(12) United States Patent
Plettner et al.

(10) Patent No.: US 9,125,406 B2
(45) Date of Patent: Sep. 8, 2015

(54) **METHODS AND COMPOSITIONS FOR CONTROL OF CABBAGE LOOPER, *TRICHOPLUSIA NI***

(71) Applicants: Simon Fraser University, Burnaby (CA); The University of British Columbia, Vancouver (CA)

(72) Inventors: Erika Plettner, Burnaby (CA); Murray Bruce Isman, Vancouver (CA)

(73) Assignees: Simon Fraser University, Burnaby (CA); The University of British Columbia, Vancouver (CA)

( * ) Notice: Subject to any disclaimer, the term of this patent is extended or adjusted under 35 U.S.C. 154(b) by 63 days.

(21) Appl. No.: 13/734,418

(22) Filed: Jan. 4, 2013

(65) Prior Publication Data
US 2013/0131185 A1 May 23, 2013

Related U.S. Application Data

(63) Continuation-in-part of application No. 12/622,421, filed on Nov. 19, 2009, now abandoned.

(60) Provisional application No. 61/116,235, filed on Nov. 19, 2008.

(51) Int. Cl.
*A01N 31/16* (2006.01)
*C07C 39/08* (2006.01)
(Continued)

(52) U.S. Cl.
CPC ............... *A01N 31/16* (2013.01); *A01N 43/12* (2013.01); *C07C 39/08* (2013.01); *C07D 307/79* (2013.01)

(58) Field of Classification Search
None
See application file for complete search history.

(56) References Cited

U.S. PATENT DOCUMENTS 2,355,974 A 8/1944 Harvill
2013/0045178 A1 2/2013 Plettner

FOREIGN PATENT DOCUMENTS

JP 2001 187702 7/2001

OTHER PUBLICATIONS

JP 2001187702, Maekawa et al. machine translation p. 1-5, Jul. 2001.
(Continued)

*Primary Examiner* — Bethany Barham
*Assistant Examiner* — Barbara Frazier
(74) *Attorney, Agent, or Firm* — Steptoe & Johnson LLP

(57) ABSTRACT

The invention provides in part dialkoxybenzene compounds for controlling infestation by a *Trichoplusia ni*, and methods thereof. The compounds include a compound of Formula I:

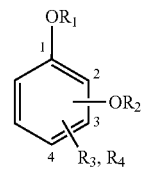

Formula I where R1 may be methyl, ethyl, propyl, n-butyl, isopentyl (3-methylbutyl) or allyl; R2 may be at positions 2, 3 or 4 and may be H, methyl, ethyl, propyl, n-butyl, isopentyl (3-methylbutyl) or allyl; and R3 may be optionally present at positions 2, 3 and 4, and is allyl; except that when R2 is at position 2, R3 if present is at position 3, and when R2 is at position 3, R3 if present is at positions 2 or 4, and when R2 is at position 4, R3 if present is at position 2, and when R2 is at position 4 and R3, if present, has reacted with an OH group at position 1 in a Markovnikov sense, then R3 becomes R4, a dihydrofuran.

19 Claims, 5 Drawing Sheets

(51) Int. Cl.
*A01N 43/12* (2006.01)
*C07D 307/79* (2006.01)

(56) References Cited

OTHER PUBLICATIONS

JP 2001 187702, English language abstract accessed via CAPLUS accession No. 2001:495266, p. 1, Jul. 2001.
Janmaat, A. F. and Myers, J. H., The cost of resistance to *Bacillus thuringiensis* varies with the host plant of *Trichoplusia ni*. Proc Biol Sci. May 2005;272:1031-1038.
Jeffery, E. H., Jarrell, V. Cruciferous Vegetables and Cancer Prevention. In: Handbook of Nutraceuticals and Functional Foods. (Wildman, R.E.C., Ed.) CRC Press, Boca Raton:Florida. 2001; Chp 11:169-191.
Jermy, T., Feeding Inhibitors and Food Preference in Chewing Phytophagous Insects. Entomologia Experimentalis et Applicata. Mar. 1966;9:1-12 (Abstract).
Johnson E.T., et al., Colored and white sectors from star-patterned petunia flowers display differential resistance to corn earworm and cabbage looper larvae J Chem Ecol. 2008;34(6):757-65.
Kain, W. C., et al., Inheritance of resistance to *Bacillus thuringiensis* Cry1Ac toxin in a greenhouse-derived strain of cabbage looper (Lepidoptera: Noctuidae). J. Econ. Entomol. 2004;97(6):2073-2078. sent.
Khambay, B. P., et al., The pyrethrins and related compounds. Part XLII:+Structure-activity relationships in fluoro-olefin non-ester pyrethroids. Pestic Sci. 1999;55:703-710.
Kim, D.H., and Ahn,Y. Contact and fumigant activities of constituents of *Foeniculum vulgare* fruit against three coleopteran stored-product insects, Pest Manag. Sci. 2001;57:301-306.
Kotkar, H. M., et al., Antimicrobial and pesticidal activity of partially purified flavonoids of *Annona squamosa*, Pest Manag. Sci. 2001;58:33-37.
Kuntz, E., et al., Palladium TPPTS catalyst in water: C-allylation of phenol and guaiacol with allyl alcohol and novel isomerisation of allyl ethers of phenol and guaiacol. J. Mol. Catal. A: Chemical. 2006;244:124-138.
Landolt, P. J, and Heath, R. R. Sexual role reversal in mate-finding strategies of the cabbage looper moth. Am Assoc for the Adv Science. Aug. 31, 1990;249(4972):1026-1028.
Lane, G. A., et al., Isoflavonoids as insect feeding deterrents and antifungal components from root of *Lupinus angustifolius*, J. Chem. Ecol. 1987;13:771-782.
Lee, J. C., et al., Facile Synthesis of Alkyl Phenyl Ethers Using Cesium Carbonate. Synth. Commun. 1995;25 (9):1367-1370.
Li, G. Q. and Ishikawa, Y. Oviposition deterrents in larval frass of four Ostrinia species fed on an artificial diet. Journal of Chemical Ecology. 2004;30(7):1445-1456.
Luthria, D. L., et al., Insect Antifeedants from Aralantia racemosa, J. Agric. Food Chem. 1989;37:1435-1437.
Markovic, I., et al., Volatiles involved in the nonhost rejection of Fraxinus pennsylvanica by Lymantria dispar larvae. J. Agric. Food Chem. 1996;44:929-935.
Mathew, N. T., et al., Rearrangement of allyl phenyl ether over AI-MCM-41. J. of Catalysis. 2005;229:105-113.
Mcewen, F. L. and Hervey, G. E. R., An Evaluation of Newer Insecticides for Control of DDT-Resistant Cabbage Loopers, J. Econ. Ent. Jun. 1956;49 (3):385-387.
Meijerink, J., et al., Identification of olfactory stimulants for Anopheles gambiae from human sweat samples. J. Chem. Ecol. 2000;26(6):1367-1382.
Miller, J. R. and Cowles, R. S., Stimulo-deterrent diversion: A concept and its possible application to onion maggot control. J. Chem. Ecol., 1990;16(11):3197-3212.
Minkenberg, O.P.J.M., et al., Egg load as a major source of variability in insect foraging and oviposition behaviour. Oikos. 1992;65:134-142.

Mota-Sanchez, D., et al., Arthropod Resistance to Pesticides: Status and Overview. In: Pesticides in Agriculture and the Environment (Wheeler, W. B. Ed.) Marcel Dekker: New York. 2002:241-272.
Munakata, K. Insect antifeedants from plants. In: Control of Insect Behaviour by Natural Products (Wood, D. L. Silverstein, R. M.; Nakajima, M. Eds.) Academic Press: New York.1970:179-187.
Murugan, K., et al, Larvicidal and repellent potential of Alibizzia amara Boivin and *Ocimum basilicum* Linn against dengue vector, Aedes aegypti (Insecta: Diptera: Culicidae). Bioresource Tech. 2006;98:198-201.
Nagabandi, S. and Plettner, E., Synthesis of Disparlure Analogues and Inhibitory Activity, Volcano Conference Feb. 23-25, 2007.
Neuhaus, E. M., et al., Odorant receptor heterodimerization in the olfactory system of *Drosophila melanogaster*, Nature Neurosci. 2005;8:15-17.
Obeng-Ofori, D. and Reichmuth, C. H., Bioactivity of eugenol, a major component of essential oil of *Ocimum suave* (Wild.) against four species of stored-product Coleoptera. Intl. J. Pest Management. 1997;43(1):89-94.
Ollevier, T., and Mwene-Mbeja,T. M., Bismuth Triflate Catalyzed [1,3] Rearrangement of Aryl 3-Methylbut-2-enyl Ethers. Synthesis. 2006;23:3963-3966.
Paduraru, P. M., et al., Synthesis of Substituted Alkoxy Benzene Minilibraries, for the Discovery of New Insect Olfaction of Gustation Inhibitors, J. Combin. Chem., 2008;10:123-134.
Paduraru, P. M., Plettner, E., Synthesis and small-scale screening of dialkoxy benzene mini-libraries for the discovery of new insect olfaction or gestation inhibitors; Volcano Conference, Park Forest, Washington, Feb. 23-25, 2007.
Park, I. K., et al., Larvicidal activity of lignans identified in *Phryma leptostachya* var. Asiatica roots against three mosquito species, J. Agric. Food Chem. 2005;53:969-972.
Parrish, J. P., et al., Improved Cs2CO3-Promoted O-Alkylation of Phenols. Synth Commun. 1999;29:4423-4431.
Plettner, E., "Structure and Function of Insect Odorant-Binding Proteins" Cambridge, UK Presentation, Apr. 25, 2008.
Plettner, "Structure and Function of Insect Odorant-Binding Proteins" Germany (Bremen, Stuttgart, Wuerzburg) Presentation, Apr. 15-21, 2008 sent (same presentation as in Cambridge).
Plettner, E., "Synthesis and Activity of Olfaction and Gustation Inhibitors against Pest Insects" CSC Conference, May 24-28, 2008.
Plettner, E., et al., "Stereoselective Synthesis and Biological Activity of Gypsy Moth Analogs"; CSC Conference, May 24-28, 2008. Abstract and Presentation.
Popoff, R. T. W. and Plettner, E., Synthesis of N-alkyl alkoxy benzenes from aminophenol; Volcano Conference Feb. 23-25, 2007.
Raffa, K.F. and Frazier, J. L., A general model for quantifying behavioural desensitization to antifeedants. Entomol. Exp. Appl., 1988;46:93-100.
Reich, N. W., et al., Gold(I)-Catalyzed Synthesis of Dihydrobenzofurans from Aryl Allyl Ethers. Synlett. 2006;8:1278-1280.
Reimer, S., et al., Partition coefficients of disparlure at hydrophobic/aqueous interfaces: A comparative experimental and theoretical study. Can. J. Chem. 2011;89:568-572.
Renwick. J.A.A., et al., Leaf surface chemicals stimulation oviposiiton by *Pieris rapae* (Lepidoptera, Pieridae) on cabbage. Chemoecology, 1992;3:33-38.
Renwick, J. A. A. and Radke,C. D., An Oviposition Deterrent Associated with Frass from Feeding Larvae of the Cabbage Looper, *Trichoplusia ni* (Lepidoptera: Noctuidae) Environmental Entomology. 1980;9(3): 318-320.
Resetarits, W. J., Oviposition site and choice of life history evolution. Am. Zool. 1996;36:205-215.
Sachdev-Gupta, K, et al., Isolation and identification of oviposition deterrents to the cabbage butterfly, *Pieris rapae*, from *Erysimum cheiranthoides*. J. Chem. Ecol., 1989;16(4):1059-1067. sent.
Salunke, B. K., et al., Efficacy of flavonoids in controlling *Callosobruchus chinensis* (L.) (Coleoptera: Bruchidae), a post-harvest pest of grain legumes, Crop Protect. 2005;24:888-893.
Sarfraz M., et al., Diamondback moth-host plant interactions: Implications for pest management. Crop Protection. 2006;25:625-639.

(56) References Cited

OTHER PUBLICATIONS

Sarfraz M. and Keddie, B. A., Conserving the efficacy of insecticides against *Plutella xylostella* (L.) (Lep., Plutellidae). Journal of Applied Entomology. 2005;129(3):149-157.

Schneider, C., et al., Insecticidal rocaglamide derivatives from *Aglaia spectabilis* (Meliaceae), Phytochem. 2000;54:731-736.

Schoonhoven, L. M. and Van Loon, J. J. A., An inventory of taste in caterpillars: each species its own key. Acta Zool. Acad. Sci. Hung. 2002;48(Suppl 1):215-263.

Simmonds, M. S. J. and Blaney, W. M., Gustatory codes in *Lepidopterous larvae*. Sym. Biol. Hungarica. 1990;39:17-27. [Journal carried as Insects-Plants, 39, 17-27, 1991].

Singh, D.V., et al., Terminalia arjuna as an insect feeding-deterrent and growth inhibitor. Phytother. Res., 2004;18:131-134.

Akhtar, Y. and Isman, M.B., Mitigating decreased feeding deterrent response to antifeedants following prolonged exposure in *Trichoplusia ni* by binary mixtures of antifeedants. Chemoecology. 2003;13:177-182.

Akhtar, Y. and Isman, M. B., Larval exposure to oviposition deterrents alters subsequent oviposition behaviour in generalist *Trichoplusia ni* and specialist, *Plutella xylostella* moths. J Chem Ecol. Aug. 2003; 29 (8):1853-1870.

Akhtar, Y. and Isman, M. B., Comparative growth inhibitory and antifeedant effects of plant extracts and pure allelochemicals on four phytophagous insect species. Journal of Applied Entomology. 2004;128:32-38.

Akhtar, Y.; Isman, M. B. Comparative growth inhibitory and antifeedant effects of plant extracts and pure allelochemicals on four phytophagous insect species. Journal of Applied Entomology 2004, 128, 32-38.

Akhtar, Y., Rankin, C. A. and Isman, M. B., Decreased response to feeding deterrents following prolonged exposure in the larvae of a generalist herbivore, *Trichoplusia ni* (Lepidoptera:Noctuidae). J Insect Behav. Nov. 2003;16(6): 811-831.

Akhtar, Y. and Isman, M.B., Feeding responses of specialist herbivores to plant extracts and pure allelochemicals: effects of prolonged exposure. Entomol. Exp. Appl. 2004;111, 201-208. sent.

Akhtar Y., et al., Screening of Dialkoxy Benzenes and Disubstituted Cyclopentene Derivatives against a Noctuid Caterpillar *Trichoplusia ni*, for the Discovery of New Feeding and Oviposition Deterrents, J. Agric. Food Chem. 2007;55:10323-10330.

Akhtar, Y., Yu, Y., Isman, M. B., Plettner, E. (2010) Dialkoxybenzene and Dialkoxyallylbenzene Feeding and Oviposition Deterrents against the Cabbage Looper, *Trichoplusia ni*: Potential Insect Behavior Control Agents. J. Agric. Food Chem. 2010;58:4983-4991.

Akhtar, Y., et al., Comparative bioactivity of selected extracts from *Meliaceae* and some commercial botanical insecticides against two noctuid caterpillars, *Trichoplusia ni and Pseudaletia unipuncta*, Phytochem Rev. 2008;7:77-88.

Ave, D. A., Stimulation of feeding: insect control agents. In: Regulatory Mechanisms in Insect Feeding (Chapman, R. F and de Boer, G. Eds.) Chapman & Hall: New York, 1995; Chp. 12:345-63.

Berenbaum, M.R., Postingestive effects of phytochemicals on insects: On Paracelsus and plant products. In: Insect-Plant Interactions (Miller, T.A., Miller, J., Eds.) Springer-Verlag: New York, 1986; Chp. 5:123-153.

Berger, R. S., Isolation, identification and synthesis of the sex attractant of the cabbage looper, *Trichoplusia ni*. Ann. Entomol. Soc. Amer. Jul. 1966;59(4):767-771.

Bernays, E.A. and Chapman, R.F., The evolution of deterrent responses in plant feeding insects. In: Perspectives in Chemoreceptions and Behavior (Chapman, R.F., Bernays, E.A. Stoffolano, J.G., Jr., Eds.) Springer-Verlag: New York, 1987; Chp. 10:159-173.

Bjostad, L. B., et al., Identification of New Sex Pheromone Components in *Trichoplusia ni*, Predicted from Biosynthetic Precursors. J. Chem.Ecol. 1984;10(9):1309-1323.

Blom, F., Sensory activity and food intake, a study of input-output relationships in two phytophagous insects. Neth. J. Zool., 1978;28(3-4):277-340.

Bortolomeazzi, R., et al., Comparative evaluation of the antioxidant capacity of smoke flavouring phenols by crocin bleaching inhibition, DPPH radical scavenging and oxidation potential. Food Chem. 2007;100 (4):1481-1489.

Burkness E.C. and Hutchison, W. D., Implementing reduced-risk integrated pest management in fresh-market cabbage: Improved net returns via scouting and timing of effective control. J Econ Entomol. 2008;101(2): 461-471.

Castillo, C., Gong, Y. and Plettner, E., "Binding Properties Comparison between Native and C-Terminus Truncated Pheromone Binding Proteins in Gypsy Moths". Abstract of Presentation at CSC Conference, Edmonton, May 24-28, 2008.

Chapman, R.F., The chemical inhibition of feeding by phytophagous insects, a review. Bull. Entomol. Res., 1974;64:339-363.

Chapman, R. F., Contact chemoreception in feeding by phytophagous insects. Annu Rev Entomol. 2003;48:455-484.

Chen, H., et al., A route to enantiomericallypure5-(2'-hydroxyethyl)cyclopent-2-en-1-ol and its absolute configuration by Mosher esters. Tetrahedron: Asymmetry. 2009;20(4):449-456.

Chow, J. K., et al., The effects of larval experience with a complex plant latex on subsequent feeding and oviposition by the cabbage looper moth: *Trichoplusia ni* (Lepidoptera: Noctuidae). Chemoecology 2005;15:129-133.

Chyb, S., et al., Identification of sensilla involved in taste mediation in adult western corn rootworm (*Diabrotica virgifera virgifera* LeConte). J. of Chem. Ecol. 1995;21(3):313-329.

Cui, F., et al., Insecticide resistance of vector mosquitoes in China. Pest Management Science. 2006;62:1013-1022.

Datta, S. and Saxena, D. B., Pesticidal properties of parthenin (from *Parthenium hysterophorus*) and related compounds. Pest Manag. Sci. 2001;57:95-101.

Davidson, R. H. and Lyion, W. F., Pests of Cucurbit and Cruciferous Crops. In: Insect Pests of Farm, Garden and Orchard (R.H. Davidson and W.F. LyonJohn Wiley, Eds.) 5th Ed. J. Wiley & Sons: New York. 1987;Chp 15:299-315.

Dethier, V.G., Electrophysiological studies of gestation in lepidopterous larvae. II. Taste spectra in relation to food-plant discrimination. J. Comp. Physiol. 1973;82:103-134.

Dewick, P. M., The Shikimate Pathway: Aromatic Amino Acids and Phenylpropanoids. In: Medicinal Natural Products: A Biosynthetic Approach, Second Edition, John Wiley & Sons, Ltd, Chichester, UK. Nov. 2001:130-140.

Dimock, M.B., et al., Chemical constituents of an unacceptable crucifer, *Erysimum cheiranthoides*, deter feeding by *Pieris rapae*. J. Chem. Ecol. 2001;17(3):525-533.

Feeny, P., et al., Chemical aspects of oviposition behavior in butterflies. In: Herbivorous Insects: Host-Seeking Behavior and Mechanisms. Ahmad (Ed.) Academic Press: New York. 1983:27-76.

Foster, S. P., and Marris, M.O., Behavior manipulation methods for insect pest-management, Annu. Rev. Entomol. 1997;42:123-146.

Frazier, J. L., The perception of plant allelochemicals that inhibit feeding. In Molecular Aspects of Insect-Plant Associations (Brattsten, L.B., Ahmad, S. Eds.) Plenum Press: New York. 1986:1-42.

Goering, H. L. and Jacobson, R.R., A Kinetic Study of the ortho-Claisen Rearrangement. J. Am. Chem. Soc. 1958;80:3277-3285.

Gong Y., et al., Ligand-interaction kinetics of the pheromone- binding protein from the gypsy moth, L. dispar: insights into the mechanism of binding and release. Chem Biol. 2009;16(2):162-172.

Gong, Y. and Plettner, E., "Ligand-Interaction Kinetics of the Pheromone-binding Protein from the Gypsy Moth, Lymantria Dispar". Presentation at 91st CSC Conference, Edmonton, May 24-28, 2008.

Gong, Y., et al., Binding Conformation and Kinetics of Two Pheromone-Binding Proteins from the Gypsy Moth Lymantria dispar with Biological and Nonbiological Ligands. Biochemistry. 2010;49:793-801.

Gozzo, F. C., et al., Regioselectivity in aromatic Claisen rearrangements. J. Org. Chem. 2003;68:5493-5499.

(56) References Cited

OTHER PUBLICATIONS

Grant, V. H., and Liu, B., Iridium(III)-catalyzed tandem Claisen rearrangement-intramolecular hydroaryloxylation of aryl allyl ethers to form dihydrobenzofurans. Tetrahedron Lett. 2005;46:1237-1240.

Griffiths, D. C., et al., Laboratory evaluation of pest management strategies combining antifeedants with insect growth regulator insecticides. Crop Prot., 1991;10:145-151.

Guillen, M. D. and Manzanos, M. J., Characteristics of smoke flavourings obtained from mixtures of oak (*Quercus* sp.) wood and aromatic plants (*Thymus vulgaris L. and Salvia lavandulifolia Vahl.*). Flavour and Fragrance J. 2005;20,676-685.

Hallem, E. A., et al., Mosquito receptor for human-sweat odorant. Nature 2004;427:212-213.

Harborne, J.B., Recent Advances in Chemical Ecology. Nat. Prod Rep. 1989;6(1):85-109.

Heath, R. R., et al., Identification of male cabbage looper sex pheromone attractive to females. J. Chem. Ecol. 1992;18(3):441-453.

Hirao, T. and Arai N., Electrophysiological studies on gustatory responses in common cutworm larvae, *Spodoptera litura*. J. Appl. Entomol. Zool. 1993;37:129-136. English Abstract with Japanese publication.

Huang, X.P. and Renwick, J. A. A., Differential selection of host plants by two Pieris species: The role of oviposition stimulants and deterrents. Entomol. Exp. Appl. 1993;68:59-69.

Isman, M. B., Problems and opportunities for the commercialization of insecticides. In: Biopesticides of Plant Origin (Regnault-Roger, C., Philogene, B.J.R., and Vincent, R. Eds.) Lavoisier: Paris, 2005:283-291.

Isman, M. B., Insect Antifeedants, Pesticide Outlook. Aug. 2002;13:152-157.

Isman, M. B. and Rodriguez, E., Larval growth inhibitors from species of *Parthenium* (*Asteraceae*). Phytochemistry. 1983;22(12):2709-2713.

Ito, F., et al., Boron Trichloride Meidated Regioselective Claisen Rearrangement of Resorcinol Derivatives: Application to Resorcinol Cawonyl Ethers. Synthesis 2007;12:1785-1796.

Ito, Y., et al., Intramolecular cyclization of phenol derivatives with C=C double bond in a side chain. J. Organometallic Chem. 2007;692:691-697.

Tamez-Guerra, P., et al., Differences in Susceptibility and Physiological Fitness of Mexican Field *Trichoplusia ni* Strains Exposed to *Bacillus thuringiensis*. J. Econ. Entomol. 2006;99(3):937-945.

Topazzini, A., et al., Electroantennogram responses of five *Lepidopteran* species to 26 general odorants, J. Insect Physiol. 1990;36(9):619-624.

Upasani, S. M., et al., Partial characterization and insecticidal properties of *Ricinus communis L. foliage flavonoids*, Pest Manag. Sci. 2003;59:1349-1354.

Usher, B.F., et al., Antifeedant tests with larvae of *Pseudaletia unipuncta* variability of behavioural response. Entomol. Exp. Appl. 1988;48:203-212.

Van Loon, J.J.A. and Schoonhoven, L.M., Specialist deterrent chemoreceptors enable *Pieris caterpillars* to discriminate between chemically different deterrents. Entomol. Exp. Appl., 1999;91:29-35.

Wang, S. F., et al., Chemical defenses of *Trifolium glanduliferum* against red legged earth mite Halotydeus destructor, J. Agric. Food Chem. 2005;53:6240-6245.

Wang, P., et al., Mechanism of Resistance to *Bacillus thuringiensis* Toxin Cry1Ac in a Greenhouse Population of the Cabbage Looper, *Trichoplusia ni*. Appl.Env. Microbiol. 2007;73:1199-1207.

White, W. N., et al., The ortho-Claisen Rearrangment. I. The Effect of Substituents on the Rearrangement of Allyl p-X-Phenyl Ethers. J. Am. Chem. Soc. Jul. 5, 1958;80:3271-3277.

White, W. N., and Slater, C. D., The ortho-Claisen rearrangement. V. The products of rearrangement of allyl m-X-phenyl ethers, J. Org. Chem. Oct. 1961;26, 3631-3638.

Xu, H., et al., Oviposition deterrents in larval frass of the cotton boll worm, *Helicoverpa armigera* (Lepidoptera: Noctuidae): Chemical identification and electroantennography analysis. Journal of Insect Physiology. 2006;52:320-326.

Yadav, G. D. and Lande, S. V., UDCaT-5: A Novel and Efficient Solid Superacid Catalyst for Claisen Rearrangement of Substituted Allyl Phenyl Ethers. Synth. Commun. 2007;37:941-946.

Schoonhoven, L. M., Insects in a Chemical Word. In: CRC Handbook Series of Naturally Occurring Pesticides. vol. VI (Morgan, E. D. and Mandava, N. B., Eds.) Insects Attractants and Repellents. 1985:1-21.

Ono, H., Kuwahara, Y. and Nishida, R., Hydroxybenzoic Acid derivatives in a nonhost rutaceous plant, *Orixa japonica*, deter both oviposition and larval feeding in a rutaceae-feeding swallowtail butterfly, *Papilio xuthus* L. J. Chem. Ecol. 2004;30(2):287-301.

U.S. Office Action Issued Jun. 3, 2014 for U.S. Appl. No. 13/592,036.

METHODS AND COMPOSITIONS FOR CONTROL OF CABBAGE LOOPER, *TRICHOPLUSIA NI*

This application claims the priority benefit of U.S. Provisional application 61/116,235, filed Nov. 19, 2008, and U.S. Utility application Ser. No. 12/622,421 the contents of which are herein incorporated by reference.

FIELD OF INVENTION

The present invention relates to insect control. More specifically, the present invention relates to methods and compositions for control of the cabbage looper, *Trichoplusia ni*.

BACKGROUND OF THE INVENTION

The behavioral manipulation of insect pests for their management, as an alternative to broad-spectrum insecticides, has been investigated for many years.

In addition to the development of resistance against insecticides by the target organism, broad-spectrum insecticides also have negative impacts on natural enemies of the pest insect, on pollinators and on other non-target organisms. Therefore, there is an increased interest in the behavioral manipulation of insect pests for their management as an alternative to broad-spectrum insecticides. Of particular interest are compounds that do not exhibit substantial toxicity or demonstrate some degree of selectivity towards a pest insect and not toward natural enemies, pollinators or the environment. In practice, manipulation may be achieved through the use of stimuli that either enhance or inhibit a particular behavior and ultimately change its expression. Many natural plant defensive chemicals discourage insect herbivory, for example, by deterring feeding and oviposition or by impairing larval growth, rather than by killing insects.

The choice of a stimulus for behavioral manipulation is usually dependent upon a number of factors including accessibility, reproducibility, specificity and practicality (Foster and Marris 1997). Various short- or long-range stimuli, involved in behavioral manipulation of insects, are perceived through contact chemoreceptors or olfactory receptors, respectively. These stimuli can either stimulate feeding or oviposition, keeping the insect at the host plant, or inhibit those behaviors, resulting in the insect abandoning the plant. Examples of feeding stimulants often include carbohydrates, proteins, or fats (Ave 1995) that are ubiquitous in plants, whereas oviposition stimulants can be highly species-specific. Feeding stimulants can be used in conjunction with toxins in "attract and kill" strategies (Ave 1995), occasionally employed in crop protection. A deterrent can be applied to a host plant to prevent feeding or oviposition. Therefore, deterrents may have potential value in crop protection, in combination with other strategies such as "attract and kill" (Jermy 1965; Munakata 1970).

Insect feeding deterrents can be found among all the major classes of plant secondary metabolites—alkaloids, phenolics and terpenoids (Frazier 1986). Especially well studied in this group are the triterpenes such as the limonoids from the neem (*Azadirachta indica*) and chinaberry (*Melia azedarach*) trees and from Citrus species and the diterpenes including the clerodanes and the abietanes (Isman 2002). Apart from terpenes, another important class of compounds involved in defense of the plant against herbivores and pathogens, as well as in attracting pollinators, are the compounds derived from aromatic amino acids—phenylpropanoids (Wildman 2006).

Eugenol is a volatile member of the phenylpropanoid class of compounds from essential oils of many spices, particularly clove (Dewick 2002). Cloves are useful in the home as moth deterrents and the main odorant from cloves, eugenol, has been reported to be perceived as a long-range stimulus by several lepidopterans (Topazzini et al. 1990). One problem with phenylpropanoids such as eugenol and compounds with a cinnamyl framework is that they can produce toxic metabolites after benzylic/allylic oxidation by certain cytochrome P450 enzymes (Dewick 2002).

Several polyphenolic compounds are also known for their toxic/insecticidal effects (Kim and Ahn 2001; Schneider et al. 2000; Khambay et al. 1999; Harborne 1989). Flavonoids isolated from *Annona squamosa* (Kotkar et al. 2002), *Ricinus communis* (Upasani 2003) and *Calotropis procera* (Salunke et al et al. 2005), are toxic to the pulse beetle. *Callosobruchus chinensis* and *R. communis* also caused oviposition deterrent and ovicidal affects in addition to toxicity. Larvicidal activity of lignans, leptostachyol acetate and analogues from the roots of *Phryma leptostachya* have been reported against three mosquito species (*Culex pipiens pallens, Aedes aegypti*, and *Ocheratatos togoi*) (Park et al et al. 2005).

Compounds derived from aromatic amino acids, such as some phenolics, have been reported to be involved in defense of the plant against herbivores and pathogens, as well as in attracting pollinators. For example phenol derivatives such as guaiacol (1-hydroxy-2-methoxybenzene), 1,2-dimethoxybenzene, 1-ethoxy-2-methoxybenzene, 1-propoxy-2-methoxybenzene, eugenol and isoeugenol, occur in smoke (Guillen and Manzanos 2005; Murugan et al et al. 2006) and are reported to have insect-repellent and insecticidal activities (Murugan et al et al. 2006). Furthermore, smoke phenolics taste and smell pleasantly (to humans) (Guillen and Manzanos 2005) and may have antioxidant activity (Bortolomeazzi, et al. 2006). Eugenol (2-methoxy-4-(2-propenyl)phenol), is found in herbs (such as basil, *Ocimum suave* (Wild.)) and has been reported to have activity against grain beetles as a toxicant and deterrent (Obeng-Ofor and Reichmuth 1997). Other benzene derivatives, such as benzyl alcohol, benzonitrile, phenylethanol, 4-methyl phenol, 4-ethylphenol, 2-methylphenol and benzaldehyde are reported components of human odor that malaria mosquitoes respond to (Hallem et al. 2004; Meijerink et al. 2000).

Widely distributed, the cabbage looper *Trichoplusia ni* is considered an important field and greenhouse pest in vegetable crop production. This species is a generalist and attacks a variety of crops including lettuce, beets, turnip, spinach, brussel sprouts, peas, celery, tomatoes, rape, tobacco, certain ornamentals, many weedy plants, as well as cruciferous plants. Moths emerge in the spring and use two mate-finding strategies (Landolt and Heath 1990). One strategy involves male attraction to the female-produced sex pheromone which includes the major component Z-7-dodecenyl acetate (Berger 1966) and several other structurally related compounds (Bjostad et al. 1984). The other strategy involves female attraction to the male pheromone composed of the major component S-(+)-linalool, as well as p-cresol and m-cresol (Heath et al. 1992). The amount of pheromone released by the male has been reported to be affected by the cabbage odour.

The mated females deposit dome-shaped, pale green eggs singly on the host-plants, chiefly at night. After hatching, the destructive larval stage reaches full development in two to four weeks; pupation then occurs and in almost 10 days the new adults emerge. In general, the larval stages damage the crop. The first two larval stages feed on the lower side of the leaf, eating through the upper epidermis, leaving "windows" in the leaf. Older larvae chew larger holes in the leaves, often resulting in extensive damage to leaves. Although this pest generally damages leaves, damage has been reported on watermelon rinds and on flowers of various host plants. Three or more generations are generally produced each season, depending on the latitude (Davidson and Lyon 1979).

The loopers overwinter in the pupal stage, the pupae enclosed in flimsy silken cocoons attached to the food plants or to nearby objects. Cabbage loopers do not generally overwinter in Canada and migrate in from the south. However, they can overwinter in greenhouses.

Chemosensory input from contact chemosensilla present on the tarsi, antennae, and other parts of the body, such as the ovipositor, affects feeding and oviposition behaviors in cabbage looper as well as other phytophagous insects. Based on the sensory information received, an insect can chose a proper feeding or an oviposition site. Neonates of many species including cabbage looper are incapable of locating a new host and are dependent on the host plant location "skills" of their mothers (Feeny et al. 1983). Therefore, the site of emergence is of importance to the larvae of many lepidopteran species (Restraits 1966).

*T. ni* has developed resistance to a number of commercial insecticides, including early generation insecticides such as DDT, carbaryl, parathion, (McEwen 1956) as well as more modern insecticides such as methomyl and Bt (*Bacillus thuringiensis* toxin), a widely used benign and specific insecticide against moth pests that are in the larval stages (Wang et al. 2007).

SUMMARY OF THE INVENTION

The present invention provides in part methods and compositions for controlling infestation by *Trichoplusia ni*.

In one aspect, the invention provides a method for controlling infestation by a *Trichoplusia ni* comprising applying an effective amount of a compound of Formula I to a site of interest whereby the infestation is controlled.

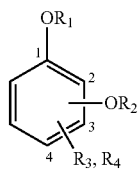

Formula I

In Formula I, R1 may be methyl, ethyl, propyl, n-butyl, isopentyl (3-methylbutyl) or allyl; R2 may be at positions 2, 3 or 4 and may be H, methyl, ethyl, propyl, n-butyl, isopentyl (3-methylbutyl) or allyl; R3 may be optionally present at positions 2, 3 and 4, and is allyl; with the provisos that when R2 is at position 2, R3 if present is at position 3; when R2 is at position 3, R3 if present is at positions 2 or 4; when R2 is at position 4, R3 if present is at position 2, or when R2 is at position 4 and R3, if present, has reacted with an OH group at position 1 in a Markovnikov sense, then R3 becomes R4, a dihydrofuran.

In an alternative aspect, the invention provides a method of protecting a plant from infestation by *Trichoplusia ni* comprising applying an effective amount of a compound of Formula I, to a site of interest whereby the plant is protected.

In alternative embodiments, the controlling may be one or more of oviposition deterrence, feeding deterrence, oviposition stimulation, feeding stimulation, or toxicity.

The compound of Formula I may be an oviposition deterrent, such as one or more of 3a{4,6}, 3a{3,4}, 5c{1,1-5}, 4b{4-5}, 3c{4,1-5}, 5b{6,1}, 4c{1-5}, 5b{5,1}, 3c{2,1-5}, 5c{2,1-5}, 3a{6,1-5}, 3a{6,1-5}, 3b{1,1-5}, or 3c{2,2}.

The compound of Formula I may be a feeding deterrent, such as one or more of 3c{1,1-5}, 5c{1,1}, 3c{2,2}, 5b{2,4-5}, 3c{4,1-5}, 3b{5,1-5}, 5c{5,1-5}, 3b{4,1-5}, 3b{2,2}, 3b{1,5}, 5b{6,2-3}, 3c{2,1-5}, 5b{3,1}, 3a{4,6}, 5c{3,1}, 5b{3,2}, 5b{3,2}, 5b{6,1}, 5b{2,1}, 5b{3,2-3}, 5b{3,2}x, 3c{3,3}, 3a{3,6}, 3c{6,6}, 3b{3,3}, 3b{3,5}, 3b{6,6}, 3b{3,1-5}, 3a{4,1-5}, 3a{3,4}, 5b{5,1}, 3c{5,1-5}, 3a{3,1-5}, 3c{6,1-5}, 3c{3,6}, 3c{2,3}, 4a{1-5}, 5a{1,1-5}, 5a{2,1-5}, 6c{1-5}, 5b{3,1}, or 5b{3,1}y.

The compound of Formula I may be a oviposition stimulant, such as one or more of 3c{5,6} and 5b{2,4-5}.

The compound of Formula I may be a feeding stimulant, such as one or more of 2b{2}, 2411, and 2c{3}.

The compound of Formula I may be non-toxic, or may be toxic. The toxicity may be selective for *Trichoplusia ni*.

In alternative embodiments, two or more compounds of Formula I may be applied simultaneously or sequentially. In alternative embodiments, a compound of Formula I may be applied in combination with another compound or treatment, such as one or more of an oviposition deterrent, an oviposition stimulant, a feeding deterrent, a feeding stimulant, an attractant, or a toxicant.

In alternative embodiments, the *T. ni* may be a larva or may be an adult, e.g. a female adult.

In alternative embodiments, the site of interest may be a plant or part thereof such as a cultivated plant within the host range of *T. ni*.

In alternative embodiments, the compound of Formula I may be provided in a formulation selected from one or more of a spray, aerosol, solid, or liquid. The liquid may be an aqueous solution, oil-in-water emulsion or dispersion.

In alternative embodiments, the compound of Formula I may be provided in a controlled release form.

In an alternative aspect, the invention provides a composition including one or more compounds selected from one or more of an oviposition deterrent, an oviposition stimulant, a feeding deterrent, a feeding stimulant and toxicant.

The feeding deterrent composition may include one or more of a compound selected from 3c{1,1-5}, 5c{1,1}, 3c{2,2}, 5b{2,4-5}, 3c{4,1-5}, 3b{5,1-5}, 5c{5,1-5}, 3b{4,1-5}, 3b{2,2}, 3b{1,5}, 5b{6,2-3}, 3c{2,1-5}, 5b{3,1}, 3a{4,6}, 5c{3,1}, 5b{3,2}, 5b{3,2}, 5b{6,1}, 5b{2,1}, 5b{3,2-3}, 5b{3,2}x, 3c{3,3}, 3a{3,6}, 3c{6,6}, 3b{3,3}, 3b{3,5}, 3b{6,6}, 3b{3,1-5}, 3a{4,1-5}, 3a{3,4}, 5b{5,1}, 3c{5,1-5}, 3a{3,1-5}, 3c{6,1-5}, 3c{3,6}, 3c{2,3}, 4a{1-5}, 5a{1,1-5}, 5a{2,1-5}, 6c{1-5}, 5b{3,1}, or 5b{3,1}y.

The oviposition deterrent composition may include one or more of a compound selected from 3a{4,6}, 3a{3,4}, 5c{1,1-5}, 4b{4-5}, 3c{4,1-5}, 5b{6,1}, 4c{1-5}, 5b{5,1}, 3c{2,1-5}, 5c{2,1-5}, 3a{6,1-5}, 3a{6,1-5}, 3b{1,1-5}, or 3c{2,2}.

The oviposition stimulant composition may include one or more of a compound selected from 3c{5,6} or 5b{2,4-5}.

The toxicant composition may include one or more of a compound selected from 2b{2}, 2c{1}, 2c{3}.

This summary of the invention does not necessarily describe all features of the invention.

BRIEF DESCRIPTION OF THE DRAWINGS

These and other features of the invention will become more apparent from the following description in which reference is made to the appended drawings wherein.

DETAILED DESCRIPTION

Figure 1:
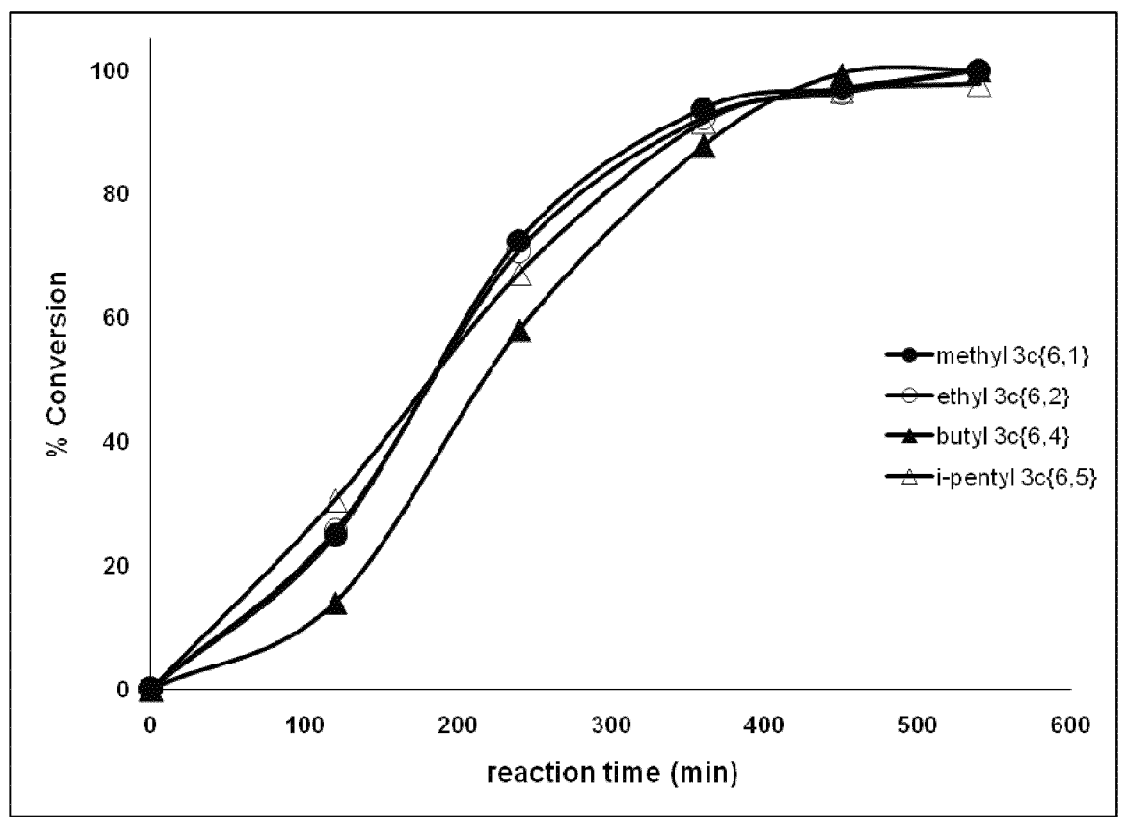
FIG. 1 shows a graph with the progress of the Claisen rearrangement reaction of 3c{6,1-5} library.

The present invention provides in part methods and compositions for controlling infestation by *Trichoplusia ni*.

The cabbage looper *T. ni* is an important plant pest and is a member of the moth family Noctuidae found throughout North America. The light green caterpillar (larva) grows to be about 2 inches long. The adult moth is a nocturnal brown moth. The caterpillar or larval stages generally cause extensive damage to plants. A "larva" or "larvae" as used herein refers to any caterpillar stage of *T. ni*. In some embodiments, a larva refers to third-instar larvae i.e., larvae that have molted twice after eclosion.

The cabbage looper is a generalist and feeds on a wide range of plants, including cultivated plants and weeds. Plants at risk for infestation by cabbage loopers, i.e., a "host plant" or a "plant within the host rage of *T. ni*" include without limitation cruciferous plants, such as cabbage, broccoli, cauliflower, Chinese cabbage, collards, kale, mustard, radish, rutabaga, Brussels sprouts, turnip, watercress, etc. Other plants attacked by cabbage loopers include without limitation crops such as lettuce, clover, beet, pea, celery, tomatoes, rape, cantaloupe, cucumber, lima bean, parsnip, pepper, potato, snap bean, peanut, soybean, spinach, squash, sweet potato, tomato, watermelon, cotton, tobacco, etc; flowers such as chrysanthemum, hollyhock, snapdragon, sweetpea, etc.; agricultural weeds such as lambsquarters, *Chenopodium album*; wild lettuce, *Lactuca* spp.; dandelion, *Taraxacum officinale*; curly dock, *Rumex crispus*, ornamental plants; etc. Although the larvae generally damage leaves, damage to other plant parts such as watermelon rinds and flowers of various host plants has been reported. Adult moths have been reported to feed on nectar from a wide range of host flowering plants, including clover, *Trifolium* spp.; goldenrod, *Solidago canadensis; dogbane, Apocynum* spp.; sunflower, *Helianthus* spp.; etc. In some embodiments, the plants are plants of economic interest, such as agricultural or crop plants.

The invention provides, in part, compounds for use in controlling infestation by *T. ni*.

By "infestation" is meant the colonization of a site or the consumption of a plant by *T. ni*. In some embodiments, infestation refers to an undesirable number of *T. ni*, sufficient to cause damage, for example, economic damage to a plant. By "control of infestation" or "controlling infestation" is meant reduction or inhibition of infestation of a plant by *T. ni* by at least about 25% to at least about 100%, or any value therebetween for example about 25%, 30%, 35%, 40%, 45%, 50%, 55%, 60%, 65%, 70%, 75%, 80%, 85%, 90%, 95%, 99%, or 100% when compared to a control plant. In alternative embodiments, by "control of infestation" or "controlling infestation" is meant reduction or inhibition of infestation of a plant by *T. ni* by at least about 1-fold or more, for example, about 1.5-fold to about 100-fold, or any value therebetween for example about 2.0, 2.5, 3.0, 3.5, 4.0, 4.5, 5.0, 5.5, 6.0, 6.5, 7.0, 7.5, 8.0, 8.5, 9.0, 9.5, 10, 15, 20, 25, 30, 35, 40, 45, 50, 55, 60, 65, 70, 75, 80, 85, 90, 95-fold when compared to a control plant. Infestation may be determined using standard techniques as known in the art or described herein. For example, infestation may be measured by comparing physical features and characteristics such as leaf damage or plant growth. By "protecting a plant from infestation" is meant reducing the probability that a *T. ni* infestation will be established in a plant. In alternative embodiments, "control of infestation" includes oviposition deterrence, feeding deterrence, oviposition stimulation, feeding stimulation, or toxicity.

By "oviposition deterrence" is meant a decrease in egg-laying by adult female *T. ni* by at least about 40% to at least about 100%, or any value therebetween for example about 40%, 45%, 50%, 55%, 60%, 65%, 70%, 75%, 80%, 85%, 90%, 95%, 99%, or 100% when compared to a control. Oviposition may be determined using standard techniques as known in the art or described herein.

By "feeding deterrence" is meant a decrease in feeding by *T. ni* larvae by at least about 50% to at least about 100%, or any value therebetween for example about 50%, 55%, 60%, 65%, 70%, 75%, 80%, 85%, 90%, 95%, 99%, or 100% when compared to a control. Feeding may be determined using standard techniques as known in the art or described herein.

By "oviposition stimulation" is meant an increase in egg-laying by adult female *T. ni* by at least about 25% to at least about 100%, or any value therebetween for example about 25%, 30%, 35%, 40%, 45%, 50%, 55%, 60%, 65%, 70%, 75%, 80%, 85%, 90%, 95%, 99%, or 100% when compared to a control. Oviposition may be determined using standard techniques as known in the art or described herein.

By "feeding stimulation" is meant an increase in feeding by *T. ni* larvae by at least about 25% to at least about 100%, or any value therebetween for example about 25%, 30%, 35%, 40%, 45%, 50%, 55%, 60%, 65%, 70%, 75%, 80%, 85%, 90%, 95%, 99%, or 100% when compared to a control. Feeding may be determined using standard techniques as known in the art or described herein.

By "toxicity" is meant an increase in mortality of adult or larval *T. ni* by at least about 25% to at least about 100%, or any value therebetween for example about 25%, 30%, 35%, 40%, 45%, 50%, 55%, 60%, 65%, 70%, 75%, 80%, 85%, 90%, 95%, 99%, or 100% when compared to a control. Toxicity may be determined using standard techniques as known in the art or described herein.

In alternative embodiments, the invention provides compounds for use in oviposition deterrence, feeding deterrence, oviposition stimulation, feeding stimulation, or toxicity as described herein.

Compounds for use in control of *T. ni* infestation include compounds according to Formula I, and mixtures thereof:

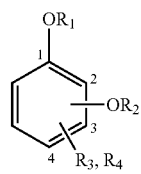

Formula I

In Formula I, R1 may be hydrogen, methyl, ethyl, propyl, n-butyl, isopentyl (3-methylbutyl) or allyl; R2 may be at positions 2, 3 or 4 and may be hydrogen, methyl, ethyl, propyl, n-butyl, isopentyl (3-methylbutyl) or allyl; R3 may be optionally present at positions 2, 3 or 4, and may be allyl.

In general, in Formula I, when R2 is at position 2, R3 if present is at position 3; when R2 is at position 3, R3 if present is at positions 2 or 4; when R2 is at position 4, R3 if present is at position 2; and when R2 is at position 4 and R3, if present, has reacted with an OH group at position 1 in a Markovnikov sense, then R3 becomes R4, a dihydrofuran.

In alternative embodiments, a compound according to Formula I also includes a compound of Formula II:

Formula II

In a compound of Formula II in general, R1 is at position 1, R2 is at position 2 and R3 if present is at position 3. For compounds 2a{R1} if R1 is not H, R2 is H and R3 is H; for compounds 3a {R2,R1} if R1 and R2 are not H and R3 is H; for compounds 4a{R1}, if R1 is not H, R2 is H and R3 is allyl; for compounds 5a{R2;R1} if R1 and R2 are not H and R3 is allyl. R1, R2 may be hydrogen, methyl, ethyl, propyl, n-butyl, isopentyl (3-methylbutyl) or allyl.

In alternative embodiments, a compound according to Formula I also includes a compound of Formula III:

Formula III

In a compound of Formula III in general, R1 is at position 1, R2 is at position 3 and R3 if present is at position 2. For compounds 2b{R1} if R1 is not H, R2 is H and R3 is H; for 3b{R2,R2} if R1 and R2 are not H and R3 is H; for compounds 4b{R1}y if R1 is not H, R2 is H and R3 is allyl; for compounds 5b{R2,R1}y if R1 and R2 are not H and R3 is allyl. R1, R2 may be hydrogen, methyl, ethyl, propyl, n-butyl, isopentyl (3-methylbutyl) or allyl.

In alternative embodiments, a compound according to Formula I also includes a compound of Formula IV:

Formula IV

In a compound of Formula IV in general; R1 is at position 1; R2 is at position 3 and R3 is at position 4. For compounds 2b{R1} if R1 is not H, R2 is H and R3 is H; for compounds 3b{R2,R1} if R1 and R2 are not H and R3 is H; for compounds 4b{R1}x if R1 is not H, R2 is H and R3 is allyl; for compounds 5b{R2,R1}x if R1 and R2 and R2 are not H and R3 is allyl. R1, R2 may be hydrogen, methyl, ethyl, propyl, n-butyl, isopentyl (3-methylbutyl) or allyl.

In alternative embodiments, a compound according to Formula I also includes a compound of Formula V:

Formula V

In a compound of Formula V in general R1 is at position 1, R2 is at position 4 and R3 is at position 3. For compounds 2c{R1} if R1 is not H, R2 is H and R3 is H; For compounds 3c{R2,R1} if R1 and R2 are not H and R3 is H; for compounds 4c{R1} if R1 is not H, R2 is H and R3 is allyl; for compounds 5c{R2,R1} if R1 and R2 are not H and R3 is allyl. R1, R2 may be hydrogen, methyl, ethyl, propyl, n-butyl, isopentyl (3-methylbutyl) or allyl.

In alternative embodiments, a compound according to Formula I also includes a compound of Formula VI:

Formula VI

In a compound of Formula VI in general R1 is at position 4; R4 is a dihydrofuran. R1 may be hydrogen, methyl, ethyl, propyl, n-butyl, isopentyl (3-methylbutyl) or allyl.

In alternative embodiments, a compound according to Formula I includes an oviposition deterrent. By "oviposition deterrent" is meant a compound according to Formula I that exhibits oviposition deterrence. In alternative embodiments, a oviposition deterrent includes a compound according to Formula I, for example, a compound of Formula I where R1 may be methyl, ethyl, propyl, butyl or isopentyl, but not H, and R2 may be methyl, ethyl, propyl, allyl, or butyl, but not H, and R3 may be H or allyl. In alternative embodiments, a oviposition deterrent includes one or more of: 3a{4,6}, 3a{3, 4}, 5c{1,1-5}, 4b{4-5}, 3c{4,1-5}, 5b{6,1}, 4c{1-5}, 5b{5, 1}, 3c{2,1-5}, 5c{2,1-5}, 3a{6,1-5}, 3a{6,1-5}, 3b{1,1-5}, or 3c{2,2}. In alternative embodiments, a oviposition deterrent includes one or more of: 4b{4-5}, 3c{4,1-5}, 5b{6,1}, 4c{1-5}, 5b{5,1}, 3c{2,1-5}, 5c{2,1-5}, 3a{6,1-5}, 3a{6,1-5}, or 3b{1,1-5}.

In alternative embodiments, a compound according to Formula I includes a feeding deterrent. By "feeding deterrent" is meant a compound according to Formula I that exhibits feeding deterrence. In alternative embodiments, a feeding deterrent includes a compound according to Formula I, for example, a compound of Formula I where R1 may be ethyl, propyl, allyl, butyl or isopentyl, but not H, and R2 may be methyl, ethyl, propyl, butyl, isopentyl or allyl but not H, and R3 may be allyl or H, and R4 if present may be dihydrofuran. In alternative embodiments, a feeding deterrent includes one or more of: 3c{1,1-5}, 5c{1,1}, 3c{2,2}, 5b{2,4-5}, 3c{4,1-5}, 3b{5,1-5}, 5c{5,1-5}, 3b{4,1-5}, 3b{2,2}, 3b{1,5}, 5b{6,2-3}, 3c{2,1-5}, 5b{3,1}, 3a{4,6}, 5c{3,1}, 5b{3,2}, 5b{3,2}, 5b{6,1}, 5b{2,1}, 5b{3,2-3}, 5b{3,2}x, 3c{3,3}, 3a{3,6}, 3c{6,6}, 3b{3,3}, 3b{3,5}, 3b{6,6}, 3b{3,1-5}, 3a{4,1-5}, 3a{3,4}, 5b{5,1}, 3c{5,1-5}, 3a{3,1-5}, 3c{6,1-5}, 3c{3,6}, 3c{2,3}, 4a{1-5}, 5a{1,1-5}, 5a{2,1-5}, 6c{1-5}, 5b{3,1}, or 5b{3,1}y.

In alternative embodiments, a feeding deterrent includes a compound according to Formula I that exhibits greater than about 80% feeding deterrence and a $DC_{50}$ of less than about 30 μg/cm$^2$, such as a $DC_{50}$ of less than about 20 μg/cm$^2$. In alternative embodiments, a feeding deterrent includes one or more of: 3c{4,1-5}, 3b{4,1-5}, 5b{6,2-3}, 3c{2,1-5}, 3a{4, 6}, 5c{3,1}, 5b{3,2}, 5b{3,2}, 5b{6,1}, 5b{3,2-3}, 3c{3,3}, 3a{3,6}, 3c{6,6}, 3b{3,3}, 3b{3,5}, 3b{6,6}, 3a{4,1-5}, 5b{5,1}, 3c{5,1-5}, 3a{3,1-5}, 3c{6,1-5}, 3c{3,6}, 5a{1,1-5}, 5a{2,1-5}, 6c{1-5}, 5b{3,1}, or 5b{3,1}y.

In alternative embodiments, a feeding deterrent includes a compound having a Feeding Deterrence Index (Feeding Deterrence/($DC_{50}$×mortality) of at least about 4, 6, or 9. In alternative embodiments, a feeding deterrent includes a compound having a Feeding Deterrence Index of at least about 35, 40, 45, 50, 55, 60, 65, 70, 75, 70, 85, 90, 95 or 100. In alternative embodiments, a feeding deterrent includes a compound having a Feeding Deterrence Index of at least about 200, 500, 1000, 1500, or 2000.

In alternative embodiments, a compound according to Formula I includes an oviposition stimulant. By "oviposition stimulant" is meant a compound according to Formula I that exhibits oviposition stimulation. In alternative embodiments, an oviposition stimulant includes a compound according to Formula I, for example, a compound of Formula I where R1 may be allyl, butyl or isopentyl and R2 may be ethyl or isopentyl and R3 may be allyl or H. In alternative embodiments, a oviposition stimulant includes one or both of: 3c{5, 6} or 5b{2,4-5}.

In alternative embodiments, a compound according to Formula I includes a feeding stimulant. By "feeding stimulant" is meant a compound according to Formula I that exhibits feeding stimulation. In alternative embodiments, a feeding stimulant includes a compound according to Formula I, for example, a compound of Formula I where R1 may be methyl, ethyl or propyl, and R2 may be H. In alternative embodiments, a feeding stimulant includes one or more of: 2b{2}, 2c{1}, or 2c{3}.

In alternative embodiments, a compound according to Formula I includes a toxicant. By "toxicant" is meant a compound according to Formula I that exhibits toxicity. In alternative embodiments, a toxicant includes a compound according to Formula I, for example, a compound of Formula I where R1 may be ethyl and —OR2 is para to OR1 (=at position 4 relative to OR1) and R2 may be methyl, ethyl, propyl, butyl or isopentyl. In alternative embodiments, a toxicant includes one or more of: 5b{6,1}, 5a{2,1-5}, 5c{5,1-5}, 3b{4,1-5}, 3b{1,5}, 3b{1,6}, 5b{6,2-3}, 5b{6,4-5}, 3b{2, 2}, 5c{1,1}, 3a{5,5}, 3b{6,4-5}, 5a{3,1-5}, 3b{3,1-5}, 4b{4-5}, 5b{1,1}, 3c{3,1-5}, 3c{4,1-5}, 3b{6,2-3}, 5b{1,2-3}, 4b{2-3}, 3b{3,3}, 3c{2,1-5}, or 3c{2,2}.

In alternative embodiments, a compound according to Formula I is non-toxic. By "non-toxic" is meant a mortality rate of adult or larval *T. ni* of less than about 25%, 30%, 35%, 40%, 45%, 50%, 55%, 60%, 65%, 70%, 75%, 80%, 85%, 90%, 95%, 99%, or 100% when compared to a control. Toxicity may be determined using standard techniques as known in the art or described herein. In alternative embodiments, a non-toxic compound includes a compound according to Formula I, for example, a compound of Formula I where R1 may be methyl, ethyl or allyl and R2 may be propyl or allyl. In alternative embodiments, a non-toxicompound includes a compound according to Formula I. In alternative embodiments, a non-toxic compound includes one or more of: 3c{3, 6}, 5b{3,1}y, 5b{6,1}, 5b{3,2}x, 5b{3,2}, 5b{3,2}, 6c{1-5}, 5b{5,1}, 5c{3,1}, 3c{6,1-5}, 5b{3,1}, 5b{2,1}, 5b{3,2-3}, 3a{4,1-5}, 3b{3,5}, 5b{2,4-5}, or 5b{3,1}.

In alternative embodiments, a compound according to the invention is selective. By "selective" is meant that a compound exhibits an activity such as one or more of oviposition deterrence, feeding deterrence, oviposition stimulation, feeding stimulation, or toxicity towards *T. ni* but not other pests, such as other noctuid moths or insects, or other organisms. In some embodiments, by "selective" is meant that a compound exhibits an activity such as one or more of oviposition deterrence, feeding deterrence, oviposition stimulation, feeding stimulation, or toxicity towards larval *T. ni* but not adults, and vice versa.

In alternative embodiments, a compound according to the invention, as used herein, may include one or more than one compound as described in Formula I, or in the Tables and Figures herein. Accordingly, in some embodiments, sets or mixtures of the compounds as described in Formula I, or in the Tables and Figures herein are included in the meaning of the term "compound". In alternative embodiments, one or more than one compound as described in in Formula I, or in the Tables and Figures herein, may be specifically excluded from the methods or compositions according to the invention.

A compound according to the invention may be applied to a site of interest to control infestation by *T. ni*. By "site of interest" is meant any area or region that is infested with, or at risk of infestation by, *T. ni* or is in the vicinity of such an area or region. Sites of interest include without limitation a plant, an area that contains a plant, an area that is intended to contain a plant, an area that is in the vicinity of a plant, etc. Accordingly, a site of interest may be a host plant, field (e.g., a vegetable field), greenhouse, habitat, garden, bait, lure, trap, film, etc. In alternative embodiments, a site of interest may be an area or region planted with alternative host plants, so that the *T. ni* may be lured to the alternative host plants. In some embodiments, a site of interest may specifically exclude a greenhouse. In alternative embodiments, a site of interest may specifically exclude a site that contains substantial quantities of grass, such as greater than 10%, 20%, 30%, 40%, 50%, 60%, 70%, 80%, or 90% grass. In alternative embodiments, a site of interest may specifically exclude a site that contains grass.

By "applied" or "applying" is meant contacting a T. ni with an effective amount of a compound. In alternative embodiments, by "applied" or "applying" is meant placing an effective amount of a compound on, in, or in the vicinity of a site of interest, as appropriate. The application method may take any form such as spraying, fogging, dusting, sprinkling, aerosolizing, e.g., of a field or greenhouse, or targeted applications such as direct application to a host plant or part thereof, or placement in a bait or trap, etc.

By "effective amount" is meant an amount or concentration of a compound that is sufficient to modulate the number of T. ni in a site of interest by at least about 25% to at least about 100%, or any value therebetween for example about 25%, 30%, 35%, 40%, 45%, 50%, 55%, 60%, 65%, 70%, 75%, 80%, 85%, 90%, 95%, 99%, or 100% when compared to a similar site in the absence of the compound. In alternative embodiments, by "effective amount" is meant an amount or concentration of a compound that is sufficient to modulate the number of T. ni in a site of interest by at least about 1-fold or more, for example, about 1.5-fold to about 100-fold, or any value therebetween for example about 2.0, 2.5, 3.0, 3.5, 4.0, 4.5, 5.0, 5.5, 6.0, 6.5, 7.0, 7.5, 8.0, 8.5, 9.0, 9.5, 10, 15, 20, 25, 30, 35, 40, 45, 50, 55, 60, 65, 70, 75, 80, 85, 90, 95-fold when compared to a similar site in the absence of the compound. By "modulate," "modulation" or "modulating" is meant changing, by either increase or decrease. Accordingly, for a compound having for example oviposition deterrent, feeding deterrent, or toxicant activity, the appropriate modulation would be to decrease the number of T. ni in a site of interest (such as a field or greenhouse or also, for a toxicant, bait or trap). Conversely, for a compound having for example oviposition stimulation or feeding stimulation activity, the appropriate modulation would be to increase the number of T. ni in a site of interest (such as a bait or trap). It is to be understood that the effective amount of a compound will vary, depending on such factors as contemplated use, life stage of T. ni, population density, site of interest, release rate, time of year, host crop, ambient moisture, temperature, etc.

In alternative embodiments, two or more compounds according to the invention may be applied to control infestation by T. ni.

In alternative embodiments, a compound according to the invention may be applied in combination with one or more other compounds, treatments, or systems to control infestation by T. ni. For example, feeding stimulants such as fructose, fucose, glucose, or sucrose; feed such as molasses; toxicants such as insecticides, fungicides, nematocides, bactericides, acaricides; attractants such as pheromones; growth regulators such as rooting stimulants; repellents, etc. may be combined with a compound according to the invention. In some embodiments, a compound according to the invention may be applied in combination with azadirachtin or a neem tree extract such as TreeAzin, which is a commercial extract of neem tree seeds.

The application may be simultaneous or sequential. For example, an oviposition or feeding stimulant as described herein may be combined with a toxicant, such as an insecticide, in a "lure and kill" or "attract and kill" treatment. In other embodiments, a toxicant as described herein may be combined with a feeding stimulant, feed, or attractant. Alternatively, a feeding deterrent may be applied to target larvae and an oviposition deterrent may be applied to target female adults at different times. Similarly, a feeding deterrent may be applied to target larvae and an oviposition stimulant may be applied to target female adults at different times. The application may be varied to, for example, minimize the build up of resistance to a particular treatment or compound.

The compounds or compositions according to the invention may be substantially pure compounds or mixtures thereof or may be formulated with a suitable additive as appropriate depending on the contemplated end use. For example, a compound or composition may be formulated with suitable additives such as carriers, diluents, emulsifiers, antioxidants, thickeners, fillers, preservatives, surfactants, etc., including without limitation crop spray oils, or any other suitable additive. In alternative embodiments, a compound according to the invention (e.g., compound 3c{3,6}) may be applied in combination with emulsifiers, such as Tween (polysorbate) 20, 40, 60, 65 or 80 and/or salts of fatty acids (e.g., sodium palmitate, sodium stearate, ammonium palmitate or ammonium stearate) and/or fatty acids (palmitic acid or stearic acid), compounds that reduce or prevent the rapid evaporation of a compound according to the invention (e.g., compound 3c{3,6}), such as Tween 20, 40, 60, 65 or 80 and/or salts of palmitic or stearic acid, palmitic or stearic acid and/or compounds that act as inducers for soil bacteria that can biodegrade a compound according to the invention (e.g., compound 3c{3,6}), such as camphor and/or benzoic acid. In alternative embodiments, a compound according to the invention (e.g., compound 3c{3,6}) may be applied in a suitable vehicle, such as one or more of palmitic acid, cetyl alcohol, isopropanol and/or combinations thereof. In alternative embodiments, a compound according to the invention (e.g., compound 3c{3,6}) may be applied in a suitable vehicle, such as deionized water, isopropanol, Tween, palmitic and/or stearic acid and/or their respective sodium or ammonium salts, camphor and/or combinations thereof. It is to be understood that any suitable formulation may be used, depending on the contemplated end use. For example, the formulations may be generally non-toxic, except for those containing a toxicant or insecticide where high mortality is a desired outcome.

In some embodiments, the compounds or compositions may be formulated in controlled release forms. The formulations may be solid, such as granules, dusts, or pellets, such as granules for direct use (i.e., without admixture with a liquid), water-dispersible granules; powders, wettable powders, dry (soluble) powders; etc. or may be liquid, such as an aqueous solution, flowable formulation, an emulsion e.g., oil-in-water emulsion, a suspension, a dispersion, etc. In some embodiments, the compounds may be formulated with a co-solvent, such as isopropanol. The compounds may be formulated for direct use (i.e., "ready-to-use" formulation) or as a concentrate.

In some embodiments, the compounds or compositions may be provided in any appropriate trap, dispensor or device known in the art.

The compounds or compositions may be used to control infestion by T. ni. In alternative embodiments, selected compounds or compositions may be used to deter or stimulate larval feeding or to deter or stimulate adult female oviposition. Accordingly, in alternative embodiments, the compounds or compositions may be used to influence host plant selection by T. ni.

Kits

The invention provides kits for use in control of T. ni infestation. In one embodiment, the kit includes a composition containing an effective amount of a compound according to the invention for application to a site of interest. In alternative embodiments, the kit may include a container containing another compound or treatment such as a toxicant such as an insecticide, attractant, etc.; the container may be any suitable container depending on the contemplated end use. The compound according to the invention may be provided together with instructions for administration to a site of interest. The instructions may include directions for use and may be provided as part of the kit or separately.

EXAMPLES

The following examples are intended to illustrate embodiments of the invention and should not be construed as limiting.

Example 1

Synthesis of Dialkoxybenzene Test Compounds

Synthesis Scheme.

Dialkoxybenzene minilibraries (consisting of four to five compounds) and pure compounds were synthesized. Briefly, dialkoxybenzenes were synthesized from the corresponding dihydroxybenzenes (1 (a-c)) by monoalkylation (Scheme 1). The pure monoalkylated compounds were mixed in equimolar amounts, for the synthesis of minilibraries, and subjected to a second round of alkylation. Thus, the minilibraries include compounds with one alkyl group constant and the other one variable.

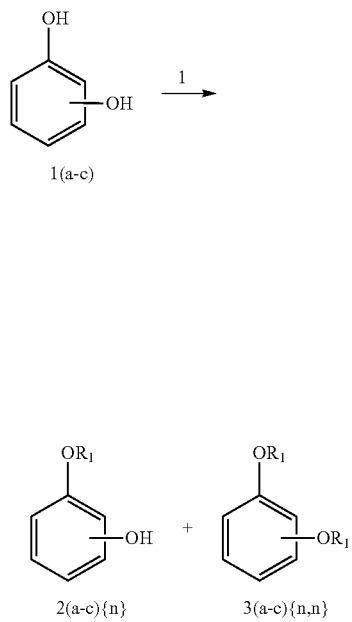

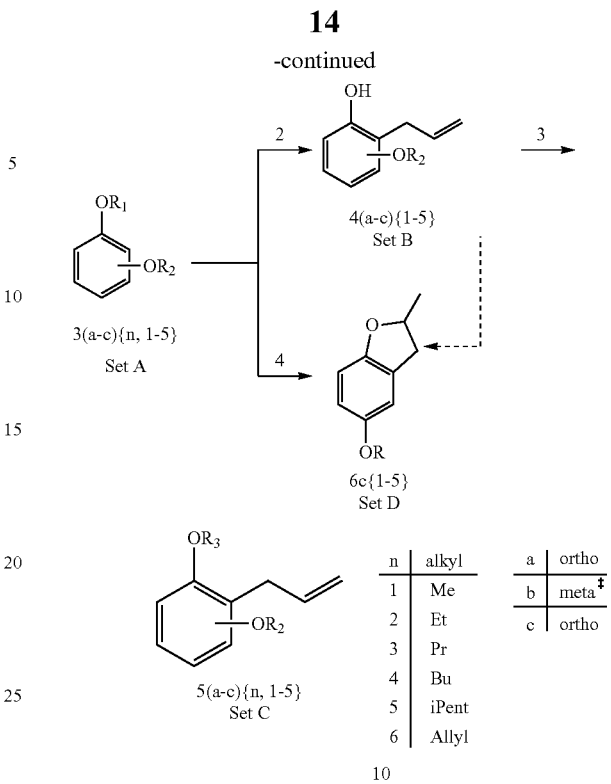

Reaction conditions: 1) base (NaH, K$_2$CO$_3$ or Cs$_2$CO$_3$), solvent (DMF or acetone), alkyl halide (MeI, EtI, PrI, BuBr, iPentBr or AllylBr), room temperature or reflux; 2) for 3(a-c){6, 1-5} neat, 180° C., 10 h (Scheme 2); (3) K$_2$CO$_3$, alkyl halide, acetone, reflux; 4) for 3c{6, 1-5} neat, 180° C., 30 h (Scheme 2). ‡The meta product from the Claisen Rearrangement (Set B) results in two products and will be identified as: 4B$^x${n} for 5-alkoxy-2-allyl phenol and 4b$^y${n} for 3-alkoxy-2-allyl phenol (see Scheme 2) (similarly for their alkylated derivatives).

An alternate depiction of Scheme 1 is described in more detail below (Scheme 1-1):

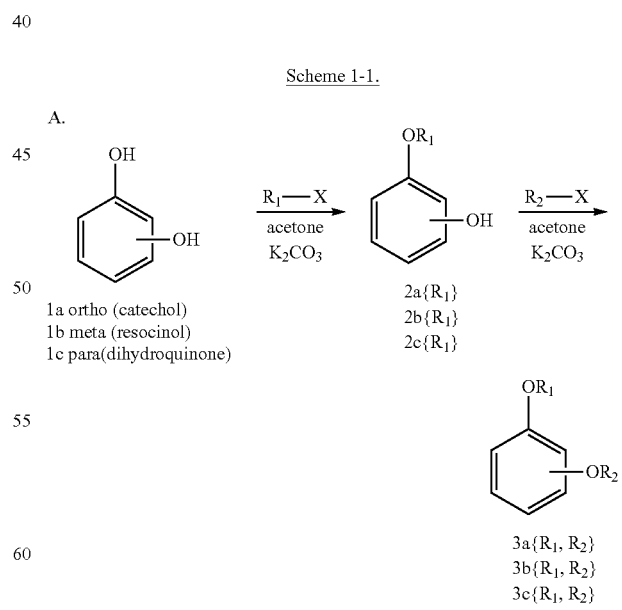

substituents, R$_1$ or R$_2$: 1 = methyl, 2 = ethyl, 3 = propyl, 4 = n-butyl, 5 = isopentyl (3methylbutyl), 6 = allyl
Sets contain equimolar amounts of the substituent that was attached first; these substituents are indicated as a range of numbers.

B.

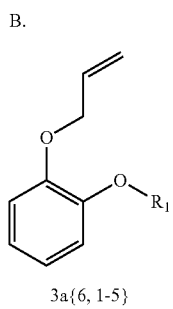

3a{6, 1-5}

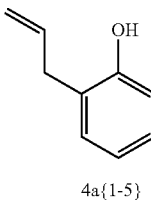

4a{1-5}    5a{R$_2$, 1-5}

C.

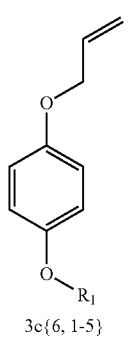

3c{6, 1-5}

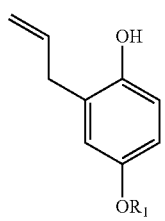

4c{1-5}    5c{R$_2$, 1-5}

D.

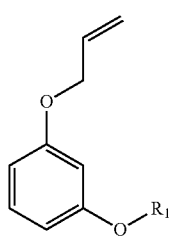

3b{6, 1-5}

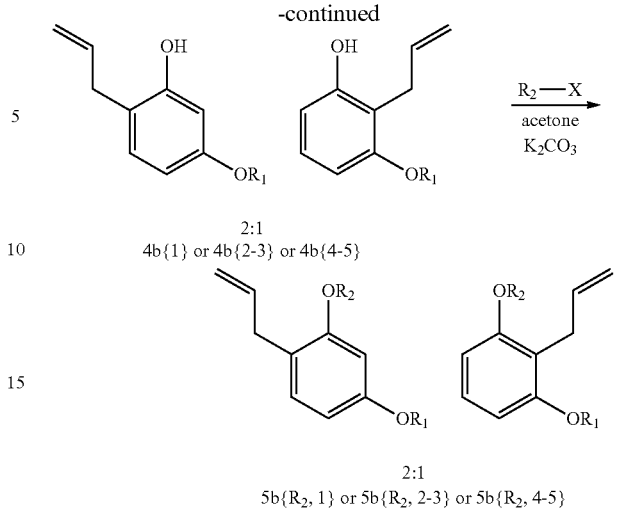

2:1
4b{1} or 4b{2-3} or 4b{4-5}

2:1
5b{R$_2$, 1} or 5b{R$_2$, 2-3} or 5b{R$_2$, 4-5}

A. Synthesis of dialkoxybenzenes from catechol (1a), resorcinol (1b) or dihydroquinone (1c). Details of the synthesis and analyses are described below. B. Synthesis of Claisen rearranged products from 1-allyl-2-alkoxybenzenes. C. Synthesis of Claisen rearranged products from 1-allyl-4-alkoxybenzene. D. Synthesis of Claisen rearranged products from 1-allyl-3-alkoxybenzene.

All solvents used were of analytical grade. Resorcinol monoacetate was from Aldrich. Compounds 2c{1}, 2c{2} and 2c{3} were synthesized and also purchased from Aldrich. Commercial grade solvents were distilled under nitrogen prior to use with the exceptions as follow: dried THF was obtained from a MBRAUN LTS 350 solvent purification system and HPLC grade acetone was used without further treatment. Reagents were used without further purification. The $^1$H and $^{13}$C NMR spectra were recorded in CDCl$_3$ on Bruker 400 or 600 MHz spectrometers or a Varian 500 MHz spectrometer.

Gas chromatography (GC) was done on Hewlett Packard 5890 using a SPB-5 column Supelco, 30 m, 0.25 mm i.d., (0.25 nm film), programmed at 100° C. (5 min), 10° C./min, and 200° C. (0 min), 50° C./min, 250° C. (4-14 min). The gas chromatographic data are reported as retention indices (RI). MS: GC-mass spectra were recorded on a Varian Saturn 2000 MS coupled to a CP 300 GC, equipped with a SPB-5 GC column (same type as above), programmed as above. Mass spectra were acquired in EI mode [2 μscans (0.55 s/scan), emission current (30 μamp), scanning single ion storage SIS (49-375 m/z)]. HRMS was recorded on a 6210 Series Time-of-Flight LC/MS System.

The identity of the members in each library was confirmed by $^1$H NMR and GC-MS techniques.

Optimization of the mono alkylation of dihydroxybenzenes 1(a-c) revealed that direct alkylation resulted in high yields. Ortho (a), meta (b) or para (c) substituted dihydroxy benzene 1(a-c) was deprotonated and reacted with an alkyl halide to afford mono 2(a-c){n} and dialkoxy 3(a-c) {n, n} products (Scheme 1 or 1-1). Tuning of the experimental conditions (base, solvent and reaction time, see Methods A-E) allowed the preferential synthesis of either monoalkylated or dialkylated products. Mono- and dialkylated products were separated using their acid/base properties. The monoalkoxy compounds 2(a-c){n} were used for the synthesis of libraries, and the dialkoxy compounds 3(a-c) {n, n} with identical alkyl groups were used for characterization and biological testing (Table 1).

TABLE 1

Purity of Dialkoxy Compounds 3(a-c){n, n}Synthesized for Characterization and Biological Evaluation

| no. | Compound | Purity[a] | no. | Compound | Purity[a] |
|---|---|---|---|---|---|
| 1 | 3a{1, 1} | 94 | 10 | 3b{4, 4} | 100 |
| 2 | 3a{2, 2} | 100 | 11 | 3b{5, 5} | 100 |
| 3 | 3a{3, 3} | 100 | 12 | 3b{6, 6} | 95 |
| 4 | 3a{4, 4} | 100 | 13 | 3c{1, 1} | 95 |
| 5 | 3a{5, 5} | 100 | 14 | 3c{2, 2} | 95 |
| 6 | 3a{6, 6} | 99 | 15 | 3c{3, 3} | 96 |
| 7 | 3b{1, 1} | 94 | 16 | 3c{4, 4} | 99 |
| 8 | 3b{2, 2} | 98 | 17 | 3c{5, 5} | 98 |
| 9 | 3b{3, 3} | 98 | 18 | 3c{6, 6} | 99 |

[a] Purity was determined by GC.

Synthesis of Alkoxy Phenols and Dialkoxy Benzenes

Method A:

Anhydrous $K_2CO_3$ (5 eq) was added to a solution of acetoxy-alkoxy benzene (1 eq) in $CH_3OH$ (25 mL) and the mixture was stirred at room temperature and monitored by TLC (hexanes-EtOAc, 8:2). When reaction was complete, it was concentrated under reduced pressure. The residue was then diluted with $CHCl_3$ (25 mL) and water (25 mL), the organic layer was dried over anhydrous $Na_2SO_4$ and concentrated under reduced pressure. In certain cases the crude product was purified by flash column chromatography (hexanes: EtOAc, 7:3) to afford pure alkoxy phenol.

Method B:

The dihydroxybenzene (hydroquinone, resorcinol or catechol, 1 eq) was added to a suspension of anhydrous $K_2CO_3$ (10 eq) in $CH_3OH$ (30 mL). The mixture was stirred at room temperature for 1 h then the alkylating reagent (10 eq) was added and reaction was monitored by TLC (hexanes-EtOAc, 7:3). When reaction was complete, the mixture was concentrated under reduced pressure and diluted with $CHCl_3$ (30 mL) and water (30 mL). The organic layer was separated, dried over anhydrous $Na_2SO_4$ and concentrated under reduced pressure to afford a crude solid which was purified by flash column chromatography (hexane-EtOAc, 7:3) to yield pure products.

Method C:

The dihydroxybenzene (hydroquinone, resorcinol or catechol, 1 eq) was added to a suspension of $Cs_2CO_3$ (0.5 eq) in DMF (5 mL) and the mixture was stirred at room temperature for 2 h. The alkylating reagent (1 eq) was then added and the reaction mixture was heated at reflux and monitored by TLC (hexanes-EtOAc, 25:1). When reaction was complete (usually after 20 h), HCl (1%, 20 mL) was added and the mixture was extracted with $CHCl_3$ (3×30 mL). The combined organic layers were washed with water (3×30 mL) and brine (30 mL), dried over anhydrous $Na_2SO_4$ and concentrated under reduced pressure. The crude obtained was purified by flash chromatography (hexanes-EtOAc, 25:1) to yield pure products.

Method D:

The dihydroxybenzene (hydroquinone, resorcinol or catechol, 1 eq) was added to a suspension of $K_2CO_3$ (1 eq) in acetone (20 mL) and the mixture was stirred at room temperature for 2 h. The alkylating reagent (1.2 eq) was then added and the reaction mixture was heated at reflux and monitored by TLC ($CHCl_3$). When reaction was complete, the mixture was filtered and the filtrate was concentrated under reduced pressure. The residue was diluted with $C_6H_6$ (30 mL) and washed with aqueous NaOH (10%, 40 mL). The organic layer was dried over anhydrous $Na_2SO_4$ and concentrated under reduced pressure to afford the corresponding pure dialkoxy benzene product. The basic aqueous layer was cooled in an ice bath and acidified with concentrated HCl. The solid alkoxy phenol was collected from this mixture by vacuum filtration.

Method E:

The dihydroxybenzene (hydroquinone, resorcinol or catechol, 1 eq) was added to a suspension of NaH (5 eq) in DMF (3 mL). The alkylating reagent (5 eq) was then added and the reaction mixture was stirred at room temperature and monitored by TLC. When reaction was complete, a solution of saturated $NH_4Cl$ (10 mL) was slowly added and the aqueous phase was extracted with $CHCl_3$ (2×15 mL). The combined organic layers were washed with water (10×15 mL), dried over anhydrous $Na_2SO_4$ and concentrated under reduced pressure. The crude oil was purified by flash column chromatography using hexanes:EtOAc as solvents to afford the corresponding pure compounds.

2-Ethoxy phenol 2(a){2} (Method C, 28%, Method D, 70%): GC (RI 1157, 96.7%); $^1$H NMR δ: 1.46 (t, J=7.0 Hz, 3H, $CH_3$), 4.12 (q, J=7.0 Hz, 2H, $OCH_2$), 5.76 (broad s, 1H, OH), 6.83-6.90 (m, 3H, ArH), 6.94-6.97 (m, 1H, ArH); $^{13}$C NMR δ: 14.8, 64.3, 111.6, 114.4, 120.0, 121.3, 145.7, 145.8; MS m/z (relative intensity): 139 ($M^+$+H, 41%), 138 ($M^+$, 100%); IR ($cm^{-1}$): 3535 (broad), 3054, 2984, 1611, 1596, 1502, 1040, 925, 743.

2-Propoxy phenol 2a{3} (Method C, 26%, Method D, 80%): GC (RI 1251, 100%); $^1$H NMR δ: 0.94 (t, J=7.4 Hz, 3H, $CH_3$), 1.70-1.77 (m, 2H, $CH_2$), 3.89 (q, J=6.5 Hz, 2H, $OCH_2$), 5.64 (broad s, 1H, OH), 6.70-6.86 (m, 4H, ArH); $^{13}$C NMR δ: 10.4, 22.5, 70.3, 111.6, 114.4, 120.1, 121.2, 145.8, 145.9; MS m/z (relative intensity): 153 ($M^+$+H, 19%), 152 ($M^+$, 100%); IR ($cm^{-1}$): 3540 (broad), 3054, 2968, 2878, 1612, 1596, 1503, 1260, 978, 743.

2-Butoxy phenol 2a{4} (Method C, 51%): GC (RI 1353, 98.7%); $^1$H NMR δ: 1.00 (t, J=7.4 Hz, 3H $CH_3$), 1.47-1.55 (m, 2H, $CH_2$), 1.78-1.84 (m, 2H, $CH_2$), 4.05 (t, J=6.5 Hz, 2H, $OCH_2$), 5.69 (broad s, 1H, OH), 6.82-6.88 (m, 3H, ArH), 6.92-6.95 (m, 1H, ArH); $^{13}$C NMR δ: 13.8, 19.2, 31.2, 68.5, 111.5, 114.4, 120.0, 121.2, 145.8; MS m/z (relative intensity): 165 ($M^+$+H, 20%), 166 ($M^+$, 100%); IR ($cm^{-1}$): 3542 (broad), 3054, 2962, 2872, 1612, 1597, 1503, 1261, 1106, 783, 741.

2-(3-Methyl-butyloxy)phenol 2a{5} (Method C, 52%): GC (RI 1412, 99.9%); $^1$H NMR δ: 0.99 (d, J=6.6 Hz, 6H, $CH_3$), 1.73 (apparent q, J=6.8 Hz, 2H, $CH_2$), 1.81-1.89 (m, 1H, CH), 4.08 (t, J=6.6 Hz, 2H, $OCH_2$), 5.70 (broad s, 1H, OH), 6.82-6.90 (m, 3H, ArH), 6.95-6.96 (m, 1H, ArH); $^{13}$C NMR δ: 22.5, 25.1, 37.9, 67.2, 111.5, 114.4, 120.0, 121.2, 145.7, 145.9; MS m/z (relative intensity): 181 ($M^+$+H, 19%), 180 ($M^+$, 100%); IR ($cm^{-1}$): 3544 (broad), 3054, 2872, 1611, 1597, 1503, 1260, 742.

2-Allyloxy phenol 2a{6} (Method D, 54%): GC (RI 1240, 100%); $^1$H NMR δ: 4.61 (dt, J=5.5, 1.4 Hz, 2H, $OCH_2$), 5.32 (dq, 10.5, 1.3 Hz, 1H, $CH_2$), 5.41 (dq, J=17.3, 1.5 Hz, 1H, $CH_2$), 5.66 (s, 1H, OH), 6.03-6.11 (m, 1H, CH), 6.81-6.95 (m, 4H, ArH); $^{13}$C NMR δ: 69.8, 112.2, 114.7, 118.3, 120.0, 121.7, 132.8, 145.5, 145.9; MS m/z (relative intensity): 151 ($M^+$+H, 25%), 150 ($M^+$, 100%); IR ($cm^{-1}$): 3526 (broad), 2870, 1597, 1503, 1465, 1107, 791, 746.

3-Methoxy phenol 2b{1} (Method A, 50%): GC (RI 1219, 100%); $^1$H NMR δ: 3.7 (s, 3H, $CH_3$), 5.38 (s, 1H, OH), 6.46-6.49 (m, 2H, ArH), 6.52-6.54 (m, 1H, ArH), 7.14 (t, J=8.1 Hz, 1H, ArH); $^{13}$C NMR δ: 55.2, 101.5, 106.4, 108.0, 130.2, 156.6, 160.6; IR ($cm^{-1}$): 3397 (broad), 1598, 1286, 1148, 1041, 765.

3-Ethoxy phenol 2b {2} (Method A, 50%): GC (RI 1311, 96.7%); $^1$H NMR δ: 1.39 (t, J=7.0 Hz, 3H, $CH_3$), 3.99 (q, J=7.0 Hz, 2H, OCH$_2$), 6.26 (broad s, 1H, OH), 6.45-6.48 (m, 2H, ArH), 6.50-6.53 (m, 1H, ArH), 7.13 (t, J=8.0 Hz, ArH); $^{13}$C NMR δ: 14.6, 63.6, 102.1, 107.1, 107.9, 130.1, 156.6, 160.0; IR (cm$^{-1}$): 3449 (broad), 2981, 1596, 976, 765.

3-Propoxy phenol 2b{3} (Method A, 47%): GC (RI 1404, 100%); $^1$H NMR δ: 1.03 (t, J=7.4 Hz, 3H, CH$_3$), 1.76-1.83 (m, 2H, CH$_2$), 3.89 (q, J=6.7 Hz, 2H, OCH$_2$), 5.67 (broad s, 1H, OH), 6.43-6.45 (m, 2H, ArH), 6.50-6.53 (m, 1H, ArH), 7.11-7.14 (m, 1H, ArH); $^{13}$C NMR δ: 10.4, 22.4, 69.6, 102.1, 107.1, 107.7, 130.1, 156.5, 160.3; IR (cm$^{-1}$): 3415 (broad), 2966, 2878, 1596, 1493, 1146, 1004, 766.

3-(3-Methyl-butyloxy)phenol 2b{4} (Method B, 9%): GC (RI 1556, 99.9%); $^1$H NMR δ: 0.96 (d, J=6.7 Hz, 6H, CH$_3$), 1.67 (apparent q, J=6.7 Hz, 2H, CH$_2$), 1.78-1.86 (m, 1H, CH), 3.96 (t, J=6.7 Hz, 2H, OCH$_2$), 5.46 (broad s, 1H, OH), 6.42-6.44 (m, 2H, ArH), 6.50-6.52 (m, 1H, ArH), 7.10-7.15 (m, 1H, ArH); $^{13}$C NMR δ: 22.53, 25.00, 37.9, 66.5, 102.1, 107.1, 107.6, 130.1, 156.6, 160.4; IR (cm$^{-1}$): 3419 (broad), 2955, 2870, 1599, 1467, 1142, 839, 764.

4-Methoxy phenol (Method A, 77%) 2c{1}: GC (RI 1170, 98.0%); $^1$H NMR δ: 3.76 (s, 3H, CH$_3$), 5.53 (s, 2H, OH), 6.76-6.80 (m, 4H, ArH); $^{13}$C NMR δ: 55.8, 114.9, 116.1, 149.5, 153.5; MS m/z (relative intensity): 125 (M$^+$+H, 31%), 124 (M$^+$, 100%), 109 (80, 81 (54).

4-Ethoxy phenol 2c{2}: GC (RI 1248, 98.5%); $^1$H NMR δ: 1.39 (t, J=7.0 Hz, 3H, CH$_3$), 3.99 (q, J=7.0 Hz, 2H, OCH$_2$), 5.91 (s, 1H, OH), 6.75-6.80 (m, 4H, ArH); $^{13}$C NMR δ: 14.8, 64.3, 115.8, 116.1, 149.5, 152.7.

4-Propoxy phenol 2c{3}: GC (RI 1325, 95.0%); $^1$H NMR δ: 1.01 (t, J=7.4 Hz, 3H, CH$_3$), 1.74-1.81 (m, 2H, CH$_2$), 3.86 (q, J=6.5 Hz, 2H, OCH$_2$), 1.68 (broad s, 1H, OH), 6.74-6.80 (m, 4H, ArH); $^{13}$C NMR δ: 10.1, 22.3, 70.2, 115.5, 115.9, 149.6, 152.5; IR (cm$^{-1}$): 3397 (broad), 2873, 1511, 1455, 1237, 982, 823, 793.

4-Butoxy phenol 2c{4} (Method C, 42%, Method D, 40%): GC (RI 1483, 99.9%); $^1$H NMR δ: 0.96 (t, J=7.3 Hz, 3H, CH$_3$), 1.44-1.52 (m, 2H, CH$_2$), 1.71-1.77 (m, 2H, CH$_2$), 3.91 (t, J=6.5 Hz, 2H, OCH$_2$), 4.79 (broad s, 1H, OH), 6.74-6.80 (m, 4H, ArH); $^{13}$C NMR δ: 13.8, 19.2, 68.5, 115.7, 116.0, 149.3, 153.1; MS m/z (relative intensity): 167 (M$^+$+H, 43%), 166 (M$^+$, 100%); IR (cm$^{-1}$): 3403 (broad), 2957, 2871, 1514, 1374, 1242, 971, 822, 768.

4-(3-Methyl-butyloxy)phenol 2c{5} (Method B, 24%, Method C, 29%; Method D, 32%): GC (RI 1552, 100%); $^1$H NMR δ: 0.96 (d, J=6.7 Hz, 5H, CH$_3$), 1.65 (apparent q, J=6.8 Hz, 2H, CH$_2$), 1.78-1.86 (m, 1H, CH), 3.92 (t, J=6.6 Hz, 2H, OCH$_2$), 4.67 (broad s, 1H, OH), 6.74-6.80 (m, 4H, ArH); $^{13}$C NMR δ: 22.6, 25.0, 38.1, 67.1, 115.6, 116.0, 149.3, 153.3; MS m/z (relative intensity): 181 (M$^+$+H, 18%), 180 (M$^+$, 100%), 110 (95%); IR (cm$^{-1}$): 3404 (broad), 2959, 2866, 1622, 1426, 1386, 1236, 820, 749.

4-Allyloxy phenol 2c{6} (Method D, 18%): GC (RI 1372, 100%); $^1$H NMR δ: 4.48 (d, J=5.4 Hz, 2H), 5.28 (dd, J=10.5, 1.1 Hz, 1H), 5.40 (dd, J=17.3, 1.6 Hz, 1H), 5.45 (broad s, 1H, OH), 6.01-6.09 (m, 1H), 6.75-6.77 (m, 2H, ArH), 6.80-6.82 (m, 2H, ArH); $^{13}$C NMR δ: 69.7, 115.9, 116.0, 117.7, 133.4, 149.5, 152.5; MS m/z (relative intensity): 151 (M$^+$+H, 55%), 150 (M$^+$, 100%).

1,2-Dimethoxy benzene 3a{1,1} (Method E from 2c-1 as starting material, 72%): GC (RI 1152, 99%); $^1$H NMR δ: 3.88 (s, 6H, CH$_3$), 6.87-6.94 (m, 4H, ArH); $^{13}$C NMR δ: 55.6, 111.2, 120.7, 148.9; MS m/z (relative intensity): 139 (M$^+$+H, 11%), 138 (M$^+$, 100%), 123 (50%), 95 (56%), 77 (69%); IR (cm$^{-1}$): 3065, 2936, 2835, 1593, 1254, 1123, 1028, 746.

1,2-Diethoxy benzene 3a{2,2} (Method D, 24%): GC (RI 1240, 100%); $^1$H NMR δ: 1.46 (t, J=7.0 Hz, 6H, CH$_3$), 4.10 (q, J=7.0 Hz, 4H, CH$_2$), 6.90 (s, 4H, ArH); $^{13}$C NMR δ: 14.8, 64.4, 113.5, 120.9, 128.2, 148.7; MS m/z (relative intensity): 167 (M$^+$+H, 100%), 166 (M$^+$, 96%); IR (cm$^{-1}$): 3063, 2987, 2871, 1592, 1506, 1392, 1034, 930, 738.

1,2-Dipropoxy benzene 3a{3,3} (Method D, 18%): GC (RI 1420, 100%); $^1$H NMR δ: 0.94 (t, J=7.4 Hz, 6H, CH$_3$), 1.70-1.78 (m, 4H, CH$_2$), 3.86 (q, J=6.6 Hz, 4H, CH$_2$), 6.74-6.82 (m, 4H, ArH); $^{13}$C NMR δ: 10.5, 22.6, 70.7, 114.1, 121.0, 149.2; MS m/z (relative intensity): 195 (M$^+$+H, 100%), 194 (M$^+$, 84%); IR (cm$^{-1}$): 3064, 2963, 2876, 1593, 1503, 1255, 1125, 981, 739.

1,2-Dibutoxy benzene 3a{4,4} (Method E from 2a{4} as starting material, 30%): GC (RI 1603, 100%); $^1$H NMR δ: 0.98 (t, J=7.4 Hz, 6H, CH$_3$), 1.47-1.56 (m, 4H, CH$_2$), 1.77-1.83 (m, 4H, CH$_2$), 4.00 (t, J=6.6 Hz, 4H, OCH$_2$), 6.87-6.91 (m, 4H, ArH); $^{13}$C NMR δ: 13.9, 19.2, 31.4, 68.9, 114.0, 120.9, 149.2; MS m/z (relative intensity): 223 (M$^+$+H, 6%), 222 (M$^+$, 41%); 110 (100%); IR (cm$^{-1}$): 2958, 2872, 1593, 1502, 1253, 1221, 737.

1,2-Di-(3-methyl-butyloxy)benzene 3a{5,5} (Method E from 2c-i5 as starting material, 53%): GC (RI 1708, 100%); $^1$H NMR δ: 0.96 (d, J=6.7 Hz, 12H, CH$_3$), 1.71 (apparent q, J=6.8 Hz, 4H, CH$_2$), 1.82-1.90 (m, 2H, CH), 4.02 (t, J=6.7 Hz, 4H, OCH$_2$), 6.87-6.91 (m, 4H, ArH); $^{13}$C NMR δ: 22.6, 25.1, 38.0, 67.6, 114.0, 120.9, 149.2; MS m/z (relative intensity): 251 (M$^+$+H, 10%), 250 (M$^+$, 53%), 180 (21%), 110 (100%); IR (cm$^{-1}$): 3064, 2953, 2870, 1593, 1506, 1385, 1055, 982, 739.

1,2-Diallyloxy benzene 3a{6,6} (Method D, 24%): GC (RI 1411, 100%); $^1$H NMR δ: 4.62 (dt, J=5.3, 1.5 Hz, 4H, OCH$_2$), 5.27-5.30 (m, 2H, CH$_2$), 5.41-5.45 (m, 2H, CH$_2$), 6.06-6.14 (m, 2H, CH), 6.89-6.94 (m, 4H, ArH); $^{13}$C NMR δ: 69.8, 114.2, 117.4, 121.2, 133.5, 148.5; MS m/z (relative intensity): 191 (M$^+$+H, 62%), 190 (M$^+$, 100%); IR (cm$^{-1}$): 3081, 2858, 1648, 1591, 1507, 1124, 921, 740.

1,3-Dimethoxy benzene 3b{1,1} (Method E, 76%): GC (RI 1181, 94.0%); $^1$H NMR δ: 3.81 (s, 6H, CH$_3$), 6.51-6.56 (m, 3H, ArH), 7.16 (t, J=8.2 Hz, 1H, ArH); $^{13}$C NMR δ 55.1, 100.4, 106.1, 129.8, 160.8; IR (cm$^{-1}$): 3001, 2957, 2835, 1593, 1337, 1152, 1050, 763.

1,3-Diethoxy benzene 3b{2,2} (Method E): GC (RI 1321, 98.3%); $^1$H NMR δ: 1.42 (t, J=7.0 Hz, 6H, CH$_3$), 4.02 (q, J=7.0 Hz, 4H, CH$_2$), 6.47-6.51 (m, 3H, ArH), 7.16 (t, J=8.2 Hz, 1H, ArH); $^{13}$C NMR δ: 14.8, 63.3, 101.3, 106.6, 129.7, 160.1; IR (cm$^{-1}$): 2980, 1603, 1493, 1475, 1150, 1048.

1,3-Dipropoxy benzene 3b{3,3} (Method E, 65%): GC (RI 1504, 98%); $^1$H NMR δ: 1.04 (t, J=7.4 Hz, 6H, CH$_3$), 1.77-1.85 (m, 4H, CH$_2$), 3.91 (q, J=6.5 Hz, 4H, CH$_2$), 6.48-6.51 (m, 3H, ArH), 7.16 (t, J=8.2 Hz, 1H, ArH); $^{13}$C NMR δ: 10.5, 22.6, 69.4, 101.4, 106.6, 129.7, 160.3; IR (cm$^{-1}$): 2964, 2877, 1601, 1492, 1470, 1287, 1263, 759.

1,3-Dibutoxy benzene 3b{4,4} (Method B, 16%): GC (RI 1701, 100%); $^1$H NMR δ: 0.97 (t, J=7.4 Hz, 6H, CH$_3$), 1.44-1.52 (m, 4H, CH$_2$), 1.73-1.78 (m, 4H, CH$_2$) 3.94 (t, J=6.5 Hz, 4H, CH$_2$), 6.46-6.49 (m, 3H, ArH), 7.15 (t, J=8.1 Hz, 1H, ArH); $^{13}$C NMR δ: 13.9, 19.2, 31.3, 67.6, 101.4, 106.6, 129.7, 160.3; MS m/z (relative intensity): 223 (M$^+$+H, 36%), 222 (M$^+$, 100%).

1,3-Di-(3-methyl-butyloxy)benzene 3b{5,5} (Method E, 63%): GC (RI 1826, 100%); $^1$H NMR δ: 0.97 (d, J=6.5 Hz, 12H, CH$_3$), 1.68 (apparent q, J=6.8 Hz, 4H, CH$_2$), 1.80-1.88 (m, 2H, CH), 3.98 (t, J=6.7 Hz, 4H, OCH$_2$), 6.47-6.61 (m, 3H, ArH), 7.16 (t, J=8.2 Hz, 1H, ArH); $^{13}$C NMR δ: 22.6, 25.0, 38.0, 66.3, 101.4, 106.6, 129.7, 160.4; MS m/z (relative intensity): 251 (M$^+$+H, 48%), 250 (M$^+$, 100%); IR (cm$^{-1}$): 2948, 2866, 1580, 1471, 1288, 1158, 850, 762, 689.

1,3-Diallyloxy benzene 3b{6,6} (Method B, 41%): GC (RI 1486, 95%); $^1$H NMR δ: 4.52 (dt, J=1.5 and 5.3 Hz, 4H, OCH$_2$), 5.29 (dq, J=1.3 and 10.5 Hz, 2H, CH=CH$_2$), 5.42 (dq, J=1.6 and 17.3 Hz, 2H, CH=CH$_2$), 6.06 (ddt, J=5.3, 10.6 and 17.2 Hz, 2H, CH), 6.51-6.54 (m, 3H, ArH), 7.17 (t, J=8.0 Hz, 1H, ArH); $^{13}$C NMR δ: 68.8, 101.9, 107.1, 117.7, 129.8, 133.2, 159.7; MS m/z (relative intensity): 191 (M$^+$+H, 70%), 190 (M$^+$, 100%).

1,4-Dimethoxy benzene 3c{1,1} (Method B, 65%): GC (RI 1115, 95.0%); $^1$H NMR δ: 3.77 (s, 6H, CH$_3$), 6.84 (s, 4H, ArH); $^{13}$C NMR δ 55.7, 114.6, 153.7.

1,4-Diethoxy benzene 3c{2,2} (Method B): GC (RI 1250, 95.0%); $^1$H NMR δ: 1.40 (t, J=6.8 Hz, 6H, CH$_3$), 3.98 (q, J=7.1 Hz, 4H, CH$_2$), 6.84 (s, 4H, ArH); $^{13}$C NMR δ: 14.9, 63.9, 115.3, 153.0; IR (cm$^{-1}$): 2985, 1508, 1394, 1116, 1048, 926, 749, 533.

1,4-Dipropoxy benzene 3c{3,3} (Method B): GC (RI 1434, 96.0%); $^1$H NMR δ: 1.03 (t, J=7.4 Hz, 6H, CH$_3$), 1.75-1.86 (m, 4H, CH$_2$), 3.87 (q, J=6.5 Hz, 4H, CH$_2$), 6.83 (s, 4H, ArH); $^{13}$C NMR δ: 10.5, 22.7, 70.1, 115.4, 153.2; IR (cm$^{-1}$): 2964, 2876, 1509, 1228, 981, 825, 531.

1,4-Dibutoxy benzene 3c{4,4} (Method B, 6%; Method C, 28%; Method D, 15%, Method E, 80%): GC (RI and ratio) 1849, 99.0%; $^1$H NMR δ: 0.96 (d, J=6.7 Hz, 12H, CH$_3$), 1.65 (apparent q, J=6.8 Hz, 4H, CH$_2$), 1.78-1.86 (m, 2H, CH), 3.93 (t, J=6.6 Hz, 4H, OCH$_2$), 6.83 (s, 4H, ArH); $^{13}$C NMR δ: 22.6, 25.0, 38.1, 67.0, 115.4, 153.2; MS m/z (relative intensity): 223 (M$^+$+H, 20%), 222 (M$^+$, 100%); IR (cm$^{-1}$): 2954, 2871, 1511, 1399, 1237, 1043, 830, 767, 535.

1,4-Di-(3-methyl-butyloxy)benzene 3c{5,5} (Method C, 28%, Method D, 20%): GC (RI and ratio) 1623, 98.0%; $^1$H NMR δ: 0.98 (d, J=7.4 Hz, 6H, CH$_3$), 1.45-1.53 (m, 4H, CH$_2$), 1.72-1.78 (m, 4H, CH$_2$), 3.91 (t, J=6.5 Hz, 4H, OCH$_2$), 6.83 (s, 4H, ArH); $^{13}$C NMR δ: 13.9, 19.2, 31.4, 68.3, 115.3, 153.2; MS m/z (relative intensity): 251 (M$^+$+H, 24%), 250 (M$^+$, 100%); IR (cm$^{-1}$): 2954, 2868, 1509, 1474, 1237, 1061, 821, 740, 523.

1,4-Diallyloxy benzene 3c{6,6} (Method D, 48%): GC (RI and ratio) 1481, 100%; $^1$H NMR δ: 4.49 (dt, J=5.4, 1.5 Hz, 4H), 5.27-5.30 (m, 2H), 5.39-5.44 (m, 2H), 6.03-6.10 (m, 2H), 6.86 (s, 4H, ArH); $^{13}$C NMR δ: 69.36, 115.5, 117.4, 133.5, 152.8; MS m/z (relative intensity): 191 (M$^+$+H, 21%), 190 (M$^+$, 100%).

Synthesis of Compounds 4c{3} and 6c{3}

Compound 4c{3} was obtained according to method D in 88% yield. GC (RI and ratio) 1495, 100%; $^1$H NMR δ: 1.04 (t, J=7.4 Hz, 3H, CH$_3$), 1.76-1.83 (m, 2H), 3.88 (t, J=6.6 Hz, 2H, OCH$_2$), 4.49 (dt, J=5.3, 1.5 Hz, 2H), 5.27-5.30 (m, 1H), 5.39-5.43 (m, 1H), 6.02-6.10 (m, 1H), 6.83-6.87 (m, 4H, ArH); $^{13}$C NMR δ: 10.5, 22.6, 69.4, 70.0, 115.3, 115.6, 117.4, 133.6, 152.6, 153.4; MS m/z (relative intensity): 193 (M$^+$+H, 48%), 192 (M$^+$, 100%).

The 4c{3} compound (0.3277 g) was heated at 180° C. in a sealed tube, under a nitrogen atmosphere for 5 days. The viscous dark black oil was purified by column chromatography with chloroform to afford 0.1253 g of pure 6c{3} library in 38% yield.

GC (RI and ratio) 1529, 98%; $^1$H NMR δ: 1.02 (t, J=7.4 Hz, 3H, CH$_3$), 1.45 (d, J=6.3 Hz, 3H, CH$_3$), 1.73-1.80 (m, 2H), 2.77-2.81 (m, 1H), 3.24-3.29 (m, 1H), 3.85 (t, J=6.6 Hz, 2H, OCH$_2$), 4.85-4.92 (m, 1H), 6.64 (d, J=1.5 Hz, 2H, ArH), 6.77 (s, 1H, ArH); $^{13}$C NMR δ: 10.5, 21.7, 22.7, 37.6, 70.5, 79.6, 109.0, 112.2, 113.6, 127.9, 153.4, 153.5; MS m/z (relative intensity): 193 (M$^+$+H, 27%), 192 (M$^+$, 100%).

The following procedures were used to generate mini-libraries in Set A and Set C as set out in Table 2.

Method F:

A mixture of mono-alkoxy phenols (1 eq) in DMF (2 mL) was added to a suspension of NaH (5 eq) in DMF (3 mL). The alkylating reagent (MeI, EtI, PrI, BuBr, bromo-3-methyl butane or allyl bromide, 3 eq) was then added and the reaction mixture was stirred at room temperature and monitored by GC. When reaction was complete (between 1 to 4 h), a solution of saturated NH$_4$Cl (25 mL) was slowly added and the aqueous phase was extracted with CHCl$_3$ (3×20 mL). The combined organic layers were washed with water (4×25 mL) and brine (2×25 mL), dried over anhydrous Na$_2$SO$_4$ and concentrated under reduced pressure. The crude oil was purified by flash column chromatography using hexane:EtOAc (4:1) to afford the corresponding library as pure oil. (Note: the 1,3 dialkoxy benzene libraries required a second purification by flash column chromatography, with hexanes:EtOAc, 4:1).

Method G:

A mixture of mono-alkoxy phenols (1 eq) in acetone (5 mL) was added to a suspension of K$_2$CO$_3$ (10 eq) in acetone (20 mL) and the mixture was stirred at room temperature for 2 h. The alkylating reagent (MeI, EtI, PrI, BuBr, 1-bromo-3-methylbutane or allyl bromide, 3 eq) was then added and the reaction mixture was heated at reflux and monitored by GC. When the reaction was complete, the mixture was filtered and the filtrate was concentrated under reduced pressure. The residue obtained was diluted with CHCl$_3$ (30 mL) and water (20 mL). The layers were separated; the organic layer was dried over anhydrous Na$_2$SO$_4$ and concentrated under reduced pressure to afford the corresponding library as pure oil. For compound sets 5b {n,n}, the oils were decolorized with flash chromatography (5% EtOAc in Hexane), even though GC analysis indicated that the compounds were pure.

Method H:

A mixture of mono-alkoxy phenols (1 eq) in acetone (5 mL) was added to a suspension of Cs$_2$CO$_3$ (2 eq) in acetone (15 mL) and the mixture was stirred at room temperature for 2 h. The alkylating reagent (3 eq) was then added and the reaction mixture was heated at reflux and monitored by GC. When the reaction was complete, the mixture was filtered and the filtrate was concentrated under reduced pressure. The residue obtained was diluted with CHCl$_3$ (30 mL) and water (20 mL). The layers were separated; the organic layer was dried over anhydrous Na$_2$SO$_4$ and concentrated under reduced pressure to afford the corresponding library as pure oil.

The following data were generated for mini-libraries in Set A and Set C as set out in Table 2.

3a{1,1-5} Methyl library (Method A, 27% yield; Method C, 72% yield): $^1$H NMR δ: 0.95-0.99 (m, 8.9H), 1.04 (t, J=7.5 Hz, 3H, CH$_3$ (Pr)), 1.45-1.52 (m, 5H), 1.75 (q, J=7.0 Hz, 2H, CH$_2$ (i-Pent)), 1.80-1.91 (m, 5.4H), 3.86, 3.865, 3.87 (s, 8.5H), 3.88 (s, 3H, OCH$_3$ (Me)), 3.89 (s, 6H, OCH$_3$ (Me)), 3.98 (t, J=6.9 Hz, 2H), 4.01-4.06 (m, 4.3H), 4.11 (q, J=7.0 Hz, 2H, OCH$_2$ (Et)), 6.88-6.94 (m, 19H, ArH); GC RI: MS m/z (relative intensity, %): 1,2-dimethoxy benzene 3a{1,1} 1145: 139 (M$^+$+H, 29), 138 (M$^+$, 100), 123 (44); 1-ethoxy-2-methoxy benzene 3a{1,2} 1190: 153 (M$^+$+H, 23), 152 (M$^+$, 100), 124 (58), 109 (91); 1-methoxy-2-propoxy benzene 3a{1,3} 1280: 167 (M$^+$+H, 18), 166 (M$^+$, 100), 124 (66), 109 (76); 1-butoxy-2-methoxy benzene 3a{1,4} 1377: 181 (M$^+$+H, 15), 180 (M$^+$, 100), 124 (57), 109 (52); 1-methoxy-2-(3-methyl-butoxy)benzene 3a{1,5} 1434: 195 (M$^+$+H, 15), 194 (M$^+$, 100), 124 (68), 109 (46).

3a{2,1-5} Ethyl library (Method A, 57% yield), 3a{3,1-5} propyl library (Method A, 67% yield), 3a{4,1-5} butyl library (Method A, 62% yield), 3a{5,1-5} isopentyl library (Method A, 43% yield), 3a{6,1-5} allyl library (Method B, 94% yield): $^1$H NMR and GC-MS data:

3a{2,1-5} Ethyl library (Method A, 57% yield): $^1$H NMR δ: 0.96-0.99 (m, 9.4H), 1.04 (t, J=7.5 Hz, 3H, CH$_3$ (Pr)), 1.41-1.53 (m, 5H), 1.73 (q, J=6.9 Hz, 2H, CH$_2$ (i-Pent)), 1.79-1.89 (m, 5.4H), 3.88 (s, 3H, OCH$_3$ (Me)), 3.97 (t, J=6.8 Hz, 2H), 4.01 (t, J=6.7 Hz, 2H), 4.04 (t, J=6.8 Hz, 2H), 4.05-4.13 (m, 14H), 6.86-6.93 (m, 19H, ArH); GC RI: MS m/z (relative intensity, %): 1,2-diethoxy benzene 3a{2,2} 1244: 167 (M$^+$+H, 100), 166 (M$^+$, 81); 1-ethoxy-2-propoxy benzene 3a{2,3} 1335: 181 (M$^+$+H, 100), 180 (M$^+$, 60); 1-ethoxy-2-butoxy benzene 3a{2,4} 1429: 195 (M$^+$+H, 100), 194 (M$^+$, 83); 1-ethoxy-2-(3-methyl-butoxy)benzene 3a{2,5} 1486: 209 (M$^+$+H, 100), 208 (M$^+$, 72).

3a{3,1-5} Propyl library (Method A, 67% yield): $^1$H NMR δ: 0.96-0.99 (m, 7.4H), 1.04 (t, J=7.4 Hz, 16.5H, CH$_3$ (Pr)), 1.44 (t, J=7.0 Hz, 3H), 1.48-1.53 (m, 1.6H), 1.72 (q, J=6.8 Hz, 1.7H, CH$_2$ (i-Pent)), 1.77-1.91 (m, 14H), 3.87 (s, 3H, OCH$_3$ (Me)), 3.94-4.04 (m, 14.7H), 4.09 (q, J=7.0 Hz, 2H), 6.86-6.92 (m, 17H, ArH); GC RI: MS m/z (relative intensity, %): 1,2-dipropoxy benzene 3a{3,3} 1424: 195 (M$^+$+H, 100), 194 (M$^+$, 60); 1-butoxy-2-propoxy benzene 3a{3,4} 1518: 209 (M$^+$+H, 100), 208 (M$^+$, 84); 1-(3-methyl-butoxy)-2-propoxy benzene 3a{3,5} 1576: 223 (M$^+$+H, 100), 222 (M$^+$, 62).

3a{4,1-5} Butyl library (Method A, 62% yield): $^1$H NMR δ: 0.96-0.99 (m, 24H), 1.04 (t, J=7.5 Hz, 3.4H, CH$_3$ (Pr)), 1.44 (t, J=7.0 Hz, 3H), 1.46-1.54 (m, 12.6H), 1.71 (q, J=6.8 Hz, 2H, CH$_2$ (i-Pent)), 1.77-1.88 (m, 16H), 3.87 (s, 3H, OCH$_3$ (Me)), 3.96 (t, J=6.6 Hz, 2H), 3.98-4.05 (m, 15H), 4.07 (q, J=7.0 Hz, 2.4H), 6.82-6.94 (m, 20H, ArH); GC RI: MS m/z (relative intensity, %): 1,2-dibutoxy benzene 3a{4,4} 1608: 223 (M$^+$+H, 100), 222 (M$^+$, 64); 1-butoxy-2-(3-methyl-butoxy)benzene 3a{4,5} 1664: 237 (M$^+$+H, 100), 236 (M$^+$, 64).

3a{5,1-5} Isopentyl library. (Method A, 43% yield): $^1$H NMR δ: 0.96-0.99 (m, 41H), 1.04 (t, J=7.5 Hz, 3.4H, CH$_3$ (Pr)), 1.43 (t, J=7.0 Hz, 3.8H), 1.50 (q, J=7.5 Hz, 2.6H), 1.69-1.90 (m, 24H), 3.86 (s, 3H, OCH$_3$ (Me)), 3.96 (t, J=6.6 Hz, 2H), 3.98-4.10 (m, 18H), 6.84-6.93 (m, 20H, ArH); GC RI: MS m/z (relative intensity, %): 1,2-di(3-methyl-butoxy)benzene 3a{5,5} 1720: 251 (M$^+$+H, 20), 250 (M$^+$, 100).

3a{6,1-5} Allyl library. (Method B, 94% yield): $^1$H NMR δ: 0.96-1.00 (m, 7H), 1.05 (t, J=7.4 Hz, 3H, CH$_3$ (Pr)), 1.45 (t, J=7.0 Hz, 3.7H), 1.49-1.53 (m, 1.7H), 1.73 (q, J=6.9 Hz, 1.4H), 1.79-1.89 (m, 4.6H), 3.88 (s, 4H, OCH$_3$ (Me)), 3.98 (t, J=6.7 Hz, 1.8H), 4.01-4.06 (m, 3.3H), 4.10 (q, J=7.0 Hz, 2.4H), 4.58-4.63 (m, 10.6H), 5.25-5.30 (m, 5.1H), 5.38-5.44 (m, 5H), 6.04-6.14 (m, 5H), 6.84-6.95 (m, 21H, ArH); GC RI: MS m/z (relative intensity, %): 1-allyloxy-2-methoxy benzene 3a{6,1} 1281: 165 (M$^+$+H, 42), 164 (M$^+$, 100); 1-allyloxy-2-ethoxy benzene 3a {6,2} 1327: 179 (M$^+$+H, 100), 178 (M$^+$, 67); 1-allyloxy-2-propoxy benzene 3a {6,3} 1416: 193 (M$^+$+H, 100), 192 (M$^+$, 91); 1-allyloxy-2-butoxy benzene 3a {6,4} 1510: 207 (M$^+$+H, 100), 206 (M$^+$, 72); 1-allyloxy-2-(3-methyl-butoxy)benzene 3a{6,5} 1569: 221 (M$^+$+H, 100), 220 (M$^+$, 70).

3b {1,1-5} Methyl library (Method A, 85% yield): $^1$H NMR δ: 0.97 (d, J=6.6 Hz, 6H, CH$_3$ (i-Pent)), 1.04 (t, J=7.4 Hz, 3H, CH$_3$ (Pr)), 1.42 (t, J=7.0 Hz, 3H, CH$_3$ (Et)), 1.68 (apparent q, J=6.8 Hz, 2H, CH$_2$ (i-Pent)), 1.78-1.87 (m, 3H), 3.79-3.80 (m, 15H, OCH$_3$), 3.91 (t, J=6.6 Hz, 2H, OCH$_2$ (Pr)), 3.98 (t, J=6.7 Hz, 2H, OCH$_2$ (i-Pent)), 4.02 (q, J=7.0 Hz, 2H, OCH$_2$ (Et)), 6.47-6.53 (m, 9.6H, ArH), 7.18 (t, J=8.2 Hz, 3H, ArH); GC RI: MS m/z (relative intensity, %): 1,3-dimethoxy benzene 3b{1,1} 1180: 138 (M$^+$, 100); 1-ethoxy-3-methoxy benzene 3b{1,2} 1253: 153 (M$^+$+H,25), 152 (M$^+$, 100); 1-methoxy-3-propoxy benzene 3b {1,3} 1345: 167 (M$^+$+H, 32), 166 (M$^+$., 100), 124 (22); 1-methoxy-3-(3-methyl-butyloxy)benzene 3b{1,5} 1508: 195 (M$^+$+H, 30), 194 (M$^+$., 100).

3b {2,1-5} Ethyl library (Method A, 66% yield), 3b {3,1-5} propyl library (Method A, 53% yield), 3b {4,1-5} butyl library (Method A, 69% yield) 3b {5,1-5} isopentyl library (Method A, 72% yield), 3b {6,1} (Method B, % yield), 3b {6,2-3} (Method B, % yield), 3b {6,4-5} (Method B, % yield) $^1$H NMR and GC-MS data:

3b{2,1-5} Ethyl library. (Method A, 66% yield): $^1$H NMR δ: 0.96 (d, J=6.6 Hz, 6H, CH$_3$ (i-Pent)), 1.03 (t, J=7.4 Hz, 3H, CH$_3$ (Pr)), 1.39-1.43 (m, 12.8H), 1.67 (apparent q, J=6.8 Hz, 2H, CH$_2$ (i-Pent)), 1.78-1.84 (m, 3H), 3.79 (s, 3H, CH$_3$ (Me)), 3.90 (t, J=6.6 Hz, 2H, OCH$_2$ (Pr)), 3.98 (t, J=6.7 Hz, 2H, OCH$_2$ (i-Pent)), 3.99-4.04 (m, 8H), 6.46-6.51 (m, 10H, ArH), 7.16 (t, J=8.2 Hz, 3H, ArH); GC RI: MS m/z (relative intensity, %): 1,3-diethoxy benzene 3b {2,2} 1318: 167 (M$^+$+H, 31), 166 (M$^+$, 100); 1-ethoxy-3-propoxy benzene 3b{2,3} 1409: 181 (M$^+$+H, 40), 180 (M$^+$, 100); 1-ethoxy-3-(3-methyl-butyloxy)benzene 3b{2,5} 1570: 209 (M$^+$+H, 35), 208 (M$^+$, 100).

3b{3,1-5} Propyl library (Method A, 53% yield): $^1$H NMR δ: 0.96 (d, J=6.6 Hz, 6H, CH$_3$ (i-Pent)), 1.02-1.05 (m, 10H), 1.40 (t, J=7.0 Hz, 2H, CH$_3$ (Et)), 1.67 (apparent q, J=6.8 Hz, 2H, CH$_2$ (i-Pent)), 1.77-1.85 (m, 8H), 3.79 (s, 1.5H, OCH$_3$ (Me)), 3.89-3.92 (m, 7H), 3.97 (t, J=6.7 Hz, 2H, OCH$_2$ (i-Pent)), 4.02 (q, J=7.0 Hz, 1.2H, OCH$_2$ (Et)), 6.46-6.51 (m, 7H, ArH), 7.16 (t, J=8.2 Hz, 2.5H, ArH); GC RI: MS m/z (relative intensity, %): 1,3-dipropoxy benzene 3b {3,3} 1501: 195 (M$^+$+H, 45), 194 (M$^+$, 100), 110 (85), 82(22); 1-(3-methyl-butyloxy)-3-propoxy benzene 3b {3,5} 1657: 223 (M$^+$+H, 44), 222 (M$^+$, 100).

3b{4,1-5} Butyl library (Method A, 69% yield): $^1$H NMR δ: 0.99-1.02 (m, 19H), 1.05 (t, J=7.0 Hz, 3H, CH$_3$ (Pr)), 1.41-1.45 (m, 3H), 1.48-1.56 (m, 8H), 1.70 (apparent q, J=6.7 Hz, 2.5H, CH$_2$ (i-Pent)), 1.76-1.91 (m, 8H), 3.81 (s, 3H, OCH$_3$ (Me)), 3.93 (t, J=6.6 Hz, 2H, OCH$_2$ (Pr)), 3.95-4.01 (m, 11H), 4.03 (q, J=7.0 Hz, 2H, OCH$_2$ (Et)), 6.45-6.54 (m, 11.7H, ArH), 7.16 (t, J=8.2 Hz, 4H, ArH); GC RI: MS m/z (relative intensity, %): 1-butoxy-3-methoxy benzene 3b {4,1} 1440: 181 (M$^+$+H, 25), 180 (M$^+$, 100); 1-butoxy-3-ethoxy benzene 3b{4,2} 1506: 193 (M$^+$+H, 33), 194 (M$^+$, 100); 1-butoxy-3-propoxy benzene 3b {4,3} 1596: 209 (M$^+$+H, 48), 208 (M$^+$, 100); 1-butoxy-3-(3-methyl-butyloxy)benzene 3b {4,5} 1754: 237 (M$^+$+H, 42), 236 (M$^+$, 100).

3b{5,1-5} Isopentyl library. (Method A, 72% yield): $^1$H NMR δ: 0.99 (d, J=6.7 Hz, 26H), 1.06 (t, J=7.4 Hz, 3H, CH$_3$ (Pr)), 1.41-1.45 (m, 3H), 1.70 (apparent q, J=6.7 Hz, 9H), 1.81-1.88 (m, 6.3H), 3.81 (s, 3H, OCH$_3$ (Me)), 3.92 (t, J=6.6 Hz, 2H, OCH$_2$ (Pr)), 3.98-4.04 (m, 11H), 6.50-6.54 (m, 11H, ArH), 7.18 (t, J=8.2 Hz, 4H, ArH); GC RI: MS m/z (relative intensity, %): 1-methoxy-3-(3-methyl-butyloxy)benzene 3b {5,1} 1500: 195 (M$^+$+H, 26), 194 (M$^+$, 100); 1-ethoxy-3-(3-methyl-butyloxy)benzene 3b {5,2} 1566: 209 (M$^+$+H, 35), 208 (M+, 100); 1-(3-methyl-butyloxy)-3-propoxy benzene 3b{5,3} 1653: 223 (M$^+$+H, 48), 222 (M$^+$, 100); 1,3-di(3-methyl-butyloxy)benzene 3b{5,5} 1826: 251 (M$^+$+H, 40), 250 (M$^+$, 100).

The meta allyl library was synthesized in three portions (methyl by itself, ethyl+propyl and butyl+isopentyl), because upon Claisen rearrangement each compound gave rise to two rearrangement products.

3b {6,1}1-allyloxy-3-methoxybenzene. (Method D, 98% yield): $^1$H NMR δ: 3.80 (s, 3H, CH$_3$), 4.53 (apparent d, J=5.5 Hz, 2H, allyl CH$_2$), 5.30 (apparent d, J=14 Hz, 1H), 5.43 (apparent d, J=22 Hz, 1H), 6.07 (m, 1H), 6.52 (m, 3H, ArH), 7.19 (apparent t, J=7.7 Hz, 1H ArH). GC R1: 1334 MS m/z (relative intensity, %): 164 (M$^{+*}$, 100), 149 (M-CH$_3$, 10), 136 (M-28, 12).

3b {6,2-3}Allyl library (ethyl, propyl). (Method D, 60% yield, 35% 3b {6,2} by GC and 39% by $^1$H NMR and the rest is 3b {6,3}): $^1$H NMR δ: 1.04 (t, J=4 Hz, 3H, CH$_3$ propyl), 1.42 (t, J=3.7 Hz, 3H, CH$_3$ ethyl), 1.81 (m, 2H, CH$_2$, propyl), 3.95 (t, J=3.7 Hz, 2H propyl CH$_2$), 4.02 (q, J=7 Hz, 2H, ethyl), 4.53 (apparent d, J=7 Hz, 2H for each component), 5.29 (m, J=14 Hz, 1H for each component), 5.41 (m, J=22 Hz, 1H for each component), 6.07 (m, 1H for each component), 6.53 (m, 3H for each component), 7.17 (apparent t, J=8 Hz, 1H for each component). GC RI: MS m/z (relative intensity, %): 1-allyloxy-3-ethoxybenzene 3b {6,2} 1398: 179 (M+1, 72), 178 (M$^{+\cdot}$, 100), 150 (M−28, 35); 1-allyloxy-3-propoxybenzene 3b {6,3} 1491: 193 (M+1, 93), 192 (M$^{+\cdot}$, 100), 164 (M−28, 12), 150 (31).

3b {6,4-5} Allyl library (butyl, isopentyl). (Method D, 71% yield, 3b {6,4} 34% by GC and 40% by $^1$H NMR and the rest is 3b {6,5}): $^1$H NMR δ: 0.98 (m, 6H, CH$_3$ isopentyl, 3H CH$_3$ butyl), 1.48 (m, 2H, CH$_2$ butyl), 1.68 (m, 2H, CH$_2$, isopentyl), 1.75 (m, 2H, CH$_2$, butyl), 1.83 (m, 1H, isopentyl), 3.96 (m, 2H for each component, CH$_2$), 4.52 (apparent d, J=8 Hz, 2H for each component), 5.29 (apparent d, J=14 Hz, 1H for each component), 5.42 (apparent d, J=22 Hz, 1H for each component), 6.06 (m, 1H for each component), 6.51 (m, 3H for each component, ArH), 7.17 (apparent t, J=7 Hz, 1H for each component, ArH). GC RI: MS m/z (relative intensity, %): 1-allyloxy-3-n-butoxybenzene 3b {6,4} 1592: 207 (M+1, 83), 206 (M$^{+\cdot}$, 100), 178 (M−28, 12), 150 (33). 1-allyloxy-3-isopentyloxybenzene 3b {6,5} 1654: 221 (M+1, 81), 220 (M$^{+\cdot}$, 100), 192 (M−28, 7), 150 (21).

3c{1,1-5} Methyl library (Method A, 65% yield): $^1$H NMR δ: 0.96 (d, J=6.7 Hz, 9H, CH$_3$ (i-Pent)), 1.03 (t, J=7.4 Hz, 3.3H, CH$_3$ (Pr)), 1.39 (t, J=6.7 Hz, 4H, CH$_3$ (Et)), 1.66 (apparent q, J=6.7 Hz, 3H, CH$_2$ (i-Pent)), 1.77-1.85 (m, 3H), 3.77, 3.78 (s, 15H, OCH$_3$), 3.87 (t, J=6.6 Hz, 2H, CH$_2$ (Pr)), 3.94 (t, J=6.6 Hz, 3H, CH$_2$ (i-Pent)), 3.98 (q, J=7.1 Hz, 3H, CH$_2$ (Et)), 6.83-6.85 (m, 16H, ArH); GC RI: MS m/z (relative intensity, %): 1,4-dimethoxy benzene 3c{1,1} 1122: 139 (M$^+$+H, 80), 138 (M$^+$, 100); 1-ethoxy-4-methoxy benzene 3c{1,2} 1188: 153 (M$^+$+H, 73), 152 (M$^+$, 100); 1-methoxy-4-propoxy-benzene 3c{1,3} 1281: 167 (M$^+$+H, 48), 166 (M$^+$, 100); 1-methoxy-4-(3-methyl-butyloxy)benzene 3c{1,5} 1442: 195 (M$^+$+H, 48), 194 (M$^+$, 100).

3c{2,1-5} Ethyl library (Method A, 31% yield), 3c{3,1-5} propyl library (Method A, 82% yield), 3c{4,1-5} butyl library (Method A, 76% yield), 3c{5,1-5} isopentyl (3-methyl-butyloxy) library (Method A, 82% yield), 3c{6,1-5} allyl library (Method B, 95% yield); $^1$H NMR and GC-MS data:

3c{2,1-5} Ethyl library (Method A, 31% yield): $^1$H NMR δ: 0.96 (d, J=6.7 Hz, 6H, CH$_3$ (i-Pent)), 1.03 (t, J=7.4 Hz, 3H, CH$_3$ (Pr)), 1.39 (t, J=7.0 Hz, 15H, CH$_3$ (Et)), 1.66 (apparent q, J=6.8 Hz, 3H, CH$_2$ (i-Pent)), 1.77-1.83 (m, 4H), 3.77 (s, 3H, OCH$_3$ (Me)), 3.87 (t, J=6.6 Hz, 2H, OCH$_2$ (Pr)), 3.94 (q, J=6.7 Hz, 2H, OCH$_2$ (i-Pent)), 3.98 (q, J=7.0 Hz, 10H, OCH$_2$ (Et)), 6.83-6.84 (m, 16H, ArH); GC RI: MS m/z (relative intensity, %): 1,4-diethoxy benzene 3c{2,2} 1248: 167 (M$^+$+H, 33), 166 (M$^+$, 100); 1-ethoxy-4-propoxy benzene 3c{2,3} 1337: 181 (M$^+$+H, 28), 180 (M+, 100); 1-ethoxy-4-(3-methyl-butyloxy)benzene 3c{2,5} 1492: 209 (M$^+$+H, 31), 208 (M$^+$, 100).

3c{3,1-5} Propyl library (Method A, 82% yield): $^1$H NMR δ: 0.97 (d, J=6.6 Hz, 7H, CH$_3$ (i-Pent)), 1.03 (t, J=7.4 Hz, 15H, CH$_3$ (Pr)), 1.40 (t, J=6.9 Hz, 3H, CH$_3$ (Et)), 1.66 (apparent q, J=6.8 Hz, 3H, CH$_2$ (i-Pent)), 1.77-1.85 (m, 12H), 3.77 (s, 3H, OCH$_3$ (Me)), 3.87 (t, J=6.5 Hz, 10H, OCH$_2$ (Pr)), 3.94 (t, J=6.6 Hz, 2.8H, OCH$_2$ (i-Pent)), 3.98 (q, J=7.1 Hz, 2H, OCH$_2$ (Et)), 6.83-6.84 (m, 16H, ArH); GC RI: MS m/z (relative intensity, %): 1,4-dipropoxy benzene 3c{3,3} 1431: (M$^+$+H, 25), 194 (M$^+$, 100); 1-(3-methyl-butyloxy)-4-propoxy benzene 3c{3,5} 1589: 223 (M$^+$+H, 28), 222 (M$^+$, 100).

3c{4,1-5} Butyl library (Method A, 76% yield): $^1$H NMR δ: 0.96-0.99 (m, 18H), 1.02 (t, J=7.4 Hz, 3H, CH$_3$ (Pr)), 1.39 (t, J=6.9 Hz, 4H, CH$_3$ (Et)), 1.45-1.53 (m, 8H, CH$_2$ (Bu)), 1.66 (apparent q, J=6.7 Hz, 2H, CH$_2$ (i-Pent)), 1.72-1.81 (m, 11.6H), 3.77 (s, 3H, OCH$_3$ (Me)), 3.87 (t, J=6.6 Hz, 2H, OCH$_2$ (Pr)), 3.90-3.95 (m, 10.4H), 3.98 (q, J=7.0 Hz, 2H, OCH$_2$ (Et)), 6.83-6.84 (m, 16H, ArH); GC RI: MS m/z (relative intensity, %): 1-butoxy-4-methoxy benzene 3c{4,1} 1371: 181 (M$^+$+H, 29), 180 (M$^+$, 100); 1-butoxy-4-ethoxy benzene 3c{4,2} 1437: 195 (M$^+$+H, 23), 194 (M$^+$, 100); 1-butoxy-4-propoxy benzene 3c{4,3} 1529: 209 (M$^+$+H, 40), 208 (M$^+$, 100); 1-butoxy-4-(3-methyl-butyloxy)benzene 3c{4,5} 1681: 237 (M$^+$+H, 42), 236 (M$^+$, 100).

3c{5,1-5} Isopentyl (3-methyl-butyloxy) library. (Method A, 82% yield): $^1$H NMR δ: 0.96 (d, J=7.0 Hz 30H, CH$_3$ (i-Pent)), 1.02 (t, J=7.4 Hz, 3H, CH$_3$ (Pr)), 1.39 (t, J=6.9 Hz, 3H, CH$_3$ (Et)), 1.66 (apparent q, J=6.8 Hz, 10H, CH$_2$ (i-Pent)), 1.75-1.86 (m, 7.5H), 3.77 (s, 3H, OCH$_3$ (Me)), 3.87 (t, J=6.4 Hz, 2H, OCH$_2$ (Pr)), 3.94 (t, J=6.9 Hz, 10H, OCH$_2$ (i-Pent)), 3.98 (q, J=6.8 Hz, 2H, OCH$_2$ (Et)), 6.83-6.84 (m, 16H, ArH); GC RI: MS m/z (relative intensity, %): 1,4-di(3-methyl-butyloxy)-benzene 3c{5,5} 1850: 251 (M$^+$+H, 25), 250 (M$^+$, 100).

3c{6,1-5} Allyl library. (Method B, 95% yield): GC (RI): $^1$H NMR δ: 0.95-0.98 (m, 8H), 1.03 (t, J=7.4 Hz, 3H, CH$_3$ (Pr)), 1.39 (t, J=7.0 Hz, 3.9H, CH$_3$ (Et)), 1.46-1.50 (m, 1.5H), 1.56 (d, J=3.8 Hz, 1.3H), 1.65 (apparent q, J=6.8 Hz, 2H, CH$_2$ (i-Pent)), 1.71-1.85 (m, 5H), 3.78 (s, 4H, OCH$_3$ (Me)), 3.87 (t, J=6.6 Hz, 2H, OCH$_2$ (Pr)), 3.90-3.95 (m, 3.7H), 3.98 (q, J=7.0 Hz, 2.5H, OCH$_2$ (Et)), 4.47-4.49 (m, 10.9H), 5.25-5.29 (m, 5H), 5.38-5.42 (m, 5H), 6.01-6.09 (m, 5H), 6.81-6.87 (m, 21H, ArH); GC RI: MS m/z (relative intensity, %): 1-allyloxy-4-methoxy benzene 3c{6,1} 1326: 165 (M$^+$+H, 20), 164 (M$^+$, 100); 1-allyloxy-4-ethoxy benzene 3c{6,2} 1394: 179 (M$^+$+H, 70), 178 (M$^+$, 100); 1-allyloxy-4-propoxy benzene 3c{6,3} 1491: 193 (M$^+$+H, 65), 192 (M$^+$, 100); 1-allyloxy-4-butoxy benzene 3c{6,4} 1594: 207 (M$^+$+H, 56), 206 (M$^+$, 100); 1-allyloxy-4-(3-methyl-butoxy)benzene 3c{6,5} 1659: 221 (M$^+$+H, 46), 220 (M+, 100).

The following procedures were used to generate mini-libraries in Set B as set out in Table 2.

The allyloxy-alkoxy mini-library 3(a-c){6,1-5} was heated at 180° C. in a sealed tube, under a nitrogen atmosphere. Reaction progress was monitored by GC. In order to remove the color, the crude libraries were passed through a silica column (top charcoal layer, chloroform as eluent).

The following data were generated for mini-libraries in Set B

4a{1-5} 95% yield: $^1$H NMR δ: 0.97-1.00 (m, 7.3H), 1.05 (t, J=7.4 Hz, 3H, CH$_3$ (Pr)), 1.44 (t, J=7.0 Hz, 3.8H, CH$_3$ (Et)), 1.50 (q, J=7.6 Hz, 1.7H), 1.71 (apparent q, J=6.8 Hz, 1.5H, CH$_2$ (i-Pent)), 1.77-1.88 (m, 4.4H), 3.42 (d, J=6.6 Hz, 9.3H), 3.89 (s, 3.7H, OCH$_3$ (Me)), 3.99 (t, J=6.5 Hz, 2H, OCH$_2$ (Pr)), 4.02-4.07 (m, 3.8H), 4.10 (q, J=7.0 Hz, 2.7H, OCH$_2$ (Et)), 5.04-5.11 (m, 10.2H), 1.69 (s, 1.2H, OH), 5.73 (s, 0.5H, OH), 5.74 (s, 0.8H, OH), 5.75 (s, 1.8H, OH), 5.98-6.06 (m, 4H), 6.70-6.86 (m, 13.8H, ArH); GC RI: MS m/z (relative intensity, %): 2-allyl-6-methoxy phenol 4a{1} 1358: 165 (M$^+$+H, 23), 164 (M$^+$, 100); 2-allyl-6-ethoxy phenol 4a{2} 1413: 179 (M$^+$+H, 25), 178 (M$^+$, 100); 2-allyl-6-propoxy phenol 4a{3} 1504: 193 (M$^+$+H, 22), 192 (M$^+$, 100); 2-allyl-6-butoxy phenol 4a{4} 1603: 207 (M$^+$+H, 22), 206 (M$^+$, 100); 2-allyl-6-(3-methyl-butoxy)phenol 4a{5} 1664: 221 (M$^+$+H, 21), 220 (M$^+$, 100).

4b$^{x,y}${1} 82% yield: $^1$H NMR δ: 3.35 (m, 3.8H, CH$_2$ (Allyl$^x$)), 3.47 (m, 2H, CH$_2$ (Allyl$^y$)), 3.77 (s, 6.6H, OCH$_3$ (Me$^x$)), 3.81 (s, 3H, OCH$_3$(Me$^y$)), 5.01 (s, 1H, OW), 5.04 (s, 1.7H, OH$^x$), 5.08-5.13 (m, 2.1H), 5.14-5.18 (m, 3.8H), 5.95-6.04 (m, 2.6H), 6.42 (d, J=2.5 Hz, 1.7H, ArH$^x$), 6.46 (dd, J=2.5 and 8.3 Hz, 1.7H, ArH$^x$), 6.50 (dd, J=6.5 and 7.9 Hz, 2H, ArH$^y$), 7.00 (d, J=8.3 Hz, 1.7H, ArH$^x$), 7.08 (t, J=8.2 Hz, 1H, ArH$^y$); GC RI: MS m/z (relative intensity, %): 2-allyl-5-methoxy phenol 4b$^x${1} 1393: 165 (M$^+$+H, 30), 164 (M$^+$, 100); 2-allyl-3-methoxy phenol 4b$^y${1} 1446: 165 (M$^+$+H, 37), 164 (M$^+$, 100).

4b$^{x,y}${2-3} 64% yield: $^1$H NMR δ: 1.01-1.06 (m, 10.9H, CH$_3$ (Pr)), 1.38-1.42 (m, 7.7H, CH$_3$ (Et)), 1.75-1.84 (m, 7.6H, CH$_2$CH$_3$ (Pr)), 3.34-3.35 (m, 7.3H), 3.47-3.49 (m, 4.2H), 3.86-3.92 (m, 7.5H, OCH$_2$ (Pr)), 3.97-4.04 (m, 5.4H, OCH$_2$ (Et)), 5.06-5.09 (m, 7.4H), 5.11-5.12 (m, 1.3H), 5.13-5.15 (m, 6.5H), 5.17-5.18 (m, 2H), 5.94-6.04 (m, 5.6H), 6.41-6.49 (m, 11.5H, ArH), 6.98 (m, 3.5H, ArH$^x$), 7.05 (m, 2H, ArH$^y$); GC RI: MS m/z (relative intensity, %): 2-allyl-5-ethoxy phenol 4b$^x${2} 1455: 179 (M$^+$+H, 54), 178 (M$^+$, 100); 2-allyl-3-ethoxy phenol 4W{2} 1517: 179 (M$^+$+H, 38), 178 (M$^+$, 100); 2-allyl-5-propoxy phenol 4b$^x${3} 1549: 193 (M$^+$+H, 62), 192 (M$^+$, 100); 2-allyl-3-propoxy phenol 4b$^y${3} 1615: 193 (M$^+$+H, 47), 192 (M$^+$, 100).

4b$^{x,y}${4-5} 31% yield: $^1$H NMR δ: 0.94-0.99 (m, 30.1H), 1.44-1.53 (m, 8.5H, CH$_2$CH$_3$ (Bu)), 1.61-1.87 (m, 17.6H), 3.34-3.35 (m, 9.5H), 3.46-3.48 (m, 4.4H), 3.90-3.98 (m, 14.6H), 5.01-5.03 (m, 6.0H), 5.06-5.09 (m, 2.2H), 5.10-5.12 (m, 1.1H), 5.13-5.18 (m, 10.1H), 5.93-6.04 (m, 6.1H), 6.41-6.50 (m, 13.6H), 6.97-6.98 (m, 4.4H, ArH$^x$), 7.03-7.07 (m, 2H, ArH$^y$); GC RI: MS m/z (relative intensity, %): 2-allyl-5-butoxy phenol 4b$^x${4} 1649: 207 (M$^+$+H, 11), 206 (M$^+$, 54), 135 (M−71, 100); 2-allyl-3-butoxy phenol 4b$^y${4} 1721: 207 (M$^+$+H, 17), 206 (M$^+$, 94), 149 (M−57, 100); 2-allyl-5-isopentoxy phenol 4b$^x${5} 1706: 221 (M$^+$+H, 11), 220 (M$^+$, 54), 135 (M−85, 100); 2-allyl-3-(3-methyl-butoxy)phenol 4b$^y${5} 1786: 221 (M$^+$+H, 17), 220 (M$^+$, 90), 150 (M−70, 100).

4c{1-5} 97% yield: $^1$H NMR δ: 0.97-0.99 (m, 8.8H), 1.03 (t, J=7.4 Hz, 3.7H, CH$_3$ (Pr)), 1.39 (t, J=7.0 Hz, 4.2H, CH$_3$ (Et)), 1.45-1.53 (m, 2H), 1.66 (apparent q, J=6.8 Hz, 2H, CH$_2$ (i-Pent)), 1.72-1.86 (m, 5.4H), 3.37-3.40 (m, 11.5H), 3.77 (s, 4.3H, OCH$_3$ (Me)), 3.86 (t, J=6.6 Hz, 2.5H, OCH$_2$ (Pr)), 3.89-3.95 (m, 3.5H), 3.98 (q, J=7.0 Hz, 2.6H, OCH$_2$ (Et)), 5.21 (broad s, 5.2H, OH), 5.13-5.17 (m, 10.6H), 5.98-6.06 (m, 5H), 6.66-6.77 (m, 16H, ArH); GC RI: MS m/z (relative intensity, %): 2-allyl-4-methoxy phenol 4c{1} 1432: 165 (M$^+$+H, 31), 164 (M$^+$, 100); 2-allyl-4-ethoxy phenol 4c{2} 1494: 179 (M$^+$+H, 31), 178 (M$^+$, 100); 2-allyl-4-propoxy phenol 4c{3} 1587: 193 (M$^+$+H, 31), 192 (M$^+$, 100); 2-allyl-4-butoxy phenol 4c{4} 1687: 207 (M$^+$+H, 29), 206 (M$^+$, 100); 2-allyl-4-(3-methyl-butoxy)phenol 4c{5} 1750: 221 (M$^+$+H, 31), 220 (M$^+$, 100).

The following data were generated for Set C

5a{1,1-5} Allyl-methyl library. (Method B, 90% yield): $^1$H NMR δ: 0.96-1.00 (m, 8.4H), 1.06 (t, J=7.4, 3.2H, CH$_3$ (Pr)), 1.44-1.47 (m, 4.4H), 1.50-1.55 (m, 2.3H), 1.73 (apparent q, J=6.8 Hz, 1.7H, CH$_2$ (i-Pent)), 1.79-1.91 (m, 5.9H), 3.40-3.43 (m, 10H), 3.81, 3.82, 3.83, 3.834, 3.84 (s, 15.2H, OCH$_3$), 3.86 (s, 4.8H, OCH$_3$), 3.95 (t, J=6.5 Hz, 2H, OCH$_2$ (Pr)), 3.98-4.03 (m, 4.4H), 4.07 (q, J=7.0 Hz, 2.7H, OCH$_2$ (Et)), 5.02-5.09 (m, 10H), 5.94-6.02 (m, 5H), 6.71-6.82 (m, 12H, ArH), 6.95-7.01 (m, 5H, ArH); GC RI: MS m/z (relative intensity, %): 1-allyl-2,3-dimethoxy benzene 5a{1,1} 1333: 179 (M$^+$+H, 50), 178 (M$^+$, 100); 1-allyl-3-ethoxy-2-methoxy benzene 5a{1,2} 1386: 193 (M$^+$+H, 79), 192 (M$^+$, 100); 1-allyl-2-methoxy-3-propoxy benzene 5a{1,3} 1481: 207 (M$^+$+H, 65), 206 (M$^+$, 100); 1-allyl-2-butoxy-3-methoxy benzene 5a{1,4} 1578: 221 (M$^+$+H, 66), 220 (M$^+$, 100); 1-allyl-2-methoxy-3-(3-methyl-butoxy)benzene 5a{1,5} 1632: 235 (M$^+$+H, 62), 234 (M$^+$, 100).

5a{2,1-5} Allyl-ethyl library (Method B, 91% yield), 5a{3,1-5} allyl-propyl library (Method B, 96% yield), 5a{4,1-5} allyl-butyl library (Method B, 92% yield), 5a{5,1-5} allyl-iPentyl library (Method B, 90% yield), 5a{6,1-5} allyl-allyl library (Method B, 90% yield); $^1$H NMR and GC-MS data:

5a{2,1-5} Allyl-ethyl library. (Method B, 91% yield): $^1$H NMR δ: 0.97-1.00 (m, 11.5H), 1.35-1.40 (m, 14.8H), 1.42-1.16 (m, 10.5H), 1.72 (apparent q, J=6.7 Hz, 1.8H, CH$_2$ (i-Pent)), 1.78-1.91 (m, 5.7H), 3.43 (d, J=6.6 Hz, 9.2H), 3.84 (s, 3.9H, OCH$_3$), 3.91-4.12 (m, 20.9H), 5.01-5.10 (m, 10.3H), 5.94-6.02 (m, 5H), 6.69-6.83 (m, 11.4H, ArH), 6.90-7.00 (m, 6.7H, ArH); GC RI: MS m/z (relative intensity, %): 1-allyl-2,3-diethoxy benzene 5a{2,2} 1435: 207 (M++H, 63), 206 (M+, 100); 1-allyl-2-ethoxy-3-propoxy benzene 5a{2,3} 1523: 221 (M$^+$+H, 56), 220 (M+, 100); 1-allyl-2-butoxy-3-ethoxy benzene 5a{2,4} 1616: 235 (M$^+$+H, 88), 234 (M$^+$, 100); 1-allyl-2-ethoxy-3-(3-methyl-butoxy)benzene 5a{2,5} 1669: 249 (M$^+$+H, 79), 248 (M$^+$, 100).

5a{3,1-5} Allyl-propyl library. (Method B, 96% yield): $^1$H NMR δ: 0.97-1.08 (m, 27.8H), 1.44 (t, J=7.0 Hz, 4H), 1.49-1.56 (m, 2.3H), 1.69-1.89 (m, 16.3H), 3.42 (d, J=6.6 Hz, 9.5H), 3.84 (s, 4H, OCH$_3$), 3.86-4.09 (m, 21H), 5.02-5.08 (m, 10H), 5.94-6.02 (m, 5H), 6.69-6.83 (m, 11.4H, ArH), 6.89-6.99 (m, 6H, ArH); GC RI: MS m/z (relative intensity, %): 1-allyl-2,3-dipropoxy benzene 5a{3,3} 1608: 235 (M$^+$+H, 57), 234 (M$^+$, 100); 1-allyl-3-butoxy-2-propoxy benzene 5a{3,4} 1699: 249 (M$^+$+H, 100), 248 (M$^+$, 72); 1-allyl-3-(3-methyl-butoxy)-2-propoxy benzene 5a{3,5} 1751: 263 (M$^+$+H, 50), 262 (M$^+$, 90), 249 (100).

5a{4,1-5} Allyl-butyl library. (Method B, 92% yield): $^1$H NMR δ: 0.96-0.99 (m, 22.3H), 1.05 (t, J=7.4 Hz, 2.7H), 1.43 (t, J=6.9 Hz, 4.2H), 1.47-1.54 (m, 12.2H), 1.69-1.89 (m, 16.7H), 3.42 (d, J=6.6 Hz, 9.2H), 3.84 (s, 4H, OCH$_3$), 3.88-4.11 (m, 19H), 5.02-5.10 (m, 10.3H), 5.93-6.01 (m, 5H), 6.69-6.83 (m, 11.4H, ArH), 6.89-6.99 (m, 6.5H, ArH); GC RI: MS m/z (relative intensity, %): 1-allyl-2,3-dibutoxy benzene 5a{4,4} 1784: 263 (M$^+$+H, 27), 262 (M$^+$, 100); 1-allyl-2-butoxy-3-(3-methyl-butoxy)benzene 5a{4,5} 1833: 277 (M$^+$+H, 25), 276 (M$^+$, 100).

5a{5,1-5} Allyl-iPentyl library. (Method B, 90% yield): $^1$H NMR δ: 0.95-1.00 (m, 37.6H), 1.06 (t, J=7.5 Hz, 2.7H), 1.44 (t, J=7.0 Hz, 4.3H), 1.49-1.55 (m, 2.1H), 1.65-1.72 (m, 12.4H), 1.78-1.90 (m, 10H), 3.41 (d, J=6.6 Hz, 9.4H), 3.84 (s, 4H, OCH$_3$), 3.91-4.08 (m, 19H), 5.01-5.09 (m, 10.2H), 5.93-6.01 (m, 5H), 6.69-6.83 (m, 11.1H, ArH), 6.89-6.99 (m, 7.2H, ArH); GC RI: MS m/z (relative intensity, %): 1-allyl-2,3-di(3-methyl-butoxy)benzene 5a{5,5} 1879: 291 (M$^+$+H, 23), 290 (M$^+$, 100).

5a{6,1-5} Allyl-allyl library. (Method B, 90% yield): $^1$H NMR δ: 0.88-0.93 (m, 11.3H), 0.96-1.01 (m, 2.7H), 1.36-1.39 (m, 2.7H), 1.45 (t, J=7.3 Hz, 2.7H), 1.65 (q, J=6.7 Hz, 2.3H), 1.70-1.83 (m, 6H), 3.25 (d, J=7.0 Hz, 1.5H), 3.35 (d, J=6.6 Hz, 8.7H), 3.78 (s, 2.5H, OCH$_3$), 3.86-4.04 (m, 9.5H), 4.40-4.54 (m, 10.3H), 4.95-5.02 (m, 10.2H), 5.13-5.20 (m, 5H), 5.27-5.36 (m, 5H), 5.84-5.92 (m, 5H), 5.97-6.08 (m, 5H), 6.61-6.76 (m, 11.1H, ArH), 6.82-6.94 (m, 5H, ArH); GC RI: MS m/z (relative intensity, %): 1-allyl-2-allyloxy-3-metoxy benzene 5a{6,1} 1463: 205 (M$^+$+H, 84), 204 (M$^+$, 100); 1-allyl-2-allyloxy-3-ethoxy benzene 5a{6,2} 1509: 219 (M$^+$+H, 100), 218 (M$^+$, 95); 1-allyl-2-allyloxy-3-propoxy benzene 5a{6,3} 1597: 233 (M$^+$+H, 100), 232 (M$^+$, 87); 1-allyl-2-allyloxy-3-butoxy benzene 5a{6,4} 1688: 247 (M$^+$+H, 100), 246 (M$^+$, 91); 1-allyl-2-allyloxy-3-(3-methyl-butoxy)benzene 5a{6,5} 1740: 261 (M$^+$+H, 100), 260 (M$^+$, 92).

5b$^{x,y}${1,1} Allyl-methyl library A. (Method B, 90% yield): $^1$H NMR δ: 3.30-3.31 (m, 3.9H, CH$_2$(Allyl$^x$)), 3.41 (dt, J=1.6 and 6.1 Hz, 2H, CH$_2$ (Allyl$^y$)), 3.79 (s, 6H (Me$^y$)), 3.80 (s, 5.4H (Me$^x$)), 3.81 (s, 5.4H (Me$^x$)), 4.91-4.95 (m, 1.6H), 4.97-5.04 (m, 4.2H), 5.91-6.01 (m, 2.8H), 6.42-6.45 (m, 3.7H, ArH$^x$), 6.55 (d, J=8.3 Hz, 2H, ArH$^y$), 7.03 (d, J=8.1 Hz, 1.7H, ArH$^x$), 7.15 (t, J=8.3 Hz, 1H, ArH$^y$); GC RI: MS m/z (relative intensity, %): 2-allyl-1,3-dimethoxy benzene 5b$^y${1,1} 1378: 179 (M$^+$+H, 30), 178 (M$^+$, 100), 1-allyl-2,4-dimethoxy benzene 5b$^x${1,1} 1411: 179 (M$^+$+H, 28), 178 (M$^+$, 100).

5b$^{x,y}${1,2-3} Allyl-methyl library B. (Method B, 61% yield): $^1$H NMR δ: 1.02-1.06 (m, 11.4H, CH$_3$ (Pr)), 1.38-1.42 (m, 7.6H, CH$_3$ (Et)), 1.77-1.84 (m, 7.9H, CH$_2$ (Pr)), 3.30-3.31 (m, 7.1H), 3.42-3.44 (m, 4.4H), 3.80 (m, 10.4H (Me$^x$)), 3.81 (m, 6.1H (Me$^y$)), 3.89-3.93 (m, 7.8H), 4.00-4.05 (m, 4.9H), 4.91-4.93 (m, 2.1H), 4.98-5.04 (m, 8.8H), 5.91-6.01 (m, 5.2H), 6.42-6.46 (m, 7.3H, ArH$^x$), 6.52-6.54 (m, 4.2H, ArH$^y$), 7.00-7.01 (m, 3.2H, ArH$^x$), 7.10-7.13 (m, 2.0H, ArH$^y$); GC RI: MS m/z (relative intensity, %): 2-allyl-1-ethoxy-3-methoxy benzene 5b$^y${1,2} 1435: 193 (M$^+$+H, 30), 192 (M$^+$, 70), 163 (M−29, 100); 1-allyl-4-ethoxy-2-methoxy benzene 5b$^x${1,2} 1480: 193 (M$^+$+H, 41), 192 (M$^+$, 100), 163 (M−29, 28); 2-allyl-1-methoxy-3-propoxy benzene 5b$^y${1,3} 1527: 207 (M$^+$+H, 62), 206 (M$^+$, 100), 177 (M−29, 68); 1-allyl-2-methoxy-4-propoxy benzene 5b$^x${1,3} 1573: 207 (M$^+$+H, 52), 206 (M$^+$, 100), 177 (M−29, 1).

5b$^{x,y}${1,4-5} Allyl-methyl library C. (Method B, 77% yield): $^1$H NMR δ: 0.95-0.99 (m, 30.7H), 1.45-1.54 (m, 8.7H, CH$_2$ (Bu)), 1.65-1.69 (m, 6.4H), 1.73-1.90 (m, 11.8H), 3.29-3.31 (m, 8.3H), 3.41-3.42 (m, 4.4H), 3.80 (m, 11.7H (Me$^x$)), 3.81 (m, 6.0H (Me$^y$)), 3.93-3.99 (m, 14.4H), 4.90-4.93 (m, 2.1H), 4.96-5.04 (m, 10.1H), 5.90-6.01 (m, 5.6H), 6.41-6.45 (m, 8.6H, ArH$^x$), 6.52-6.54 (m, 4.2H, ArH$^y$), 6.99-7.01 (m, 3.8H, ArH$^x$), 7.10-7.14 (m, 2H, ArH$^y$); GC RI: MS m/z (relative intensity, %): 2-allyl-3-methoxy-1-butoxy benzene 5b$^y${1,4} 1624: 221 (M$^+$+H, 36), 220 (M$^+$, 100), 191 (M−29, 79); 1-allyl-2-methoxy-4-butoxy benzene 5b$^x${1,4} 1672: 221 (M$^+$+H, 34), 220 (M$^+$, 100), 191 (M−29, 1); 2-allyl-1-methoxy-3-(3-methyl-butoxy)benzene 5b$^y${1,5} 1680: 235 (M$^+$+H, 32), 234 (M$^+$, 100), 205 (M−29, 47); 1-allyl-2-methoxy-4-(3-methyl-butoxy)benzene 5b$^x${1,5} 1731: 235 (M$^+$+H, 31), 234 (M$^+$, 100), 205 (M−29, 0).

5b$^{x,y}${2,1} Allyl-ethyl library A (Method B, 70% yield), 5b$^{x,y}${2,2-3} allyl-ethyl library B (Method B, 80% yield), 5b$^{x,y}${2,4-5} allyl-ethyl library C (Method B, 48% yield), 5b$^{x,y}${3,1} allyl-propyl library A (Method B, 88% yield), 5b$^{x,y}${3,2-3} allyl-propyl library B (Method B, 80% yield), 5b$^{x,y}${3,4-5} allyl-propyl library C (Method B, 62% yield), 5b$^{x,y}${4,1} allyl-butyl library A (Method B, 81% yield), 5b$^{x,y}${4,2-3} allyl-butyl library B (Method B, 52% yield), 5b$^{x,y}${4,4-5} allyl-butyl library C (Method B, 64% yield), 5b$^{x,y}${5,1} allyl-ipentyl library A (Method B, 64% yield), 5b$^{x,y}${5,2-3} allyl-ipentyl library B (Method B, 74% yield), 5b$^{x,y}${5,4-5} allyl-ipentyl library C (Method B, 82% yield), 5b$^{x,y}${6,1} allyl-allyl library A (Method B, 67% yield), 5b$^{x,y}${6,2-3} allyl-allyl library B (Method B, 53% yield), 5b$^{x,y}${6,4-5} allyl-allyl library C (Method B, 76% yield): $^1$H NMR and GC-MS:

5b$^{x,y}${2,1} Allyl-ethyl library A. (Method B, 70% yield): $^1$H NMR δ: 1.38-1.42 (m, 8.9H, CH$_3$ (Et)), 3.31-3.32 (m, 3.5H, CH$_2$(Allyl$^x$)), 3.42 (dt, J=1.5 and 6.3 Hz, 2H CH$_2$ (Allyl$^y$)), 3.78 (s, 5.2H (Me$^x$)), 3.82 (s, 3H (Me$^y$)), 3.99-4.05 (m, 6.2H), 4.91-4.94 (m, 1H), 4.98-5.07 (m, 4.6H), 5.91-6.01 (m, 2.5H), 6.42-6.44 (m, 3.4H, ArH$^x$), 6.54 (d, J=8.3 Hz, 2H, ArH$^y$), 7.03 (d, J=7.9 Hz, 1.6H, ArH$^x$), 7.12 (t, J=8.3 Hz, 1H, ArH$^y$); GC RI: MS m/z (relative intensity, %): 2-allyl-1-ethoxy-3-methoxy benzene 5b$^y${2,1} 1435: 193 (M$^+$+H, 75), 192 (M$^+$, 100); 1-allyl-2-ethoxy-4-methoxy benzene 5b$^x${2,1} 1471: 193 (M$^+$+H, 47), 192 (M$^+$, 100).

5b$^{x,y}${2,2-3} Allyl-ethyl library B. (Method B, 80% yield): $^1$H NMR δ: 1.01-1.06 (m, 11.6H, CH$_3$ (Pr)), 1.39-1.42 (m, 26.6H, CH$_3$ (Et)), 1.76-1.84 (m, 8H, CH$_2$ (Pr)), 3.31-3.32 (m, 7.7H), 3.42-3.45 (m, 4.4H), 3.88-3.93 (m, 8H, OCH$_2$ (Pr)), 3.98-4.04 (m, 18.1H, OCH$_2$ (Et)), 4.91-4.93 (m, 2.1H), 4.99-5.07 (m, 9.5H), 5.91-6.01 (m, 5.4H), 6.40-6.45 (m, 7.6H, ArH$^x$), 6.50-6.52 (d, 4.1H, ArH$^y$), 7.00-7.02 (m, 3.5H, ArH$^x$), 7.07-7.11 (m, 2H, ArH$^y$); GC RI: MS m/z (relative intensity, %): 2-allyl-1,3-diethoxy benzene 5b$^y${2,2} 1490: 207 (M$^+$+H, 80), 206 (M$^+$, 100); 1-allyl-2,4-diethoxy benzene 5b$^x${2,2} 1535: 207 (M$^+$+H, 62), 206 (M$^+$, 100); 2-allyl-1-ethoxy-3-propoxy benzene 5b$^y${2,3} 1587: 221 (M$^+$+H, 100), 220 (M$^+$, 94); 1-allyl-2-ethoxy-4-propoxy benzene 5b$^x${2,3} 1627: 221 (M$^+$+H, 67), 220 (M$^+$, 100).

5b$^{x,y}${2,4-5} Allyl-ethyl library C. (Method B, 48% yield): $^1$H NMR δ: 0.95-0.99 (m, 29.6H), 1.38-1.42 (m, 21.5H, CH$_3$ (Et)), 1.45-1.53 (m, 8.5H, CH$_2$CH$_3$ (Bu)), 1.64-1.70 (m, 6.4H, CH$_2$CH (iPent)), 1.72-1.91 (m, 11.2H), 3.30-3.32 (m, 9.1H), 3.42-3.43 (m, 4.3H), 3.92-4.04 (m, 29.2H), 4.90-4.93 (m, 2.1H), 4.98-5.06 (m, 10.7H), 5.90-6.01 (m, 6H), 6.40-6.44 (m, 9H, ArH$^x$), 6.50-6.53 (m, 4.2H, ArH$^y$), 7.00-7.01 (m, 4.2H, ArH$^x$), 7.07-7.11 (m, 2H ArH$^y$); GC RI: MS m/z (relative intensity, %): 2-allyl-1-butoxy-3-ethoxy benzene 5b$^y${2,4} 1682: 235 (M$^+$+H, 43), 234 (M$^+$, 85), 149 (M−86, 100); 1-allyl-4-butoxy-2-ethoxy benzene 5b$^x${2,4} 1724: 235 (M$^+$+H, 42), 234 (M$^+$, 100); 2-allyl-1-ethoxy-3-(3-methyl-butoxy) benzene 5W{2,5} 1739: 249 (M$^+$+H, 31), 248 (M$^+$, 69), 149 (M−99, 100); 1-allyl-2-ethoxy-4-(3-methyl-butoxy)benzene 5b$^x${2,5} 1784: 249 (M$^+$+H, 34), 248 (M$^+$, 98), 149 (M−99, 100).

5b$^{x,y}${3,1} Allyl-propyl library A. (Method B, 88% yield): $^1$H NMR δ: 1.03-1.06 (m, 9.1H, CH$_3$ (Pr)), 1.77-1.85 (m, 6.4H, CH$_2$CH$_3$ (Pr)), 3.32-3.33 (m, 3.9H, CH$_2$ (Allyl$^x$)), 3.43-3.44 (m, 2.2H, CH$_2$ (Allyl$^y$)), 3.79 (s, 5.6H (Me$^x$)), 3.82 (s, 3H (Me$^y$)), 3.89-3.93 (m, 6.2H, OCH$_2$ (Pr)), 4.91-4.94 (m, 1.1H), 4.98-5.07 (m, 4.7H), 5.91-6.01 (m, 2.8H), 6.41-6.44 (m, 3.8H, ArH$^x$), 6.52-6.54 (m, 2H, ArH$^y$), 7.03 (d, J=8.0 Hz, 1.6H, ArH$^x$), 7.12 (t, J=8.3 Hz, 1H, ArH$^y$); GC RI: MS m/z (relative intensity, %): 2-allyl-1-methoxy-3-propoxy benzene 5b$^y${3,1} 1527: 207 (M$^+$+H, 100), 206 (M$^+$, 97); 1-allyl-4-methoxy-2-propoxy benzene 5b$^x${3,1} 1573: 207 (M$^+$+H, 51), 206 (M$^+$, 100).

5b$^{x,y}${3,2-3} Allyl-propyl library B. (Method B, 80% yield): $^1$H NMR δ: 1.03-1.08 (m, 30H, CH$_3$ (Pr)), 1.40-1.43 (m, 7.4H, CH$_3$ (Et)), 1.78-1.86 (m, 20.8H, CH$_2$CH$_3$ (Pr)), 3.33-3.34 (m, 7.5H), 3.45-3.47 (m, 4.4H), 3.90-3.94 (m, 20.4H, OCH$_2$ (Pr)), 4.00-4.06 (m, 5.3H, OCH$_2$ (Et)), 4.92-4.95 (m, 2H), 5.00-5.08 (m, 9H), 5.93-6.03 (m, 4.8H), 6.41-6.46 (m, 7.3H, ArH$^x$), 6.51-6.53 (m, 4.2H, ArH$^y$), 7.01-7.03 (m, 3.4H, ArH$^x$), 7.09-7.12 (m, 2H, ArH$^y$); GC RI: MS m/z (relative intensity, %): 2-allyl-1-ethoxy-3-propoxy benzene 5b$^y${3,2} 1587: 221 (M$^+$+H, 39), 220 (M$^+$, 89), 149 (M−71, 100); 1-allyl-4-ethoxy-2-propoxy benzene 5b$^x${3,2} 1624: 221 (M$^+$+H, 29), 220 (M$^+$, 100), 149 (M−71, 53); 2-allyl-1,3-dipropoxy benzene 5b$^y${3,3} 1682: 235 (M$^+$+H, 50), 234 (M$^+$, 100); 1-allyl-2,4-dipropoxy benzene 5b$^x${3,3} 1713: 235 (M$^+$+H, 39), 234 (M$^+$, 100).

5b$^{x,y}${3,4-5} Allyl-propyl library C. (Method B, 62% yield): $^1$H NMR δ: 0.95-0.98 (m, 29.4H), 1.02-1.06 (m, 20.9H, CH$_3$ (Pr)), 1.44-1.53 (m, 8.2H, CH$_2$CH$_3$ (Bu)), 1.64-1.69 (m, 6.4H, CH$_2$CH (iPent)), 1.72-1.89 (m, 26.1H), 2.17 (m, 5.8H (Me)), 3.31-3.32 (m, 9H), 3.42-3.44 (m, 4.3H), 3.88-3.98 (m, 29.1H), 4.89-4.92 (m, 2H), 4.98-5.06 (m, 10.6H), 5.89-6.00 (m, 5.8H), 6.39-6.43 (m, 8.9H, ArH$^x$), 6.49-6.52 (m, 4.9H, ArH$^y$), 6.99-7.01 (m, 4.2H, ArH$^x$), 7.07-7.10 (m, 2H, ArH$^y$); GC RI: MS m/z (relative intensity, %): 2-allyl-1-butoxy-3-propoxy benzene 5W{3,4} 1778: 249

(M$^+$+H, 85), 248 (M$^+$, 100); 1-allyl-4-butoxy-2-propoxy benzene 5b$^x$\{3,4\} 1813: 249 (M$^+$+H, 46), 248 (M$^+$, 100); 2-allyl-1-(3-methyl-butoxy)-3-propoxy benzene 5b$^y$\{3,5\} 1835: 263 (M$^+$+H, 69), 262 (M$^+$, 100); 1-allyl-2-propoxy-4-(3-methyl-butoxy)benzene 5b$^x$\{3,5\} 1870: 263 (M$^+$+H, 45), 262 (M$^+$, 100).

5b$^{x,y}$\{4,1\} Allyl-butyl library A. (Method B, 81% yield): $^1$H NMR δ: 0.95-0.98 (m, 9.9H, CH$_3$ (Bu)), 1.46-1.54 (m, 6.1H, CH$_2$CH$_3$ (Bu)), 1.73-1.79 (m, 6.3H, OCH$_2$CH$_2$ (Bu)), 3.30-3.32 (m, 3.7H, CH$_2$ (Allyl$^x$)), 3.42 (dt, J=1.3 and 6.3 Hz, 2H, CH$_2$ (Allyl$^y$)), 3.78 (s, 5.3H (Me$^x$)), 3.81 (s, 3H (Me$^y$)), 3.92-3.96 (m, 6.3H, OCH$_2$ (Bu)), 4.99-4.93 (m, 1H), 4.96-5.05 (m, 4.7H), 5.90-6.00 (m, 2.7H), 6.40-6.43 (m, 3.6H, ArH$^x$), 6.53 (d, J=8.3 Hz, 2H, ArH$^y$), 7.02 (d, J=8.1 Hz, 1.7H, ArH$^x$), 7.11 (t, J=8.3 Hz, 1H, ArH$^y$); GC RI: MS m/z (relative intensity, %): 2-allyl-1-butoxy-3-methoxy benzene 5W\{4,1\} 1625: 221 (M$^+$+H, 66), 220 (M$^+$, 100); 1-allyl-2-butoxy-4-methoxy benzene 5b$^x$\{4,1\} 1656: 221 (M$^+$+H, 37), 220 (M$^+$, 100).

5b$^{x,y}$\{4,2-3\} Allyl-butyl library B. (Method B, 52% yield): $^1$H NMR δ: 0.95-0.98 (m, 17.7H, CH$_3$ (Bu)), 1.01-1.06 (m, 8.6H, CH$_3$ (Pr)), 1.38-1.41 (m, 9.5H, CH$_3$ (Et)), 1.46-1.54 (m, 12.3H), 1.74-1.83 (m, 18.4H), 3.31-3.32 (m, 7.8H), 3.43-3.45 (m, 3.9H), 3.88-4.04 (m, 25.8H), 4.91-4.93 (m, 1.9H), 4.99-5.06 (m, 9.6H), 5.90-6.01 (m, 5.7H), 6.40-6.45 (m, 8H, ArH$^x$), 6.50-6.52 (m, 4H, ArH$^y$), 7.00-7.01 (m, 3.8H, ArH$^x$), 7.07-7.11 (m, 2H, ArH$^y$); GC RI: MS m/z (relative intensity, %): 2-allyl-1-butoxy-3-ethoxy benzene 5b$^y$\{4,2\} 1681: 235 (M$^+$+H, 55), 234 (M$^+$, 88), 149 (M−85, 100); 1-allyl-2-butoxy-4-ethoxy benzene 5b$^x$\{4,2\} 1714: 235 (M$^+$+H, 38), 234 (M$^+$, 100); 2-allyl-1-butoxy-3-propoxy benzene 5b$^y$\{4,3\} 1777: 249 (M$^+$+H, 59), 248 (M$^+$, 100); 1-allyl-2-butoxy-4-propoxy benzene 5b$^x$\{4,3\} 1803: 249 (M$^+$+H, 41), 248 (M$^+$, 100).

5b$^{x,y}$\{4,4-5\} Allyl-butyl library C. (Method B, 64% yield): $^1$H NMR δ: 0.95-0.99 (m, 48.9H), 1.43-1.55 (m, 20H, CH$_2$CH$_3$ (Bu)), 1.64-1.70 (m, 8.2H), 1.72-1.90 (m, 25.5H), 3.30-3.32 (m, 7H), 3.42-3.44 (m, 4.1H), 3.92-3.99 (m, 25.5H), 4.90-4.93 (m, 2H), 4.98-5.05 (m, 9.1H), 5.89-6.01 (m, 5.2H), 6.39-6.44 (m, 7.3H, ArH$^x$), 6.50-6.52 (m, 4.1H, ArH$^y$), 6.99-7.01 (m, 3.3H, ArH$^x$), 7.07-7.11 (m, 2H, ArH$^y$); 2-allyl-1,3-dibutoxy benzene 5b$^y$\{4,4\} 1871: 263 (M$^+$+H, 72), 262 (M$^+$, 100); 1-allyl-2,4-dibutoxy benzene 5b$^x$\{4,4\} 1899: 263 (M$^+$+H, 41), 262 (M$^+$, 100); 2-allyl-1-butoxy-3-(3-methyl-butoxy)benzene 5b$^y$\{4,5\} 1926: 277 (M$^+$+H, 65), 276 (M$^+$, 100); 1-allyl-2-butoxy-4-(3-methyl-butoxy)benzene 5b$^x$\{4,5\} 1955: 277 (M$^+$+H, 42), 276 (M$^+$, 100).

5b$^{x,y}$\{5,1\} Allyl-ipentyl library A. (Method B, 64% yield): $^1$H NMR δ: 0.95-0.97 (m, 16.8H, CH$_3$ (iPent)), 1.66-1.71 (m, 5.8H, CH$_2$CH (iPent)), 1.82-1.91 (m, 3H, CH (iPent)), 3.31-3.32 (m, 3.6H, CH$_2$ (Allyl$^x$)), 3.41-3.43 (dt, J=1.3 and 6.3 Hz, 2.2H, CH$_2$ (Allyl$^y$)), 3.79 (s, 5.2H, CH$_3$ (Me$^x$)), 3.81 (s, 3H, CH$_3$ (Me$^y$)), 3.95-3.99 (m, 6H, OCH$_2$ (iPent)), 4.90-4.93 (m, 1H), 4.97-5.06 (m, 4.7H), 5.90-6.00 (m, 2.7H), 6.41-6.45 (m, 3.5H), 6.53-6.55 (m, 2H), 7.03 (d, J=8.2 Hz, 1.7H), 7.12 (t, J=8.3 Hz, 1H); GC RI: MS m/z (relative intensity, %): 2-allyl-1-methoxy-3-(3-methyl-butoxy)benzene 5b$^y$\{5,1\} 1684: 235 (M$^+$+H, 43), 234 (M$^+$, 100); 1-allyl-4-methoxy-2-(3-methyl-butoxy)benzene 5b$^x$\{5,1\} 1711: 235 (M$^+$+H, 30), 234 (M$^+$, 100).

5b$^{x,y}$\{5,2-3\} Allyl-ipentyl library B. (Method B, 74% yield): $^1$H NMR δ: 0.94-0.96 (m, 37.1H, CH$_3$ (iPent)), 1.01-1.05 (m, 9.6H, CH$_3$ (Pr)), 1.38-1.41 (m, 10.4H, CH$_3$ (Et)), 1.65-1.69 (m, 13H), 1.74-1.89 (m, 13.8H), 3.29-3.30 (m, 8.1H), 3.40-3.43 (m, 4.3H), 3.88-4.04 (m, 27H), 4.89-4.92 (m, 2.1H), 4.98-5.05 (m, 10.6H), 5.89-5.99 (m, 6.2H), 6.39-6.44 (m, 8.4H), 6.49-6.52 (m, 4.2H), 6.99-7.00 (m, 4H), 7.07-7.10 (m, 2H); GC RI: MS m/z (relative intensity, %): 2-allyl-1-ethoxy-3-(3-methyl-butoxy)benzene 5b$^y$\{5,2\} 1736: 249 (M$^+$+H, 14), 248 (M$^+$, 52), 149 (M−99, 100); 1-allyl-4-ethoxy-2-(3-methyl-butoxy)benzene 5b$^x$\{5,2\} 1820: 249 (M$^+$+H, 22), 248 (M$^+$, 100); 2-allyl-1-(3-methyl-butoxy)-3-propoxy benzene 5b$^y$\{5,3\} 1834: 263 (M$^+$+H, 22), 262 (M$^+$, 80), 135 (M−127, 100); 1-allyl-2-(3-methyl-butoxy)-4-propoxy benzene 5b$^x$\{5,3\} 1855: 263 (M$^+$+H, 26), 262 (M$^+$, 100).

5b$^{x,y}$\{5,4-5\} Allyl-ipentyl library C. (Method B, 82% yield): $^1$H NMR δ: 0.96-1.00 (m, 68H), 1.45-1.54 (m, 8.6H, CH$_2$CH$_3$ (Bu)), 1.65-1.92 (m, 40.4H), 3.31-3.32 (m, 6.2H), 3.42-3.44 (m, 4H), 3.93-4.00 (m, 24.7H), 4.90-4.93 (m, 2H), 4.99-5.06 (m, 9.41H), 5.89-6.01 (m, 5.65H), 6.41-6.45 (m, 7.3H), 6.51-6.53 (m, 3.8H), 7.00-7.01 (m, 3.2H), 7.07-7.11 (m, 2H); GC RI: MS m/z (relative intensity, %): 2-allyl-1-butoxy-3-isopentoxy benzene 5b$^y$\{5,4\} 1927: 277 (M$^+$+H, 42), 276 (M$^+$, 100); 1-allyl-4-butoxy-2-isopentoxy benzene 5b$^x$\{5,4\} 1950: 277 (M$^+$+H, 32), 276 (M$^+$, 100); 2-allyl-1,3-di(3-methyl-butoxy)benzene 5b$^y$\{5,5\} 1984: 291 (M$^+$+H, 36), 290 (M$^+$, 89), 150 (M−140, 100); 1-allyl-2,4-di(3-methyl-butoxy)benzene 5b$^x$\{5,5\} 2006: 291 (M$^+$+H, 32), 290 (M$^+$, 100).

5b$^{x,y}$\{6,1\} Allyl-allyl library A. (Method B, 67% yield): $^1$H NMR δ: 3.35-3.36 (m, 3.8H, CH$_2$ (Allyl$^x$)), 3.46-3.47 (m, 2H, CH$_2$ (Allyl$^y$)), 3.79 (s, 5.4H, CH$_3$ (Me$^x$)), 3.83 (s, 3H, CH$_3$ (Me$^y$)), 4.52-4.55 (m, 6.3H), 4.92-4.95 (m, 1.1H), 4.99-5.08 (m, 5H), 5.25-5.30 (m, 3H), 5.41-5.46 (m, 3H), 5.93-6.10 (m, 5.7H), 6.44-6.47 (m, 3.6H), 6.55 (t, J=8.5 Hz, 2H), 7.05 (d, J=8.7 Hz, 1.7H), 7.13 (t, J=8.3 Hz, 1H); GC RI: MS m/z (relative intensity, %): 2-allyl-1-allyloxy-3-methoxy benzene 5b$^y$\{6,1\} 1524: 205 (M$^+$+H, 29), 204 (M$^+$, 100); 1-allyl-2-allyloxy-4-methoxy benzene 5b$^x$\{6,1\} 1554: 205 (M$^+$+H, 31), 204 (M$^+$, 100).

5b$^{x,y}$\{6,2-3\} Allyl-allyl library B. (Method B, 53% yield): $^1$H NMR δ: 1.02-1.07 (m, 8.8H, CH$_3$ (Pr)), 1.39-1.42 (m, 9.4H, CH$_3$ (Et)), 1.76-1.85 (m, 6.2H, CH$_2$CH$_3$ (Pr)), 3.34-3.35 (m, 7.7H), 3.46-3.48 (m, 4.3H), 3.88-3.93 (m, 6H, OCH$_2$ (Pr)), 3.98-4.05 (m, 6.5H, OCH$_2$ (Et)), 4.51-4.54 (m, 12.2H), 4.91-4.94 (m, 2H), 5.00-5.07 (m, 10H), 5.24-5.28 (m, 6H), 5.40-5.45 (m, 6H), 5.92-6.09 (m, 12.1H), 6.42-6.45 (m, 7.6H), 6.51-6.54 (m, 4.2H), 7.01-7.03 (m, 3.7H), 7.08-7.11 (m, 2H); GC RI: MS m/z (relative intensity, %): 2-allyl-1-allyloxy-3-ethoxy benzene 5b$^y$\{6,2\} 1581: 219 (M$^+$+H, 42), 218 (M$^+$, 100); 1-allyl-2-allyloxy-4-ethoxy benzene 5b$^x$\{6,2\} 1613: 219 (M$^+$+H, 46), 218 (M$^+$, 100); 2-allyl-1-allyloxy-3-propoxy benzene 5b$^y$\{6,3\} 1674: 233 (M$^+$+H, 31), 232 (M$^+$, 59), 149 (M−83, 100); 1-allyl-2-allyloxy-4-propoxy benzene 5b$^x$\{6,2\} 1706: 233 (M$^+$+H, 50), 232 (M$^+$, 100).

5b$^{x,y}$\{6,4-5\} Allyl-allyl library C. (Method B, 76% yield): $^1$H NMR δ: 0.96-0.99 (m, 28.1H), 1.45-1.54 (m, 7.5H, CH$_2$CH$_3$ (Bu)), 1.65-1.71 (m, 7H), 1.73-1.92 (m, 10.9H), 3.34-3.36 (m, 6.2H), 3.46-3.47 (m, 3.9H), 3.92-4.00 (m, 12.8H), 4.51-4.55 (m, 10.6H), 4.91-4.94 (m, 2.1H), 5.00-5.07 (m, 9.2H), 5.24-5.29 (m, 5.8H), 5.40-5.45 (m, 5.7H), 5.92-6.10 (m, 11.9H), 6.42-6.45 (m, 6.6H), 6.51-6.55 (m, 4.1H), 7.02-7.04 (m, 3.1H), 7.08-7.12 (m, 2H); GC RI: MS m/z (relative intensity, %): 2-allyl-1-allyloxy-3-butoxy benzene 5b$^y$\{6,4\} 1771: 247 (M$^+$+H, 43), 246 (M$^+$, 63), 149 (M−97, 100); 1-allyl-2-allyloxy-4-butoxy benzene 5b$^x$\{6,4\} 1801: 247 (M$^+$+H, 61), 246 (M$^+$, 100); 2-allyl-1-allyloxy-3-(3-methyl-butoxy)benzene 5b$^y$\{6,5\} 1827: 261 (M$^+$+H, 74), 260 (M$^+$, 78), 149 (M−111, 100); 1-allyl-2-allyloxy-4-(3-methyl-butoxy)benzene 5b$^x$\{6,5\} 1861: 261 (M$^+$+H, 62), 260 (M$^+$, 100).

5c\{1,1-5\} Allyl-methyl library. (Method B, 98% yield): $^1$H NMR δ: 0.95-0.99 (m, 8.6H), 1.03 (t, J=7.5, 3.2H, CH$_3$ (Pr)), 1.38 (t, J=7.0 Hz, 4H), 1.45-1.52 (m, 2H), 1.65 (apparent q, J=6.7 Hz, 2H, CH$_2$ (i-Pent)), 1.71-1.86 (m, 5.2H), 3.35-3.36 (m, 10.8H), 3.76 (s, 4H, OCH$_3$), 3.78-3.79 (m, 16.5H, OCH$_3$), 3.86 (t, J=6.6 Hz, 2.3H, OCH$_2$ (Pr)), 3.89-3.94 (m, 3.6H), 3.97 (q, J=7.0 Hz, 2.4H, OCH$_2$ (Et)), 5.04-5.08 (m, 10H), 5.94-6.02 (m, 4.7H), 6.70-6.80 (m, 15.6H, ArH); GC RI: MS m/z (relative intensity, %): 1-allyl-2,5-dimethoxy benzene 5c{1,1} 1397: 179 (M$^+$+H, 28), 178 (M$^+$, 100); 1-allyl-5-ethoxy-2-methoxy benzene 5c{1,2} 1462: 193 (M$^+$+H, 32), 192 (M$^+$, 100); 1-allyl-2-methoxy-5-propoxy benzene 5c{1,3} 1557: 207 (M$^+$+H, 33), 206 (M$^+$, 100); 1-allyl-5-butoxy-2-methoxy benzene 5c{1,4} 1650: 221 (M$^+$+H, 32), 220 (M$^+$, 100); 1-allyl-2-methoxy-5-(3-methyl-butoxy)benzene 5c{1,5} 1709: 235 (M$^+$+H, 29), 234 (M$^+$, 100).

5c{2,1-5} Allyl-ethyl library. (Method B, 89% yield), 5c{3,1-5} Allyl-propyl library. (Method B, 95% yield), 5c{4,1-5} Allyl-butyl library. (Method B, 95% yield), 5c{5,1-5} Allyl-iPentyl library. (Method B, 95% yield); $^1$H NMR and GC-MS data:

5c{2,1-5} Allyl-ethyl library. (Method B, 89% yield): $^1$H NMR δ: 0.94-0.98 (m, 8.7H), 1.02 (t, J=7.4 Hz, 3.7H), 1.36-1.41 (m, 21H), 1.44-1.52 (m, 2.2H), 1.62-1.66 (m, 4.5H), 1.70-1.86 (m, 5.6H), 3.36-3.38 (m, 10.9H), 3.76 (s, 4H, OCH$_3$), 3.86 (t, J=6.6 Hz, 2.6H), 3.88-3.93 (m, 4H), 3.95-3.99 (m, 14H), 5.03-5.10 (m, 10H), 5.93-6.02 (m, 4.7H), 6.66-6.78 (m, 16.2H, ArH); GC RI: MS m/z (relative intensity, %): 1-allyl-2,5-diethoxy benzene 5c{2,2} 1518: 207 (M$^+$+H, 31), 206 (M$^+$, 100); 1-allyl-2-ethoxy-5-propoxy benzene 5c{2,3} 1605: 221 (M$^+$+H, 29), 220 (M$^+$, 100); 1-allyl-5-butoxy-2-ethoxy benzene 5c{2,4} 1704: 235 (M$^+$+H, 29), 234 (M$^+$, 100); 1-allyl-2-ethoxy-5-(3-methyl-butoxy)benzene 5c{2,5} 1763: 249 (M$^+$+H, 27), 248 (M$^+$, 100).

5c{3,1-5} Allyl-propyl library. (Method B, 95% yield): $^1$H NMR δ: 0.96-1.06 (m, 27.6H), 1.37-1.41 (m, 4H), 1.44-1.53 (m, 2H), 1.64-1.68 (m, 2.9H), 1.72-1.92 (m, 16H), 3.38 (d, J=6.4 Hz, 10.9H), 3.80 (s, 3.8H, OCH$_3$), 3.82-3.99 (m, 19.9H), 4.99-5.18 (m, 10.5H), 5.92-6.05 (m, 5H), 6.67-6.85 (m, 17.5H, ArH); GC RI: MS m/z (relative intensity, %): 1-allyl-2,5-dipropoxy benzene 5c{3,3} 1699: 235 (M$^+$+H, 26), 234 (M$^+$, 100); 1-allyl-5-butoxy-2-propoxy benzene 5c{3,4} 1798: 249 (M$^+$+H, 27), 248 (M$^+$, 100); 1-allyl-5-(3-methyl-butoxy)-2-propoxy benzene 5c{3,5} 1857: 263 (M$^+$+H, 27), 262 (M$^+$, 90), 249 (100).

5c{4,1-5} Allyl-butyl library. (Method B, 95% yield): $^1$H NMR δ: 0.94-0.98 (m, 19.5H), 1.00-1.04 (m, 3.4H), 1.36-1.39 (m, 3.6H), 1.44-1.54 (m, 9.3H), 1.57-1.58 (m, 2H), 1.64 (t, J=6.8 Hz, 1.8H), 1.70-1.85 (m, 12.5H), 3.35-3.39 (m, 10H), 3.76 (s, 3.7H, OCH$_3$), 3.86 (t, J=6.6 Hz, 2.2H), 3.88-3.93 (m, 11.2H), 3.97 (q, J=6.9 Hz, 2.4H), 5.03-5.17 (m, 9.5H), 5.93-6.06 (m, 4.5H), 6.65-6.87 (m, 16.1H, ArH); GC RI: MS m/z (relative intensity, %): 1-allyl-2,5-dibutoxy benzene 5c{4,4} 1892: 263 (M$^+$+H, 28), 262 (M$^+$, 100); 1-allyl-2-butoxy-5-(3-methyl-butoxy)benzene 5c{4,5} 1949: 277 (M$^+$+H, 28), 276 (M$^+$, 100).

5c{5,1-5} Allyl-iPentyl library. (Method B, 95% yield): $^1$H NMR δ: 0.93-0.99 (m, 27.7H), 1.03 (t, J=7.4 Hz, 3.7H), 1.39 (t, J=7.0 Hz, 4H), 1.44-1.52 (m, 2.2H), 1.63-1.88 (m, 18.5H), 3.36-3.39 (m, 10.7H), 3.76 (s, 4H, OCH$_3$), 3.84-3.99 (m, 15.7H), 5.01-5.18 (m, 10.5H), 5.93-6.05 (m, 5H), 6.66-6.85 (m, 17H, ArH); GC RI: MS m/z (relative intensity, %): 1-allyl-2,5-di(3-methyl-butoxy)benzene 5c{5,5} 2001: 291 (M$^+$+H, 27), 290 (M$^+$, 100).

The following procedures were used to generate mini-libraries in Set D as set out in Table 2.

The 3c{6,1-5} mini-library (2.7224 g) was heated at 180° C. in a sealed tube, under a nitrogen atmosphere for 30 hours. The viscous dark black oil was purified by column chromatography with chloroform to afford 1.6334 g of pure 6W-51 library in 60% yield.

The following data were generated for Set D.

$^1$H NMR δ: 0.92-0.97 (m, 9.5H), 1.02 (t, J=7.4 Hz, 3.6H), 1.37 (t, J=7.0 Hz, 4.2H), 1.45 (d, J=6.2 Hz, 15.7H), 1.57-1.58 (m, 1.4H), 1.64 (q, J=6.8 Hz, 2H), 1.70-1.85 (m, 5.7H), 2.77-2.82 (m, 4.8H), 3.24-3.30 (m, 5H), 3.75 (s, 3.4H, OCH$_3$), 3.85 (t, J=6.6 Hz, 2.2H), 3.87-3.92 (m, 3.9H), 3.96 (q, J=7.0 Hz, 2.3H), 4.85-4.93 (m, 4.2H), 6.63-6.82 (m, 17.6H, ArH); GC RI: MS m/z (relative intensity, %): 5-methoxy-2-methyl-2,3-dihydro benzofuran 6c{1} 1365: 165 (M$^+$+H, 24), 164 (M$^+$, 100), 149 (65); 5-ethoxy-2-methyl-2,3-dihydro benzofuran 6c{2} 1434: 179 (M$^+$+H, 22), 178 (M$^+$, 100), 149 (25); 5-propoxy-2-methyl-2,3-dihydro benzofuran 6c{3} 1533: 193 (M$^+$+H, 22), 192 (M$^+$, 100); 5-butoxy-2-methyl-2,3-dihydro benzofuran 6c{4} 1634: 207 (M$^+$+H, 22), 206 (M$^+$, 100); 5-(3-methyl-butoxy)-2-methyl-2,3-dihydro benzofuran 6c{5} 1699: 221 (M$^+$+H, 22), 220 (M$^+$, 100).

Spectral Data and Analysis of Ethyl, Propyl, Butyl, Isopentyl and Allyl Sets

Data for Compounds in Set A (dialkoxybenzenes)

Ortho

3a{2,1-5} Ethyl library (Method A, 57% yield): $^1$H NMR δ: 0.96-0.99 (m, 9.4H), 1.04 (t, J=7.5 Hz, 3H, CH$_3$ (Pr)), 1.41-1.53 (m, 5H), 1.73 (q, J=6.9 Hz, 2H, CH$_2$ (i-Pent)), 1.79-1.89 (m, 5.4H), 3.88 (s, 3H, OCH$_3$ (Me)), 3.97 (t, J=6.8 Hz, 2H), 4.01 (t, J=6.7 Hz, 2H), 4.04 (t, J=6.8 Hz, 2H), 4.05-4.13 (m, 14H), 6.86-6.93 (m, 19H, ArH); GC RI: MS m/z (relative intensity, %): 1,2-diethoxy benzene 3a{2,2} 1244: 167 (M$^+$+H, 100), 166 (M$^+$, 81); 1-ethoxy-2-propoxy benzene 3a{2,3} 1335: 181 (M$^+$+H, 100), 180 (M$^+$, 60); 1-ethoxy-2-butoxy benzene 3a{2,4} 1429: 195 (M$^+$+H, 100), 194 (M$^+$, 83); 1-ethoxy-2-(3-methyl-butoxy)benzene 3a{2,5} 1486: 209 (M$^+$+H, 100), 208 (M$^+$, 72).

3a{3,1-5} Propyl library (Method A, 67% yield): $^1$H NMR δ: 0.96-0.99 (m, 7.4H), 1.04 (t, J=7.4 Hz, 16.5H, CH$_3$ (Pr)), 1.44 (t, J=7.0 Hz, 3H), 1.48-1.53 (m, 1.6H), 1.72 (q, J=6.8 Hz, 1.7H, CH$_2$ (i-Pent)), 1.77-1.91 (m, 14H), 3.87 (s, 3H, OCH$_3$ (Me)), 3.94-4.04 (m, 14.7H), 4.09 (q, J=7.0 Hz, 2H), 6.86-6.92 (m, 17H, ArH); GC RI: MS m/z (relative intensity, %): 1,2-dipropoxy benzene 3a{3,3} 1424: 195 (M$^+$+H, 100), 194 (M$^+$, 60); 1-butoxy-2-propoxy benzene 3a{3,4} 1518: 209 (M$^+$+H, 100), 208 (M$^+$, 84); 1-(3-methyl-butoxy)-2-propoxy benzene 3a{3,5} 1576: 223 (M$^+$+H, 100), 222 (M$^+$, 62).

3a{4,1-5} Butyl library (Method A, 62% yield): $^1$H NMR δ: 0.96-0.99 (m, 24H), 1.04 (t, J=7.5 Hz, 3.4H, CH$_3$ (Pr)), 1.44 (t, J=7.0 Hz, 3H), 1.46-1.54 (m, 12.6H), 1.71 (q, J=6.8 Hz, 2H, CH$_2$ (i-Pent)), 1.77-1.88 (m, 16H), 3.87 (s, 3H, OCH$_3$ (Me)), 3.96 (t, J=6.6 Hz, 2H), 3.98-4.05 (m, 15H), 4.07 (q, J=7.0 Hz, 2.4H), 6.82-6.94 (m, 20H, ArH); GC RI: MS m/z (relative intensity, %): 1,2-dibutoxy benzene 3a{4,4} 1608: 223 (M$^+$+H, 100), 222 (M$^+$, 64); 1-butoxy-2-(3-methyl-butoxy)benzene 3a{4,5} 1664: 237 (M$^+$+H, 100), 236 (M$^+$, 64).

3a{5,1-5} Isopentyl library. (Method A, 43% yield): $^1$H NMR δ: 0.96-0.99 (m, 41H), 1.04 (t, J=7.5 Hz, 3.4H, CH$_3$ (Pr)), 1.43 (t, J=7.0 Hz, 3.8H), 1.50 (q, J=7.5 Hz, 2.6H), 1.69-1.90 (m, 24H), 3.86 (s, 3H, OCH$_3$ (Me)), 3.96 (t, J=6.6 Hz, 2H), 3.98-4.10 (m, 18H), 6.84-6.93 (m, 20H, ArH); GC RI: MS m/z (relative intensity, %): 1,2-di(3-methyl-butoxy) benzene 3a{5,5} 1720: 251 (M$^+$+H, 20), 250 (M$^+$, 100).

3a{6,1-5} Allyl library. (Method B, 94% yield): $^1$H NMR δ: 0.96-1.00 (m, 7H), 1.05 (t, J=7.4 Hz, 3H, CH$_3$ (Pr)), 1.45 (t, J=7.0 Hz, 3.7H), 1.49-1.53 (m, 1.7H), 1.73 (q, J=6.9 Hz, 1.4H), 1.79-1.89 (m, 4.6H), 3.88 (s, 4H, OCH$_3$ (Me)), 3.98 (t, J=6.7 Hz, 1.8H), 4.01-4.06 (m, 3.3H), 4.10 (q, J=7.0 Hz, 2.4H), 4.58-4.63 (m, 10.6H), 5.25-5.30 (m, 5.1H), 5.38-5.44

(m, 5H), 6.04-6.14 (m, 5H), 6.84-6.95 (m, 21H, ArH); GC RI: MS m/z (relative intensity, %): 1-allyloxy-2-methoxy benzene 3a{6,1} 1281: 165 (M$^+$+H, 42), 164 (M$^+$, 100); 1-allyloxy-2-ethoxy benzene 3a{6,2} 1327: 179 (M$^+$+H, 100), 178 (M$^+$, 67); 1-allyloxy-2-propoxy benzene 3a{6,3} 1416: 193 (M$^+$+H, 100), 192 (M$^+$, 91); 1-allyloxy-2-butoxy benzene 3a{6,4} 1510: 207 (M$^+$+H, 100), 206 (M$^+$, 72); 1-allyloxy-2-(3-methyl-butoxy)benzene 3a{6,5} 1569: 221 (M$^+$+H, 100), 220 (M$^+$, 70).

Meta

3b{2,1-5} Ethyl library. (Method A, 66% yield): $^1$H NMR δ: 0.96 (d, J=6.6 Hz, 6H, CH$_3$ (i-Pent)), 1.03 (t, J=7.4 Hz, 3H, CH$_3$ (Pr)), 1.39-1.43 (m, 12.8H), 1.67 (apparent q, J=6.8 Hz, 2H, CH$_2$ (i-Pent)), 1.78-1.84 (m, 3H), 3.79 (s, 3H, CH$_3$ (Me)), 3.90 (t, J=6.6 Hz, 2H, OCH$_2$ (Pr)), 3.98 (t, J=6.7 Hz, 2H, OCH$_2$ (i-Pent)), 3.99-4.04 (m, 8H), 6.46-6.51 (m, 10H, ArH), 7.16 (t, J=8.2 Hz, 3H, ArH); GC RI: MS m/z (relative intensity, %): 1,3-diethoxy benzene 3b{2,2} 1318: 167 (M$^+$+H, 31), 166 (M$^+$, 100); 1-ethoxy-3-propoxy benzene 3b{2,3} 1409: 181 (M$^+$+H, 40), 180 (M$^+$, 100); 1-ethoxy-3-(3-methyl-butyloxy)benzene 3b{2,5} 1570: 209 (M$^+$+H, 35), 208 (M$^+$, 100).

3b{3,1-5} Propyl library (Method A, 53% yield): $^1$H NMR δ: 0.96 (d, J=6.6 Hz, 6H, CH$_3$ (i-Pent)), 1.02-1.05 (m, 10H), 1.40 (t, J=7.0 Hz, 2H, CH$_3$ (Et)), 1.67 (apparent q, J=6.8 Hz, 2H, CH$_2$ (i-Pent)), 1.77-1.85 (m, 8H), 3.79 (s, 1.5H, OCH$_3$ (Me)), 3.89-3.92 (m, 7H), 3.97 (t, J=6.7 Hz, 2H, OCH$_2$ (i-Pent)), 4.02 (q, J=7.0 Hz, 1.2H, OCH$_2$ (Et)), 6.46-6.51 (m, 7H, ArH), 7.16 (t, J=8.2 Hz, 2.5H, ArH); GC RI: MS m/z (relative intensity, %): 1,3-dipropoxy benzene 3b{3,3} 1501: 195 (M$^+$+H, 45), 194 (M$^+$, 100), 110 (85), 82(22); 1-(3-methyl-butyloxy)-3-propoxy benzene 3b {3,5} 1657: 223 (M$^+$+H, 44), 222 (M$^+$, 100).

3b{4,1-5} Butyl library (Method A, 69% yield): $^1$H NMR δ: 0.99-1.02 (m, 19H), 1.05 (t, J=7.0 Hz, 3H, CH$_3$ (Pr)), 1.41-1.45 (m, 3H), 1.48-1.56 (m, 8H), 1.70 (apparent q, J=6.7 Hz, 2.5H, CH$_2$ (i-Pent)), 1.76-1.91 (m, 8H), 3.81 (s, 3H, OCH$_3$ (Me)), 3.93 (t, J=6.6 Hz, 2H, OCH$_2$ (Pr)), 3.95-4.01 (m, 11H), 4.03 (q, J=7.0 Hz, 2H, OCH$_2$ (Et)), 6.45-6.54 (m, 11.7H, ArH), 7.16 (t, J=8.2 Hz, 4H, ArH); GC RI: MS m/z (relative intensity, %): 1-butoxy-3-methoxy benzene 3b{4,1} 1440: 181 (M$^+$+H, 25), 180 (M$^+$, 100); 1-butoxy-3-ethoxy benzene 3b{4,2} 1506: 193 (M$^+$+H, 33), 194 (M$^+$, 100); 1-butoxy-3-propoxy benzene 3b {4,3} 1596: 209 (M$^+$+H, 48), 208 (M$^+$, 100); 1-butoxy-3-(3-methyl-butyloxy)benzene 3b {4,5} 1754: 237 (M$^+$+H, 42), 236 (M$^+$, 100). 3b{5,1-5} Isopentyl library. (Method A, 72% yield): $^1$H NMR δ: 0.99 (d, J=6.7 Hz, 26H), 1.06 (t, J=7.4 Hz, 3H, CH$_3$ (Pr)), 1.41-1.45 (m, 3H), 1.70 (apparent q, J=6.7 Hz, 9H), 1.81-1.88 (m, 6.3H), 3.81 (s, 3H, OCH$_3$ (Me)), 3.92 (t, J=6.6 Hz, 2H, OCH$_2$ (Pr)), 3.98-4.04 (m, 11H), 6.50-6.54 (m, 11H, ArH), 7.18 (t, J=8.2 Hz, 4H, ArH); GC RI: MS m/z (relative intensity, %): 1-methoxy-3-(3-methyl-butyloxy)benzene 3b{5,1} 1500: 195 (M$^+$+H, 26), 194 (M$^+$, 100); 1-ethoxy-3-(3-methyl-butyloxy)benzene 3b{5,2} 1566: 209 (M$^+$+H, 35), 208 (M+, 100); 1-(3-methyl-butyloxy)-3-propoxy benzene 3b {5,3} 1653: 223 (M$^+$+H, 48), 222 (M$^+$, 100); 1,3-di(3-methyl-butyloxy)benzene 3b {5,5} 1826: 251 (M$^+$+H, 40), 250 (M$^+$, 100).

The meta allyl library was synthesized in three portions (methyl by itself, ethyl+propyl and butyl+isopentyl), because upon Claisen rearrangement each compound gave rise to two rearrangement products.

3b {6,1}1-allyloxy-3-methoxybenzene. (Method D, 98% yield): $^1$H NMR δ: 3.80 (s, 3H, CH$_3$), 4.53 (apparent d, J=5.5 Hz, 2H, allyl CH$_2$), 5.30 (apparent d, J=14 Hz, 1H), 5.43 (apparent d, J=22 Hz, 1H), 6.07 (m, 1H), 6.52 (m, 3H, ArH), 7.19 (apparent t, J=7.7 Hz, 1H ArH). GC R1: 1334 MS m/z (relative intensity, %): 164 (M$^+$, 100), 149 (M-CH$_3$, 10), 136 (M−28, 12).

3b {6,2-3}Allyl library (ethyl, propyl). (Method D, 60% yield, 35% 3b {6, 2} by GC and 39% by $^1$H NMR and the rest is 3b {6,3}): $^1$H NMR δ: 1.04 (t, J=4 Hz, 3H, CH$_3$ propyl), 1.42 (t, J=3.7 Hz, 3H, CH$_3$ ethyl), 1.81 (m, 2H, CH$_2$, propyl), 3.95 (t, J=3.7 Hz, 2H propyl CH$_2$), 4.02 (q, J=7 Hz, 2H, ethyl), 4.53 (apparent d, J=7 Hz, 2H for each component), 5.29 (m, J=14 Hz, 1H for each component), 5.41 (m, J=22 Hz, 1H for each component), 6.07 (m, 1H for each component), 6.53 (m, 3H for each component), 7.17 (apparent t, J=8 Hz, 1H for each component). GC RI: MS m/z (relative intensity, %): 1-allyloxy-3-ethoxybenzene 3b {6,2} 1398: 179 (M+1, 72), 178 (M$^{+\cdot}$, 100), 150 (M−28, 35); 1-allyloxy-3-propoxybenzene 3b {6,3} 1491: 193 (M+1, 93), 192 (M$^{+\cdot}$, 100), 164 (M−28, 12), 150 (31).

3b {6,4-5}Allyl library (butyl, isopentyl). (Method D, 71% yield, 3b {6,4} 34% by GC and 40% by $^1$H NMR and the rest is 3b {6,5}): $^1$H NMR δ: 0.98 (m, 6H, CH$_3$ isopentyl, 3H CH$_3$ butyl), 1.48 (m, 2H, CH$_2$ butyl), 1.68 (m, 2H, CH$_2$, isopentyl), 1.75 (m, 2H, CH$_2$, butyl), 1.83 (m, 1H, isopentyl), 3.96 (m, 2H for each component, CH$_2$), 4.52 (apparent d, J=8 Hz, 2H for each component), 5.29 (apparent d, J=14 Hz, 1H for each component), 5.42 (apparent d, J=22 Hz, 1H for each component), 6.06 (m, 1H for each component), 6.51 (m, 3H for each component, ArH), 7.17 (apparent t, J=7 Hz, 1H for each component, ArH). GC RI: MS m/z (relative intensity, %): 1-allyloxy-3-n-butoxybenzene 3b {6, 4} 1592: 207 (M+1, 83), 206 (M$^+$, 100), 178 (M−28, 12), 150 (33). 1-allyloxy-3-isopentyloxybenzene 3b {6,5} 1654: 221 (M+1, 81), 220 (M$^+$, 100), 192 (M−28, 7), 150 (21).

Para

3c{2,1-5} Ethyl library (Method A, 31% yield): $^1$H NMR δ: 0.96 (d, J=6.7 Hz, 6H, CH$_3$ (i-Pent)), 1.03 (t, J=7.4 Hz, 3H, CH$_3$ (Pr)), 1.39 (t, J=7.0 Hz, 15H, CH$_3$ (Et)), 1.66 (apparent q, J=6.8 Hz, 3H, CH$_2$ (i-Pent)), 1.77-1.83 (m, 4H), 3.77 (s, 3H, OCH$_3$ (Me)), 3.87 (t, J=6.6 Hz, 2H, OCH$_2$ (Pr)), 3.94 (t, J=6.7 Hz, 2H, OCH$_2$ (i-Pent)), 3.98 (q, J=7.0 Hz, 10H, OCH$_2$ (Et)), 6.83-6.84 (m, 16H, ArH); GC RI: MS m/z (relative intensity, %): 1,4-diethoxy benzene 3c{2,2} 1248: 167 (M$^+$+H, 33), 166 (M$^+$, 100); 1-ethoxy-4-propoxy benzene 3c{2,3} 1337: 181 (M$^+$+H, 28), 180 (M+, 100); 1-ethoxy-4-(3-methyl-butyloxy)benzene 3c{2,5} 1492: 209 (M$^+$+H, 31), 208 (M$^+$, 100).

3c{3,1-5} Propyl library (Method A, 82% yield): $^1$H NMR δ: 0.97 (d, J=6.6 Hz, 7H, CH$_3$ (i-Pent)), 1.03 (t, J=7.4 Hz, 15H, CH$_3$ (Pr)), 1.40 (t, J=6.9 Hz, 3H, CH$_3$ (Et)), 1.66 (apparent q, J=6.8 Hz, 3H, CH$_2$ (i-Pent)), 1.77-1.85 (m, 12H), 3.77 (s, 3H, OCH$_3$ (Me)), 3.87 (t, J=6.5 Hz, 10H, OCH$_2$ (Pr)), 3.94 (t, J=6.6 Hz, 2.8H, OCH$_2$ (i-Pent)), 3.98 (q, J=7.1 Hz, 2H, OCH$_2$ (Et)), 6.83-6.84 (m, 16H, ArH); GC RI: MS m/z (relative intensity, %): 1,4-dipropoxy benzene 3c{3,3} 1431: (M$^+$+H, 25), 194 (M$^+$, 100); 1-(3-methyl-butyloxy)-4-propoxy benzene 3c{3,5} 1589: 223 (M$^+$+H, 28), 222 (M$^+$, 100).

3c{4,1-5} Butyl library (Method A, 76% yield): $^1$H NMR δ: 0.96-0.99 (m, 18H), 1.02 (t, J=7.4 Hz, 3H, CH$_3$ (Pr)), 1.39 (t, J=6.9 Hz, 4H, CH$_3$ (Et)), 1.45-1.53 (m, 8H, CH$_2$ (Bu)), 1.66 (apparent q, J=6.7 Hz, 2H, CH$_2$ (i-Pent)), 1.72-1.81 (m, 11.6H), 3.77 (s, 3H, OCH$_3$ (Me)), 3.87 (t, J=6.6 Hz, 2H, OCH$_2$ (Pr)), 3.90-3.95 (m, 10.4H), 3.98 (q, J=7.0 Hz, 2H, OCH$_2$ (Et)), 6.83-6.84 (m, 16H, ArH); GC RI: MS m/z (relative intensity, %): 1-butoxy-4-methoxy benzene 3c{4,1} 1371: 181 (M$^+$+H, 29), 180 (M$^+$, 100); 1-butoxy-4-ethoxy benzene 3c{4,2} 1437: 195 (M$^+$+H, 23), 194 (M$^+$, 100); 1-butoxy-4-propoxy benzene 3c{4,3} 1529: 209 (M$^+$+H, 40), 208 (M+, 100); 1-butoxy-4-(3-methyl-butyloxy)benzene 3c{4,5} 1681: 237 (M++H, 42), 236 (M+, 100).

3c{5,1-5} Isopentyl (3-methyl-butyloxy) library. (Method A, 82% yield): $^1$H NMR δ: 0.96 (d, J=7.0 Hz 30H, CH$_3$ (i-Pent)), 1.02 (t, J=7.4 Hz, 3H, CH$_3$ (Pr)), 1.39 (t, J=6.9 Hz, 3H, CH$_3$ (Et)), 1.66 (apparent q, J=6.8 Hz, 10H, CH$_2$ (i-Pent)), 1.75-1.86 (m, 7.5H), 3.77 (s, 3H, OCH$_3$ (Me)), 3.87 (t, J=6.4 Hz, 2H, OCH$_2$ (Pr)), 3.94 (t, J=6.9 Hz, 10H, OCH$_2$ (i-Pent)), 3.98 (q, J=6.8 Hz, 2H, OCH$_2$ (Et)), 6.83-6.84 (m, 16H, ArH); GC RI: MS m/z (relative intensity, %): 1,4-di(3-methyl-butyloxy)-benzene 3c{5,5} 1850: 251 (M++H, 25), 250 (M+, 100).

3c{6,1-5} Allyl library. (Method B, 95% yield): GC (RI): $^1$H NMR δ: 0.95-0.98 (m, 8H), 1.03 (t, J=7.4 Hz, 3H, CH$_3$ (Pr)), 1.39 (t, J=7.0 Hz, 3.9H, CH$_3$ (Et)), 1.46-1.50 (m, 1.5H), 1.56 (d, J=3.8 Hz, 1.3H), 1.65 (apparent q, J=6.8 Hz, 2H, CH$_2$ (i-Pent)), 1.71-1.85 (m, 5H), 3.78 (s, 4H, OCH$_3$ (Me)), 3.87 (t, J=6.6 Hz, 2H, OCH$_2$ (Pr)), 3.90-3.95 (m, 3.7H), 3.98 (q, J=7.0 Hz, 2.5H, OCH$_2$ (Et)), 4.47-4.49 (m, 10.9H), 5.25-5.29 (m, 5H), 5.38-5.42 (m, 5H), 6.01-6.09 (m, 5H), 6.81-6.87 (m, 21H, ArH); GC RI: MS m/z (relative intensity, %):

1-allyloxy-4-methoxy benzene 3c{6,1} 1326: 165 (M++H, 20), 164 (M+, 100); 1-allyloxy-4-ethoxy benzene 3c{6,2} 1394: 179 (M++H, 70), 178 (M+, 100); 1-allyloxy-4-propoxy benzene 3c{6,3} 1491: 193 (M++H, 65), 192 (M+, 100); 1-allyloxy-4-butoxy benzene 3c{6,4} 1594: 207 (M++H, 56), 206 (M+, 100); 1-allyloxy-4-(3-methyl-butoxy)benzene 3c{6,5} 1659: 221 (M++H, 46), 220 (M+, 100).

Data for Compounds in Set C (Allyl Dialkoxybenzenes)
Ortho

5a{2,1-5} Allyl-ethyl library. (Method B, 91% yield): $^1$H NMR δ: 0.97-1.00 (m, 11.5H), 1.35-1.40 (m, 14.8H), 1.42-1.16 (m, 10.5H), 1.72 (apparent q, J=6.7 Hz, 1.8H, CH$_2$ (i-Pent)), 1.78-1.91 (m, 5.7H), 3.43 (d, J=6.6 Hz, 9.2H), 3.84 (s, 3.9H, OCH$_3$), 3.91-4.12 (m, 20.9H), 5.01-5.10 (m, 10.3H), 5.94-6.02 (m, 5H), 6.69-6.83 (m, 11.4H, ArH), 6.90-7.00 (m, 6.7H, ArH); GC RI: MS m/z (relative intensity, %): 1-allyl-2,3-diethoxy benzene 5a{2,2} 1435: 207 (M++H, 63), 206 (M+, 100); 1-allyl-2-ethoxy-3-propoxy benzene 5a{2,3} 1523: 221 (M++H, 56), 220 (M+, 100); 1-allyl-2-butoxy-3-ethoxy benzene 5a{2,4} 1616: 235 (M++H, 88), 234 (M+, 100); 1-allyl-2-ethoxy-3-(3-methyl-butoxy)benzene 5a{2,5} 1669: 249 (M++H, 79), 248 (M+, 100).

5a{3,1-5} Allyl-propyl library. (Method B, 96% yield): $^1$H NMR δ: 0.97-1.08 (m, 27.8H), 1.44 (t, J=7.0 Hz, 4H), 1.49-1.56 (m, 2.3H), 1.69-1.89 (m, 16.3H), 3.42 (d, J=6.6 Hz, 9.5H), 3.84 (s, 4H, OCH$_3$), 3.86-4.09 (m, 21H), 5.02-5.08 (m, 10H), 5.94-6.02 (m, 5H), 6.69-6.83 (m, 11.4H, ArH), 6.89-6.99 (m, 6H, ArH); GC RI: MS m/z (relative intensity, %): 1-allyl-2,3-dipropoxy benzene 5a{3,3} 1608: 235 (M++H, 57), 234 (M+, 100); 1-allyl-3-butoxy-2-propoxy benzene 5a{3,4} 1699: 249 (M++H, 100), 248 (M+, 72); 1-allyl-3-(3-methyl-butoxy)-2-propoxy benzene 5a{3,5} 1751: 263 (M++H, 50), 262 (M+, 90), 249 (100).

5a{4,1-5} Allyl-butyl library. (Method B, 92% yield): $^1$H NMR δ: 0.96-0.99 (m, 22.3H), 1.05 (t, J=7.4 Hz, 2.7H), 1.43 (t, J=6.9 Hz, 4.2H), 1.47-1.54 (m, 12.2H), 1.69-1.89 (m, 16.7H), 3.42 (d, J=6.6 Hz, 9.2H), 3.84 (s, 4H, OCH$_3$), 3.88-4.11 (m, 19H), 5.02-5.10 (m, 10.3H), 5.93-6.01 (m, 5H), 6.69-6.83 (m, 11.4H, ArH), 6.89-6.99 (m, 6.5H, ArH); GC RI: MS m/z (relative intensity, %): 1-allyl-2,3-dibutoxy benzene 5a{4,4} 1784: 263 (M++H, 27), 262 (M+, 100); 1-allyl-2-butoxy-3-(3-methyl-butoxy)benzene 5a{4,5} 1833: 277 (M++H, 25), 276 (M+, 100).

5a{5,1-5} Allyl-iPentyl library. (Method B, 90% yield): $^1$H NMR δ: 0.95-1.00 (m, 37.6H), 1.06 (t, J=7.5 Hz, 2.7H), 1.44 (t, J=7.0 Hz, 4.3H), 1.49-1.55 (m, 2.1H), 1.65-1.72 (m, 12.4H), 1.78-1.90 (m, 10H), 3.41 (d, J=6.6 Hz, 9.4H), 3.84 (s, 4H, OCH$_3$), 3.91-4.08 (m, 19H), 5.01-5.09 (m, 10.2H), 5.93-6.01 (m, 5H), 6.69-6.83 (m, 11.1H, ArH), 6.89-6.99 (m, 7.2H, ArH); GC RI: MS m/z (relative intensity, %): 1-allyl-2,3-di (3-methyl-butoxy)benzene 5a{5,5} 1879: 291 (M++H, 23), 290 (M+, 100).

5a{6,1-5} Allyl-allyl library. (Method B, 90% yield): $^1$H NMR δ: 0.88-0.93 (m, 11.3H), 0.96-1.01 (m, 2.7H), 1.36-1.39 (m, 2.7H), 1.45 (t, J=7.3 Hz, 2.7H), 1.65 (q, J=6.7 Hz, 2.3H), 1.70-1.83 (m, 6H), 3.25 (d, J=7.0 Hz, 1.5H), 3.35 (d, J=6.6 Hz, 8.7H), 3.78 (s, 2.5H, OCH$_3$), 3.86-4.04 (m, 9.5H), 4.40-4.54 (m, 10.3H), 4.95-5.02 (m, 10.2H), 5.13-5.20 (m, 5H), 5.27-5.36 (m, 5H), 5.84-5.92 (m, 5H), 5.97-6.08 (m, 5H), 6.61-6.76 (m, 11.1H, ArH), 6.82-6.94 (m, 5H, ArH); GC RI: MS m/z (relative intensity, %): 1-allyl-2-allyloxy-3-methoxy benzene 5a{6,1} 1463: 205 (M++H, 84), 204 (M+, 100); 1-allyl-2-allyloxy-3-ethoxy benzene 5a{6,2} 1509: 219 (M++H, 100), 218 (M+, 95); 1-allyl-2-allyloxy-3-propoxy benzene 5a{6,3} 1597: 233 (M++H, 100), 232 (M+, 87); 1-allyl-2-allyloxy-3-butoxy benzene 5a{6,4} 1688: 247 (M++H, 100), 246 (M+, 91); 1-allyl-2-allyloxy-3-(3-methyl-butoxy)benzene 5a{6,5} 1740: 261 (M++H, 100), 260 (M+, 92).

Meta

5b$^{x,y}${2,1} Allyl-ethyl library A. (Method B, 70% yield): $^1$H NMR δ: 1.38-1.42 (m, 8.9H, CH$_3$ (Et)), 3.31-3.32 (m, 3.5H, CH$_2$(Allyl$^x$)), 3.42 (dt, J=1.5 and 6.3 Hz, 2H CH$_2$ (Allyl$^y$)), 3.78 (s, 5.2H (Me$^x$)), 3.82 (s, 3H (Me$^y$)), 3.99-4.05 (m, 6.2H), 4.91-4.94 (m, 1H), 4.98-5.07 (m, 4.6H), 5.91-6.01 (m, 2.5H), 6.42-6.44 (m, 3.4H, ArH$^x$), 6.54 (d, J=8.3 Hz, 2H, ArH$^y$), 7.03 (d, J=7.9 Hz, 1.6H, ArH$^x$), 7.12 (t, J=8.3 Hz, 1H, ArH$^y$); GC RI: MS m/z (relative intensity, %): 2-allyl-1-ethoxy-3-methoxy benzene 5b$^y${2,1} 1435: 193 (M++H, 75), 192 (M+, 100); 1-allyl-2-ethoxy-4-methoxy benzene 5b$^x${2,1} 1471: 193 (M++H, 47), 192 (M+, 100).

5b$^{x,y}${2,2-3} Allyl-ethyl library B. (Method B, 80% yield): $^1$H NMR δ: 1.01-1.06 (m, 11.6H, CH$_3$ (Pr)), 1.39-1.42 (m, 26.6H, CH$_3$ (Et)), 1.76-1.84 (m, 8H, CH$_2$ (Pr)), 3.31-3.32 (m, 7.7H), 3.42-3.45 (m, 4.4H), 3.88-3.93 (m, 8H, OCH$_2$ (Pr)), 3.98-4.04 (m, 18.1H, OCH$_2$ (Et)), 4.91-4.93 (m, 2.1H), 4.99-5.07 (m, 9.5H), 5.91-6.01 (m, 5.4H), 6.40-6.45 (m, 7.6H, ArH$^x$), 6.50-6.52 (d, 4.1H, ArH$^y$), 7.00-7.02 (m, 3.5H, ArH$^x$), 7.07-7.11 (m, 2H, ArH$^y$); GC RI: MS m/z (relative intensity, %): 2-allyl-1,3-diethoxy benzene 5b$^y${2,2} 1490: 207 (M++H, 80), 206 (M+, 100); 1-allyl-2,4-diethoxy benzene 5b$^x${2,2} 1535: 207 (M++H, 62), 206 (M+, 100); 2-allyl-1-ethoxy-3-propoxy benzene 5b$^y${2,3} 1587: 221 (M++H, 100), 220 (M+, 94); 1-allyl-2-ethoxy-4-propoxy benzene 5b$^x${2,3} 1627: 221 (M++H, 67), 220 (M+, 100).

5b$^{x,y}${2,4-5} Allyl-ethyl library C. (Method B, 48% yield): $^1$H NMR δ: 0.95-0.99 (m, 29.6H), 1.38-1.42 (m, 21.5H, CH$_3$ (Et)), 1.45-1.53 (m, 8.5H, CH$_2$CH$_3$ (Bu)), 1.64-1.70 (m, 6.4H, CH$_2$CH (iPent)), 1.72-1.91 (m, 11.2H), 3.30-3.32 (m, 9.1H), 3.42-3.43 (m, 4.3H), 3.92-4.04 (m, 29.2H), 4.90-4.93 (m, 2.1H), 4.98-5.06 (m, 10.7H), 5.90-6.01 (m, 6H), 6.40-6.44 (m, 9H, ArH$^x$), 6.50-6.53 (m, 4.2H, ArH$^y$), 7.00-7.01 (m, 4.2H, ArH$^x$), 7.07-7.11 (m, 2H ArH$^y$); GC RI: MS m/z (relative intensity, %): 2-allyl-1-butoxy-3-ethoxy benzene 5b$^y${2,4} 1682: 235 (M++H, 43), 234 (M+, 85), 149 (M−86, 100); 1-allyl-4-butoxy-2-ethoxy benzene 5b$^x${2,4} 1724: 235 (M++H, 42), 234 (M+, 100); 2-allyl-1-ethoxy-3-(3-methyl-butoxy)benzene 5b$^y${2,5} 1739: 249 (M++H, 31), 248 (M+, 69), 149 (M−99, 100); 1-allyl-2-ethoxy-4-(3-methyl-butoxy)benzene 5b$^x${2,5} 1784: 249 (M++H, 34), 248 (M+, 98), 149 (M−99, 100).

5b$^{x,y}${3,1} Allyl-propyl library A. (Method B, 88% yield): $^1$H NMR δ: 1.03-1.06 (m, 9.1H, CH$_3$ (Pr)), 1.77-1.85 (m, 6.4H, CH$_2$CH$_3$ (Pr)), 3.32-3.33 (m, 3.9H, CH$_2$ (Allyl$^x$)), 3.43-3.44 (m, 2.2H, CH$_2$ (Allyl$^y$)), 3.79 (s, 5.6H (Me$^x$)), 3.82 (s, 3H (Me$^y$)), 3.89-3.93 (m, 6.2H, OCH$_2$ (Pr)), 4.91-4.94 (m, 1.1H), 4.98-5.07 (m, 4.7H), 5.91-6.01 (m, 2.8H), 6.41-6.44 (m, 3.8H, ArH$^x$), 6.52-6.54 (m, 2H, ArH$^y$), 7.03 (d, J=8.0 Hz, 1.6H, ArH$^x$), 7.12 (t, J=8.3 Hz, 1H, ArH$^y$); GC RI: MS m/z (relative intensity, %): 2-allyl-1-methoxy-3-propoxy benzene 5b$^y${3,1} 1527: 207 (M$^+$+H, 100), 206 (M$^+$, 97); 1-allyl-4-methoxy-2-propoxy benzene 5b$^x${3,1} 1573: 207 (M$^+$+H, 51), 206 (M$^+$, 100).

5b$^{x,y}${3,2-3} Allyl-propyl library B. (Method B, 80% yield): $^1$H NMR δ: 1.03-1.08 (m, 30H, CH$_3$ (Pr)), 1.40-1.43 (m, 7.4H, CH$_3$ (Et)), 1.78-1.86 (m, 20.8H, CH$_2$CH$_3$ (Pr)), 3.33-3.34 (m, 7.5H), 3.45-3.47 (m, 4.4H), 3.90-3.94 (m, 20.4H, OCH$_2$ (Pr)), 4.00-4.06 (m, 5.3H, OCH$_2$ (Et)), 4.92-4.95 (m, 2H), 5.00-5.08 (m, 9H), 5.93-6.03 (m, 4.8H), 6.41-6.46 (m, 7.3H, ArH$^x$), 6.51-6.53 (m, 4.2H, ArH$^y$), 7.01-7.03 (m, 3.4H, ArH$^x$), 7.09-7.12 (m, 2H, ArH$^y$); GC RI: MS m/z (relative intensity, %): 2-allyl-1-ethoxy-3-propoxy benzene 5b$^y${3,2} 1587: 221 (M$^+$+H, 39), 220 (M$^+$, 89), 149 (M−71, 100); 1-allyl-4-ethoxy-2-propoxy benzene 5b$^x${3,2} 1624: 221 (M$^+$+H, 29), 220 (M$^+$, 100), 149 (M−71, 53); 2-allyl-1,3-dipropoxy benzene 5b$^y${3,3} 1682: 235 (M$^+$+H, 50), 234 (M$^+$, 100); 1-allyl-2,4-dipropoxy benzene 5b$^x${3,3} 1713: 235 (M$^+$+H, 39), 234 (M$^+$, 100).

5b$^{x,y}${3,4-5} Allyl-propyl library C. (Method B, 62% yield): $^1$H NMR δ: 0.95-0.98 (m, 29.4H), 1.02-1.06 (m, 20.9H, CH$_3$ (Pr)), 1.44-1.53 (m, 8.2H, CH$_2$CH$_3$ (Bu)), 1.64-1.69 (m, 6.4H, CH$_2$CH (iPent)), 1.72-1.89 (m, 26.1H), 2.17 (m, 5.8H (Me)), 3.31-3.32 (m, 9H), 3.42-3.44 (m, 4.3H), 3.88-3.98 (m, 29.1H), 4.89-4.92 (m, 2H), 4.98-5.06 (m, 10.6H), 5.89-6.00 (m, 5.8H), 6.39-6.43 (m, 8.9H, ArH$^x$), 6.49-6.52 (m, 4.9H, ArH$^y$), 6.99-7.01 (m, 4.2H, ArH$^x$), 7.07-7.10 (m, 2H, ArH$^y$); GC RI: MS m/z (relative intensity, %): 2-allyl-1-butoxy-3-propoxy benzene 5b$^y${3,4} 1778: 249 (M$^+$+H, 85), 248 (M$^+$, 100); 1-allyl-4-butoxy-2-propoxy benzene 5b$^x${3,4} 1813: 249 (M$^+$+H, 46), 248 (M$^+$, 100); 2-allyl-1-(3-methyl-butoxy)-3-propoxy benzene 5b$^y${3,5} 1835: 263 (M$^+$+H, 69), 262 (M$^+$, 100), 1-allyl-2-propoxy-4-(3-methyl-butoxy)benzene 5b$^x${3,5} 1870: 263 (M$^+$+H, 45), 262 (M$^+$, 100).

5b$^{x,y}${4,1} Allyl-butyl library A. (Method B, 81% yield): $^1$H NMR δ: 0.95-0.98 (m, 9.9H, CH$_3$ (Bu)), 1.46-1.54 (m, 6.1H, CH$_2$CH$_3$ (Bu)), 1.73-1.79 (m, 6.3H, OCH$_2$CH$_2$ (Bu)), 3.30-3.32 (m, 3.7H, CH$_2$ (Allyl$^x$)), 3.42 (dt, J=1.3 and 6.3 Hz, 2H, CH$_2$ (Allyl$^y$)), 3.78 (s, 5.3H (Me$^x$)), 3.81 (s, 3H (Me$^y$)), 3.92-3.96 (m, 6.3H, OCH$_2$ (Bu)), 4.99-4.93 (m, 1H), 4.96-5.05 (m, 4.7H), 5.90-6.00 (m, 2.7H), 6.40-6.43 (m, 3.6H, ArH$^x$), 6.53 (d, J=8.3 Hz, 2H, ArH$^y$), 7.02 (d, J=8.1 Hz, 1.7H, ArH$^x$), 7.11 (t, J=8.3 Hz, 1H, ArH$^y$); GC RI: MS m/z (relative intensity, %): 2-allyl-1-butoxy-3-methoxy benzene 5b$^y${4,1} 1625: 221 (M$^+$+H, 66), 220 (M$^+$, 100); 1-allyl-2-butoxy-4-methoxy benzene 5b$^x${4,1} 1656: 221 (M$^+$+H, 37), 220 (M$^+$, 100).

5b$^{x,y}${4,2-3} Allyl-butyl library B. (Method B, 52% yield): $^1$H NMR δ: 0.95-0.98 (m, 17.7H, CH$_3$ (Bu)), 1.01-1.06 (m, 8.6H, CH$_3$ (Pr)), 1.38-1.41 (m, 9.5H, CH$_3$ (Et)), 1.46-1.54 (m, 12.3H), 1.74-1.83 (m, 18.4H), 3.31-3.32 (m, 7.8H), 3.43-3.45 (m, 3.9H), 3.88-4.04 (m, 25.8H), 4.91-4.93 (m, 1.9H), 4.99-5.06 (m, 9.6H), 5.90-6.01 (m, 5.7H), 6.40-6.45 (m, 8H, ArH$^x$), 6.50-6.52 (m, 4H, ArH$^y$), 7.00-7.01 (m, 3.8H, ArH$^x$), 7.07-7.11 (m, 2H, ArH$^y$); GC RI: MS m/z (relative intensity, %): 2-allyl-1-butoxy-3-ethoxy benzene 5b$^y${4,2} 1681: 235 (M$^+$+H, 55), 234 (M$^+$, 88), 149 (M−85, 100); 1-allyl-2-butoxy-4-ethoxy benzene 5b$^x${4,2} 1714: 235 (M$^+$+H, 38), 234 (M$^+$, 100); 2-allyl-1-butoxy-3-propoxy benzene 5b$^y${4,3} 1777: 249 (M$^+$+H, 59), 248 (M$^+$, 100); 1-allyl-2-butoxy-4-propoxy benzene 5b$^x${4,3} 1803: 249 (M$^+$+H, 41), 248 (M$^+$, 100).

5b$^{x,y}${4,4-5} Allyl-butyl library C. (Method B, 64% yield): $^1$H NMR δ: 0.95-0.99 (m, 48.9H), 1.43-1.55 (m, 20H, CH$_2$CH$_3$ (Bu)), 1.64-1.70 (m, 8.2H), 1.72-1.90 (m, 25.5H), 3.30-3.32 (m, 7H), 3.42-3.44 (m, 4.1H), 3.92-3.99 (m, 25.5H), 4.90-4.93 (m, 2H), 4.98-5.05 (m, 9.1H), 5.89-6.01 (m, 5.2H), 6.39-6.44 (m, 7.3H, ArH$^x$), 6.50-6.52 (m, 4.1H, ArH$^y$), 6.99-7.01 (m, 3.3H, ArH$^x$), 7.07-7.11 (m, 2H, ArH$^y$); 2-allyl-1,3-dibutoxy benzene 5b$^y${4,4} 1871: 263 (M$^+$+H, 72), 262 (M$^+$, 100); 1-allyl-2,4-dibutoxy benzene 5b$^x${4,4} 1899: 263 (M$^+$+H, 41), 262 (M$^+$, 100); 2-allyl-1-butoxy-3-(3-methyl-butoxy)benzene 5b$^y${4,5} 1926: 277 (M$^+$+H, 65), 276 (M$^+$, 100); 1-allyl-2-butoxy-4-(3-methyl-butoxy)benzene 5b$^x${4,5} 1955: 277 (M$^+$+H, 42), 276 (M$^+$, 100).

5b$^{x,y}${5,1} Allyl-ipentyl library A. (Method B, 64% yield): $^1$H NMR δ: 0.95-0.97 (m, 16.8H, CH$_3$ (iPent)), 1.66-1.71 (m, 5.8H, CH$_2$CH (iPent)), 1.82-1.91 (m, 3H, CH (iPent)), 3.31-3.32 (m, 3.6H, CH$_2$ (Allyl$^x$)), 3.41-3.43 (dt, J=1.3 and 6.3 Hz, 2.2H, CH$_2$ (Allyl$^y$)), 3.79 (s, 5.2H, CH$_3$ (Me$^x$)), 3.81 (s, 3H, CH$_3$ (Me$^y$)), 3.95-3.99 (m, 6H, OCH$_2$ (iPent)), 4.90-4.93 (m, 1H), 4.97-5.06 (m, 4.7H), 5.90-6.00 (m, 2.7H), 6.41-6.45 (m, 3.5H), 6.53-6.55 (m, 2H), 7.03 (d, J=8.2 Hz, 1.7H), 7.12 (t, J=8.3 Hz, 1H); GC RI: MS m/z (relative intensity, %): 2-allyl-1-methoxy-3-(3-methyl-butoxy)benzene 5b$^y${5,1} 1684: 235 (M$^+$+H, 43), 234 (M$^+$, 100); 1-allyl-4-methoxy-2-(3-methyl-butoxy)benzene 5b$^x${5,1} 1711: 235 (M$^+$+H, 30), 234 (M$^+$, 100).

5b$^{x,y}${5,2-3} Allyl-ipentyl library B. (Method B, 74% yield): $^1$H NMR δ: 0.94-0.96 (m, 37.1H, CH$_3$ (iPent)), 1.01-1.05 (m, 9.6H, CH$_3$ (Pr)), 1.38-1.41 (m, 10.4H, CH$_3$ (Et)), 1.65-1.69 (m, 13H), 1.74-1.89 (m, 13.8H), 3.29-3.30 (m, 8.1H), 3.40-3.43 (m, 4.3H), 3.88-4.04 (m, 27H), 4.89-4.92 (m, 2.1H), 4.98-5.05 (m, 10.6H), 5.89-5.99 (m, 6.2H), 6.39-6.44 (m, 8.4H), 6.49-6.52 (m, 4.2H), 6.99-7.00 (m, 4H), 7.07-7.10 (m, 2H); GC RI: MS m/z (relative intensity, %): 2-allyl-1-ethoxy-3-(3-methyl-butoxy)benzene 5b$^y${5,2} 1736: 249 (M$^+$+H, 14), 248 (M$^+$, 52), 149 (M−99, 100); 1-allyl-4-ethoxy-2-(3-methyl-butoxy)benzene 5b$^x${5,2} 1820: 249 (M$^+$+H, 22), 248 (M$^+$, 100); 2-allyl-1-(3-methyl-butoxy)-3-propoxy benzene 5b$^y${5,3} 1834: 263 (M$^+$+H, 22), 262 (M$^+$, 80), 135 (M−127, 100); 1-allyl-2-(3-methyl-butoxy)-4-propoxy benzene 5b$^x${5,3} 1855: 263 (M$^+$+H, 26), 262 (M$^+$, 100).

5b$^{x,y}${5,4-5} Allyl-ipentyl library C. (Method B, 82% yield): $^1$H NMR δ: 0.96-1.00 (m, 68H), 1.45-1.54 (m, 8.6H, CH$_2$CH$_3$ (Bu)), 1.65-1.92 (m, 40.4H), 3.31-3.32 (m, 6.2H), 3.42-3.44 (m, 4H), 3.93-4.00 (m, 24.7H), 4.90-4.93 (m, 2H), 4.99-5.06 (m, 9.41H), 5.89-6.01 (m, 5.65H), 6.41-6.45 (m, 7.3H), 6.51-6.53 (m, 3.8H), 7.00-7.01 (m, 3.2H), 7.07-7.11 (m, 2H); GC RI: MS m/z (relative intensity, %): 2-allyl-1-butoxy-3-isopentoxy benzene 5b$^y${5,4} 1927: 277 (M$^+$+H, 42), 276 (M$^+$, 100); 1-allyl-4-butoxy-2-isopentoxy benzene 5b$^x${5,4} 1950: 277 (M$^+$+H, 32), 276 (M$^+$, 100); 2-allyl-1,3-di(3-methyl-butoxy)benzene 5b$^y${5,5} 1984: 291 (M$^+$+H, 36), 290 (M$^+$, 89), 150 (M−140, 100); 1-allyl-2,4-di(3-methyl-butoxy)benzene 5b$^x${5,5} 2006: 291 (M$^+$+H, 32), 290 (M$^+$, 100).

5b$^{x,y}${6,1} Allyl-allyl library A. (Method B, 67% yield): $^1$H NMR δ: 3.35-3.36 (m, 3.8H, CH$_2$ (Allyl$^x$)), 3.46-3.47 (m, 2H, CH$_2$ (Allyl$^y$)), 3.79 (s, 5.4H, CH$_3$ (Me$^x$)), 3.83 (s, 3H, CH$_3$ (Me$^y$)), 4.52-4.55 (m, 6.3H), 4.92-4.95 (m, 1.1H), 4.99-5.08 (m, 5H), 5.25-5.30 (m, 3H), 5.41-5.46 (m, 3H), 5.93-6.10 (m, 5.7H), 6.44-6.47 (m, 3.6H), 6.55 (t, J=8.5 Hz, 2H), 7.05 (d, J=8.7 Hz, 1.7H), 7.13 (t, J=8.3 Hz, 1H); GC RI: MS m/z (relative intensity, %): 2-allyl-1-allyloxy-3-methoxy benzene 5b[y]{6,1} 1524: 205 (M[+]+H, 29), 204 (M[+], 100); 1-allyl-2-allyloxy-4-methoxy benzene 5b[x]{6,1} 1554: 205 (M[+]+H, 31), 204 (M[+], 100).

5b[x,y]{6,2-3} Allyl-allyl library B. (Method B, 53% yield): $^1$H NMR δ: 1.02-1.07 (m, 8.8H, $CH_3$ (Pr)), 1.39-1.42 (m, 9.4H, $CH_3$ (Et)), 1.76-1.85 (m, 6.2H, $CH_2CH_3$ (Pr)), 3.34-3.35 (m, 7.7H), 3.46-3.48 (m, 4.3H), 3.88-3.93 (m, 6H, $OCH_2$ (Pr)), 3.98-4.05 (m, 6.5H, $OCH_2$ (Et)), 4.51-4.54 (m, 12.2H), 4.91-4.94 (m, 2H), 5.00-5.07 (m, 10H), 5.24-5.28 (m, 6H), 5.40-5.45 (m, 6H), 5.92-6.09 (m, 12.1H), 6.42-6.45 (m, 7.6H), 6.51-6.54 (m, 4.2H), 7.01-7.03 (m, 3.7H), 7.08-7.11 (m, 2H); GC RI: MS m/z (relative intensity, %): 2-allyl-1-allyloxy-3-ethoxy benzene 5b[y]{6,2} 1581: 219 (M[+]+H, 42), 218 (M[+], 100); 1-allyl-2-allyloxy-4-ethoxy benzene 5b[x]{6,2} 1613: 219 (M[+]+H, 46), 218 (M[+], 100); 2-allyl-1-allyloxy-3-propoxy benzene 5b[y]{6,3} 1674: 233 (M[+]+H, 31), 232 (M[+], 59), 149 (M−83, 100); 1-allyl-2-allyloxy-4-propoxy benzene 5b[x]{6,2} 1706: 233 (M[+]+H, 50), 232 (M[+], 100).

5b[x,y]{6,4-5} Allyl-allyl library C. (Method B, 76% yield): $^1$H NMR δ: 0.96-0.99 (m, 28.1H), 1.45-1.54 (m, 7.5H, $CH_2CH_3$ (Bu)), 1.65-1.71 (m, 7H), 1.73-1.92 (m, 10.9H), 3.34-3.36 (m, 6.2H), 3.46-3.47 (m, 3.9H), 3.92-4.00 (m, 12.8H), 4.51-4.55 (m, 10.6H), 4.91-4.94 (m, 2.1H), 5.00-5.07 (m, 9.2H), 5.24-5.29 (m, 5.8H), 5.40-5.45 (m, 5.7H), 5.92-6.10 (m, 11.9H), 6.42-6.45 (m, 6.6H), 6.51-6.55 (m, 4.1H), 7.02-7.04 (m, 3.1H), 7.08-7.12 (m, 2H); GC RI: MS m/z (relative intensity, %): 2-allyl-1-allyloxy-3-butoxy benzene 5b[y]{6,4} 1771: 247 (M[+]+H, 43), 246 (M[+], 63), 149 (M−97, 100); 1-allyl-2-allyloxy-4-butoxy benzene 5b[x]{6,4} 1801: 247 (M[+]+H, 61), 246 (M[+], 100); 2-allyl-1-allyloxy-3-(3-methyl-butoxy)benzene 5b[y]{6,5} 1827: 261 (M[+]+H, 74), 260 (M[+], 78), 149 (M−111, 100); 1-allyl-2-allyloxy-4-(3-methyl-butoxy)benzene 5b[x]{6,5} 1861: 261 (M[+]+H, 62), 260 (M[+], 100).

Para

5c{2,1-5} Allyl-ethyl library. (Method B, 89% yield): $^1$H NMR δ: 0.94-0.98 (m, 8.7H), 1.02 (t, J=7.4 Hz, 3.7H), 1.36-1.41 (m, 21H), 1.44-1.52 (m, 2.2H), 1.62-1.66 (m, 4.5H), 1.70-1.86 (m, 5.6H), 3.36-3.38 (m, 10.9H), 3.76 (s, 4H, $OCH_3$), 3.86 (t, J=6.6 Hz, 2.6H), 3.88-3.93 (m, 4H), 3.95-3.99 (m, 14H), 5.03-5.10 (m, 10H), 5.93-6.02 (m, 4.7H), 6.66-6.78 (m, 16.2H, ArH); GC RI: MS m/z (relative intensity, %): 1-allyl-2,5-diethoxy benzene 5c{2,2} 1518: 207 (M[+]+H, 31), 206 (M[+], 100); 1-allyl-2-ethoxy-5-propoxy benzene 5c{2,3} 1605: 221 (M[+]+H, 29), 220 (M[+], 100); 1-allyl-5-butoxy-2-ethoxy benzene 5c{2,4} 1704: 235 (M[+]+H, 29), 234 (M[+], 100); 1-allyl-2-ethoxy-5-(3-methyl-butoxy)benzene 5c{2,5} 1763: 249 (M[+]+H, 27), 248 (M[+], 100).

5c{3,1-5} Allyl-propyl library. (Method B, 95% yield): $^1$H NMR δ: 0.96-1.06 (m, 27.6H), 1.37-1.41 (m, 4H), 1.44-1.53 (m, 2H), 1.64-1.68 (m, 2.9H), 1.72-1.92 (m, 16H), 3.38 (d, J=6.4 Hz, 10.9H), 3.80 (s, 3.8H, $OCH_3$), 3.82-3.99 (m, 19.9H), 4.99-5.18 (m, 10.5H), 5.92-6.05 (m, 5H), 6.67-6.85 (m, 17.5H, ArH); GC RI: MS m/z (relative intensity, %): 1-allyl-2,5-dipropoxy benzene 5c{3,3} 1699: 235 (M[+]+H, 26), 234 (M[+], 100); 1-allyl-5-butoxy-2-propoxy benzene 5c{3,4} 1798: 249 (M[+]+H, 27), 248 (M[+], 100); 1-allyl-5-(3-methyl-butoxy)-2-propoxy benzene 5c{3,5} 1857: 263 (M[+]+H, 27), 262 (M[+], 90), 249 (100).

5c{4,1-5} Allyl-butyl library. (Method B, 95% yield): $^1$H NMR δ: 0.94-0.98 (m, 19.5H), 1.00-1.04 (m, 3.4H), 1.36-1.39 (m, 3.6H), 1.44-1.54 (m, 9.3H), 1.57-1.58 (m, 2H), 1.64 (t, J=6.8 Hz, 1.8H), 1.70-1.85 (m, 12.5H), 3.35-3.39 (m, 10H), 3.76 (s, 3.7H, $OCH_3$), 3.86 (t, J=6.6 Hz, 2.2H), 3.88-3.93 (m, 11.2H), 3.97 (q, J=6.9 Hz, 2.4H), 5.03-5.17 (m, 9.5H), 5.93-6.06 (m, 4.5H), 6.65-6.87 (m, 16.1H, ArH); GC RI: MS m/z (relative intensity, %): 1-allyl-2,5-dibutoxy benzene 5c{4,4} 1892: 263 (M[+]+H, 28), 262 (M[+], 100); 1-allyl-2-butoxy-5-(3-methyl-butoxy)benzene 5c{4,5} 1949: 277 (M[+]+H, 28), 276 (M[+], 100).

5c{5,1-5} Allyl-iPentyl library. (Method B, 95% yield): $^1$H NMR δ: 0.93-0.99 (m, 27.7H), 1.03 (t, J=7.4 Hz, 3.7H), 1.39 (t, J=7.0 Hz, 4H), 1.44-1.52 (m, 2.2H), 1.63-1.88 (m, 18.5H), 3.36-3.39 (m, 10.7H), 3.76 (s, 4H, $OCH_3$), 3.84-3.99 (m, 15.7H), 5.01-5.18 (m, 10.5H), 5.93-6.05 (m, 5H), 6.66-6.85 (m, 17H, ArH); GC RI: MS m/z (relative intensity, %): 1-allyl-2,5-di(3-methyl-butoxy)benzene 5c{5,5} 2001: 291 (M[+]+H, 27), 290 (M[+], 100).

$^1$H NMR Data for Individual Compounds (Group II)

1-allyloxy-2-propoxybenzene, 3a{3,6} (5.1 g, 74%): liquid; GC (RI 12.51, 99%); $^1$H NMR (600 MHz, $CDCl_3$) δ: 6.68-7.15 (m, 4H), 6.14 (ddt, 1H, J=17.3, 10.5, 5.3 Hz), 5.42 (dq, 1H, J=17.3, 1.6 Hz), 5.26 (dq, 1H, J=10.5, 1.6 Hz), 4.60 (dt, 2H, J=5.3, 1.6 Hz), 3.98 (t, 2H, J=6.7 Hz), 1.80-1.91 (m, 2H), 1.05 (t, 3H, J=7.4 Hz). MS m/z (relative intensity): 193 (M[+]+1, 100%), 109 (78%), 81 (42%).

1-allyloxy-2-butoxybenzene, 3a{4,6}, (1.3 g, 98%): $^1$H NMR (400 MHz, $CDCl_3$) δ: 6.91 (m, 4H), 6.08 (m, 1H), 5.41 (br dd, 1H, J=17.2, 1.2 Hz), 5.26 (br dd, 1H, J=10.4, 1.2 Hz), 4.60 (br d, 2H, J=5.2 Hz), 4.02 (t, 2H, J=6.4 Hz), 1.83 (m, 1H), 1.52 (m, 2H), 0.99 (t, 3H, J=6.8 Hz). MS m/z (relative intensity): 206 (25%), 109 (100%), 81 (26%).

1-propoxy-2-butoxybenzene, 3a{3,4}, (1.0 g, 85%): $^1$H NMR (400 MHz, $CDCl_3$) δ: 6.90 (br s, 4H), 4.01 (t, 2H, J=6.4 Hz), 3.97 (t, 2H, J=6.8 Hz), 1.84 (m, 4H), 1.51 (m, 2H), 1.05 (t, 3H, J=6.8 Hz), 0.98 (t, 3H, J=7.6 Hz). MS m/z (relative intensity): 208 (27%), 110 (100%).

1-allyloxy-2-isopentoxybenzene, 3a {5,6}, (440 mg, 64%): $^1$H NMR (400 MHz, $CDCl_3$) δ: 6.90 (m, 4H), 6.08 (m, 1H), 5.42 (m, 1H), 5.26 (m, 1H), 4.59 (dt, 2H, J=5.2, 1.2 Hz), 4.04 (t, 2H, J=6.8 Hz), 1.84 (m, 1H), 1.75 (q, 2H, J=6.8 Hz), 0.97 (d, 6H, J=6.8 Hz). MS m/z (relative intensity): 220 (65%), 150 (25%), 121 (30%), 109 (100%), 43 (32%).

3-propoxy-1-isopentoxybenzene, 3b{3,5} (7.4 g, 57%): liquid; GC (RI 1251, 100%); $^1$H NMR (400 MHz, $CDCl_3$) δ 0.97 (d, 6H, J=6.7 Hz), 1.05 (t, 3H, J=7.4 Hz), 1.69 (q, 2H, J=6.8 Hz), 1.74-1.90 (m, 3H), 3.92 (t, 2H, J=6.6 Hz), 3.97 (t, 2H, J=6.6 Hz), 6.52-6.46 (m, 3H), 7.15 (t, 1H, J=8.1 Hz); MS m/z (relative intensity): 223 (M[+]+1, 100%), 110 (61%).

1-methoxy-2-isopentoxybenzene, 3b{1,5}, (1.3 g, 85%): $^1$H NMR (400 MHz, $CDCl_3$) δ: 7.17 (t, 1H, J=8.4 Hz), 6.50 (br dt, 2H, J=8.4, 2.4 Hz), 6.46 (br t, 1H, J=2.0 Hz), 3.97 (t, 2H, J=6.8 Hz), 3.79 (s, 3H), 1.82 (m, 1H), 1.67 (dt, 2H, J=6.8, 6.8 Hz), 0.96 (d, 6H, J=6.4 Hz). MS m/z (relative intensity): 194 (20%), 124 (100%), 95 (22%).

1-methoxy-2-allyloxybenzene, 3b{1,6}, (499 mg, 38%): $^1$H NMR (400 MHz, $CDCl_3$) δ: 7.16 (br t, 1H, J=8.4 Hz), 6.53 (br t, 1H, J=2.0 Hz), 6.50 (m, 2H), 6.05 (m, 1H), 5.41 (br dq, 1H, J=17.2, 1.6 Hz), 5.28 (br dq, 1H, J=10.4, 1.2 Hz), 4.52 (dt, 2H, J=5.2, 1.6 Hz), 3.79 (s, 3H). MS m/z (relative intensity): 164 (5%), 57 (45%), 56 (99%), 41 (100%).

1-allyloxy-2-allyloxybenzene, 3b {6,6}, (1.1 g, 90%): $^1$H NMR (400 MHz, $CDCl_3$) δ: 7.20 (br dt, 1H, J=5.2, 0.4 Hz), 6.56 (m, 3H), 6.09 (m, 2H), 5.45 (ddd, 2H, J=11.6, 2.4, 1.2 Hz), 5.32 (ddd, 2H, J=6.8, 2.0, 0.8 Hz), 4.55 (dt, 4H, J=3.6, 0.8 Hz). MS m/z (relative intensity): 190 (70%), 120 (30%).

1-allyloxy-3-isopentoxybenzene, 3b{5,6}, (616 mg, 99%): $^1$H NMR (400 MHz, $CDCl_3$) δ: 7.16 (br t, 1H, J=8.8 Hz), 6.52 (br d, 1H, J=2.4 Hz), 6.49 (m, 2H), 6.06 (m, 1H, J=Hz), 5.42 (dq, 1H, J=17.2, 1.6 Hz), 5.28 (dq, 1H, J=10.4, 1.2 Hz), 4.52 (dt, 2H, J=5.2, 1.6 Hz), 3.97 (t, 2H, J=6.8 Hz), 1.82 (m, 1H), 1.67 (q, 2H, J=6.4 Hz), 0.96 (d, 3H, J=6.4 Hz). MS m/z (relative intensity): 220 (25%), 150 (100%), 149 (30%), 135 (20%), 107 (22%).

1-allyloxy-4-methoxybenzene, 3c{1,6} (10.4 g, 99%): liquid; GC (RI 1251, 97%); $^1$H NMR (600 MHz, CDCl$_3$) δ: 3.78 (s, 3H), 4.50 (dt, 2H, J=5.3, 1.5 Hz), 5.27 (dq, 1H, J=10.5, 1.4 Hz), 5.40 (dq, 1H, J=17.3, 1.6 Hz), 6.01-6.09 (ddt, 1H, J=17.2, 10.6, 5.3 Hz), 6.81-6.89 (m, 4H); MS m/z (relative intensity): 164 (M$^+$, 38%), 123 (100%), 95 (43%).

1-allyloxy-4-ethoxybenzene, 3c{2,6} (6.2 g, 82%): solid; GC (RI 1251, 98%); $^1$H NMR (600 MHz, CDCl$_3$) δ: 1.39 (t, 3H, J=7.0 Hz), 3.98 (q, 2H, J=7.0 Hz), 4.48 (dt, 2H, J=5.3, 1.5 Hz), 5.27 (dq, 1H, J=10.5, 1.4 Hz), 5.40 (dq, 1H, J=17.3, 1.6 Hz), 6.05 (ddt, 1H, J=17.2, 10.6, 5.3 Hz), 6.78-6.89 (m, 4H); MS m/z (relative intensity): 179 (M$^+$+1, 84%), 178 (M$^+$, 100%), 137(74%).

1-allyloxy-4-propoxybenzene, 3c{3,6} (4.2 g, 81%): solid; GC (RI 1251, 100%); $^1$H NMR (600 MHz, CDCl$_3$) δ: 1.01 (t, 3H, J=7.4 Hz), 1.73-1.80 (m, 2H), 3.85 (t, 2H, J=6.6 Hz), 4.47 (dt, 2H, J=5.3, 1.5 Hz), 5.25 (dq, 1H, J=10.5, 1.4 Hz), 5.38 (dq, 1H, J=17.3, 1.6 Hz), 6.03 (ddt, 1H, J=17.3, 10.5, 5.3 Hz), 6.86-6.79 (m, 4H); $^{13}$C NMR (400 MHz, CDCl$_3$) δ: 153.4, 152.6, 133.6, 117.4, 115.7 (2C), 115.3 (2C), 70.1, 69.5, 22.6, 10.5. MS m/z (relative intensity): 193 (M$^+$+1, 53%), 192 (M, 88%), 151 (40%), 109 (100%). HRMS-ESI calcd for C$_{12}$H$_{17}$O$_2$ (M+H)$^+$, m/z 193.1223. found m/z 193.1215.

1-allyloxy-4-isopentoxybenzene, 3c{5,6}, (510 mg, 84%): $^1$H NMR (400 MHz, CDCl$_3$) δ: 6.84 (m, 4H), 6.05 (m, 1H), 5.40 (dq, 1H, J=17.2, 1.6 Hz), 5.27 (dq, 1H, J=10.4, 1.2 Hz), 4.49 (dt, 2H, J=5.2, 1.2 Hz), 3.94 (t, 2H, J=6.4 Hz), 1.82 (m, 1H), 1.65 (q, 2H, J=6.8 Hz), 0.96 (d, 3H, J=6.8 Hz). MS m/z (relative intensity): 220 (60%), 150 (24%), 109 (100%), 71 (84%), 43 (82%).

4-ethoxy-1-propoxybenzene, 3c{2,3}, (700 mg, 49%): solid; $^1$H NMR (400 MHz, CDCl$_3$) δ: 1.02 (t, 3H, J=7.6 Hz), 1.39 (t, 3H, J=7.2 Hz), 1.78 (m, 2H), 3.87 (t, 1H, J=6.4 Hz), 3.98 (q, 1H, J=6.8 Hz), 6.82 (s, 4H). MS m/z (relative intensity): 180(25%), 138 (20%), 110 (100%), 41 (28%).

1,4-dimethoxy-2-allyl-benzene, 5c{1,1}: (9.4 g, 58% yield of the Claisen rearrangement): liquid, $^1$H NMR (600 MHz, CDCl$_3$) δ: 3.40 (d, 2H, J=6.7 Hz), 3.80 (s, 3H), 3.82 (s, 3H), 5.14-5.06 (m, 2H), 6.02 (ddt, 1H, J=6.6, 10.1, 16.8 Hz), 6.88-6.70 (m, 3H).

1-methoxy-2-allyl-4-propoxy-benzene, 5c{3,1}: (7.7 g, 81% yield of the Claisen rearrangement): liquid; $^1$H NMR (600 MHz, CDCl$_3$) δ: 1.03 (t, 3H, J=7.4 Hz), 1.84-1.73 (m, 2H, J=7.5 Hz), 3.37 (d, 2H, J=6.7 Hz), 3.75 (s, 3H), 3.86 (t, 2H, J=6.4 Hz), 5.16-4.98 (m, 2H), 6.06-5.89 (m, 1H), 6.86-6.58 (m, 3H), MS m/z (relative intensity): 208 (100%), 206 (M$^+$, 61%), 164 (41%), 150 (94%), 149 (56%).

1-allyl-2,4-dimethoxybenzene and 1,3-dimethoxy-2-allylbenzene, 5b{1,1} (isomers x and y, ratio 1.8:1), 2.6 g, 79% yield of the Claisen rearrangement, liquid, $^1$H NMR (600 MHz, CDCl$_3$) δ: 3.37 (d, 2H, J=6.5 Hz, isomer x), 3.48 (d, 2H, J=4.6 Hz, isomer y), 3.92-3.80 (s, 3H, isomers x and y), 5.00 (m, 1H, isomer y), 5.09 (m, 1H, isomer y), 5.16-5.25 (m, 2H, isomer x), 6.10-5.96 (m, isomers x and y), 6.49 (d, 1H, J=8.3 Hz, isomer x), 6.51 (br s, 1H, isomer x) 6.60 (d, 2H, J=8.3 Hz, isomer y), 7.08 (d, 1H, J=8.3 Hz, isomer x), 7.20 (t, 1H, J=8.3 Hz, isomer y), MS m/z (relative intensity): isomer x (retention time 5.81 min): 178 (M$^+$, 100%), 177 (41%), 151 (26%), 149 (28%), 147 (40%), 121 (40%), 91 (27%). isomer y (retention time 5.48 min): 178 (M$^+$, 100%), 149 (57%), 121 (26%), 91 (41%). HRMS-ESI calcd for C$_{11}$H$_{15}$O$_2$ (M+H)$^+$, m/z 179.1067. found m/z 179.1061.

1-allyl-4-methoxy-2-propoxy-benzene and 1-methoxy-2-allyl-3-propoxy-benzene, 5b{3,1} (isomers x and y, ratio 1.2:1), 11.1 g, 88% yield of Claisen rearrangement, liquid, $^1$H NMR (600 MHz, CDCl$_3$) δ: 1.07 (dt, 6H, J=7.4, 1.3 Hz), 1.79-1.87 (m, 4H), 3.35 (d, 2H, J=6.7 Hz), 3.46 (d, 2H, J=6.3 Hz), 3.79-3.81 (m, 3H), 3.82-3.84 (m, 3H), 3.92 (td, 4H, J=9.7, 6.4 Hz), 4.92-5.10 (m, 4H), 5.93-6.04 (m, 2H), 6.42-6.47 (m, 2H), 6.55 (d, 2H, J=8.3 Hz), 7.05 (d, 1H, J=8.1 Hz), 7.14 (t, 1H, J=8.3 Hz). HRMS-ESI calcd for C$_{13}$H$_{19}$O$_2$ (M+H)$^+$, m/z 207.1380. found m/z 207.1371.

1-allyl-4-methoxy-2-propoxy-benzene, 5b{3,1} (isomer x), 15 mg, 96% enriched, liquid, $^1$H NMR of isomer x (600 MHz, CDCl$_3$) δ: 1.05 (t, 3H, J=7.4 Hz), 1.77-1.85 (m, 2H), 3.43 (td, 2H, J=6.3, 1.4 Hz), 3.78 (s, 3H), 3.92 (t, 2H, J=6.4 Hz), 5.00 (ddd, 1H, J=10.0, 3.6, 1.4 Hz), 5.03 (ddd, 1H, J=17.1, 3.6, 1.4 Hz), 5.95 (tdd, 1H, J=17.1, 10.0, 6.3 Hz), 6.46 (m, 2H), 7.12 (d, 1H, J=8.3 Hz), MS m/z (relative intensity): 206 (M$^+$, 100%), 177 (25%), 164 (38%), 163 (74%), 149 (27%).

1-methoxy-2-allyl-3-propoxy-benzene, 5b{3,1} (isomer y), 48 mg, 100% enriched, 2.6 g 86% enriched, liquid, $^1$H NMR of pure y (600 MHz, CDCl$_3$) δ: 1.04 (t, 3H, J=7.4 Hz), 1.76-1.84 (m, 2H), 3.30-3.34 (m, 2H), 3.78 (s, 3H), 3.87-3.93 (t, 2H, J=Hz), 4.89-5.06 (m, 2H), 5.90-6.00 (m, 1H), 6.39-6.45 (d, 2H, J=8.3 Hz), 7.02 (d, 1H, J=8.3 Hz). $^{13}$C NMR (400 MHz, CDCl$_3$) δ: 158.2, 157.7, 137.0, 127.0, 116.8, 114.0, 104.8, 103.6, 69.9, 55.8, 27.4, 22.8, 10.7. MS m/z (relative intensity): 206 (M$^+$, 100%), 177 (90%), 164 (25%), 163 (30%), 149 (71%), 135 (81%), 133 (34%), 121 (76%), 107 (52%). HRMS-ESI calcd for C$_{13}$H$_{19}$O$_2$ (M+H)$^+$, m/z 207.1380. found m/z 207.1370.

1-allyl-4-ethoxy-2-propoxy-benzene and 1-ethoxy-2-allyl-3-propoxy-benzene, 5b{3,2} (isomers x and y, ratio: 2.3:1), 2.6 g, 89% yield of the Claisen rearrangement, liquid, $^1$H NMR (600 MHz, CDCl$_3$) δ: 1.09 (m, 6H), 1.44 (m, 6H), 1.79-1.92 (m, 4H), 3.36 (m, 2H), 3.50 (m, 2H), 3.94 (m, 4H), 3.99-4.10 (m, 4H), 4.91-5.12 (m, 4H), 6.00 (m, 2H), 6.42-6.56 (m, 4H), 7.00-7.16 (m, 2H). HRMS-ESI calcd for C$_{14}$H$_{21}$O$_2$ (M+H)$^+$, m/z 221.1536. found m/z 221.1528.

1-allyl-4-ethoxy-2-propoxy-benzene, 5b{3,2} (isomer x), 13.2 mg, 96% enriched, liquid, $^1$H NMR (600 MHz, CDCl$_3$) δ: 1.02 (t, 3H, J=7.4 Hz), 1.38 (t, 3H, J=7.0 Hz), 1.72-1.85 (m, 2H), 3.30 (d, 2H, J=6.7 Hz), 3.88 (m, 2H), 4.05 (q, 2H, J=7.0 Hz), 4.94 (ddd, 1H, J=10.2, 2.1, 1.2 Hz), 5.05 (ddd, 1H, J=16.8, 2.4, 1.2 Hz), 5.88-5.99 (m, 1H), 6.38 (dd, 1H, J=8.4, 2.4 Hz), 6.42 (d, 1H, J=2.4 Hz), 6.98 (d, 1H, J=8.4 Hz), MS m/z (relative intensity): 220 (M$^+$, 100%), 191 (25%), 177 (16%), 149 (58%).

1-ethoxy-2-allyl-3-propoxy-benzene, 5b{3,2} (isomer y), 49.7 mg, 100% enriched, liquid, $^1$H NMR (600 MHz, CDCl$_3$) δ: 1.07 (t, 3H, J=7.4 Hz), 1.42 (t, 3H, J=7.0 Hz), 1.77-1.89 (m, 2H), 3.46 (dt, 2H, J=6.5, 1.3 Hz), 3.94 (t, 2H, J=6.4 Hz), 4.05 (q, 2H, J=7.0 Hz), 4.94 (ddt, 1H, J=10.0, 2.4, 1.3 Hz), 5.05 (ddd, 1H, J=17.0, 3.8, 1.6 Hz), 5.97 (ddt, 1H, J=17.0, 10.0, 6.5 Hz), 6.53 (d, 2H, J=8.3 Hz), 7.11 (t, 1H, J=8.3 Hz). $^{13}$C NMR (400 MHz, CDCl$_3$) δ: 157.7, 157.6, 137.1, 126.9, 117.1, 114.0, 104.7, 104.6, 69.8, 63.9, 27.6, 22.8, 15.0, 10.7. MS m/z (relative intensity): 220 (M$^+$, 60%), 191 (62%), 177 (12%), 149 (100%), 135 (46%), 121 (59%), 107 (29%). HRMS-ESI calcd for C$_{14}$H$_{21}$O$_2$ (M+H)$^+$, m/z 221.1536. found m/z 221.1532.

1-allyl-4-methoxy-3-isopentoxybenzene and 1-methoxy-2-allyl-3-isopentoxybenzene, 5b{5,1} (isomers x and y, ratio 1.8:1), 11.0 g, 91% yield of the Claisen rearrangement, liquid, $^1$H NMR (600 MHz, CDCl$_3$) δ: 0.99 (d and s, 12H, J=6.9 Hz), 1.75-1.68 (m, 4H), 1.95-1.85 (m, 2H), 3.34 (d, 2H, J=6.7 Hz), 3.45 (d, 2H, J=6.3 Hz), 3.80-3.82 (m, 3H), 3.83-3.84 (m, 3H), 3.97-4.03 (m, 6H), 4.93-5.09 (m, 4H), 5.93-6.04 (m, 2H), 6.43-6.48 (m, 2H), 6.56 (d, 2H, J=8.3, 5.3 Hz), 7.05 (d, 1H, J=8.3 Hz), 7.15 (t, 1H, J=8.3 Hz), MS m/z (relative intensity): isomer x (retention time 8.03 min): 234 (M$^+$, 80%), 177 (2%), 164 (95%), 163 (100%), 149 (33%), 147 (37%), 133 (28%). isomer y (retention time 7.83 min): 234 (M+, 100%), 205 (35%), 177 (7%), 164 (72%), 163 (39%), 135 (99%), 133 (41%), 121 (71%), 107 (40%), 77 (28%). HRMS-ESI calcd for $C_{15}H_{23}O_2$ (M+H)+, m/z 235.1693. found m/z 235.1691.

1-allyl-3-allyloxy-4-methoxybenzene and 1-methoxy-2-allyl-3allyloxybenzene, 5b{6,1} (isomers x and y, ratio 2.3:1), 8.6 g, 69% yield of the Claisen rearrangement, liquid, $^1$H NMR (600 MHz, CDCl$_3$) δ: 3.37 (br d, 2H, J=6.6 Hz, isomer x), 3.48 (br d, 2H, J=6.0 Hz, isomer y), 3.80 (s, 3H, isomer x), 3.85 (s, 3H, isomer y), 4.54 (ddd, 2H, J=5.4, 1.8, 1.8 Hz, isomer x), 4.55 (ddd, 2H, J=4.8, 1.2, 1.2 Hz, isomer y), 4.90 (m, 1H, isomer y), 5.02 (m, 1H, isomer y), 5.03 (m, 1H, isomer x), 5.07 (m, 1H, isomer x), 5.00-5.10 (m, 2H isomer x+1H isomer y), 5.27 (m, 1H, isomer y), 5.28 (m, 1H, isomer x), 5.44 (ddd, 1H, J=17.4, 3.6, 1.8 Hz, isomer y), 5.45 (ddd, 1H, J=16.8, 3.0, 1.2 Hz, isomer x), 5.95-6.12 (m, 2H, isomer x+2H, isomer y), 6.44-6.49 (m, 2H, isomer x), 6.55 (d, J=8.4 Hz, 1H isomer y), 6.57 (d, J=9.0 Hz, 1H isomer y), 7.04-7.08 (br d, J=9.0 Hz, 2H, isomer x), 7.14 (t, 1H, J=8.4 Hz, isomer y), MS m/z (relative intensity): isomer x (retention time 6.92 min): 204 (M+•, 100%), 203 (32%), 177 (9%), 163 (44%), 161 (28%), 135 (43%), isomer y (retention time 6.70 min): 204 (M+, 100%), 189 (26%), 177 (20%), 175 (25%), 163 (85%), 161 (42%), 147 (30%), 135 (89%), 107 (88%), 105 (42%), 103 (50%), 91 (47%), 77 (52%). HRMS-ESI calcd for $C_{13}H_{17}O_2$ (M+H)+, m/z 205.1223. found m/z 205.1232.

For the synthesis of the first set of mini-libraries (Set A, Scheme 1 or 1-1, and Table 2), equimolar mixtures of monoalkoxy 2(a-c){n} compounds were alkylated to afford chemsets of 4 or 5 members 3(a-c){n,1-5}. In order to effect complete deprotonation of the monoalkoxy compounds 2(a-c){n}, the alkylation was conducted with NaH as the base, in DMF, at room temperature. The reaction was monitored by GC and it proceeded at similar rates for all the components, affording crude products of high purity (>90% by GC). However, the removal of DMF resulted in losses of material. Further, the more volatile dialkoxy members 3(a-c){n,1-5}evaporated in sufficient quantities to introduce biases (e.g. Table 2, entry 2). Following optimization, the K$_2$CO$_3$/acetone base/solvent system afforded better yields and much less bias (e.g. Table 2, entry 6).

TABLE 2

Purity of the Libraries and % Distribution of the Members in Libraries

| no. | Library$^a$ | n | Purity$^b$ | Distribution of members in library (%)$^d$ | | | | |
|---|---|---|---|---|---|---|---|---|
| | | | | {n, 1}$^c$ | {n, 2} | {n, 3} | {n, 4} | {n, 5} |
| Set A | | | | | | | | |
| 1 | 3a{1, 1-5} | 1 | 100 | 13.7 | 13.0 | 16.9 | 26.0 | 30.4 |
| 2 | 3a{2 1-5} | 2 | 99 | 7.0 | 8.8 | 15.3 | 32.5 | 35.0 |
| 3 | 3a{3, 1-5} | 3 | 99 | 9.7 | 12.3 | 20.2 | 25.8 | 30.7 |
| 4 | 3a{4, 1-5} | 4 | 99 | 9.0 | 14.7 | 18.8 | 27.9 | 27.2 |
| 5 | 3a{5, 1-5} | 5 | 99 | 7.7 | 12.9 | 17.9 | 31.2 | 29.6 |
| 6 | 3a{6, 1-5} | 6 | 100 | 13.2 | 15.9 | 19.2 | 27.3 | 24.3 |
| 7 | 3b{1, 1-5}* | 1 | 99 | 21.1 | 21.7 | 26.1 | — | 30.0 |
| 8 | 3b{2, 1-5}* | 2 | 95 | 16.2 | 20.4 | 26.4 | — | 32.3 |
| 9 | 3b{3, 1-5}* | 3 | 97 | 12.0 | 16.2 | 28.6 | — | 39.7 |
| 10 | 3b{4, 1-5}* | 4 | 100 | 19.1 | 20.7 | 27.7 | — | 32.2 |
| 11 | 3b{5, 1-5}* | 5 | 97 | 22.5 | 22.9 | 27.3 | — | 24.3 |
| 12 | 3b{6, 1} | 6 | 100 | 100 | — | — | — | — |
| 13 | 3b{6, 2-3} | 6 | 97 | — | 62 | 38 | — | — |
| 14 | 3b{6, 4-5} | 6 | 97 | — | — | — | 59 | 41 |
| 15 | 3c{1, 1-5}* | 1 | 97 | 15.1 | 20.2 | 23.2 | — | 38.2 |
| 16 | 3c{2, 1-5}* | 2 | 98 | 20.1 | 23.6 | 23.9 | — | 30.7 |
| 17 | 3c{3, 1-5}* | 3 | 96 | 19.7 | 18.6 | 24.9 | — | 32.9 |
| 18 | 3c{4, 1-5}* | 4 | 97 | 24.6 | 23.0 | 24.7 | — | 24.8 |
| 19 | 3c{5, 1-5}* | 5 | 95 | 22.7 | 21.2 | 24.5 | — | 26.7 |
| 20 | 3c{6, 1-5} | 6 | 100 | 10.1 | 13.6 | 18.6 | 23.8 | 33.9 |
| Set B | | | | | | | | |
| 21 | 4a{1-5} | — | 95 | 13.7 | 17.3 | 18.9 | 23.1 | 22.0 |
| 22 | 4b{1}$^e$ | — | 100 | 61/39 | — | — | — | — |
| 23 | 4b{2-3}$^e$ | — | 100 | — | 22/20 | 32/27 | — | — |
| 24 | 4b{4-5}$^e$ | — | 100 | — | — | — | 26/24 | 28/22 |
| 25 | 4c{1-5} | — | 100 | 9.1 | 14.3 | 20.6 | 22.9 | 33.1 |
| Set C | | | | | | | | |
| 26 | 5a{1, 1-5} | 1 | 92 | 12.9 | 14.5 | 17.2 | 24.1 | 23.7 |
| 27 | 5a{2, 1-5} | 2 | 93 | 14.3 | 15.5 | 17.0 | 23.2 | 23.1 |
| 28 | 5a{3, 1-5} | 3 | 94 | 14.0 | 15.2 | 17.6 | 23.7 | 23.1 |
| 29 | 5a{4, 1-5} | 4 | 90 | 16.7 | 16.7 | 15.7 | 22.3 | 18.5 |
| 30 | 5a{5, 1-5} | 5 | 90 | 19.9 | 20.7 | 15.6 | 19.7 | 14.5 |
| 31 | 5a{6, 1-5} | 6 | 96 | 17.6 | 21.5 | 18.0 | 22.5 | 16.4 |
| 32 | 5b{1, 1}$^e$ | 1 | 99 | 60/40 | — | — | — | — |
| 33 | 5b{1, 2-3}$^e$ | 1 | 96 | — | 23/16 | 38/24 | — | — |
| 34 | 5b{1, 4-5}$^e$ | 1 | 100 | — | — | — | 34/20 | 29/17 |
| 35 | 5b{2, 1}$^e$ | 2 | 100 | 62/38 | — | — | — | — |
| 36 | 5b{2, 2-3}$^e$ | 2 | 98 | — | 24/16 | 38/22 | — | — |
| 37 | 5b{2, 4-5}$^e$ | 2 | 100 | — | — | — | 36/20 | 27/17 |
| 38 | 5b{3, 1}$^e$ | 3 | 100 | 61/39 | — | — | — | — |
| 39 | 5b{3, 2-3}$^e$ | 3 | 100 | — | 25/16 | 35/23 | — | — |
| 40 | 5b{3, 4-5}$^e$ | 3 | 100 | — | — | — | 35/19 | 31/15 |
| 41 | 5b{4, 1}$^{e,f}$ | 4 | 98 | 62/38 | — | — | — | — |
| 42 | 5b{4, 2-3}$^{e,f}$ | 4 | 98 | — | 34/20 | 31/15 | — | — |
| 43 | 5b{4, 4-5}$^{e,f}$ | 4 | 95 | — | — | — | 30/18 | 32/20 |
| 44 | 5b{5, 1}$^{e,f}$ | 5 | 99 | 62/38 | — | — | — | — |
| 45 | 5b{5, 2-3}$^{e,f}$ | 5 | 100 | — | 34/20 | 31/15 | — | — |
| 46 | 5b{5, 4-5}$^{e,f}$ | 5 | 99 | — | — | — | 30/19 | 31/20 |
| 47 | 5b{6, 1}$^{e,f}$ | 6 | 94 | 61/39 | — | — | — | — |
| 48 | 5b{6, 2-3}$^{e,f}$ | 6 | 94 | — | 36/21 | 26/17 | — | — |
| 49 | 5b{6, 4-5}$^{e,f}$ | 6 | 88 | — | — | — | 29/20 | 30/21 |
| 50 | 5c{1, 1-5} | 1 | 99 | 11.0 | 14.0 | 19.9 | 23.7 | 30.0 |
| 51 | 5c{2, 1-5} | 2 | 100 | 12.6 | 16.5 | 22.8 | 21.3 | 26.8 |
| 52 | 5c{3, 1-5} | 3 | 100 | 12.5 | 15.9 | 21.9 | 22.7 | 26.9 |
| 53 | 5c{4, 1-5} | 4 | 100 | 9.8 | 14.5 | 23.1 | 24.1 | 28.5 |
| 54 | 5c{5, 1-5} | 5 | 99 | 16.5 | 18.9 | 22.0 | 20.3 | 21.3 |
| 55 | 5c{6, 1-5} | 6 | 100 | 14.1 | 21.5 | 27.5 | 18.6 | 18.3 |
| Set D | | | | | | | | |
| 56 | 6c{1-5} | — | 100 | 10.5 | 15.1 | 19.9 | 24.6 | 29.9 |

*These libraries do not contain the {n, 4} member;
$^a$Sequence of alkyl substituents in the brackets is interchangeable: e.g. member 3a{1, 2} is identical with member 3a{2, 1};
$^b$Purity was determined by GC;
$^c$"n" has the same significance as in Scheme 1 and it corresponds to the first number in the bracket of the respective chemset;
$^d$Percent distribution of the library members was determined by GC and validated by NMR and GC-MS data;
$^e$Meta compounds undergoing a Claisen Rearrangement yielded two products, and the "5-alkoxy-2-allyl phenol" (x) is listed first; the same format holds for the alkylated derivatives of the meta Claisen Rearrangement products;
$^f$Initial lot of starting material, 4b{n}, was used completely and re-synthesized as a second lot.

Further expansion of the libraries was accomplished via the ortho-Claisen rearrangement of chemsets 3(a-c){6,1-5} at 180° C. and afforded pure libraries (Set B, Table 2). For the ortho library, 4a{1-5}, traces (2-5%) of the para-Claisen rearrangement products were detected (Scheme 2). For the meta 4b libraries no para-Claisen rearrangement was detected and for para 4c libraries the para-Claisen rearrangement was not possible and not observed (Scheme 2). Under thermal conditions, the para-Claisen rearrangement of allyl phenyl ethers is not an important pathway (Ito, F et al. 2007). Under selected Lewis acid or metal catalysis conditions, and when the ortho positions are blocked the para-Claisen rearrangement can be significant Kuntz et al. 2006; Ollevier et al. 2006; Yadav et al. 2007. The meta compounds 3b{6,1-5} yielded two products:

5-alkoxy-2-allylphenol, x, and 3-alkoxy-2-allylphenol, y (Table 2, Scheme 2) upon ortho-Claisen rearrangement. The rearrangement to the less sterically hindered side was slightly more prevalent (1.4-1.8×) than the alternative rearrangement to the hindered position, consistent with previous literature on the thermal Claisen rearrangement of meta-substituted allyl phenol ethers (Ito, F et al. 2007; Gozzo et al 2003; White and Slater 1961).

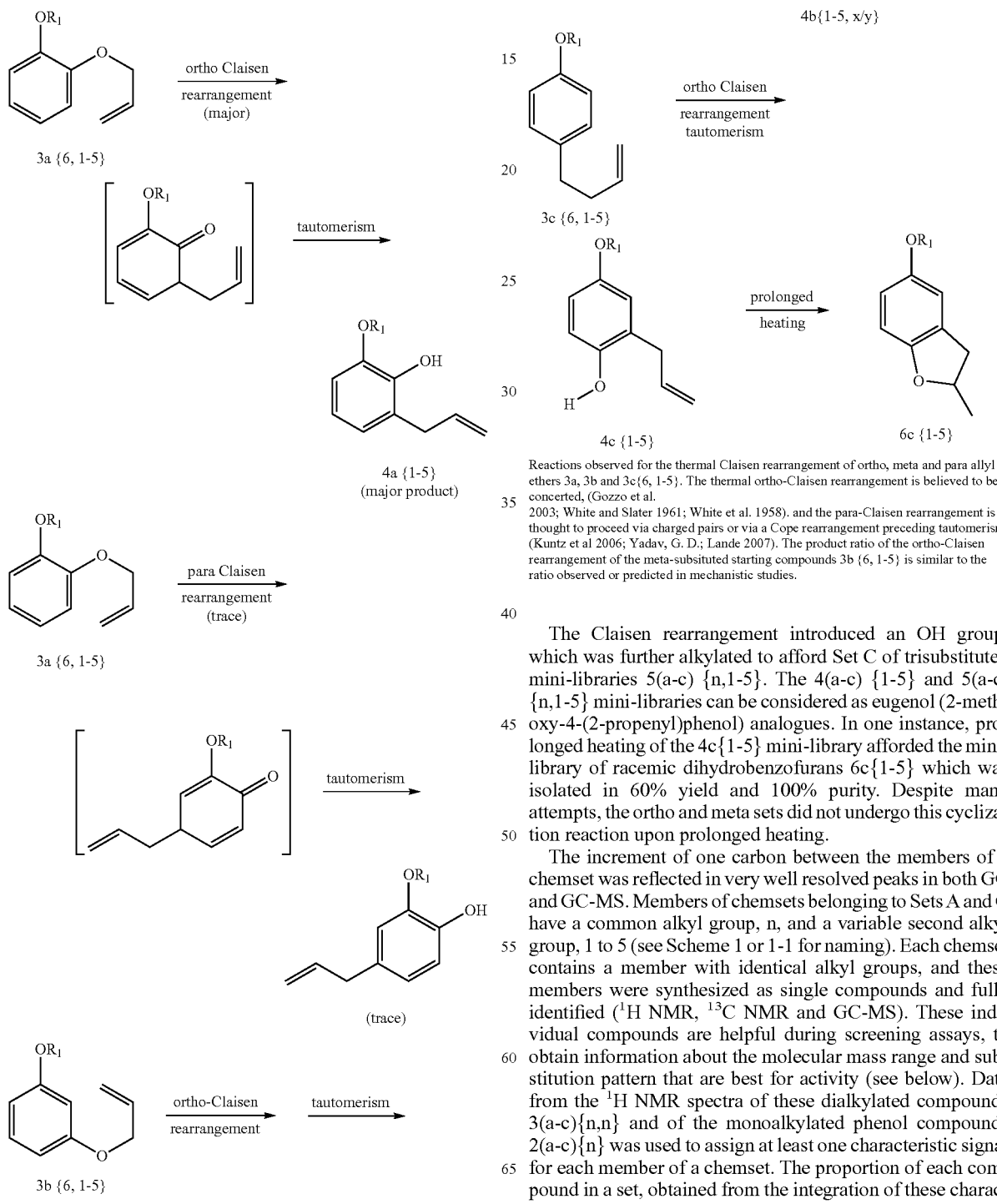

Scheme 2.

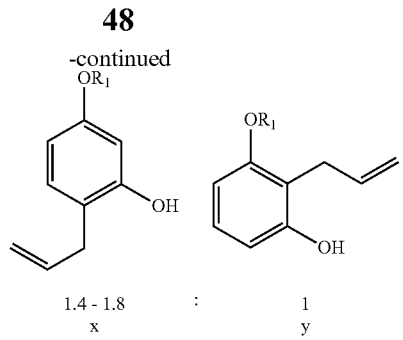

Reactions observed for the thermal Claisen rearrangement of ortho, meta and para allyl ethers 3a, 3b and 3c{6, 1-5}. The thermal ortho-Claisen rearrangement is believed to be concerted, (Gozzo et al. 2003; White and Slater 1961; White et al. 1958). and the para-Claisen rearrangement is thought to proceed via charged pairs or via a Cope rearrangement preceding tautomerism (Kuntz et al 2006; Yadav, G. D.; Lande 2007). The product ratio of the ortho-Claisen rearrangement of the meta-subsituted starting compounds 3b {6, 1-5} is similar to the ratio observed or predicted in mechanistic studies.

The Claisen rearrangement introduced an OH group, which was further alkylated to afford Set C of trisubstituted mini-libraries 5(a-c) {n,1-5}. The 4(a-c) {1-5} and 5(a-c) {n,1-5} mini-libraries can be considered as eugenol (2-methoxy-4-(2-propenyl)phenol) analogues. In one instance, prolonged heating of the 4c{1-5} mini-library afforded the mini-library of racemic dihydrobenzofurans 6c{1-5} which was isolated in 60% yield and 100% purity. Despite many attempts, the ortho and meta sets did not undergo this cyclization reaction upon prolonged heating.

The increment of one carbon between the members of a chemset was reflected in very well resolved peaks in both GC and GC-MS. Members of chemsets belonging to Sets A and C have a common alkyl group, n, and a variable second alkyl group, 1 to 5 (see Scheme 1 or 1-1 for naming). Each chemset contains a member with identical alkyl groups, and these members were synthesized as single compounds and fully identified ($^1$H NMR, $^{13}$C NMR and GC-MS). These individual compounds are helpful during screening assays, to obtain information about the molecular mass range and substitution pattern that are best for activity (see below). Data from the $^1$H NMR spectra of these dialkylated compounds 3(a-c){n,n} and of the monoalkylated phenol compounds 2(a-c){n} was used to assign at least one characteristic signal for each member of a chemset. The proportion of each compound in a set, obtained from the integration of these characteristic signals, was the same as the proportion of that compound obtained by GC. This congruence of $^1$H NMR and GC data validates the composition of the libraries (Table 2). Each library composition was further confirmed during GC-MS calibrations.

Reaction rates of components in the libraries. Within each set, 2a {1-5}, 2b {1-5} or 2c{1-5}, the rates of the second alkylation were similar for all compounds in the mixture, suggesting that the size of the substituent did not influence the rate of the reaction. This was especially surprising in the case of the ortho substituted substrates for which, regardless of the differences in size of the alkyl substituent or alkyl halide reagent (methyl to iso-pentyl), complete conversion was achieved at the same time for all the members of the set.

To determine whether the Claisen rearrangement of the 3(a-c){6,1-5} libraries was also independent of substituent size, the rearrangement was monitored by GC at regular time intervals. For the para library, 3c{6,1-5}, the GC peaks corresponding to the substrates were better resolved and the percent conversion of four of the starting materials was calculated and plotted against time (FIG. 1). The graph confirms that the size of the substituent did not influence the reaction progress, and that complete conversion of all compounds in a set was achieved after about 9 hours of reaction time. A similar behavior was also obtained for the ortho and meta libraries 3(a,b){6,1-5}. A previous kinetic study of the Claisen rearrangement of various para-substituted allyl phenyl ethers also suggested that the rate of the rearrangement is mildly dependent on the nature of the substituents; electron-releasing groups accelerated the reaction. The methoxy and ethoxy members of that study gave the same rates of rearrangement (Goering and Jacobson 1958).

Figure 2:
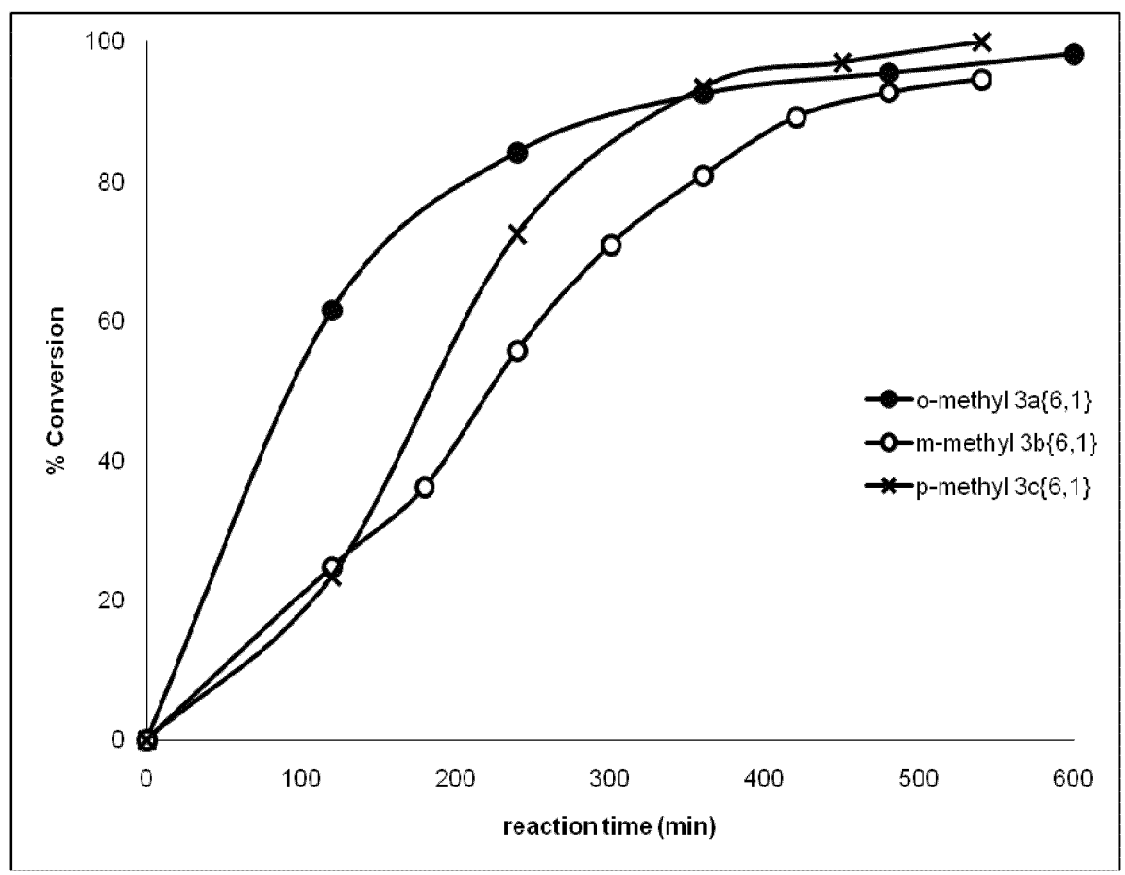
FIG. 2 shows a graph with the progress of the Claisen rearrangement reaction: comparison between the ortho methoxy 3a {6,1}, meta methoxy 3b{6,1} and para methoxy 3c{6, 1} library members.

Comparison between the conversion profile of ortho, meta and para substituted library members showed differences in the half-time to total conversion, but not in the total reaction time. Members of the ortho library 3a{6,1-5} achieved 50% conversion in 1 hour while it took 3 and 4 hours for the members of the para library 3c{6,1-5} and meta library 3b{6,1-5}, respectively, to reach the same point. The time necessary to achieve total conversion was not dependent upon the substitution pattern. For clarity, only data for one member in each library are shown (FIG. 2). In a previous kinetic study, the rearrangement of para and meta methoxy substituted allyl phenyl ether had the same rate constants (Goering and Jacobson 1958).

Dihydrobenzofuran Formation.

When the para library 3c{6,1-5} was heated three times longer (30 hours) than required for the completion of the Claisen rearrangement, dihydrobenzofurans 6W-51 were obtained. Reported spectral data for the known compound, 6c{1}, was used to confirm the identity of the products (Grant and Liu 2005). As a further proof we synthesized 6c{3} as a single compound, and its spectra as well as GC retention time matched the data for the respective library member. Interestingly, cyclization occurred only on the para substituted compounds 3c{6,1-5} and not on the ortho 3a{6,1-5} or meta 3b {6,1-5} substituted ones. Ortho and meta allyl ethers began decomposing when heated longer than was necessary to complete the Claisen rearrangement. Further, we learned that the cyclization reaction followed the Claisen rearrangement and, therefore library 6W-51 could also be obtained directly from the 4c{1-5} library. The cyclization reaction proceeded in a Markovnikov sense, and this selectivity has been observed also with (3'-methyl)-2'-butenyl(dimethylallyl) substituents (Ollevier et al. 2006). In previous literature, allyl aryl ethers were rearranged and cyclized to dihydrobenzofurans in the presence of a copper (II) triflate catalyst (Ito et al. 2007), an iridium (III)/silver triflate catalyst (Grant and Liu 2005), aluminum-containing mesoporous molecular sieves (Mathew et al. 2004), a gold (I)-catalyst (Reich et al. 2006) or a bismuth triflate catalyst (Ollevier et al. 2006). These studies also suggest that the Claisen rearrangement occurs first, followed by the Markovnikov addition of the new phenol OH to the allyl double bond (Reich et al. 2006). In fact, few catalysts promoted the tandem reaction; some only catalyzed the Claisen reaction and others caused decomposition. Further, the allyl phenyl ethers that cyclized best, generally had electron-releasing groups or no additional substituents on the benzene ring.

Preparation of Compounds Group II

For the meta compounds, the Claisen rearrangement gave two isomers. For the alkoxy substituents that were used, the isomer in which the allyl group migrates to position 4 (isomer x) is slightly favoured thermodynamically over the isomer in which the allyl group migrates to position 2 (isomer y) (White and Slater 1961; Gozzo et al. 2003). Typical ratios of compounds x:y range from 2.3:1 to 1.2:1. Isomers x and y from the Claisen rearrangement of meta substituted allyloxybenzenes were separated by flash chromatography on AgNO$_3$-silica.

The two isomers x and y were separated for selected cases of series 5b (see Table 7). Briefly, 1% (w/v) AgNO$_3$ was dissolved in water, to which was added silica gel to form a thick slurry. The slurry dried overnight (120° C.), before being packed into the column. Care was taken not to expose the silver nitrate silica to light, by wrapping the beaker with the slurry and later the column with aluminum foil. The silver-silica column was equilibrated with hexane-toluene: 99:1, and the loaded compounds were eluted with 90:10 hexane-toluene. To monitor the separation, 1% AgNO$_3$ TLC plates were prepared by running the silver nitrate solution up the plates and drying them. The plates could be stained with anisaldehyde solution. Isomer y ran faster than x, and it was possible to obtain several fractions that contained pure y. However, y also tailed into the x peak, so that it was not possible to obtain fractions with 100% x by FCC. Alternatively, 5b{3,1}y and 5b{3,1}x as well as 5b{3,2}y and 5b{3,2}x could be separated by preparative TLC (100% hexanes) with multiple developments.

The more compact isomer y was more volatile than x, eluting usually 0.5-1 min earlier from the GC (DB-5 column). Also, in general, isomer y formed an M+1 ion in the mass spectrum more readily and fragmented more extensively (for example, to the tropylium ion m/z 91) than isomer x.

Example 2

Testing of Compounds for Toxicity, Oviposition and Feeding

Materials and Methods
Plant Material

Cabbage plants (*Brassica oleraceae* var. *Stonehead*) used in the bioassays were routinely grown in plastic pots with a mixture of sandy loam soil and peat moss (4:1) in a greenhouse at the University of British Columbia, Vancouver, BC, Canada. Leaves were collected from cabbage plants that were 5-6 weeks old.

Test Insects

*T. ni* larvae and moths were obtained from a long established colony (>50 generations) maintained on an artificial diet, Velvetbean Caterpillar Diet No. F9796 [Bio-Sery Inc. (Frenchtown, NIL)] in the insectary of the University of British Columbia (UBC). The diet was supplemented with finely ground alfalfa, to improve acceptability, and vitamins [No. 8045; Biosery Inc. (Frenchtown, NIL)].

General Testing Procedure

Initial screening for feeding deterrent effects was conducted at 50 μg/cm² in feeding deterrent bioassays. Compounds that exhibited >50% feeding deterrence at this concentration were subjected to further testing for oviposition deterrent effects and contact toxicity at 0.25% of the test substance. For compounds exhibiting ≥50% values for feeding deterrence and ≥70% mortality by contact, $DC_{50}$ (concentration causing 50% feeding deterrence compared with the control) and $LC_{50}$ (concentration causing 50% mortality compared with the control) were determined, respectively, based on bioassays involving a minimum of four concentrations (3.12-25 μg/cm²).

Feeding Deterrence Bioassays

Leaf disk choice bioassays (Akhtar et al. 2003; Akhtar and Isman 2004) were conducted to determine feeding deterrent effects of the synthetic compounds using freshly molted third instar larvae starved for 4-5 h prior to each bioassay. Larvae were given the choice of feeding on two leaf disks, one treated with 10 μL of a solution of the test substance painted on each side and the other treated with a carrier solvent alone. The number of larvae was 25 per treatment. Bioassays were terminated when approximately 50% of the control disk had been eaten (normally 3-5 h). Areas of control and treated leaf disks consumed by the larvae were measured using Scion Image software, and feeding deterrence was calculated (Akhtar and Isman 2004) using the formula $[(C-T)/(C+T)] \times 100$, where C and T are areas consumed of the control and treated leaf disks, respectively.

Oviposition Deterrence Bioassays

Oviposition response of *T. ni* moths was measured according to the oviposition choice bioassay described in Akhtar and Isman 2003 and Chow et al. 2005. *T. ni* larvae were reared on normal diet from neonates (<24 h old) until pupation. Pupae were sexed and put in separate plastic containers until emergence. After eclosion, pairs of moths (one male and one female) were introduced into each cage with a control and a treated cabbage leaf. Pairs of moths (n=25) were used per treatment. Each leaf (approximately 100-110 cm²) was sprayed with 0.5 mL of MeOH or a methanolic solution of the test chemical on each side. Eggs were counted on each cabbage leaf after 48 h. ODI (oviposition deterrence index) was calculated using the formula $ODI=[(C-T)/(C+T)] \times 100$, where C and T are the numbers of eggs laid on the control and treated leaf disks, respectively (Akhtar and Isman 2003; Chow et al. 2005).

Contact Toxicity Bioassay

Mortality was determined 24 h after spraying larvae directly with test solutions. Third instar *T. ni* larvae were sprayed in 90 mm×15 mm Petri dishes (Falcon) lined with Fisher Scientific filter paper (90 mm diameter). Small plastic hand spraying bottles (50 mL capacity) were used. Larvae were then transferred to Petri dishes (90 mm×15 mm) with a small piece of artificial diet. Each Petri dish contained 10 larvae. Three replicates, each consisting of 10 larvae, were used per treatment.

Comparison of Toxicity, Oviposition, and Feeding Deterrence Values

The mortality of each test material was plotted against its respective oviposition deterrence value (determined at 0.25%) to explore the relationship between the two bioassays using correlation analysis. Similarly, feeding deterrence was plotted against oviposition deterrence and mortality.

Data Analysis

Feeding deterrence data (percent) for initial screening concentration were analyzed by analysis of variance (ANOVA) after arcsin transformation using statistics software (Statistix 7. Analytical Software, Statistix 7 for Windows 95, 98, NT, 2000. Analytical Software, Tallahassee). Where significant F values were found, Tukey's HSD multiple comparison tests were used to test for significant differences between individual treatments.

Results for Test Compound Group I

Example 3

Effects of p-Dialkoxybenzene Libraries, Pure Compounds, and 1-Hydroxy-4-alkoxy Compounds All six of the p-dialkoxybenzene libraries and five individual compounds (3c{$R_1;R_2$}) exhibited >50% feeding deterrence at the initial screening concentration (50 μg/cm²) and, therefore, were subjected to further testing (Table 3) against third instar *T. ni* larvae for toxic and oviposition deterrent effects. The response of the larvae to the initial screening concentration varied significantly in most cases (one-way ANOVA; $F1_{6405}=9.6$, $p<0.0001$).

Feeding Deterrence Effects

1-Isopentyloxy-4-alkoxybenzene 3c{5,1-5} had the lowest $DC_{50}$ value (8.5 μg/cm²) followed by 1-butyloxy-4-alkoxybenzene 3c{4,1-5} (14.5 μg/cm²) and 1-allyloxy-4-isopentoxybenzene 3c{5,6} (15.7 μg/cm²) (Table 3). 1-Hydroxy-4-methoxybenzene 2c{1} and 1-hydroxy-4-propoxybenzene 2c{3} acted as feeding stimulants at the screening concentration. 1-Hydroxy-4-ethoxybenzene 2c{2} (a precursor to diethyl and the ethyl minilibrary) was a weak feeding deterrent.

Toxic Effects 1,4-Diethoxybenzene 3c{2,2} and the 1-ethoxy-4-alkoxybenzene 3c{2,1-5} library were the most toxic (Table 3) at 0.25% ($LC_{50}$ values were 0.03% for both) followed by 1-butyloxy-4-alkoxybenzene 3c{4,1-5} and 1-propoxy-4-alkoxybenzene 3c{3,1-5}.

TABLE 3

Bioactivities of 1,4-dialkoxybenzene libraries and analogues (3c{$R_1$; $R_2$}) against third instar *T. ni* larvae[a]

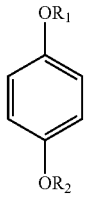

| compound | R1 | R2 | FD (%), mean ± SE (n = 25) | DC50, µg/cm2 (r2)b (n = 25) | mortality (%) (n = 3 × 10) | OD (%), mean ± SE (n = 25-33) |
|---|---|---|---|---|---|---|
| 1,4-dimethoxybenzene | CH3 | CH3 | 9.9 ± 18.0cd | —c | — | — |
| 1,4-diethoxybenzene | C2H5 | C2H5 | 80.8 ± 11.3b | 25.9 (0.91) 20.3 | 100.0d | 74.7 ± 13.3a |
| 1,4-dipropoxybenzene | C3H7 | C3H7 | 96.0 ± 2.8a | (0.99) | 22.6 | 11.8 ± 13.1b |
| 1,4-diisopentoxybenzene | C5H11 | C5H11 | 44.0 ± 18.3abc | — | — | — |
| 1,4-diallyloxybenzene | C3H5 | C3H5 | 96.9 ± 3.6a | 23.9 (0.97) | 16.0 | 14.1 ± 13.1b |
| Me library (1-methoxy-4-alkoxybenzene) | CH3 | CH3, C2H5, C3H7, C5H11 | 80.2 ± 9.8b | 34.6 (0.90) | 23.3 | 6.0 ± 5.1b |
| Et library (1-ethoxy-4-alkoxybenzene) | C2H5 | CH3, C2H5, C3H7, C5H11 | 90.7 ± 10.2a | 23.4 (0.99) | 96.8e | 56.6 ± 16.9ab |
| Pr library (1-propoxy-4-alkoxybenzene) | C3H7 | CH3, C2H5, C3H7, C5H11 | 53.4 ± 15.8abc | 39.7 (0.94) 14.5 | 53.1 | 9.6 ± 13.8b |
| Bu library (1-butyloxy-4-alkoxybenzene) | C4H9 | CH3, C2H5, C3H7, C5H11 | 83.4 ± 9.7b | (0.83) | 58.1 | 50.1 ± 14.5ab |
| iPent library (1-isopentyloxy-4-alkoxy-benzene allyl small | C5H11 | CH3, C2H5, C3H7, C5H11 | 100.0 ± 0.0a | 5.8 (0.85) | 18.8 | 22.9 ± 14.2ab |
| library (1-allyloxy-4-alkoxybenzene) | C3H7 | CH3, C2H5C3H7 | 82.4 ± 10.7b | 27.9 (0.93) | 10.0 | 5.4 ± 13.9b |
| 1-allyloxy-4-butoxybenzene | C3H7 | C4H9 | 84.0 ± 10.7b | 22.6 (0.90) 15.7 | 10.0 | 16.8 ± 13.8ab |
| 1-allyloxy-4-isopentoxybenzene | C3H7 | C5H11 | 75.1 ± 12.7abc | (0.90) | 7.0 | 18.8 ± 14.3ab |
| 1-hydroxy-4-methoxybonzene | H | CH3 | −26.5 ± 18.6d | — | — | — |
| 1-hydroxy-4-ethoxybenzene | H | C2H5 | 29.8 ± 18.2bcd | — | — | — |
| 1-hydroxy-4-propoxybenzene | H | C3H7 | −28.0 ± 18.4d | — | — | — |
| 1-hydroxy-4-isopentoxybenzene | H | C5H11 | 29.5 ± 16.6bcd | — | — | — | aFeeding deterrent (FD) effects (mean ± SE) at 50 µg/cm$^2$ are expressed in %. $DC_{50}$s (concentrations causing 50% feeding deterrence compared with the control) were calculated for samples showing >50% feeding deterrence in initial screening (≥50 µg/cm$^2$) using Excel; linear regression analysis was conducted for all dose-response experimental data. Mortality and oviposition deterrent effects were determined at 0.25% for samples showing >50% feeding deterrence in initial screening. $LC_{50}$ (concentrations causing 50% mortality compared with the control) was calculated for test compounds exhibiting ≥70% mortality at 0.25%. Means followed by the same letters within a column do not differ significantly (Tukey's test, p < 0.05).
bCoefficient of determination.
cNot tested.
d$LC_{50}$ = 0.03%.
e$LC_{50}$ = 0.03%.
fPrecursor to diethyl and the ethyl minilibrary.

Oviposition Deterrence Effects 1,4-Diethoxybenzene 3c{2,2}, the 1-ethoxy-4-alkoxybenzene library 3c{2,1-5}, and the 1-butyloxy-4-alkoxybenzene 3c{4,1-5} library showed the strongest oviposition deterrent effects (74.7%, 56.6%, and 50.1%, respectively) when tested at 0.25% (Table 3). Other members in the group demonstrated weak oviposition deterrent effects (<23%). Responses of moths varied significantly in most cases (one-way ANOVA; $F_{10304}$=2.8, p<0.003).

Example 4 m-Dialkoxybenzene Libraries, Pure Compounds, and 1-Hydroxy-3-alkoxy Compounds

All five of the m-dialkoxybenzene libraries and two pure compounds (3b {$R_1$;$R_2$}) exhibited >50% feeding deterrence in initial screening (50 µg/cm$^2$) and therefore were subjected to further testing (Table 4). The response of the larvae to initial screening concentration varied significantly in most cases (one-way ANOVA; $F_{12307}$=8.6, p<0.0001).

Feeding Deterrence Effects

The 1-butoxy-3-alkoxybenzene 3b{4,1-5} library had the lowest $DC_{50}$ value (14.4 µg/cm$^2$) followed by the 1-isopentoxy-3-alkoxybenzene 3b{5,1-5} library ($DC_{50}$) 19.8 µg/cm$^2$). Three compounds acted as feeding stimulants to third instar *T. ni* larvae.

Toxic Effects 1,3-Dipropoxybenzene 3b{3,3} was the most toxic (Table 4) at 0.25% and had a $LC_{50}$ value of 0.16% followed by the 1-propoxy-3-alkoxybenzene library 3b {3,1-5} (50% mortality).

Oviposition Deterrence Effects

The 1-methoxy-3-alkoxybenzene 3b {1,1-5} library demonstrated the strongest oviposition deterrent effect (70.2%) followed by the 1-isopentoxy-3-alkoxybenzene 3b {5,1-5} library (35.7%) (Table 4) when tested at 0.25%. Responses of moths varied significantly in most cases (one-way ANOVA; $F_{6199}$=2.19, p<0.04).

TABLE 4

Bioactivities of 1,3-Dialkoxybenzene Libraries and Analogues (3b{R1; R2}) against Third Instar *T. ni* Larvae[a]

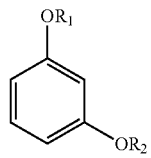

| compound | R1 | R2 | FD (%), mean (SE (n = 25) | DC50, µg/cm2 (r2)b (n = 25) | mortality (%) (n = 3 × 10) | OD (%), mean ± SE (n = 25-33) |
|---|---|---|---|---|---|---|
| 1,3-dimethoxybenzene | CH3 | CH3 | 20.4 ± 19.1bcde | —c | — | — |
| 1,3-diethoxybenzene | C2H5 | C2H5 | 89.4 ± 8.3ab | 28.7 (0.85) | 36.7 | 3.4 ( 14.1b |
| 1,3-dipropoxybenzene | C3H7 | C3H7 | 96.9 ± 3.1a | 26.8 (0.79) | 76.7d | 33.0 ( 14.6ab |
| 1,3-diisopentoxybenzene | C5H11 | C5H11 | -12.2 ± 18.8de | — | — | — |
| Me library (1-methoxy-3-alkoxybenzene) | CH3 | CH3, C2H5, C3H7, C5H11 | 54.8 ± 16.6abcd | 61.5 (0.94) | 16.7 | 70.2 ( 17.3a |
| Et library (1-ethoxy-3-alkoxybenzene) | C2H5 | CH3, C2H5, C3H7, C5H11 | 69.8 ± 13.8abc | 26.5 (0.98) | 20.0 | 14.3 ( 13.5ab |
| Pr library (1-propoxy-3-alkoxybenzene) | C3H7, | CH3, C2H5, C3H7, C5H11 | 98.0 ± 1.5a | 21.5 (0.96) | 50.0 | 2.7 ( 14.2b |
| Bu library (1-butyloxy-3-alkoxybenzene) | C4H9, | CH3, C2H5, C3H7, C5H11 | 84.1 ± 8.9ab | 14.4 (0.85) | 30.0 | 25.9 ( 13.9ab |
| iPent library (1-isopentyloxy-3-alkoxybenzene | C5H11 | CH3, C2H5, C3H7, C5H11 | 82.6 ± 12.0ab | 19.8 (0.96) | 20.8 | 35.7 ( 13.4ab |
| 1-hydroxy-3-methoxybenzene | H | CH3 | 44.7 ± 17.5abcde | — | — | — |
| 1-hydroxy-3-ethoxybenzene | H | C2H5 | -18.7 ± 17.8e | — | — | — |
| 1-hydroxy-3-propoxybenzene | H | C3H7 | 4.0 ± 20.4cde | — | — | — |
| 1-hydroxy-3-isopentoxybenzene | H | C5H11 | -5.8 ± 18.7de | — | — | — | aFeeding deterrent (FD) effects (mean ± SE) at 50 µg/cm² are expressed in %. $DC_{50}$s (concentrations causing 50% feeding deterrence compared with the control) were calculated for samples showing >50% feeding deterrence in initial screening concentration (≥50 µg/cm²) using Excel; linear regression analysis was conducted for all dose-response experimental data. Mortality and oviposition deterrent effects were determined at 0.25% for samples showing >50% feeding deterrence in initial screening. $LC_{50}$ (concentrations causing 50% mortality compared with the control) was calculated for test compounds exhibiting ≥70% mortality at 0.25%. Means followed by the same letters within a column do not differ significantly (Tukey's test, p < 0.05).
bCoefficient of determination.
cNot tested.
d$LC^{50}$ = 0.16%.

Example 5 o-Dialkoxybenzene Libraries, Pure Compounds, and 1-Hydroxy-2-alkoxy Compounds Six o-dialkoxybenzene libraries and three individual compounds (3a{R1;R2}) exhibited >50% feeding deterrence in initial testing and therefore were subjected to further testing (Table 5) as explained above. The response of the larvae to initial screening concentration varied significantly in most cases (one-way ANOVA; $F_{16401}$=5.4, p<0.0001).

Feeding Deterrence Effects

The 1-butoxy-2-alkoxybenzene 3a{4,1-5} library had the lowest DC50 value (16.8 µg/cm²) followed by the 1-propoxy-2-alkoxybenzene library ($DC_{50}$=19.4 µg/cm²).

Toxic Effects

None of the o-dialkoxybenzene libraries or pure compounds caused >40% mortality at 0.25% (Table 5).

Oviposition Deterrence Effects

The 1-allyloxy-2-alkoxybenzene 3a{6,1-5} library demonstrated strong oviposition deterrent activity (66.7%) at 0.25%. The 1-allyloxy-2-alkoxybenzene library demonstrated strong oviposition deterrent activity (66.7%) at 0.25%. Other libraries and compounds had modest oviposition deterrent activities (Table 5; one-way ANOVA; $F_{7205}$=1.07, p=0.38).

TABLE 5

Bioactivities of 1,2-Dialkoxybenzene Libraries and Analogues (3a{R1; R2}) against Third Instar *T. ni* Larvae[a]

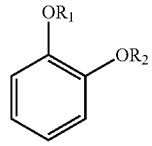

| compound | R1 | R2 | FD (%), mean ± SE (n = 25) | DC50, µg/cm2 (r2)b (n = 25) | mortality (%) (n = 3 × 10) | OD (%), mean ± SE (n = 25-33) |
|---|---|---|---|---|---|---|
| 1,2-dimethoxybenzene | CH3 | CH3 | 26.0 ± 17.6abcd | —c | — | — |
| 1,2-diethoxybenzene | C2H5 | C2H5 | -2.1 ± 18.6bcd | — | — | — |
| 1,2-dipropoxybenzene | C3H7 | C3H7 | 26.2 ± 17.6abcd | — | — | — |
| 1,2-dibutoxybenzene | C4H9 | C4H9 | 56.4 ± 13.8abcd | 43.8 (0.90) | 10.0 | 19.6 ( 14.4a |
| 1,2-diisopentoxybenzene | C5H11 | C5H11 | 69.9 ± 11.5abc | 19.6 (0.96) | 40.0 | 11.5 ( 13.8a |
| 1,2-diallyloxybenzene | C3H5 | C3H5 | 70.4 ± 13.2abc | 22.4 (0.99) | 20.0 | 15.0 ( 16.6a |
| Me library (1-methoxy-2-alkoxybenzeno) | CH3 | CH3, C2H5, C3H7, C4H9, C5H11 | 23.5 ± 15.9abcd | — | — | — |
| Et library (1-ethoxy-2-alkoxybenzene) | C2H5 | CH3, C2H5, C3H7, C4H9, C5H11 | 71.0 ± 10.6ab | 24.1 (0.95) | 6.7 | 28.7 ( 16.4a |
| Pr library (1-propoxy-2-alkoxybenzene) | C3H7 | CH3, C2H5, C3H7, C4H9, C5H11 | 100.0 ± 0.0a | 19.4 (0.89) | 13.8 | 31.7 ( 17.4a |
| Bu library (1-butoxy-2-alkoxybenzene) | C4H9 | CH3, C2H5, C3H7, C4H9, C5H11 | 98.0 ± 1.9a | 16.8 (0.90) | 6.7 | 28.7 ( 16.7a |

TABLE 5-continued

Bioactivities of 1,2-Dialkoxybenzene Libraries and Analogues (3a{$R_1$; $R_2$}) against Third Instar *T. ni* Larvae[a]

| compound | R1 | R2 | FD (%), mean ± SE (n = 25) | DC50, µg/cm2 (r2)b (n = 25) | mortality (%) (n = 3 × 10) | OD (%), mean ± SE (n = 25-33) |
|---|---|---|---|---|---|---|
| iPent library (1-isopentoxy-2-alkoxybenzene) | C5H11 | CH3, C2H5, C3H7, C4H9, C5H11 | 66.9 ± 12.7abc | 32.5 (0.90) | 10.0 | 29.4 ( 16.7a |
| allyl library (1-allyloxy-2-alkoxybenzene) | C3H7 | CH3, C2H5, C3H7, C4H9, C5H11 | 67.8 ± 13.5abc | 30.0 (0.90) | 23.3 | 66.7 ( 16.9a |
| 1-hydroxy-2-allyloxybenzene | H | | 31.1 ± 15.5abcd | — | — | — |
| 1-hydroxy-2-methoxybenzene | H | CH3 | −7.5 ± 19.8cd | — | — | — |
| 1-hydroxy-2-butoxybenzene | H | C4H9 | 12.0 ± 20.3bcd | — | — | — |
| 1-hydroxy-2-ethoxybenzene | H | C2H5 | −5.3 ± 19.8bcd | — | — | — |
| 1-hydroxy-2-propoxybenzene | H | C3H7 | −12.0 ± 20.0e | — | — | — | aFeeding deterrent (FD) effects (mean ± SE) at 50 µg/cm² are expressed in %. $DC_{50}$s (concentrations causing 50% feeding deterrence compared with the control) were calculated for samples showing >50% feeding deterrency in initial screening (≥50 µg/cm2) using Excel; linear regression analysis was conducted for all dose-response experimental data. Mortality and oviposition deterrent effects were determined at 0.25% for samples showing >50% feeding deterrency in initial screening. Means followed by the same letters within a column do not differ significantly (Tukey's test, $p < 0.05$).
bCoefficient of determination.
cNot tested.

Example 6

Comparison of Toxicity, Oviposition, and Feeding Deterrence Values of Test Compounds (Group I)

Toxicity and Oviposition Deterrence:
There was a very slight positive correlation (y=0.33x+18.0, $R^2$=0.18) although there were some strong deterrents that were not toxic in the data set. Feeding deterrence and oviposition deterrence: There was no correlation (y=−0.26x+48.0, $R^2$=0.04) within the data set. Feeding deterrence and toxicity: There was no correlation (y=0.07x+77.0, $R^2$=0.01) within the data set.

TABLE 6

Summary of Exemplary Feeding and Oviposition Deterrents, Grouped According to Their Contact Toxicity to Third Instar *T. ni* Larvae[a]

| Toxic lead compounds and mini libraries | | | | * | |
|---|---|---|---|---|---|
| Feeding deterrency | strong | strong | strong | strong | strong |
| Oviposition deterrency | strong | moderate | strong | strong | none |

$R_2$ = Me, Et, Pr, isopentyl
* moderate toxicity (58% mortality)

TABLE 6-continued

| | | | | | |
|---|---|---|---|---|---|
| Low toxicity lead compounds and mini libraries | [1,4-dipropoxybenzene] | [1-allyloxy-4-allyloxybenzene] | [1-allyloxy-4-butoxybenzene] | [4-allyloxyphenyl-OR$_2$] | [4-isopentyloxyphenyl-OR$_2$] |
| Feeding deterrency | strong | strong | strong | strong | strong |
| Oviposition deterrency | weak | weak | weak | none | weak |
| | [3-isopentyloxyphenyl-OR$_2$] | [2-propoxyphenyl-OR$_2$] | [2-butoxyphenyl-OR$_2$] | [2-allyloxyphenyl-OR$_2$] | |
| Feeding deterrency | strong | strong | strong | moderate | |
| Oviposition deterrency | moderate | moderate | moderate | strong | |

R$_2$ = Me, Et, Pr, Bu, isopentyl $^a$Compounds with >80% mortality were considered toxic and compounds with <25% mortality were considered of low toxicity. See Tables 1-3 for the activity data. Strong feeding deterrency, >80%; >60%. Strong oviposition deterrency, >50%; moderate, >25%; weak, >10%; none, <10%.

Example 7

Testing of Compounds of Group II for Toxicity, Oviposition and Feeding Deterrence Individual Compounds or Compound Sets (Group II)

All four of the dialkoxybenzene sets and thirteen individual compounds along with DEET exhibited >50% feeding deterrence at the initial screening concentration (50 µg/cm$^2$) and, therefore, were subjected to further testing (Table 8) against third instar $T.$ $ni$ larvae for toxic and oviposition deterrent effects. The response of larvae to sets or compounds at the initial screening concentration varied significantly in most cases (one-way ANOVA; $F_{18, 462}$=4.4, p<0.0001).

DC$_{50}$ values varied from 0.5-42.1 µg/cm$^2$ (Table 8). The compound 1-allyloxy-4-propoxybenzene, 3c{3,6}, had the lowest DC$_{50}$ value (0.5 µg/cm$^2$) followed by the 1-allyloxy-4-alkoxybenzene set (8.5 µg/cm$^2$), 3c{6,1-5}, which contains compound 3c{3,6}. DEET showed a DC$_{50}$ value of 46.7 µg/cm (Table 8).

At 0.25% the 1-allyloxy-3-ethoxyl-propoxybenzene set 3b{6,2-3} was the most toxic (65% mortality) followed by the 1-allyloxy-3-butoxy/isopentoxybenzene set 3b {6,4-5} (40% mortality) (Table 8). 1-Allyloxy-4-ethoxybenzene 3c{2,6} was the least toxic (6.7% mortality) in this group.

At 0.25% the 1-allyloxy-2-alkoxy benzene set 3a {6,1-5} showed the strongest oviposition deterrent effect (66.7%) (Table 8). Members of set 3c{6,1-5} with small alkoxy substituents (3c{1,6}, 3c{2,6} and 3c{3,6}) were poor oviposition deterrents (<30%). The meta substituted dialkoxybenzenes (3b compounds) were generally weak, with the strongest congeners being the ones with a molecular volume of 250-260 Å$^3$ and either an allyloxy or an isopentyloxy group (3b{1,5} and 3b {6,6} (25-30% oviposition deterrence).

TABLE 7

Libraries of ortho Claisen rearrangement products from 1-allyloxy-3-alkoxybenzenes.

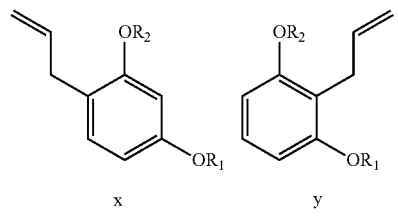

x        y

2:1

| Compound/sets [a] | $R_1$ [a] | $R_2$ [a] | F.D (%) [b] Mean ± SE N = 25 | $DC_{50}$ [c] µg/cm² ($R^2$) N = 25 | Mortality (%) [d] N = 3 × 10 | OD (%) [d] Mean ± SE N = 35-40 |
|---|---|---|---|---|---|---|
| 4b{1} | Me | H | 74 ± 11 [ABC] | 25 (0.98) | 20 | 12 ± 12 |
| 4b{2-3} | Et, Pr | H | 73 ± 11 [ABC] | 33 (0.99) | 70 | 31 ± 14 |
| 4b{4-5} | Bu, iPent | H | 66 ± 13 [ABC] | 26 (0.96) | 50 | 45 ± 15 |
| 5b{1, 1} | Me | Me | 77 ± 9 [ABC] | 25 (0.99) | 50 | −5 ± 13 |
| 5b{1, 2-3} | Et, Pr | Me | 74 ± 11 [ABC] | 23 (0.98) | 65 | 19 ± 15 |
| 5b{1, 4-5} | Bu, iPent | Me | 41 ± 16 [ABC] | — | — | — |
| 5b{2, 1} | Me | Et | 93 ± 5 [AB] | 24 (0.89) | 3.6 | −2 ± 13 |
| 5b{2, 2-3} | Et, Pr | Et | 79 ± 10 [ABC] | 17 (0.99) | 20 | 28 ± 14 |
| 5b{2, 4-5} | Bu, iPent | Et | 81 ± 11 [ABC] | 15 (0.95) | 10 | −24 ± 13 |
| 5b{3, 1} | Me | Pr | 100 ± 0 [A] | 16 (0.90) | 3.6 | −11 ± 15 |
| 5b{3, 2-3} | Et, Pr | Pr | 93 ± 5 [AB] | 8.7 (0.85) | 10 | 5 ± 13 |
| 5b{3, 4-5} | Bu, iPent | Pr | 33 ± 16 [BC] | — | — | 34 ± 15 |
| 5b{3, 2} | Et | Pr | 92 ± 6 [AB] | 17 (0.79) | 0.6 | 25 ± 13 |
| 5b{4, 1} | Me | Bu | 60 ± 16 [ABC] | 27 (0.90) | 10 | 13 ± 14 |
| 5b{4, 2-3} | Et, Pr | Bu | 54 ± 16 [ABC] | 49 (0.96) | 6.7 | 9 ± 13 |
| 5b{4, 4-5} | Bu, iPent | Bu | 26 ± 16 [C] | — | — | 18 ± 14 |
| 5b{5, 1} | Me | iPent | 71 ± 14 [ABC] | 19 (0.93) | 16 | 51 ± 14 |
| 5b{5, 2-3} | Et, Pr | iPent | 79 ± 9 [ABC] | 24 (0.98) | 6.7 | 15 ± 14 |
| 5b{5, 4-5} | Bu, iPent | iPent | 41 ± 17 [ABC] | — | — | — |
| 5b{6, 1} | Me | allyl | 76 ± 12 [ABC] | 21 (0.97) | 25 | 50 ± 14 |
| 5b{6, 2-3} | Et, Pr | allyl | 90 ± 8 [AB] | 16 (0.96) | 33 | 8 ± 13 |
| 5b{6, 4-5} | Bu, iPent | allyl | 57 ± 15 [ABC] | 43 (0.96) | 33 | 19 ± 13 |
| Second lots and purified isomers of 5b{n,1} or 5b{3, 2} compounds | | | | | | |
| 5b{1, 1} [e] | Me | Me | 58 ± 15 [ABC] | 39 (0.97) | −2.9 | 10 ± 15 |
| 5b{3, 1} [e] | Me | Pr | 91 ± 6 [AB] | 26 (0.96) | 10 | 7 ± 11 |
| 5b{3, 1} y [f] (100% y) | Me | Pr | 100 ± 0 [A] | 14 (0.98) | −4.2 | 17 ± 14 |
| 5b{3, 1} x [f] (68% x, 32% y) | Me | Pr | 68 ± 12 [ABC] | 24 (0.76) | −32 | 0 |
| 5b{3, 2} [g] | Et | Pr | 92 ± 6 [AB] | 17 (0.79) | 0.6 | 25 ± 13 |
| 5b{3, 2} y [f] (100% y) | Et | Pr | 74 ± 14 [ABC] | 27.6 (0.99) | 0 | −6.4 ± 11.4 |
| 5b{3, 2} y [f] (82% x, 18% y) | Et | Pr | 95 ± 3 [AB] | 25 (0.98) | 0 | 26 ± 8 |
| 5b{5, 1} [e] | Me | iPent | 99 ± 1 [A] | 4 (0.98) | 6.0 ± | 32 ± 12 |
| 5b{6, 1} [e] | Me | allyl | 92 ± 6 [AB] | 23 (0.92) | −1.6 ± | 10 ± 14 |

[a] Me = methyl, Et = ethyl, Pr = propyl, Bu = n-butyl, iPent = isopentyl (= 3-methylbutyl). For 5b sets, the code is 5b{$R_2$, $R_1$} (Scheme 1). The compounds are a mixture of isomers x and y in a ratio of x:y 2:1.
[b] Feeding deterrent effects (Mean ± SE) at 50 µg/cm² are expressed in %. Means followed by the same capitalized letters within a column do not differ significantly (One-way ANOVA, $F_{27, 684}$ = 3.2, p < 0.0001; Tukey's test, p < 0.05).
[c] $DC_{50}$s (concentrations causing 50% feeding deterrence compared with the control) were calculated for samples showing >50% feeding deterrence in initial screening concentration (50 µg/cm²), using Excel. Linear regression analysis was conducted for all dose-response experimental data. The $R^2$ values for the linear regressions are shown in parenthesis after the number.
[d] Mortality and oviposition deterrent (OD) effects were determined at 0.25% for samples showing >50% feeding deterrence in initial screening.
[e] These lots were prepared on a larger scale than previously (22), and the ratios of x:y were: 5b{1, 1} 1.8:1, 5b{3, 1} 1.2:1, 5b{3, 2} 2.3:1, 5b{5, 1} 1.8:1, 5b{6, 1} 2.3:1.
[f] The isomers were separated on a column of silica/silver nitrate (see methods).
[g] Same set as listed above with the sets, provided for convenience.
— not tested

TABLE 8

Activity of individual compounds or compound sets of compound set B or precursor sets for the Claisen rearrangements and subsequent alkylations. The activities of the products of those reactions are shown in Tables 9, 10 and 7. Compounds were synthesized, as shown in Scheme 1A.

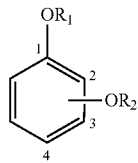

a = ortho, $OR_2$ at position 2
b = meta, $OR_2$ at position 3
c = para, $OR_2$ at position 4

| Compound/sets | $R_1$[a] | $R_2$[a] | F.D (%)[b] Mean ± SE N = 25 | $DC_{50}$[c] µg/cm$^2$ ($R^2$) N = 25 | Mortality (%)[d] N = 3 × 10 | OD (%)[d] Mean ± SE N = 35-40 |
|---|---|---|---|---|---|---|
| 3a{3, 6} | Allyl | Propyl | 96 ± 3 [A] | 12 (0.98) | 17 | 28 ± 13 |
| 3a{3, 6} | " | " | 97 ± 15 [A] | 16 (0.92) | 10 | 12 ± 13 |
| 3a{4, 6} | Allyl | Butyl | 92 ± 6 [A] | 17 (0.96) | 19 | 35 ± 17 |
| 3a{3, 4} | Propyl | Butyl | 98 ± 2 [A] | 21 (0.97) | 19 | 37 ± 14 |
| 3a{6, 1-5} | Allyl | Me, Et, Pr, Bu, iPent | 68 ± 12 [AB] | 30 (0.90) | 23 | 67 ± 15 |
| 3a{5, 6} | Allyl | iPent | — | — | — | 26 ± 13.5 |
| 3b{3, 5} | Propyl | iPent | 97 ± 3 [A] | 17 (0.98) | 10 | 9 ± 17 |
| 3b{1, 5} | Methyl | iPent | 89 ± 7 [A] | 29 (0.96) | 30 | 30 ± 14 |
| 3b{1, 6} | Methyl | Allyl | 66 ± 12 [AB] | 34 (0.89) | 33 | 9 ± 14 |
| 3b{6, 2-3} | Allyl | Et, Pr | 64 ± 12 [AB] | 42 (0.93) | 65 | −9 ± 14 |
| 3b{6, 4-5} | Allyl | Bu, iPent | 69 ± 11 [AB] | 32 (0.89) | 40 | −1 ± 15 |
| 3b{6, 6} | Allyl | Allyl | 97 ± 3 [A] | 20 (0.98) | 13 | 26 ± 16 |
| 3b{5, 6} | Allyl | iPent | — | — | — | 10 ± 13 |
| 2b{6} | H | Allyl | 36 ± 10 [B] | — | — | 5 ± 13 |
| 3c{6, 1-5} | Allyl | Me, Et, Pr, Bu, iPent | 100 ± 0 [A] | 9 (0.99) | 7 | 46 ± 15 |
| 3c{1, 6} | Methyl | Allyl | 62 ± 15 [AB] | 30 (0.96) | 6 | 13 ± 13 |
| 3c{2, 6} | Ethyl | Allyl | 73 ± 12 [AB] | 30 (0.98) | −5 | 17 ± 14 |
| 3c{3, 6} | Propyl | Allyl | 100 ± 0 [A] | 0.5 (0.98) | −11 | 21 ± 14 |
| 3c{5, 6} | iPent | Allyl | — | — | — | −25 ± 12 |
| 3c{2, 3} | Ethyl | Propyl | 100 ± 0 [A] | 33.3 (0.99) | 17 | 10 ± 13 |
| DEET | not applicable | | 60 ± 15 [AB] | 47 (0.98) | 7 | 23 ± 14 |

[a] Me = methyl, Et = ethyl, Pr = propyl, Bu = n-butyl, iPent = isopentyl (= 3-methylbutyl).
[b] Feeding deterrent effects (Mean ± SE) at 50 µg/cm$^2$ are expressed in %. Means followed by the same capitalized letters within a column do not differ significantly (One-way ANOVA, $F_{18, 462}$ = 4.4, $p < 0.0001$; Tukey's test, $p < 0.05$).
[c] $DC_{50}$s (concentrations causing 50% feeding deterrence compared with the control) were calculated for samples showing >50% feeding deterrence in initial screening concentration (50 µg/cm$^2$), using Excel. Linear regression analysis was conducted for all dose-response experimental data. The $R^2$ values for the linear regressions are shown in parenthesis after the number.
[d] Mortality and oviposition deterrent (OD) effects were determined at 0.25% for samples showing >50% feeding deterrence in initial screening.
— not tested Libraries of ortho Claisen Rearrangement Products from 1-allyloxy-2-alkoxybenzenes The 5a {1,1-5} mini library had the lowest $DC_{50}$ value (16 µg/cm$^2$) followed by 5a{2,1-5} and 4a{1-5}(—20 µg/cm$^2$) (Table 9). A structure-activity relationship was observed among these compounds: small $R_2$ groups (H, methyl or maximally ethyl) gave high feeding deterrence. This activity was lost somewhat with a one or more carbon increase in the size of group $R_2$.

Set 5a{3,1-5} was the most toxic (Table 9) at 0.25% (47% mortality). A structure-activity relationship could be seen, with $R_2$=propyl being most toxic and $R_2$ groups smaller or larger than that being less toxic. At 0.25% the sets 5a{1,1-5} and 5a{2,1-5} caused ~30% oviposition deterrence (Table 9).

TABLE 9

Libraries of ortho Claisen rearrangement products from 1-allyloxy-2-alkoxybenzenes.

| Compound/sets | $R_2$[a] | F.D (%)[b] Mean ± SE N = 25 | $DC_{50}$[c] µg/cm$^2$ ($R^2$) N = 25 | Mortality (%)[d] N = 3 × 10 | OD (%)[d] Mean ± SE N = 35-40 |
|---|---|---|---|---|---|
| 4a{1-5} | H | 100 ± 0 [A] | 20.6 (0.92) | 17 | 7 ± 15 |
| 5a{1, 1-5} | Me | 100 ± 0 [A] | 15.5 (0.86) | 17 | 32 ± 15 |
| 5a{2, 1-5} | Et | 100 ± 0 [A] | 20.0 (0.91) | 27 | 31 ± 15 |

TABLE 9-continued

Libraries of ortho Claisen rearrangement products from 1-allyloxy-2-alkoxybenzenes.

| Compound/ sets | $R_2$ [a] | F.D (%) [b] Mean ± SE N = 25 | $DC_{50}$ [c] μg/cm$^2$ ($R^2$) N = 25 | Mortality (%) [d] N = 3 × 10 | OD (%) [d] Mean ± SE N = 35-40 |
|---|---|---|---|---|---|
| 5a{3, 1-5} | Pr | 31 ± 15 [B] | — | 47 | — |
| 5a{4, 1-5} | Bu | 6 ± 17 [B] | — | 1 | — |
| 5a{5, 1-5} | iPent | 22 ± 16 [B] | — | 7 | — |
| 5a{6, 1-5} | allyl | 22 ± 18 [B] | — | 7 | — |

[a] Me = methyl, Et = ethyl, Pr = propyl, Bu = n-butyl, iPent = isopentyl (= 3-methylbutyl). For 5a sets, the code is 5a{$R_2$, $R_1$} (Scheme 1).
[b] Feeding deterrent effects (Mean ± SE) at 50 μg/cm$^2$ are expressed in %. Means followed by the same capitalized letters within a column do not differ significantly (One-way ANOVA, $F_{6, 173}$ = 12.5, p < 0.0001; Tukey's test, p < 0.05).
[c] $DC_{50}$s (concentrations causing 50% feeding deterrence compared with the control) were calculated for samples showing >50% feeding deterrence in initial screening concentration (50 μg/cm$^2$), using Excel. Linear regression analysis was conducted for all dose-response experimental data. The $R^2$ values for the linear regressions are shown in parenthesis after the number.
[d] Mortality and oviposition deterrent (OD) effects were determined at 0.25% for samples showing >50% feeding deterrence in initial screening.
— not tested

Libraries of Ortho Claisen Rearrangement Products from 1-allyloxy-4-alkoxybenzenes Set 5c{3,1} had the lowest $DC_{50}$ value (9 μg/cm$^2$) while 4c{1-5} had the highest $DC_{50}$ value (57 μg/cm$^2$). There was a moderate structure-activity relationship among the sets 5c{$R_2$,1-5}, with a$R_2$=butyl or allyl being less active than $R_2$=methyl, ethyl, propyl or isopentyl. Compounds 5c{3,1} and 5c{1,1} were more active than the entire 5c{3,1-5} or 5c{1,1-5} sets, respectively. Because sets and compounds were tested at the same concentration by weight, this result suggests that the activity detected for the sets came mostly from the most active component. Overall, the structure-activity suggests that good feeding deterrents in the 5c group have an odd-numbered (methyl or propyl) or branched (isopentyl) $R_2$ alkyl group and with a small $R_1$ (methyl) group.

Compound set 6c{1-5} was formed during the synthesis of 5c libraries (in cases when the Claisen reaction was left too long). The cyclic portion of compounds 6c{1-5} resembles a branched chain, and could fit the same type of site as the 5c compounds.

At 0.25% set 5c{1,1} was the most toxic with 38.9% mortality followed by 5c{5,1-5} (Table 10). Other members in the group exhibited <26% mortality (Table 10). Set 5c{2,1-5} demonstrated strong oviposition deterrent activity (63.6%) followed by 4c{1-5} (51.4%) and 5c{1,1-5} (37%). There was some structure-activity relationship with respect to oviposition deterrence, with the optimal $R_2$ alkyl group being ethyl: smaller or larger was less effective. Set 6c{1-5} acted as a moderate oviposition stimulant. Other libraries had modest oviposition deterrent activities (Table 10).

TABLE 10

Libraries of ortho Claisen rearrangement products from 1-allyloxy-4-alkoxybenzenes.

| Compound/ sets | $R_2$ [a] | F.D (%) [b] Mean ± SE N = 25 | $DC_{50}$ [c] μg/cm$^2$ ($R^2$) N = 25 | Mortality (%) [d] N = 3 × 10 | OD (%) [d] Mean ± SE N = 35-40 |
|---|---|---|---|---|---|
| 4c{1-5} | H | 51 ± 18 [ABC] | 57 (0.92) | 3.3 | 51 ± 17 |
| 5c{1, 1} | Me | 80 ± 11 [AB] | 20 (0.88) | 39 | 14 ± 12 |
| 5c{1, 1-5} | Me | 68 ± 12 [ABC] | 19 (0.94) | 17 | 37 ± 15 |
| 5c{2, 1-5} | Et | 66 ± 14 [ABC] | 22 (0.95) | 3.3 | 64 ± 17 |
| 5c{3, 1} | Pr | 92 ± 6 [A] | 9.4 (0.90) | 6.4 | 7 ± 15 |
| 5c{3, 1-5} | Pr | 65 ± 11 [ABC] | 33 (0.98) | 17 | 21 ± 14 |
| 5c{4, 1-5} | Bu | 23 ± 16 [C] | — | — | -14 ± 13 |
| 5c{5, 1-5} | iPent | 83 ± 12 [AB] | 15 (0.85) | 27 | 20 ± 15 |
| 5c{6, 1-5} | allyl | 29 ± 11 [BC] | — | — | — |
| 6c{1-5} | cyclic | 100 ± 0 [A] | 16 (0.95) | 1.0 | -12 ± 13 |

[a] Me = methyl, Et = ethyl, Pr = propyl, Bu = n-butyl, iPent = isopentyl (= 3-methylbutyl). For 5c sets, the code is 5c{$R_2$, $R_1$} (Scheme 1).
[b] Feeding deterrent effects (Mean ± SE) at 50 μg/cm$^2$ are expressed in %. Means followed by the same capitalized letters within a column do not differ significantly (One-way ANOVA, $F_{9-241}$ = 4.3, p < 0.0001; Tukey's test, p < 0.05).
[c] $DC_{50}$s (concentrations causing 50% feeding deterrence compared with the control) were calculated for samples showing >50% feeding deterrence in initial screening concentration (50 μg/cm$^2$), using Excel. Linear regression analysis was conducted for all dose-response experimental data. The $R^2$ values for the linear regressions are shown in parenthesis after the number.
[d] Mortality and oviposition deterrent (OD) effects were determined at 0.25% for samples showing >50% feeding deterrence in initial screening.
— not tested

Libraries of Ortho Claisen Rearrangement Products from 1-allyloxy-3-alkoxybenzenes Set 5b {5,1}, a mixture of two isomeric compounds (Table 7), exhibited the lowest $DC_{50}$ value (4 μg/cm$^2$), in one trial. A different lot of set 5b {5,1} exhibited a higher $DC_{50}$ value (16 μg/cm$^2$). With respect to feeding deterrence there were observed structure-activity relationships. For group $R_2$, propyl gave the best results, and the smaller (methyl, ethyl or allyl) or larger (butyl or isopentyl) groups gave lower feeding deterrence. For group $R_1$ the structure-activity relationship was clear: within each group with $R_2$ constant, there was a decrease in activity in going from $R_1$=methyl to the larger groups. For cases in which isomers x and y were separated, the more compact isomer y was more active as a feeding deterrent than isomer x.

Compound 4b{2-3} was the most toxic, causing 70% mortality at 0.25% (Table 7). Thus group $R_2$=H or methyl gave high mortality. For the larger $R_2$ sets, mortality was lower, and there was a slight pattern with respect to group $R_1$ within each group with constant $R_2$ (ethyl or propyl): the set with $R_1$=ethyl/propyl was more toxic than the set with $R_1$=methyl.

5b {5,1} and 5b {6,1} demonstrated the strongest oviposition deterrent effects (50%). Set 5b{2,4-5} acted as a mild oviposition stimulant (Table 7). There were observed structure-activity patterns in the oviposition data. Among the 4b sets, oviposition deterrence increased with increasing size of group $R_1$. Also in the 5b sets when $R_2$=methyl, ethyl or propyl, there was an increase in oviposition deterrence going from $R_1$=methyl to $R_1$=ethyl/propyl, but when $R_2$=isopentyl or allyl, there was a decrease in oviposition deterrence going from $R_1$=methyl to $R_1$=ethyl/propyl or butyl/isopentyl. In the $R_2$=butyl sets, oviposition deterrence was the same for all $R_1$ groups.

Example 8

Comparison of Toxicity, Oviposition and Feeding Deterrence of Compounds (Group II)

There was no correlation between toxicity and oviposition deterrence (y=−0.0738x+20.582, $R^2$=0.0044) within the data sets. Similarly, there was no correlation between feeding deterrence and oviposition deterrence (y=−0.2005x+25.333, $R^2$=0.0368) within the data sets. Further, there was no correlation between toxicity and feeding deterrence (y=−0.0235x+ 20.565, $R^2$=0.0006).

Table 11 provides a list of exemplary non-toxic oviposition deterrents.

TABLE 11

Non-toxic oviposition deterrents

| Group | compound | % deterrence | % mortality | Index = deterrence/mortality | Table |
|---|---|---|---|---|---|
| II | 5c{2, 1-5} | 64 | 3 | 21 | 10 |
| II | 4c{1-5} | 51 | 3 | 17 | 10 |
| I | 3b{1, 1-5} | 70 | 17 | 4.1 | 4 |
| II | 5b{5, 1} | 51 | 16 | 3.1 | 7 |
| I | 3a{6, 1-5} | 67 | 23 | 2.9 | 5 |
| II | butyl eugenol | 34 BL | 15 | 2.2 | 5 |
| II | 5c{1, 1-5} | 37 BL | 17 | 2.1 | 10 |
| II | 5b{6, 1} | 50 | 25 | 2 | 7 |
| II | 3a{3, 4} | 37 BL | 19 | 1.9 | 8 |
| II | 3a{4, 6} | 35 BL | 19 | 1.8 | 8 |
| II | 4b{4-5} | 45 | 50 | 0.9 | 7 |
| I | 3c{4, 1-5} | 50 | 58 | 0.86 | 3 |
| I | 3c{2, 2} | 75 | 100 | 0.75 | 3 |
| I | 3c{2, 1-5} | 57 | 97 | 0.58 | 3 |

Table 12 provides a list of exemplary non-toxic feeding deterrents.

TABLE 12

Non-toxic feeding deterrents

| Group | compound | % deterrence | $DC_{50}$ | % mortality | Index = FD/ ($DC_{50}$ × mortality) |
|---|---|---|---|---|---|
| II | 3c{3, 6} | 100 | 0.5 | −11 [b] | 2000 |
| II | 5b{3, 1}y | 100 | 14 | −4.2 [b] | 71 |
| II | 5b{6, 1} | 92 | 23 | −2 [b] | 40 |
| II | 5b{3, 2}x | 95 | 25 | 0 [b] | 38 |
| II | 5b{3, 2} | 92 | 17 | 0.6 | 9 |
| II | 5b{3, 2} | 92 | 17 | 0.6 | 9 |
| II | 6c{1-5} | 100 | 16 | 1 | 6.3 |
| II | 5b{5, 1} | 99 | 4 | 6 | 4 |
| II | 5c{3, 1} | 92 | 9 | 6 | 1.7 |
| II | 3c{6, 1-5} | 100 | 9 | 7 | 1.6 |
| II | 5b{3, 1} | 100 | 16 | 4 | 1.6 |
| II | 5b{2, 1} | 93 | 24 | 4 | 1 |
| II | 5b{3, 2-3} | 93 | 9 | 10 | 1 |
| I | 3c{5, 1-5} | 100 | 6 | 19 | 0.9 |
| I | 3a{4, 1-5} | 98 | 17 | 7 | 0.8 |
| II | 3b{3, 5} | 97 | 17 | 10 | 0.6 |
| II | 3a{3, 6} | 96 | 12-16 [a] | 10-17 [a] | 0.5 |
| II | 5b{2, 4-5} | 81 | 15 | 10 | 0.5 |
| I | 3a{3, 1-5} | 100 | 19 | 14 | 0.4 |
| II | 3b{6, 6} | 97 | 20 | 13 | 0.4 |
| II | 5a{1, 1-5} | 100 | 16 | 17 | 0.4 |
| II | 5b{3, 1} | 91 | 26 | 10 | 0.35 |
| II | 3a{4, 6} | 92 | 17 | 19 | 0.3 |
| II | 4a{1-5} | 100 | 21 | 17 | 0.3 |
| II | allyl | 86 | 15 | 18 | 0.3 |
| I | 3c{6, 6} | 97 | 24 | 16 | 0.25 |
| II | 3a{3, 4} | 98 | 21 | 19 | 0.25 |
| I | 3c{3, 3} | 96 | 20 | 23 | 0.2 |
| I | 3b{4, 1-5} | 84 | 14 | 30 | 0.2 |
| I | 3b{5, 1-5} | 83 | 20 | 21 | 0.2 |
| II | 5c{5, 1-5} | 83 | 15 | 27 | 0.2 |
| II | 5b{6, 2-3} | 90 | 16 | 33 | 0.2 |
| II | 5a{2, 1-5} | 100 | 20 | 27 | 0.19 |
| II | 3c{2, 3} | 100 | 33 | 17 | 0.18 |
| I | 3c{1, 1-5} | 80 | 35 | 23 | 0.1 |
| I | 3c{4, 1-5} | 83 | 15 | 58 | 0.1 |
| II | 3b{1.5} | 89 | 29 | 30 | 0.1 |
| II | 5c{1, 1} | 80 | 20 | 39 | 0.1 |
| I | 3b{3, 1-5} | 98 | 22 | 50 | 0.09 |
| I | 3b{2, 2} | 89 | 29 | 37 | 0.08 |
| I | 3b{3, 3} | 97 | 27 | 77 | 0.05 |
| I | 3c{2, 1-5} | 91 | 23 | 97 | 0.04 |
| I | 3c{2, 2} | 81 | 26 | 100 | 0.03 |

[a] Used the average
[b] Used 0.1, in order to get meaningful values

Example 9

Comparison of Feeding Deterrence with Botanical Insecticides

Based upon antifeedant activity, the compounds/libraries of possess levels of activity that compare to some of the most active botanical insecticides in current use. One of the compounds, 3c{3,6} in the group is more active than pyrethrum ($DC_{50}$=0.9 μg/cm$^2$) on third instar *T. ni* larvae using the feeding deterrent bioassay. Similarly, other compounds/libraries including 5c{3,1}, 3c{6,1-5}, 5b{3,2-3} and 5b {5,1} x+y were more active than rotenone against third instar, *T. ni* larvae. All of the compounds/libraries were more active than rosemary oil ($DC_{50}$ value of 158 μg/cm$^2$), clove leaf oil ($DC_{50}$ value of 217 μg/cm$^2$), *Melia azedarach* ($DC_{50}$=288 μg/cm$^2$), *Trichilia americana* ($DC_{50}$=190 μg/cm$^2$) and ryania ($DC_{50}$=725 μg/cm$^2$) (Akhtar et al. 2008).

Example 10

Comparison of Compounds (Group II) with DEET

Many of the pure compounds and libraries were more active than a commercial insect repellent, DEET, as feeding and/or oviposition deterrents against *T. ni* larvae and adult female moths, respectively. DEET exhibited the highest $DC_{50}$ value (47 μg/cm$^2$) in the whole group (Table 8) as opposed to the low $DC_{50}$ value of 0.5 μg/cm$^2$ exhibited by 3c{3,6}.

Example 11

Test of Compound 3c{3,6} on *T. ni* neonates in Greenhouse

Figure 3:
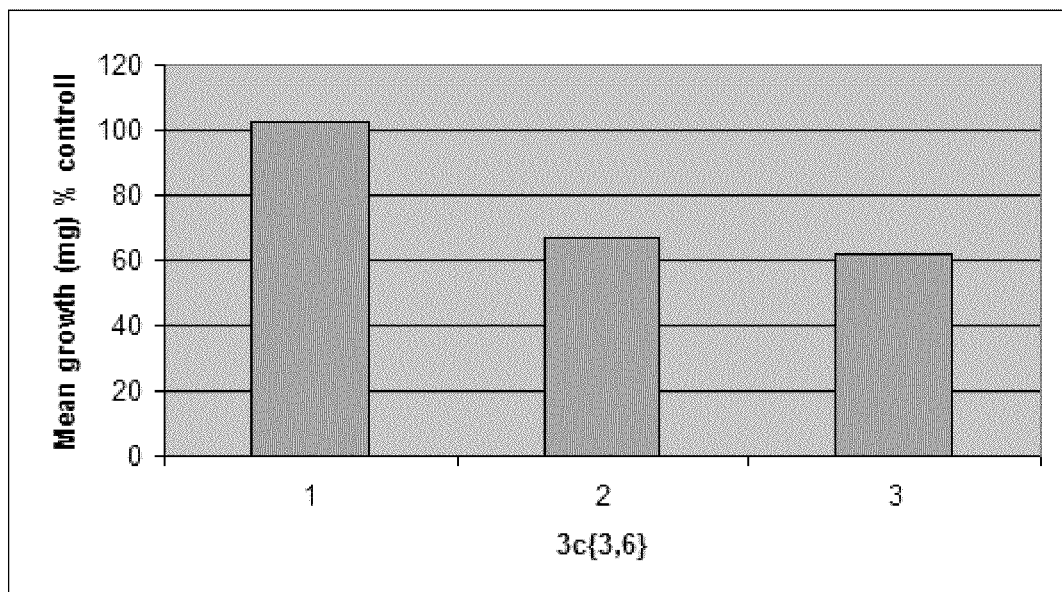
FIG. 3 is a graph showing the mean weight gain of *T. ni* larvae exposed to cabbage plants that had been treated with compound 3c{3,6}. Three doses were tested: 1=0.0002% (2 ppm), 2=0.0005% (5 ppm), 3=0.001% (10 ppm). Data are given as a percentage of the control, larvae that were feeding on untreated plants.
Figure 4:
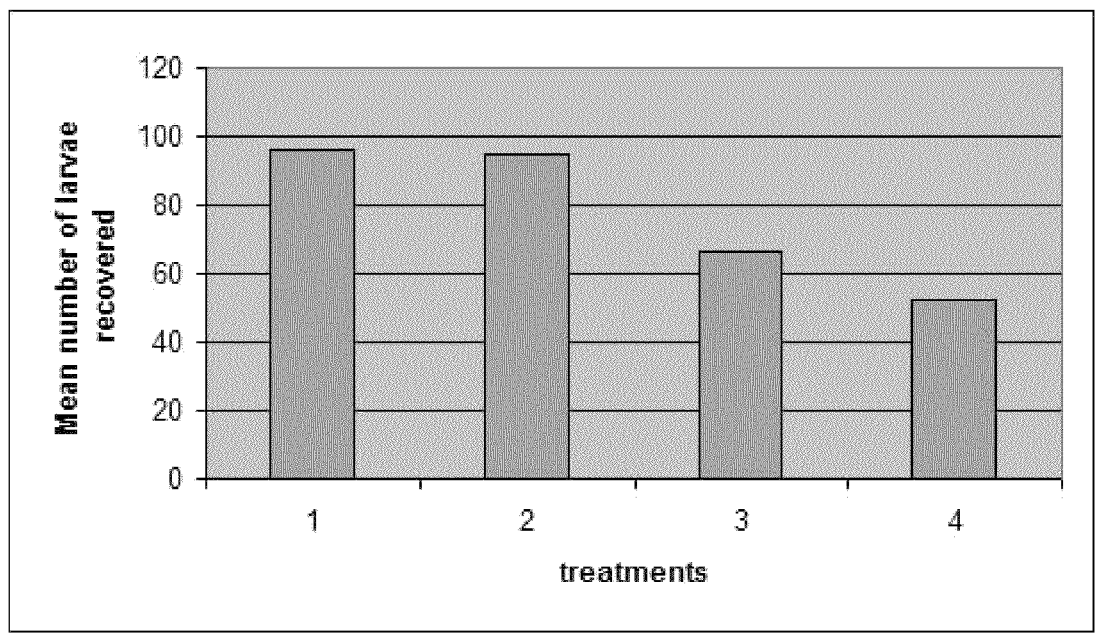
FIG. 4 is a graph showing the number of larvae recovered after 6 days in a greenhouse on cabbage plants. Column 1=non-treated control; columns 2-4 plants treated with 3c{3, 6} in three doses: 2=0.0002%, 3=0.0005%, 4=0.001%.

The compound 1-allyloxy-4-propoxybenzene, 3c{3,6}, was tested in the Greenhouse at 3 different concentrations (2 μg, 5 μg and 10 μg). Concentrations in % are as follows: 0.0002%, 0.005% and 0.01%. Cabbage plants had 3-5 leaves. Each plant was sprayed (~1 ml/leaf) and dried before the introduction of insects. There were 3 replicates of 5 plants for each treatment. Approximately nine *T. ni* neonates (<24 h old) were transferred on each plant. They were weighed after 6 days of feeding on the treatments. Numbers of larvae recovered from each treatment were also recorded. The results indicate that weight of the larvae was not affected at the lowest concentration (0.0002%), but that the weight reduction was 33.3% and 48% at 0.0005 and 0.001%, respectively (FIG. 3). This suggests that larvae are feeding less and, therefore, gaining less weight. The mean larval recovery was not affected at the lowest concentration (0.0002%). However, mean larval recovery was 66.7% and 52% at 0.0005 and 0.001%, respectively (FIG. 4). This suggests that some of the larvae were not surviving.

The highest concentration of the compound used in the experiment was 10 ppm. A growth reduction of ~50% and larval recovery was observed at this concentration. For comparison, the amount of active ingredient in most of the commercial insecticides varies from 24-24000 ppm.

Table 13 provides a list of the test compounds of Group I.

TABLE 13

| | Test Compounds Group I | | | |
|---|---|---|---|---|
| Table Reference | Compound name (IUPAC) | $R_1$ | $R_2$ | Name |
| Table 3 | 1,4-dimethoxybenzene | methyl | methyl | 3c{1, 1} |
| | 1,4-diethoxybenzene | ethyl | ethyl | 3c{2, 2} |
| | 1,4-dipropoxybenzene | propyl | propyl | 3c{3, 3} |
| | 1,4-diisopentoxybenzene | isopentyl | isopentyl | 3c{5, 5} |
| | 1,4-diallyloxybenzene | allyl | allyl | 3c{6, 6} |
| | Me library (1-methoxy-4-alkoxybenzene) | methyl | methyl, ethyl, propyl, isopentyl | 3c{1, 1-5} |
| | Et library (1-ethoxy-4-alkoxybenzene) | ethyl | methyl, ethyl, propyl, isopentyl | 3c{2, 1-5} |
| | Pr library (1-propoxy-4-alkoxybenzene) | propyl | methyl, ethyl, propyl, isopentyl | 3c{3, 1-5} |
| | Bu library (1-butoxy-4-alkoxybenzene) | butyl | methyl, ethyl, propyl, isopentyl | 3c{4, 1-5} |
| | iPent library (1-isopentyloxy-4-alkoxybenzene) | isopentyl | methyl, ethyl, propyl, isopentyl | 3c{5, 1-5} |
| | allyl small library (1-allyloxy-4-alkoxybenzene) | allyl | methyl, ethyl, propyl | 3c{6, 1-3} |
| | 1-allyloxy-4-butoxybenzene | allyl | butyl | 3c{4, 6} |
| | 1-allyloxy-4-isopetoxybenzene | allyl | isopentyl | 3c{5, 6} |
| | 1-hydroxy-4-methoxybeznene | H | methyl | 2c{1} |
| | 1-hydroxy-4-ethoxybeznene | H | ethyl | 2c{2} |
| | 1-hydroxy-4-propoxybenzene | H | propyl | 2c{3} |
| | 1-hydroxy-4-isopentoxybenzene | H | isopentyl | 2c{5} |
| Table 4 | 1,3-dimethoxybenzene | methyl | methyl | 3b{1, 1} |
| | 1,3-diethoxybenzene | ethyl | ethyl | 3b{2, 2} |
| | 1,3-dipropoxybenzene | propyl | propyl | 3b{3, 3} |
| | 1,3-diisopentoxybenzene | isopentyl | isopentyl | 3b{5, 5} |
| | Me library (1-methoxy-3-alkoxybenzene) | methyl | methyl, ethyl, propyl, isopentyl | 3b{1, 1-5} |
| | Et library (1-ethoxy-3-alkoxybenzene) | ethyl | methyl, ethyl, propyl, isopentyl | 3b{2, 1-5} |
| | Pr library (1-propoxy-3-alkoxybenzene) | propyl | methyl, ethyl, propyl, isopentyl | 3b{3, 1-5} |
| | Bu library (1-butoxy-3-alkoxybenzene) | butyl | methyl, ethyl, propyl, isopentyl | 3b{4, 1-5} |
| | iPent library (1-isopentyloxy-3-alkoxybenzene) | isopentyl | methyl, ethyl, propyl, isopentyl | 3b{5, 1-5} |
| | 1-hydroxy-3-methoxybenzene | H | methyl | 2b{1} |
| | 1-hydroxy-3-ethoxybeznene | H | ethyl | 2b{2} |
| | 1-hydroxy-3-propoxybenzene | H | propyl | 2b{3} |
| | 1-hydroxy-3-isopentoxybenzene | H | isopentyl | 2b{5} |
| Table 5 | 1,2-dimethoxybenzene | methyl | methyl | 3a{1, 1} |
| | 1,2-diethoxybenzene | ethyl | ethyl | 3a{2, 2} |
| | 1,2-dipropoxybenzene | propyl | propyl | 3a{3, 3} |
| | 1,2-dibutoxybenzene | butyl | butyl | 3a{4, 4} |
| | 1,2-diisopentoxybenzene | isopentyl | isopentyl | 3a{5, 5} |
| | 1,2-diallyloxybenzene | allyl | allyl | 3a{6, 6} |
| | Me library (1-methoxy-2-alkoxybenzene) | methyl | methyl, ethyl, propyl, butyl, isopentyl | 3a{1, 1-5} |
| | Et library (1-ethoxy-2-alkoxybenzene) | ethyl | methyl, ethyl, propyl, butyl, isopentyl | 3a{2, 1-5} |
| | Pr library (1-propoxy-2-alkoxybenzene) | propyl | methyl, ethyl, propyl, butyl, isopentyl | 3a{3, 1-5} |
| | Bu library (1-butoxy-2-alkoxybenzene) | butyl | methyl, ethyl, propyl, butyl, isopentyl | 3a{4, 1-5} |
| | iPent library (1-isopentyloxy-2- | isopentyl | methyl, ethyl, propyl, butyl, isopentyl | 3a{5, 1- |

TABLE 13-continued

Test Compounds Group I

| Table Reference | Compound name (IUPAC) | R₁ | R₂ | Name |
|---|---|---|---|---|
| | alkoxybenzene) | | | 5} |
| | allyl library (1-allyloxy-2-alkoxybenzene) | allyl | methyl, ethyl, propyl, butyl, isopentyl | 3a{6, 1-5} |
| | 1-hydroxy-2-allyloxybenzene | H | allyl | 2a{6} |
| | 1-hydroxy-2-methoxybenzene | H | methyl | 2a{1} |
| | 1-hydroxy-2-ethoxybeznene | H | ethyl | 2a{2} |
| | 1-hydroxy-2-propoxybenzene | H | propyl | 2a{3} |
| | 1-hydroxy-2-butoxybenzene | H | butyl | 2a{4} |
| Table 6 (list of most active compounds, listed in order of the table, from top left across the first row, then across the second row and across the third row) | 1,2-diethoxybenzene | ethyl | ethyl | 3c{2, 2} |
| | 1,3-dipropoxybenzene | propyl | propyl | 3b{3, 3} |
| | 1-ethoxy-4-alkoxybenzene | ethyl | methyl, ethyl, propyl, isopentyl | 3c{2, 1-5} |
| | 1-butoxy-4-alkoxybenzene | butyl | methyl, ethyl, propyl, isopentyl | 3c{4, 1-5} |
| | 1-propoxy-3-alkoxybenzene | propyl | methyl, ethyl, propyl, isopentyl | 3b{3, 1-5} |
| | 1,4-dipropoxybenzene | propyl | propyl | 3c{3, 3} |
| | 1,4-diallyloxybenzene | allyl | allyl | 3c{6, 6} |
| | 1-allyloxy-4-butoxybenzene | allyl | butyl | 3c{4, 6} |
| | allyl small library (1-allyloxy-4-alkoxybenzene) | allyl | methyl, ethyl, propyl | 3c{6, 1-3} |
| | iPent library (1-isopentyloxy-4-alkoxybenzene) | isopentyl | methyl, ethyl, propyl, isopentyl | 3c{5, 1-5} |
| | iPent library (1-isopentyloxy-3-alkoxybenzene) | isopentyl | methyl, ethyl, propyl, isopentyl | 3b{5, 1-5} |
| | Pr library (1-propoxy-2-alkoxybenzene) | propyl | methyl, ethyl, propyl, butyl, isopentyl | 3a{3, 1-5} |
| | Bu library (1-butoxy-2-alkoxybenzene) | butyl | methyl, ethyl, propyl, butyl, isopentyl | 3a{4, 1-5} |
| | allyl library (1-allyloxy-2-alkoxybenzene) | allyl | methyl, ethyl, propyl, butyl, isopentyl | 3a{6, 1-5} |

Table 14 provides a list of the test compounds of Group II.

TABLE 14

Test compounds-Group II

| Table Reference | Compound name (IUPAC) | R₁ | R₂ | Name |
|---|---|---|---|---|
| Table 8 | 1-allyloxy-2-propoxybenzne | Allyl | Propyl | 3a{3, 6} |
| | " | " | " | 3a{3, 6} |
| | 1-allyloxy-2-butoxybenzene | Allyl | Butyl | 3a{4, 6} |
| | 1-butoxy-3-propoxybenzene | Propyl | Butyl | 3a{3, 4} |
| | allyl library (1-allyloxy-2-alkoxybenzene) | Allyl | Me, Et, Pr, Bu, iPent | 3a{6, 1-5} |
| | 1-allyloxy-2-isopentoxybenzene | Allyl | iPent | 3a {5, 6} |
| | 1-propoxy-3-isopentoxybenzene | Propyl | iPent | 3b{3, 5} |
| | 1-methoxy-3-isopentoxybenzene | Methyl | iPent | 3b{1, 5} |
| | 1-allyloxy-3-methoxybenzene | Methyl | Allyl | 3b{1, 6} |
| | small allyl set (1-allyloxy-3-ethoxy/propoxybenzene) | Allyl | Et, Pr | 3b{6, 2-3} |
| | small allyl set (1-allyloxy-3-butoxy/isopentoxybenzene) | Allyl | Bu, iPent | 3b{6, 4-5} |
| | 1,3-diallyloxybenzene | Allyl | Allyl | 3b{6, 6} |
| | 1-allyloxy-3-isopentoxybenzene | Allyl | iPent | 3b{5, 6} |
| | 1-hydroxy-2-allyloxybenzne | H | Allyl | 2b{6} |
| | allyl library (1-allyloxy-4-alkoxybenzene) | Allyl | Me, Et, Pr, Bu, iPent | 3c{6, 1-5} |
| | 1-allyloxy-4-methoxybenzene | Methyl | Allyl | 3c{1, 6} |
| | 1-allyloxy-4-ethoxybenzene | Ethyl | Allyl | 3c{2, 6} |
| | 1-allyloxy-4-propoxybenzene | Propyl | Allyl | 3c{3, 6} |
| | 1-allyloxy-4-isopentoxybenzene | iPent | Allyl | 3c{5, 6} |
| | 1-ethoxy-4-propoxybenzene | Ethyl | Propyl | 3c{2, 3} |
| Table 9 | R₃ = allyl (1-alkoxy-2-(hydroxy or alkoxy)-3-allylbenzene) | Me, Et, Pr, Bu, iPent | H | 4a{1-5} |
| | | Me, Et, Pr, Bu, iPent | Me | 5a{1, 1-5} |

TABLE 14-continued

| | Test compounds-Group II | | | |
|---|---|---|---|---|
| Table Reference | Compound name (IUPAC) | R₁ | R₂ | Name |
| [structure: allyl-1,2-dialkoxybenzene with OR₂, OR₁] | | Me, Et, Pr, Bu, iPent | Et | 5a{2, 1-5} |
| | | Me, Et, Pr, Bu, iPent | Pr | 5a{3, 1-5} |
| | | Me, Et, Pr, Bu, iPent | Bu | 5a{4, 1-5} |
| | | Me, Et, Pr, Bu, iPent | iPent | 5a{5, 1-5} |
| | | Me, Et, Pr, Bu, iPent | allyl | 5a{6, 1-5} |
| Table 10 | R₃ = allyl | Me, Et, Pr, Bu, iPent | H | 4c{1-5} |
| [structure: 5c{R₂, 1-5}] | (1-(hydroxy or alkoxy)-2-allyl-4-alkoxybenzene) | Me | Me | 5c{1, 1} |
| | | Me, Et, Pr, Bu, iPent | Me | 5c{1, 1-5} |
| | | Me, Et, Pr, Bu, iPent | Et | 5c{2, 1-5} |
| | | Pr | Pr | 5c{3, 1} |
| | | Me, Et, Pr, Bu, iPent | Pr | 5c{3, 1-5} |
| | | Me, Et, Pr, Bu, iPent | Bu | 5c{4, 1-5} |
| | | Me, Et, Pr, Bu, iPent | iPent | 5c{5, 1-5} |
| | | Me, Et, Pr, Bu, iPent | allyl | 5c{6, 1-5} |
| [structure: 2-methyl-2,3-dihydrobenzofuran with OR₁; 6c{1-5}] | R₄; dihydrofuran | Me, Et, Pr, Bu, iPent | cyclic (dihydrofuran) | 6c{1-5} |
| Table 7 | | Me | H | 4b{1} |
| | | Et, Pr | H | 4b{2-3} |
| | | Bu, iPent | H | 4b{4-5} |
| | R₃ = allyl | Me | Me | 5b{1, 1} |

TABLE 14-continued

Test compounds-Group II

| Table Reference | Compound name (IUPAC) | $R_1$ | $R_2$ | Name |
|---|---|---|---|---|
| (structures x and y shown, 2:1) | isomer x: 1-allyl-2-alkoxy-4-alkoxybenzene<br>isomer y: 1-alkoxy-2-allyl-3-alkoxybenzene | Et, Pr | Me | 5b{1, 2-3} |
| | | Bu, iPent | Me | 5b{1, 4-5} |
| | | Me | Et | 5b{2, 1} |
| | | Et, Pr | Et | 5b{2, 2-3} |
| | | Bu, iPent | Et | 5b{2, 4-5} |
| | | Me | Pr | 5b{3, 1} |
| | | Et, Pr | Pr | 5b{3, 2-3} |
| | | Bu, iPent | Pr | 5b{3, 4-5} |
| | | Et | Pr | 5b{3, 2} |
| | | Me | Bu | 5b{4, 1} |
| | | Et, Pr | Bu | 5b{4, 2-3} |
| | | Bu, iPent | Bu | 5b{4, 4-5} |
| | | Me | iPent | 5b{5, 1} |
| | | Et, Pr | iPent | 5b{5, 2-3} |
| | | Bu, iPent | iPent | 5b{5, 4-5} |
| | | Me | allyl | 5b{6, 1} |
| | | Et, Pr | allyl | 5b{6, 2-3} |
| | | Bu, iPent | allyl | 5b{6, 4-5} |
| | | Me | Me | 5b{1, 1} |
| | | Me | Pr | 5b{3, 1} |
| | | Me | Pr | 5b{3, 1} y (100% y) |
| | | Me | Pr | 5b{3, 1} x (68% x, 32% y) |
| | | Et | Pr | 5b{3, 2} |
| | | Et | Pr | 5b{3, 2} y (100% y) |
| | | Et | Pr | 5b{3, 2} y (82% x, 18% y) |
| | | Me | iPent | 5b{5, 1} |
| | | Me | allyl | 5b{6, 1} |

Example 12

The Feeding Deterrent Effect of 1-alkoxy-4-propoxybenzene Alone and in a Blend with Azadirachtin Against the Cabbage Looper, Trichoplusia ni on Different Plants and in the Greenhouse The feeding deterrent effect of 3c{3,6} (1-alkoxy-4-propoxybenzene) alone and in a blend with azadirachtin was evaluated against T. ni. Antifeedant activity was assayed using a leaf-disc bioassay in choice and no-choice tests. The $DC_{50}$ value of 3c{3,6} was found to be 27 μg/cm². The blend was assayed on several different types of vegetables to determine if the feeding deterrence first measured on cabbage was transferable. The blend (8.9 μg/cm² 3c{3,6} and 3.7 μg/cm² azadirachtin) had a high feeding deterrent effect on all vegetable types tested against third instar T. ni larvae. This blend can be used in a greenhouse-like setting and the concentration of the blend is correlated positively with feeding deterrence in this environment. The experimental procedure and results are described in greater detail, as follows.

Materials and Methods

Insect Care

T. ni larvae were raised from eggs (Insect Production Services, Natural Resources Canada) on a wheat-germ based artificial diet (McMorran diet, Insect Production Services, Natural Resources Canada), or raised from eggs from a laboratory colony of T. ni adults, at 22±1° C., 32-40% humidity, 9 h/15 h light/dark photoperiod.

Cabbage Plants

Cabbage (Brassica oleracea L. cv. Golden Acre) plants were grown from seed (Pacific Northwest Seeds, Vernon, B.C.) in sandy loam soil in the laboratory at 21±1° C. beside a south-facing window. Plants received supplemental lighting from grow-lights emitting light of wavelengths 430 and 662 nm for 2 h/d. Plants were about 2-3 months old (with about 8-12 fully expanded leaves) at time of leaf collection for disc choice bioassays.

Chemicals

3c{3,6} was synthesized as described herein. Azadirachtin in a neem oil preparation (TreeAzin [5% azadirachtins A and B]) was obtained from BioForest Technologies Inc., Sault Step. Marie, Canada. Azadirachtin solutions were prepared fresh on the day of the bioassay to avoid degradation. Cetyl alcohol was obtained from Sigma, palmitic acid from BDH Chemicals Ltd., methanol (HPLC-grade) from Calcdon, and isopropanol (2-propanol-205, distilled in glass) from Calcdon Ammonium hydroxide solution was obtained from CanLab.

Blend and whole plant studies used a "vehicle" that consisted of palmitic acid (25 mM), cetyl alcohol (25 mM), and isopropanol (50%). The vehicle was prepared by dissolving palmitic acid and cetyl alcohol in isopropanol. The solution was neutralized with 1M NaOH, followed by step-wise dilution with water.

Bioassay Protocol

Leaf discs (disc area: 2.24 cm$^2$) cut with a no. 10 borer from cabbage plant leaves were painted on each side with 20 µL of treatment solution or solvent, using a Hamilton 25 µL glass syringe, and allowed to dry. One treatment and one control leaf disc were placed on opposite sides (5 cm apart) of a 9 cm diameter Petri dish containing moistened filter paper (Whatman #1, 70 mm). A fasting *Trichoplusia ni* larva was placed midway between the two leaf discs and oriented away from either disc. Replicate Petri dishes were kept in a plastic basin, protected from light, at 22±1° C. during the feeding period. Larvae fasted for approximately 7 h prior to the experiments.

An additional 5-10 replicates having TreeAzin as the treatment were included in each bioassay as a positive control.

The feeding period was terminated when approximately 50% of either the control or treatment leaf disc had been consumed, or, after a preset interval.

Leaf disc areas consumed were measured using a Canon CanoS can LiDE 20 scanner, CanoScan Toolbox 4.1 software, Microsoft Office Picture Manager, and Un-Scan-It Gel and Graph Digitizing Software v. 6.1. Leaf disc area remaining was subtracted from the mean area of five nonconsumed reference leaf discs, all area measurements being made at the end of the feeding period, to correct for shrinkage.

Antifeedant effect was described by the feeding deterrence index (%): FDI (%)=(C−T)/(C+T)×100, where C and T are the areas consumed of control and treatment leaf discs, respectively (Inman et al. 1990).

In cases where one leaf disc had been completely consumed and the other leaf disc partially consumed, it was assumed that the larva had first consumed the completely-consumed leaf disc. In such cases the replicate was assigned an FDI of 100% or −100% depending on which leaf disc, the control or treatment, respectively, had been completely consumed. Replicates in which neither leaf disc was consumed were omitted from the calculations.

Dose-Response

In the dose-response study leaf-disc choice bioassays were performed with larvae in day 1 or 2 of the 3$^{rd}$ and 4$^{th}$ instar. 3c{3,6} was in 83% methanol. Data compiled from several bioassays were pooled prior to analysis for DC$_{50}$ determination. There were not enough data points in the dose-response data for a sigmoidal fit, but the DC50 could be determined by linear regression analysis, as was the case for Akhtar et al. (2007).

Blend Assay

Leaf-disc choice bioassays of 3c{3,6}, azadirachtin, and a blend of 3c{3,6}+azadirachtin were conducted with larvae in day 1 or 2 of their fifth instar. Solutions were prepared in a vehicle (as described herein).

Feeding Deterrence on Different Plant Types

Antifeedant activity of the blend was assayed using a leaf disc bioassay according to section 2.4 bioassay protocol. Leaf discs were cut using a no. 10 cork borer (2.24 cm$^2$ area). Leaves for the lettuce test were removed from healthy, organic, romaine lettuce plants purchased from the grocery store. The Brussels sprouts, and red cabbage were also purchased from a grocery store and used while fresh and healthy. Because the outer leaves may be contaminated, only the inner leaves were used for all store bought plants. The cabbage leaves were from cabbage plants grown from seeds in the laboratory until the plants were about three months old (with about 10-12 fully expanded leaves). The tomato plant leaves were from a Roma tomato plant also growing in the laboratory.

Third instar larva of *T. ni*, were used for these tests. They fasted for approximately 7 h prior to the experiments and were allowed to feed for approximately 17 hours. For each treatment and negative controls, 20 replicate containers were tested. For the positive control only five replicates were done because the feeding deterrent effect is so strong.

After the discs were then scanned the remaining areas of leaf discs were measured using UN-SCAN-IT gel 6.1 software. In order for the software to recognize an area that was eaten part way through the disc, images were all edited using Microsoft Office Picture Manager so that pitted areas were white (the same as holes) and uneaten parts were black. The areas consumed from control and treatment discs in the choice tests were calculated by subtracting remaining areas from an average disc area after shrinkage (1.69 cm$^2$). The FDIs for each replicate were calculated separately and then were averaged to find the mean FDI for each plant type. Feeding deterrence was also assessed as the percentage of total control leaf area consumed as a percentage of the total leaf area consumed (Feeding deterrence percentage, FDP). The formula FDP=100[(total area of controls consumed/(total area consumed in control and treatment discs)] was used.

Protection of Whole Cabbage Plants in a Greenhouse Environment with Different Blend Concentrations The 3c{3,6} blend was tested for protection of intact cabbage plants from *T. ni* herbivory in a greenhouse-like setting, and at different concentrations of the blend. Five cabbage plants were grown until they were about four months old (12-18 leaf stage). Leaves were removed from each plant so that only six or seven large leaves remained and the surface area of each plant was approximately equal. These remaining leaves were photographed and then analyzed to determine the surface area. The five plants were kept in their individual pots with tinfoil covering the soil to prevent larvae from hiding. The pots were placed in large plastic trays and a vented Plexiglas box covered the trays to simulate a greenhouse environment. A grow light was shone on the plants for two hours each day and they were watered as needed.

The plants were each sprayed with a total of twelve squirts of the vehicle solution with a handheld sprayer. Each plant received 11.52 mL of solution covering both sides of all the leaves. The blend for this experiment was put in a modified vehicle from previous experiments to eliminate the browning of the leaves that occurred. This Vehicle was still 1:1 Isopropanol and water, but had 10 mM Cetyl alcohol, 10 mM Palmitic acid, and was neutralized with NH$_4$OH solution. After spraying, the plants were left to air dry. The concentrations of the blend were:

A. 4.8 µg/cm$^2$ Azadirachtin and 9 µg/cm$^2$ 3c{3,6}
B. 0.48 µg/cm$^2$ Azadirachtin and 0.9 µg/cm$^2$ 3c{3,6}
C. 0.048 µg/cm$^2$ Azadirachtin and 0.09 µg/cm$^2$ 3c{3,6}
D. 0 µg/cm$^2$ Azadirachtin and 0 µg/cm$^2$ 3c{3,6}
E. 0 µg/cm$^2$ Azadirachtin and 0 µg/cm$^2$ 3c{3,6}

Fifteen weighed second instar larvae were distributed over each plant (A to D) on the first day. On the second day, plants were supplemented as needed so that by the third day all plants had seven larvae to begin the experiment. The larva had a tendency to wriggle after being placed on the leaves, so the majority fell off the plants. The second application method was selected to control the number of larva starting on each plant. Plant E did not receive any larva and served as a control for natural plant growth during the experiment. Over the two week experiment, the remaining leaf areas of the plants were estimated every few days and the number of larva per plant recorded daily. At the end of the experiment, the larva were also removed and reweighed.

To measure leaf area, plant leaves were photographed on graph paper and the area remaining around the leaf could be estimated from the images. By subtracting from the total known area of the paper, the leaf area was estimated.

Data Analyses

Curve-fitting and statistical tests were performed with GraphPad Prism v.5. The $DC_{50}$ of $3c\{3,6\}$ was determined by linear regression of the dose-response data from 9 to 45 µg/cm². The effect of the blend compared to its components was analyzed by performing paired and unpaired t tests and the Wilcoxon ranked pairs test.

All leaf areas consumed were calculated in Microsoft Excel. These were then used to calculate average FDI and FDP also in Microsoft Excel. GraphPad Prism software was used to determine if the difference between controls FDI and treatment FDI was significant using a paired t test for Brussels sprouts, cabbage, and red cabbage, and a one sample t test for lettuce and tomato data.

Results

Dose-Response

Figure 5:
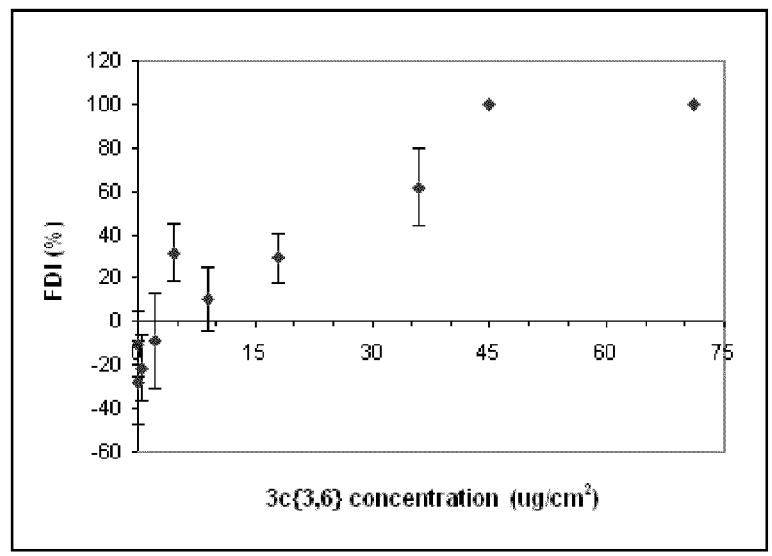
FIG. 5 is a dose-response plot of the feeding deterrent effect of 3c{3,6} alone. $DC_{50}$: 27 µg/cm$^2$. Data points with error bars indicate the mean feeding deterrence index (FDI) (%)±SE. Number of replicates ranged from 20 to 70.

At concentrations greater than 18 µg/cm² $3c\{3,6\}$ had a concentration-dependent deterrent effect on *T. ni* larval feeding (FIG. 5). The dose-response data yielded a $DC_{50}$ value of 27 µg/cm².

Feeding Deterrence of the Blend of $3c\{3,6\}$ and Azadirachtin

Individually, $3c\{3,6\}$ and the known antifeedant azadirachtin (8.9 and 4.9 µg/cm², respectively) in the vehicle had modest antifeedant effects (Table 15). In contrast, the blend of $3c\{3,6\}$ (8.9 µg/cm²) and azadirachtin (4.9 µg/cm²) completely deterred larval feeding and had a significantly stronger feeding deterrent effect than each component alone. The blend had a feeding deterrent effect as strong as a concentration of $3c\{3,6\}$ five times greater.

TABLE 15

Feeding deterrent effect of $3c\{3, 6\}$, azadirachtin, and a blend of $3c\{3, 6\}$ + azadirachtin. A statistically significant difference in mean FDI is indicated by a different letter.

| | FDI (%)* | n |
|---|---|---|
| $3c\{3, 6\}$ (8.9 ug/cm²) | 43 (20) a | 21 |
| azadirachtin (4.9 ug/cm²) | 43 (20) a | 21 |
| $3c\{3, 6\}$ (8.9 ug/cm²) + azadirachtin (4.9 ug/cm²) | 100 (0) b | 12 |
| $3c\{3, 6\}$ (45 ug/cm²) | 100 (0) b | 20 |
| vehicle/negative control | −10 (16) c | 39 |

*mean (SE)

Feeding Deterrent Effect on Different Plant types

The absolute areas consumed by the larva were similar for almost all plant types, with the exception being the tomato plant. Excluding the tomato, larvae consumed an average of 0.33 cm² on controls and 0.05 cm² on treatment leaf discs. On tomato leaf discs, they consumed an average area of just 0.01 cm² on control discs and 0.00 cm² on treated discs.

Figure 6:
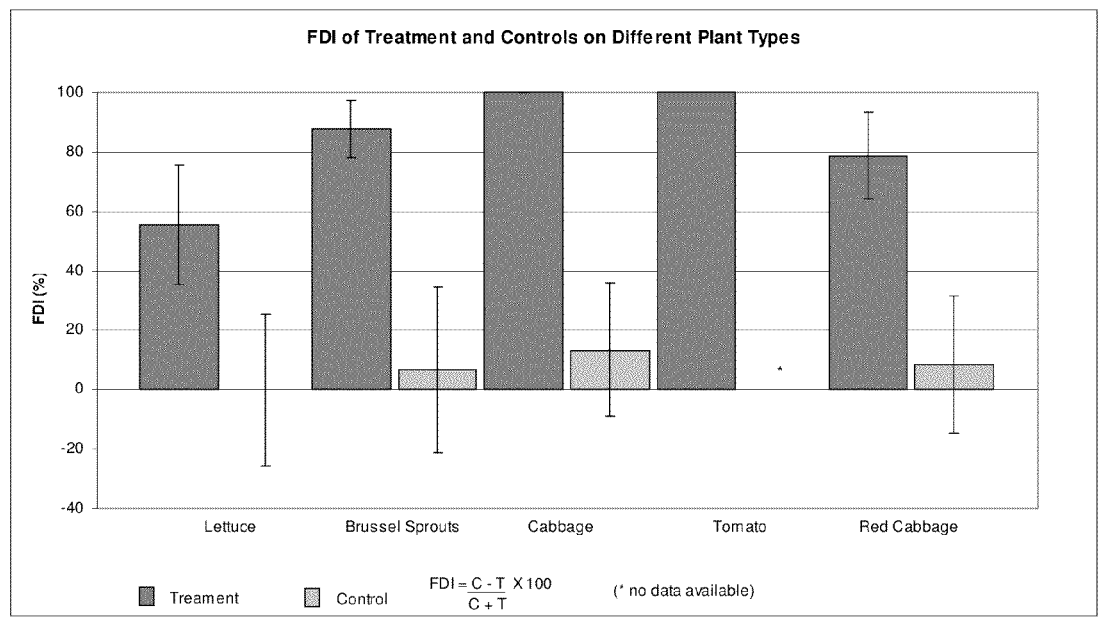
FIG. 6 is a graph showing feeding preference behavior of third instar *T. ni* larvae in leaf disc choice assays. The treated discs contained a blend of 3c{3,6} and the major active compound known from neem (8.9 µg/cm$^2$ 3c{3,6} and 3.7 µg/cm$^2$ Azadirachtin). Bars represent the mean FDI and vertical lines represent standard errors. There was a significant difference between control and treatment within each plant type but there was no significant difference between plant types.

The $3c\{3,6\}$ blend (8.9 µg/cm² $3c\{3,6\}$ and 3.7 µg/cm² Azadirachtin) in the vehicle had a feeding deterrent effect on *T. ni* larvae on all types of plant leaves tested. The larvae were able to differentiate between the discs and chose to eat from the control discs much more often than the treated discs. The blend showed feeding deterrence on lettuce (FDI=55.6; SE=20; P<0.0135; FIG. 6) compared to the control. The blend also gave feeding deterrence on Brussels Sprouts (FDI=87.8; SE=9; P<0.0395). The blend resulted in complete feeding deterrence on cabbage (FDI=100.0; SE=0; P<0.0011) and on tomato plant leaves (FDI=100.0; SE=0; P<0.0001). The blend produced a strong feeding deterrent effect on red cabbage as well (FDI=78.8; SE=14; P<0.0332). The FDI for each plant type does not differ significantly from any of the others.

Feeding deterrence was also assessed by area using the percentage of the total control leaf area consumed out of the total leaf area consumed for each plant type (Feeding deterrence percentage, FDP). This revealed an extremely strong feeding deterrent effect from the $3c\{3,6\}$ blend in all plant types tested (Table 16).

TABLE 16

Feeding deterrence as a percentage; the total control leaf area consumed out of the total leaf area consumed for each plant type. Higher percentages indicate greater feeding on controls in disc choice assays.

| | Plant Type | | | | |
|---|---|---|---|---|---|
| | Lettuce | Brussel sprouts | Cabbage | Tomato | Red cabbage |
| FDP | 93.6% | 96.7% | 100% | 100% | 99.1% |

Effect of Blend Concentrations on Feeding Deterrence with Whole Cabbage Plants in a Greenhouse Environment Larva behavior and development varied between the treatments. For instance, larvae on the plant A, treated with a higher concentration of blend, were more likely to abandon their plants sooner to forage. The larvae on plants B and C also left their plants but after a longer period of time, in which their plants sustained considerable damage. Larvae on the treated plants (A, B and C) were also much smaller than the larvae on the control plant (D) and appeared to have delayed development. The average weight gain of a larva on plant D was 0.164 g, while no larvae on the other plants survived to the end of the test period.

Figure 7:
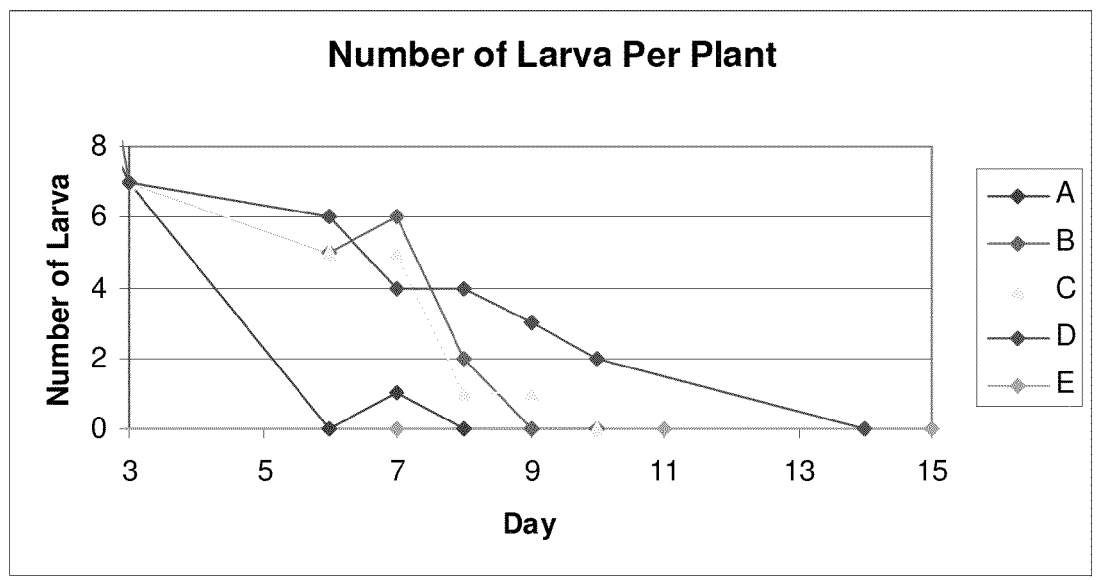
FIG. 7 is a graph showing the number of larva per plant per day in whole plant studies with blends of 3c{3,6} and a botanical feeding deterrent (neem). Initially, 15 larvae were added per plant and left for 2 days to stabilize. On day 3, 7 larvae were located per plant. A=4.8 µg/cm$^2$ Azadirachtin and 9 µg/cm$^2$ 3c{3,6}; B=0.48 µg/cm$^2$ Azadirachtin and 0.9 µg/cm$^2$ 3c{3,6}; C=0.048 µg/cm$^2$ Azadirachtin and 0.09 µg/cm$^2$ 3c{3,6}; D=no blend, with larvae; E=no blend, no larvae.

The number of larvae remaining on each of the plants declined after day three, for each of the test plants (FIG. 7). Initially on day 3, there were seven larvae per plant. The number of larvae on plant A (with the highest concentration of blend) decreased the fastest, reaching zero on day eight. Plant B and C were next to reach zero larvae, on days nine and ten respectively. Larvae on plant D, the control, lasted much longer until day fourteen. These results show that the concentration of the blend is positively correlated with the larvae being deterred.

Figure 8:
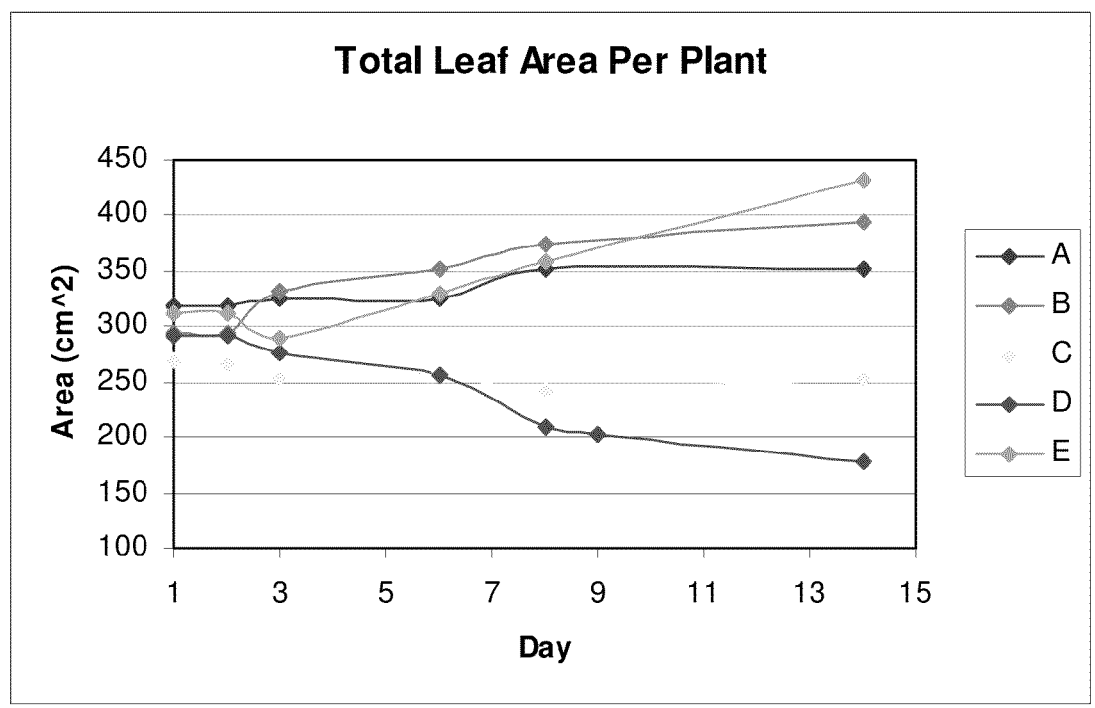
FIG. 8 is a graph showing the total leaf area per plant per day in whole plant studies described in FIG. 7.

The total leaf area for each plant also follows a distinct trend over the course of the test. By day six plants B, C, and D appeared to have been consumed about the same while plant A was consumed much less. FIG. 8 shows the long term trends of plant area. Plant E was the control, without larva, and thus increased in area over the course of the experiment. Similarly, plant A and plant B also increased in area. For plant C, the area of growth almost exactly cancelled out the area that was consumed, so there is no net change in area. The area of Plant D decreased substantially as it was untreated with the blend. In general, feeding deterrence correlated positively with the concentration of the blend.

The dose-response profile and $DC_{50}$ value of $3c\{3,6\}$ echo the findings from a group of closely related synthetic compounds tested against third instar *T. ni* larvae. In the present study $3c\{3,6\}$ at a concentration of 45 µg/cm² had an FDI of 100±0%. A small library of 1-allyloxy-4-alkoxybenzenes (including $3c\{3,6\}$) at 50 µg/cm² had an FDI of 82.4±10.7% (Akhtar et al. 2007). The $DC_{50}$ (the concentration at which 50% feeding deterrence occurred) of $3c\{3,6\}$ and that of the library of compounds were very similar (27 and 27.9 µg/cm², respectively).

For the test of $3c\{3,6\}$ and azadirachtin, individually and in combination, concentrations were selected such that the compounds by themselves had a modest effect on *T. ni* feeding.

Our results have shown that the $3c\{3,6\}$ blend exhibits a strong feeding deterrent effect when applied to many different types of vegetables. There was a significant difference between controls and choice tests with all plant types: lettuce, brussel sprouts, cabbage, tomato, and red cabbage. The differences between plant types were not significantly different. However, they all showed high, positive FDI values in the range of 55.6% to 100%. The variability between plant types may partly be due to the combination of the plant's own volatiles with the blend compounds. For example, lettuce volatiles mixed with the blend might trigger different responses on $T.$ $ni$ chemoreceptors than cabbage volatiles with the blend. In cases where larvae did eat from treated leaf discs, they always consumed very little area. This effect is summarized in the FDP values where we can see clearly that on all plant types the majority of the area consumed was on controls.

On some plants, the level of feeding deterrence activity was comparable to TreeAzin (50,000 ppm azadirachtin), even though our blend has much lower concentrations of the active compounds (418 ppm azadirachtin and 1000 ppm 3c{3,6}).

The whole plant experiments demonstrated that the blend can have a feeding deterrent effect on *T. ni* larva and that the concentration of the blend is positively correlated with feeding deterrence. The number of larvae data point to treatment A as the most effective concentration, in this study, when compared to the others (B, and C). This is because it deters larva the fastest, before they reach the most destructive instars. The total leaf area measurements indicate that treatment A and B, in this study, are most effective. The long term trend of plants A and B, in this study, is similar to plant E which shows net growth over the experiment. This is in stark contrast to the large loss of leaf area in the control (D).

Example 13

The Feeding Deterrent Effect of 1-alkoxy-4-propoxybenzene in a TreeAzin Blend Against the Cabbage Looper, *Trichoplusia ni* on Different Plants and in the Greenhouse The feeding deterrent effect of a blend of 3c{3,6} (1-alkoxy-4-propoxybenzene) (9 μg/$cm^2$) and TreeAzin; a commercial extract of neem tree seeds (4.8 μg/$cm^2$) in a vehicle was evaluated against the cabbage looper, *Trichoplusia ni*. Antifeedant activity was assayed using a leaf-disc bioassay in choice and no-choice tests. The blend was assayed on several different types of vegetables to determine if the feeding deterrence measured on cabbage was transferable. The blend has a high feeding deterrent effect on a number of vegetable types tested against third instar *T. ni* larvae. The experimental procedure and results are described in greater detail, as follows.

Materials and Methods

Feeding Deterrence on Different Plant Types

Antifeedant activity of the blend was assayed using a leaf disc bioassay. The bioassays were conducted in round, transparent, plastic petri dishes (9 cm diameter×1.5 cm height). A round filter paper (70 mm diameter) was centered in the bottom of each container and moistened with 600 μL of water prior to the experiment in order to keep the leaf discs fresh.

Leaves for the lettuce test were removed from healthy, organic, romaine lettuce plants purchased from the grocery store. The Brussels sprouts and red cabbage were also purchased from a grocery store and used while fresh and healthy. Because the outer leaves may be contaminated, only the inner leaves were used for all store bought plants. The cabbage leaves were from cabbage plants grown from seeds in the laboratory until the plants were about three months old (with about 10-12 fully expanded leaves). The tomato plant leaves were from a Roma tomato plant also growing in the laboratory.

Leaf discs were cut using a no. 10 cork borer (1.47 cm diameter, 1.69 $cm^2$ area). Then, the treatments were painted onto the discs using a 25 μL syringe. 20 μL was applied to the first side of each disc and left to dry completely in a fume hood. After flipping discs over, the second side was also painted with 20 μL and dried.

In choice tests, two discs were placed in the same container; the left disc was the control with just vehicle applied to it, and the right disc had the blend applied to it. In no-choice, negative control tests, both discs only had the vehicle applied to them. In the positive control test the left disc had just the vehicle and the right disc had TreeAzin (a known feeding deterrent) applied to it. The distance between the discs was 5 cm.

A single third instar larva of *T. ni*, was added to the centre of each Petri dish oriented away from either disc and allowed to feed for approximately 17 hours at room temperature. Test insects fasted for approximately 7 h prior to the experiments.

For each treatment and negative controls, 20 replicate containers were tested. For the positive control only five replicates were done because the feeding deterrent effect is so strong.

After the tests were run and larvae were removed, the discs were then scanned and the remaining areas of leaf discs were measured using UN-SCAN-IT gel 6.1 software. In order for the software to recognize area that was eaten part way through the disc, images were all edited using Microsoft Office Picture Manager so that pitted areas were white (the same as holes) and uneaten parts were black. The areas consumed from control and treatment discs in the choice tests were calculated subtracting remaining areas from an average original disc area (averaged from five uneaten discs scanned at the end of the feeding period to control for leaf shrinkage). A feeding deterrent index (FDI) was calculated using the formula $FDI=100[(C-T)/(C+T)]$ where C and T are the control and treated leaf areas consumed by the larvae. The FDIs for each replicate were calculated separately and then were averaged to find the mean FDI for each plant type. Feeding deterrence was also assessed as the percentage of total control leaf area consumed out of the total leaf area consumed (Feeding deterrence percentage, FDP). The formula FDP=100[(total area of controls consumed/(total area consumed in control and treatment discs)] was used.

Protection of Whole Cabbage Plants in a Greenhouse Environment with Different Blend Concentrations We also wanted to test if the 3c{3,6} blend would protect intact cabbage plants from *T. ni* herbivory in a more realistic greenhouse-like setting, and which concentration of blend was most effective. Five cabbage plants were grown until they were about four months old (12-18 leaf stage). Leaves were removed from each plant so that only six or seven large leaves remained and the surface area was approximately equal. These remaining leaves were photographed and then analyzed to determine the surface area. The five plants were kept in their individual pots with tinfoil covering the soil to prevent larvae from hiding. The pots were placed in large plastic trays and a Plexiglas box covered the trays to simulate a greenhouse environment. A grow light was shone on the plants for two hours each day and they were watered as needed.

The plants were each sprayed with a total of twelve squirts of the vehicle solution with a handheld sprayer. Each plant received 11.52 mL of solution covering both sides of all the leaves. The blend for this experiment was put in a modified vehicle from previous experiments to eliminate the browning of the leaves that occurred. This Vehicle was still 1:1 Isopropanol and water, but had 10 mM Cetyl alcohol, 10 mM Palmitic acid, and was neutralized with NH$_4$OH solution. After spraying, the plants were left to air dry for three hours. The concentrations of the blend were:

A. 4.8 µg/cm$^2$ Azadirachtin and 9 µg/cm$^2$ 3c{3,6}

B. 0.48 µg/cm$^2$ Azadirachtin and 0.9 µg/cm$^2$ 3c{3,6}

C. 0.048 µg/cm$^2$ Azadirachtin and 0.09 µg/cm$^2$ 3c{3,6}

D. 0 µg/cm$^2$ Azadirachtin and 0 μg/$cm^2$ 3c{3,6}

E. 0 μg/$cm^2$ Azadirachtin and 0 μg/$cm^2$ 3c{3,6}

Fifteen weighed second instar larvae were distributed over each plant (A to D) on the first day. On the second day, plants were supplemented as needed so that by the third day all plants had seven larvae to begin the experiment. The larva have a tendency to wriggle when moved, so the majority fall off the plants. The second application method was selected to control the number of larva starting on each plant. Plant E did not receive any larva and served as a control for natural plant growth during the experiment. Over the two week experiment, the remaining leaf areas of the plants were estimated every few days and the number of larva per plant recorded daily. At the end of the experiment, the larva were also removed and reweighed.

To measure leaf area, plant leaves were photographed on graph paper and the area remaining around the leaf could be estimated from the images. By subtracting from the total known area of the paper, the leaf area was estimated.

Data Analyses

All leaf areas consumed were calculated in Microsoft Excel. These were then used to calculate average FDI and FDP also in Microsoft Excel. GraphPad Prism software was used to determine if the difference between controls FDI and treatment FDI was significant using a paired t test for brussel sprouts, cabbage, and red cabbage, and a one sample t test for lettuce and tomato data.

Results

Feeding Deterrent Effect on Different Plant Types]

The absolute areas consumed by the larva were similar for almost all plant types, with the exception being the tomato plant. Excluding the tomato, larvae consumed an average of 0.34 $cm^2$ on controls and 0.06 $cm^2$ on treatment leaf discs. On tomato leaf discs, they consumed an average area of just 0.01 $cm^2$ on control discs and 0.00 $cm^2$ on treated discs.

The 3c{3,6} blend (9 μg/$cm^2$ 3c{3,6} and 5 μg/$cm^2$ Azadirachtin) in the vehicle had a feeding deterrent effect on *T. ni* larvae on all types of plant leaves tested. The larvae were able to differentiate between the discs and chose to eat from the control discs much more often than the treated discs. The blend showed feeding deterrence on lettuce (FDI=55.6; $P<0.0135$; FIG. 9) compared to the control. The blend also gave feeding deterrence on Brussel Sprouts (FDI=87.8; $P<0.0395$). The blend resulted in complete feeding deterrence on cabbage (FDI=100.0; $P<0.0011$) and on tomato plant leaves (FDI=100.0; $P<0.0001$). The blend produced a strong feeding deterrent effect on red cabbage as well (FDI=78.8; $P<0.0332$). The FDI for each plant type does not differ significantly from any of the others.

Feeding deterrence was also assessed by area using the percentage of the total control leaf area consumed out of the total leaf area consumed for each plant type (Feeding deterrence percentage, FDP). This revealed an extremely strong feeding deterrent effect from the 3c{3,6} blend in all plant types (Table 17).

TABLE 3.1

Feeding deterrence as a percentage; the total control leaf area consumed out of the total leaf area consumed for each plant type. Higher percentages indicate greater feeding on controls in disc choice assays.

| | Plant Type | | | | |
|---|---|---|---|---|---|
| | Lettuce | Brussel sprouts | Cabbage | Tomato | Red cabbage |
| FDP | 93.6% | 96.7% | 100% | 100% | 99.1% |

Our results have shown that the 3c{3,6} blend exhibits a strong feeding deterrent effect when applied to many different types of vegetables. There was a significant difference between controls and choice tests with all plant types: lettuce, brussel sprouts, cabbage, tomato, and red cabbage. The high feeding deterrence effect on cabbage is consistent with the results of Jozdani (2012). The differences between plant types were not significantly different, so we cannot say for certain if the blend is more effective on one type or another. However, they all showed high, positive FDI values in the range of 55.6% to 100%. The variability between plant types may partly be due to the combination of the plant's own volatiles with the blend compounds. For example, lettuce volatiles mixed with the blend might trigger different responses on *T. ni* chemoreceptors than cabbage volatiles with the blend. In cases where larvae did eat from treated leaf discs, they always consumed very little area. This effect is summarized in the FDP values where we can see clearly that on all plant types the majority of the area consumed was on controls. The FDP values can appear much higher than the FDIs because some larva did not continue to forage after finding the treatment disc. Even if they only ate a very small amount of the treatment disc and were then deterred, the FDI gets counted as −100% meaning that larvae were in fact attracted to the treatment. The FDP is calculated differently so this activity is not as significant.

On some plants, the level of feeding deterrence activity was comparable to TreeAzin (50,000 ppm azadirachtin), even though our blend has much lower concentrations of the active compounds (418 ppm azadirachtin and 1000 ppm 3c{3,6}).

Other Embodiments

Although various embodiments of the invention are disclosed herein, many adaptations and modifications may be made within the spirit and scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range, and of sub-ranges encompassed therein. As used herein, the terms "comprising", "comprises", "having" or "has" are used as an open-ended terms, substantially equivalent to the phrase "including, but not limited to". Terms such as "the," "a," and "an" are to be construed as indicating either the singular or plural. Citation of references herein shall not be construed as an admission that such references are prior art to the present invention. All publications are incorporated herein by reference as if each individual publication were specifically and individually indicated to be incorporated by reference herein and as though fully set forth herein. The invention includes all embodiments and variations substantially as hereinbefore described and with reference to the examples and drawings.

REFERENCES

Akhtar, Y.; Rankin, C. A.; Isman, M. B. Decreased response to feeding deterrents following prolonged exposure in the larvae of a generalist herbivore, *Trichoplusia ni* (Lepidoptera: Noctuidae). *J Insect Behav.* 2003, 16, 811-831.

Akhtar, Y.; Isman, M. B. Comparative growth inhibitory and antifeedant effects of plant extracts and pure allelochemicals on four phytophagous insect species. *Journal of Applied Entomology* 2004, 128, 32-38.

Akhtar, Y.; Isman, M. B. Larval exposure to oviposition deterrents alters subsequent oviposition behaviour in generalist *Trichoplusia ni* and specialist, *Plutella xylostella* moths. *J Chem. Ecol. to* 2003, 29, 1853-1870.

Akhtar, Y., Isman, M., Pudaru P., Nagabandi S., Nair R., Plettner E. 2007. Screening of dialkoxy benzenes and disubstituted cyclopentene derivatives against the cabbage looper, *Trichoplusia ni*, for the discovery of new feeding an oviposition deterrents. Agric. Food Chem. 55: 10323-10330.

Akhtar, Y., Yeoung, Y. R., and Isman, M. B. (2008) Comparative bioactivity of selected extracts from Meliaceae and some commercial botanical insecticides against two noctuid caterpillars, *Trichoplusia ni* and *Pseudaletia unipuncta, Phytochem. Rev.* 7, 77-88.

Ave, D. A. (1995) Stimulation of feeding: insect control agents. In *Regulatory Mechanisms in InsectFeeding* (Chapman, R. F and de Boer, G. Eds.), pp 345-63, Chapman & Hall, NY.

Berger, R. S. 1966. Isolation, identification and synthesis of the sex attractant of the cabbage looper, *Trichoplusia ni. Ann. Entomol. Soc. Amer.* 59, 767-771.

Bjostad, L. B., Linn, C. E., Du, J. W., Roelofs, W. L. 1984. Identification of New Sex Pheromone Components in *Trichoplusia ni*, Predicted from Biosynthetic Precursors. *J. Chem. Ecol.* 10, 1309-1323.

Chow, J. K.; Akhtar, Y.; Isman, M. B. The effects of larval experience with a complex plant latex on subsequent feeding and oviposition by the cabbage looper moth: *Trichoplusia ni* (Lepidoptera: Noctuidae). *Chemoecology* 2005, 15, 129-133.

Davidson, R. H. and Lyon, W. F. 1979. Insect Pests of Farm, Garden and Orchard, John Wiley and Sons Inc., USA.

Davidson, R. H.; Lyon, W. F. *Insect Pests of Farm, Garden, and Orchard*. John Wiley & Sons Inc: USA, 1999.

Dewick, P. M. (2002) *Medicinal Natural Products. A Biosynthetic Approach,* 2nd Ed., John Wiley & Sons, NY, p 550.

Feeny, P., Rosenberry, L., Carter, M. 1983. Chemical aspects of oviposition behavior in butterflies. In: *Herbivorous Insects: Host-Seeking Behavior and Mechanisms*. Ahmad (Ed.). Academic Press, NY, pp. 27-76.

Frazier, J. L. The perception of plant allelochemicals that inhibit feeding. In *Molecular Aspects of Insect-Plant Associations*; Brattsten, L. B., Ahmad, S. Eds.; Plenum Press: New York, 1986, 1-42.

Foster, S. P., and Maths, M. O. (1997) Behavior manipulation methods for insect pest-management, *Annu. Rev. Entomol.* 42, 123-146.

Goering, H. L.; Jacobson, R. R., A Kinetic Study of the ortho-Claisen Rearrangement. *J. Am. Chem. Soc.* 1958, 80, 3277-3285.

Gozzo, F. C., Fernandes, S. A., Rodrigues, D. C., Eberlin, M. N., Marsaioli, A. J. Regioselectivity in aromatic Claisen rearrangements. *J. Org. Chem.* 2003, 68, 5493-5499.

Grant, V. H.; Liu, B., Iridium(III)-catalyzed tandem Claisen rearrangement-intramolecular hydroaryloxylation of aryl allyl ethers to form dihydrobenzofurans. *Tetrahedron Lett.* 2005, 46, 1237-1240.

Guillen, M. D.; Manzanos, M. J., Characteristics of smoke flavourings obtained from mixtures of oak (*Quercus* sp.) wood and aromatic plants (*Thymus vulgaris* L. and Salvia lavandulifolia Vahl.). *Flavour and Fragrance J.* 2005, 20, 676-685.

Heath, R. R., Landolt, P. J., Dueben, B. D., Murphy, R. E. and Schneider, R. E. 1992. Identification of male cabbage looper sex pheromone attractive to females. *J. Chem. Ecol.* 18, 441-453.

Hallem, E. A.; Fox, A. N.; Zwiebel, L. J.; Carlson, J. R., Mosquito receptor for human sweat odorant. *Nature* 2004, 427, 212-213.

Harborne, J. B. (1989) Plant phenolics. In *Methods in plant biochemistry* (Dey, P. M. and Harborne, J. B. Eds.), pp 1-28, Academic Press, London. Isman, M. B. Problems and opportunities for the commercialization of insecticides. In *Biopesticides of Plant Origin*; Regnault-Roger, C., Philogene, B. J. R., and Vincent, R. Eds.; Lavoisier: Paris, 2005; pp 283-291.

Isman, M. B. (2002) Antifeedants, *Pesticide Outlook* 13, 152-157.

Ito, F.; Fusegi, K.; Kumamoto, T.; Ishikawa, T., Boron Trichloride Meidated Regioselective Claisen Rearrangement of Resorcinol Derivatives: Application to Resorcinol Carvonyl Ethers. *Synthesis* 2007, 12, 1785-1796.

Ito, Y.; Kato, R.; Hamashima, K.; Kataoka, Y.; Oe, Y.; Ohta, T.; Furukawa, I., Intramolecular cyclization of phenol derivatives with C=C double bond in a side chain. *J. Organometallic Chem.* 2007, 692, 691-697.

Jermy, T. (1965) The role of rejective stimuli in the host selection of phytophagous insects, *Proc. XIIth Int. Congr. Entomol.*, London, p. 547.

Khambay, B. P., Beddie, D. G., Simmonds, M. S. J. and Green, P. W. C. (1999) A new insecticidal pyranocyclohexenedione from *Kunzea ericifolia, J. Natl. Prod.* 62, 1423-1424.

Kim, D. H., and Ahn, Y. (2001) Contact and fumigant activities of constituents of *Foeniculum vulgare* fruit against three coleopteran stored-product insects, Pest Manag. Sci. 57, 301-306.

Kotkar, H. M., Mendki, P. S., Sadan, S. V., Jha, S. R., Upasani, S. M., and Maheswari, V. L. (2002) Antimicrobial and pesticidal activity of partially purified flavonoids of *Annona squamosa*, Pest Manag. Sci. 58, 33-37.

Kuntz, E.; Amgoune, A.; Lucas, C.; Godard, G., Palladium TPPTS catalyst in water: C-allylation of phenol and guaiacol with ally alcohol and novel isomerisation of allyl ethers of phenol and guaiacol. *J. Mol. Catal. A* 2006, 244, 124-138.

Lane, G. A., Sutherland, O. R. W., and Skipp. R. A. (1987) Isoflavonoids as insect feeding deterrents and antifungal components from root of *Lupinus angustifolius, J. Chem. Ecol.* 13, 771-782.

Landolt, P. J. and Heath, R. R. 1990. Sexual role reversal in mate-finding strategies of the cabbage looper moth. *Science,* 240, 1026-1028.

Luthria, D. L., Ramakrishnan, V., Verma, G. S., Prabhu, B. R., and Banerji, A. (1989) Insect Antifeedants from *Atalantia racemosa, J. Agric. Food Chem.* 37, 1435-1437.

Mathew, N. T.; Khaire, S.; Mayadevi, S.; Jha, R.; Sivasanker, S., Rearrangement of allyl phenyl ether over Al-MCM-41. *J. of Catalysis* 2004, 229, 105-113.

Meijerink, J.; Braks, M. A. H.; Brack, A. A.; Adam, W.; Dekker, T.; Posthumus, M. A.; VanBeek, T. A.; VanLoon, J. A., Identification of olfactory stimulants for *Anopheles gambiae* from human sweat samples. *J. Chem. Ecol.* 2000, 26, 1367-1382.

Munakata, K. Insect antifeedants from plants. In *Control of Insect Behaviour by Natural Products*; Wood, D. L.; Silverstein, R. M.; Nakajima, M. Eds.; Academic Press: New York, 1970, 179-187.

Murugan, K.; Murugan, P.; Noortheen, A., Larvicidal and repellent potential of *Alibizzia amara* Boivin and *Ocimum basilicum* Linn against dengue vector, *Aedes aegypti* (Insecta: Diptera: Culicidae). *Bioresource Tech.* 2006, 98, 198-201.

Neuhaus, E. M., Gisselmann, G., Zhang, W., Dooley, R., Stortkuhl, K., and Hatt. H. (2005) Odorant receptor heterodimerization in the olfactory system of *Drosophila melanogaster, Nature Neurosci.* 8, 15-17.

Obeng-Ofori, D.; Reichmuth, C. H., Bioactivity of eugenol, a major component of essential oil of *Ocimum suave* (Wild.) against four species of stored-product Coleoptera. *Intl. J. Pest Management* 1997, 43, 89-94.

Ollevier, T.; Mwene-Mbeja, T. M., Bismuth Triflate Catalyzed [1,3] Rearrangement of Aryl 3-Methylbut-2-enyl Ethers. *Synthesis* 2006, 23, 3963-3966.

Park, I. K., Shin, S. C., Kim, C. S., Lee, H. J., Choi, W. S., Ahn, Y. J. (2005) Larvicidal activity of lignans identified in *Phryma leptostachya* var. *Asiatica* roots against three mosquito species, *J. Agric. Food Chem.* 53, 969-972.

Reich, N. W.; Yang, C.-G.; Shi, Z.; He, C., Gold(I)-Catalyzed Synthesis of Dihydrobenzofurans from Aryl Allyl Ethers. *Synlett* 2006, 8, 1278-1280.

Restraits, W. J. 1966. Oviposition site and choice of life history evolution. *Am. Zool.* 36, 205-215.

Salunke, B. K., Kotkar, H. M., Mendki, P. S., Upasani, S. M., Maheshwari, V. L. (2005) Efficacy of flavonoids in controlling *Callosobruchus chinensis* (L.) (Coleoptera: Bruchidae), a post-harvest pest of grain legumes, *Crop Protect.* 24, 888-893.

Schneider, C., Bohnenstengel, F. I., Nugroho, B. W., Wray, V., Witte, L., Hung, P. D., Kiet L. C., and Proksch, P. (2000) Insecticidal rocaglamide derivatives from *Aglaia spectabilis* (Meliaceae), *Phytochem.* 54, 731-736.

Topazzini, A., Mazza, M., and Pelosi, P. (1990) Electroantennogram responses of five Lepidopteran species to 26 general odorants, *J. Insect Physiol.* 36, 619-624.

Upasani, S. M., Kotkar, H. M., Mendki, P. S., and Maheswari, V. L. (2003) Partial characterization and insecticidal properties of *Ricinus communis* L. foliage flavonoids, *Pest Manag. Sci.* 59, 1349-1354.

Wang, S. F., Ridsdill-Smith, T. J., and Ghisalberti, E. L. (2005) Chemical defenses of *Trifolium glanduliferum* against red legged earth mite *Halotydeus destructor, J. Agric. Food Chem.* 53, 6240-6245.

Wang P, Zhao J.-Z., Rodrigo-Simón A., Kain W., Janmaat A. F., Shelton A. M., Ferré J., Myers J. 2007. Mechanism of Resistance to *Bacillus Thuringiensis* Toxin CrylAc in a Greenhouse Population of the Cabbage Looper, *Trichoplusia ni. Appl. Env. Microbiol.* 73, 1199

White, W. N.; Gwynn, D.; Schlitt, R.; Girard, C.; Fife, W., The ortho-Claisen Rearrangment. I. The Effect of Substituents on the Rearrangement of Allyl p-X-Phenyl Ethers. *J. Am. Chem. Soc.* 1958, 80, 3271-3277.

White, W. N., and Slater, C. D. (1961) The ortho-Claisen rearrangement. V. The products of rearrangement of allyl m-X-phenyl ethers, *J. Org. Chem.* 26, 3631-3638.

Wildman, R. E. C. (2006) Handbook of nutraceuticals and functional foods. Second edition, CRC Press, Florida, p 560.

Yadav, G. D.; Lande, S. V., UDCaT-5: A Novel and Efficient Solid Superacid Catalyst for Claisen Rearrangement of Substituted Allyl Phenyl Ethers. *Synth. Commun.* 2007, 37, 941-946.

What is claimed is:

1. A method for controlling infestation by a *Trichoplusia ni* comprising applying an effective amount of a compound of Formula I:

$$\text{Formula I}$$

wherein

R1 is methyl, ethyl, propyl, n-butyl, isopentyl (3-methylbutyl) or allyl; and

R2 is H, methyl, ethyl, propyl, n-butyl, isopentyl (3-methylbutyl) or allyl, to a site of interest whereby the *Trichoplusia ni* infestation is controlled.

2. The method of claim 1 wherein the controlling is selected from the group consisting of one or more of oviposition deterrence, feeding deterrence, oviposition stimulation, and feeding stimulation.

3. The method of claim 1 wherein the compound of Formula I is an oviposition deterrent.

4. The method of claim 3 wherein the compound of Formula I is selected from the group consisting of one or more of 1-butoxy-4-alkoxybenzene, wherein the 4-alkoxy groups are methoxy, ethoxy, propoxy, or isopentyloxy; 1-ethoxy-4-alkoxybenzene, wherein the 4-alkoxy groups are methoxy, ethoxy, propoxy, or isopentyloxy; and 1,4-diethoxybenzene.

5. The method of claim 1 wherein the compound of Formula I is a feeding deterrent.

6. The method of claim 5 wherein the compound of Formula I is selected from the group consisting of one or more of 1-methoxy-4-alkoxybenzene, wherein the 4-alkoxy groups are methoxy, ethoxy, propoxy, or isopentyloxy; 1,4-diethoxybenzene; 1-butoxy-4-alkoxybenzene, wherein the 4-alkoxy groups are methoxy, ethoxy, propoxy, butoxy, or isopentyloxy; 1-ethoxy-4-alkoxybenzene, wherein the 4-alkoxy groups are methoxy, ethoxy, propoxy, or isopentyloxy; l-isopentyloxy-4-alkoxybenzene, wherein the 4-alkoxy groups are methoxy, ethoxy, propoxy, or isopentyloxy; 1-allyloxy-4-alkoxybenzene, wherein the 4-alkoxy groups are methoxy, ethoxy, or propoxy; 1-allyloxy-4-propoxybenzene; and 1-ethoxy-4-propoxybenzene.

7. The method of claim 1 wherein the compound of Formula I is an oviposition stimulant.

8. The method of claim 7 wherein the compound of Formula I is 1-allyloxy-4-isopentoxybenzene.

9. The method of claim 1 wherein the compound of Formula I is a feeding stimulant.

10. The method of claim 9 wherein the compound of Formula I is selected from the group consisting of one or more of 1-hydroxy-4-methoxybenzene, and 1-hydroxy-4-propoxybenzene.

11. The method of claim 1 wherein the compound of Formula I is non-toxic.

12. The method of claim 1 wherein two or more compounds of Formula I are applied simultaneously or sequentially.

13. The method of claim 1 wherein the compound of Formula I is applied in combination with another compound or treatment.

14. The method of claim 13 wherein the other compound is selected from one or more of the group consisting of an oviposition deterrent, an oviposition stimulant, a feeding deterrent, a feeding stimulant, an attractant, and a toxicant.

15. The method of claim 1 wherein the the *T. ni* is a larva or an adult.

16. The method of claim 1 wherein the site of interest comprises a plant or part thereof and wherein the plant is a plant within the host range of *Trichoplusia ni*.

17. The method of claim 1 wherein the compound of Formula I is provided in a formulation selected from one or more of the group consisting of a spray, aerosol, solid, or liquid.

18. A method of protecting a plant from infestation by a *Trichoplusia ni* comprising applying an effective amount of a compound of Formula I:

Formula I wherein
R1 is methyl, ethyl, propyl, n-butyl, isopentyl (3-methylbutyl) or allyl; and
R2 is H, methyl, ethyl, propyl, n-butyl, isopentyl (3-methylbutyl) or allyl,
to the plant or part thereof, wherein the plant is a plant within the host range of *Trichoplusia ni*, whereby the *Trichoplusia ni* infestation is controlled.

19. The method of claim 1 wherein the site of interest does not contain grass.

* * * * *